US010859577B2

(12) United States Patent
Guette et al.

(10) Patent No.: US 10,859,577 B2
(45) Date of Patent: Dec. 8, 2020

(54) METHOD FOR IN VITRO DIAGNOSING AND PROGNOSING OF TRIPLE NEGATIVE BREAST CANCER RECURRENCE

(71) Applicants: Institut de Cancerologie de L'Ouest, Angers (FR); Universite D'Angers, Angers (FR); Institut National de la Sante et de la Recherche Medicale (INSERM), Paris (FR)

(72) Inventors: Catherine Guette, La Possonniere (FR); Mario Campone, Nantes (FR); Olivier Coqueret, Angers (FR); Benjamin Barre, Bain sur Longuenee (FR)

(73) Assignees: Institut de Cancerologie de L'Ouest, Angers (FR); Universite D'Angers, Angers (FR); Institut National de la Sante et de la Recherche Medicale (INSERM), Paris (FR)

( * ) Notice: Subject to any disclaimer, the term of this patent is extended or adjusted under 35 U.S.C. 154(b) by 254 days.

(21) Appl. No.: 15/038,125

(22) PCT Filed: Nov. 24, 2014

(86) PCT No.: PCT/EP2014/075424
§ 371 (c)(1),
(2) Date: May 20, 2016

(87) PCT Pub. No.: WO2015/075240
PCT Pub. Date: May 28, 2015

(65) Prior Publication Data
US 2016/0291021 A1 Oct. 6, 2016

(30) Foreign Application Priority Data
Nov. 22, 2013 (EP) .................................. 13306603

(51) Int. Cl.
*G01N 33/574* (2006.01)
*G01N 33/50* (2006.01)

(52) U.S. Cl.
CPC ... *G01N 33/57415* (2013.01); *G01N 33/5011* (2013.01); *G01N 2800/52* (2013.01); *G01N 2800/54* (2013.01)

(58) Field of Classification Search
None
See application file for complete search history.

(56) References Cited

U.S. PATENT DOCUMENTS

| 2004/0005563 | A1* | 1/2004 | Mack | ...... C07K 14/47 435/6.14 |
| 2004/0029114 | A1* | 2/2004 | Mack | ...... C07K 14/47 435/6.14 |
| 2005/0181375 | A1* | 8/2005 | Aziz | ...... G01N 33/57415 435/6.14 |
| 2007/0054271 | A1* | 3/2007 | Polyak | ...... C07K 14/47 435/6.14 |
| 2009/0222387 | A1* | 9/2009 | Gehrmann | ...... G06F 19/24 706/12 |
| 2009/0239229 | A1* | 9/2009 | Weaver | ...... C12Q 1/6886 435/6.12 |
| 2009/0317392 | A1* | 12/2009 | Nakamura | ...... C12N 15/1135 424/139.1 |
| 2010/0210738 | A1* | 8/2010 | Leyland-Jones | ..... C12Q 1/6886 514/789 |
| 2012/0225789 | A1* | 9/2012 | Chang | ...... C12Q 1/6886 506/9 |
| 2014/0162887 | A1* | 6/2014 | Martin | ...... C12Q 1/6886 506/8 |
| 2015/0005183 | A1* | 1/2015 | Krizman | ...... G01N 33/57415 506/9 |

FOREIGN PATENT DOCUMENTS

| WO | 03/070979 | A2 | 8/2003 |
| WO | 2004/063355 | A2 | 7/2004 |
| WO | 2009/114862 | A1 | 9/2009 |
| WO | 2012/106718 | A2 | 8/2012 |

OTHER PUBLICATIONS

Sparano et al, Cancer Res, 69 Suppl S:25, 2009.*
Morita et al, Protomics, 6:5880-5890, 2006.*
Boelens et al, J Clin Pathol 60:608-614, 2007.*
Bigbee et al, J Thrac Oncol, 7:698-708, 2012.*
Young et al, Lung Cancer, 36:133-141, 2002.*
Nomura et al, Annals of Oncology, vol. 23, Suppl 9, 1701, 2012.*
Brenton, J.D. et al, Molecular Classification and Molecular Forecasting of Breast Cancer: Ready for Clinical Application?, Journal of Clinical Oncology, Oct. 10, 2005, 23(29), pp. 7350-7360.
Hudis, C.A. et al, Triple-Negative Breast Cancer: An Unmet Medical Need, The Oncologist, 2011, 16 (suppl 1), pp. 1-11.
Ernoult, E. et al, Improved Proteome Coverage by Using iTRAQ Labelling and Peptide OFFGEL Fractionation, Proteome Science, 2008, 13; 6:27.
Ernoult, E. et al, A Proteomic Approach for Plasma Biomarker Discovery with iTRAQ Labelling and OFFGEL Fractionation, Journal of Biomedicine and Biotechnology, 2010, 2010:927917.
Rakha, E.A. et al, Prognostic Significance of Nottingham Histologic Grade in Invasive Breast Carcinoma, Journal of Clinical Oncology, Jul. 1, 2008, vol. 26, No. 19, pp. 3153-3158.

(Continued)

*Primary Examiner* — Mark Halvorson
(74) *Attorney, Agent, or Firm* — Banner & Witcoff, Ltd.

(57) ABSTRACT

The present invention is in the technical field of breast cancer management, and more particularly relates to the diagnosis and/or prognosing of triple-negative breast cancer (TNBC). The invention is more particularly based on the finding that specific biomarkers are aberrantly expressed in patients suffering from a triple-negative breast cancer recurrence, and are highly related to the aggressiveness of this disease, and thus to survival of said patient.

10 Claims, 10 Drawing Sheets
Specification includes a Sequence Listing.

(56) References Cited

OTHER PUBLICATIONS

Lopez-Farre, A.J. et al, Plasma Desmoplakin I Biomarker of Vascular Recurrence After Ischemic Stroke, Journal of Neurochemistry, 2012, vol. 121, pp. 314-325.
Hou, H.W. et al, Isolation and Retrieval of Circulating Tumor Cells Using Centrifugal Forces, Scientific Reports, 2013, 3:1259.
Reeves, J.R. et al, Measurement of Protein Expression A Technical Overview, Methods in Molecular Medicine, 2000, vol. 39, Chapter 51, pp. 471-483.
Hamelinck, D. et al, Optimized Normalization for Antibody Microarrays and Application to Serum-Protein Profiling, Molecular & Cellular Proteomics, 2005, vol. 4.6, pp. 773-784.
Kohler, G. et al, Continuous Cultures of Fused Cells Secreting Antibody of Predefined Specificity, Nature, Aug. 7, 1975, vol. 256, pp. 495-497.
Kozbor, D. et al, The production of Monoclonal Antibodies from Human Lymphocytes, Immunology Today, 1983, vol. 4, No. 3, pp. 72-79.
Roder, J.C. et al, The EBV-Hybridoma Technique, Methods in Enzymology, 1986, vol. 121, pp. 140-167.
Huse, W.D. et al, Generation of a Large Combinatorial Library of the Immunoglobulin Repertoire in Phage Lambda, Science, Dec. 8, 1989, vol. 246, pp. 1275-1281.
Weigelt, B. et al, Unraveling the Microenvironmental Influences on the Normal Mammary Gland and Breast Cancer, Semin Cancer Biol, Oct. 2008, 18(5), pp. 311-321.
Kenny, P.A. et al, The Morphologies of Breast Cancer Cell Lines in Three-Dimensional Assays Correlate with their Profiles of Gene Expression, Molecular Oncology, Jun. 2007, 1(1), pp. 84-96.
Li, Q. et al, Three-Dimensional Overlay Culture Models of Human Breast Cancer Reveal a Critical Sensitivity to Mitogen-Activated Protein Kinase Kinase Inhibitors, The Journal of Pharmacology and Experimental Therapeutics, 2010, 332(3): 821-828.
Liu, B. et al, Metformin Induces Unique Biological and Molecular Responses in Triple Negative Breast Cancer Cells, Cell Cycle, 2009, 8:13, pp. 2031-2040.
Mitchell, Peter, A Perspective on Protein Microarrays, Nature Biotechnology, Mar. 2002, vol. 20, pp. 225-229.
Haab, Brian B., Antibody Arrays in Cancer Research, Molecular & Cellular Proteomics, 2005, vol. 4.4, pp. 377-383.
Eckel-Passow, J.E. et al, Experimental Design and Analysis of Antibody Microarrays: Applying Methods from cDNA Arrays, Cancer Res, 2005, 65(8), pp. 2985-2989.
Kingsmore, Stephen F., Multiplexed Protein Measurement: Technologies and Applications of Protein and Antibody Arrays, Nat Rev Drug Discov, Apr. 2006; 5(4), pp. 310-320.
Chandra, H. et al, Protein Microarrays and Novel Detection Platforms, Expert Review of Proteomics, 2011, 8:1, pp. 61-79.
Wisniewski, J.R. et al, Universal Sample Preparation Method for Proteome Analysis, Nature Methods, May 2009, vol. 6, No. 5, pp. 359-362.
Shilov, I.V. et al, The Paragon Algorithm, a Next Generation Search Engine that uses Sequence Temperature Values and Feature Probabilities to Identify Peptides from Tandem Mass Spectra, Molecular & Cellular Proteomics, 2007, vol. 6.9, pp. 1638-1655.
Schwacke, J.H. et al, iQuantitator: A Tool for Protein Expression Interference Using iTRAQ, BMC Bioinformatics, Oct. 18, 2009, 10:342.
Grant, J.E. et al, Quantification of Protein Expression Changes in the Aging Left Ventricle of Rattus Norvegicus, J. Proteome Res., Sep. 2009, 8(9), pp. 4252-4263.
Besson, D. et al, A Quantitative Proteomic Approach of the Different Stages of Colorectal Cancer Establishes OLFM4 as a New Nonmetastatic Tumor Marker, Molecular & Cellular Proteomics, 2011, 10(12): M111.009712.
Zeeberg, B.R. et al, High-Throughput GoMiner, an 'Industrial-Strength' Integrative Gene Ontology Tool for Interpretation of Multiple-Microarray Experiments, with Application to Studies of Common Variable Immune Deficiency (CVID), BMC Bioinformatics, 2005, 6:168.
International Search Report Issued in Corresponding International Application No. PCT/EP2014/075424, dated May 22, 2015.

\* cited by examiner

A

B

SEQUENCE LISTING

<160> NUMBER OF SEQ ID NOS: 24

<210> SEQ ID NO 1
<211> LENGTH: 2871
<212> TYPE: PRT
<213> ORGANISM: homo sapiens
<220> FEATURE:
<221> NAME/KEY: misc_feature
<223> OTHER INFORMATION: Desmoplakin isoform 1

<400> SEQUENCE: 1

Met Ser Cys Asn Gly Gly Ser His Pro Arg Ile Asn Thr Leu Gly Arg
1               5                   10                  15

```
Met Ile Arg Ala Glu Ser Gly Pro Asp Leu Arg Tyr Glu Val Thr Ser
            20                  25                  30
Gly Gly Gly Gly Thr Ser Arg Met Tyr Tyr Ser Arg Arg Gly Val Ile
        35                  40                  45
Thr Asp Gln Asn Ser Asp Gly Tyr Cys Gln Thr Gly Thr Met Ser Arg
    50                  55                  60
His Gln Asn Gln Asn Thr Ile Gln Glu Leu Leu Gln Asn Cys Ser Asp
65                  70                  75                  80
Cys Leu Met Arg Ala Glu Leu Ile Val Gln Pro Glu Leu Lys Tyr Gly
                85                  90                  95
Asp Gly Ile Gln Leu Thr Arg Ser Arg Glu Leu Asp Glu Cys Phe Ala
            100                 105                 110
Gln Ala Asn Asp Gln Met Glu Ile Leu Asp Ser Leu Ile Arg Glu Met
        115                 120                 125
Arg Gln Met Gly Gln Pro Cys Asp Ala Tyr Gln Lys Arg Leu Leu Gln
    130                 135                 140
Leu Gln Glu Gln Met Arg Ala Leu Tyr Lys Ala Ile Ser Val Pro Arg
145                 150                 155                 160
Val Arg Arg Ala Ser Ser Lys Gly Gly Gly Tyr Thr Cys Gln Ser
                165                 170                 175
Gly Ser Gly Trp Asp Glu Phe Thr Lys His Val Thr Ser Glu Cys Leu
            180                 185                 190
Gly Trp Met Arg Gln Gln Arg Ala Glu Met Asp Met Val Ala Trp Gly
        195                 200                 205
Val Asp Leu Ala Ser Val Glu Gln His Ile Asn Ser His Arg Gly Ile
    210                 215                 220
His Asn Ser Ile Gly Asp Tyr Arg Trp Gln Leu Asp Lys Ile Lys Ala
225                 230                 235                 240
Asp Leu Arg Glu Lys Ser Ala Ile Tyr Gln Leu Glu Glu Tyr Glu
                245                 250                 255
Asn Leu Leu Lys Ala Ser Phe Glu Arg Met Asp His Leu Arg Gln Leu
            260                 265                 270
Gln Asn Ile Ile Gln Ala Thr Ser Arg Glu Ile Met Trp Ile Asn Asp
        275                 280                 285
Cys Glu Glu Glu Glu Leu Leu Tyr Asp Trp Ser Asp Lys Asn Thr Asn
    290                 295                 300
Ile Ala Gln Lys Gln Glu Ala Phe Ser Ile Arg Met Ser Gln Leu Glu
305                 310                 315                 320
Val Lys Glu Lys Glu Leu Asn Lys Leu Lys Gln Glu Ser Asp Gln Leu
                325                 330                 335
Val Leu Asn Gln His Pro Ala Ser Asp Lys Ile Glu Ala Tyr Met Asp
            340                 345                 350
Thr Leu Gln Thr Gln Trp Ser Trp Ile Leu Gln Ile Thr Lys Cys Ile
        355                 360                 365
Asp Val His Leu Lys Glu Asn Ala Ala Tyr Phe Gln Phe Phe Glu Glu
    370                 375                 380
Ala Gln Ser Thr Glu Ala Tyr Leu Lys Gly Leu Gln Asp Ser Ile Arg
385                 390                 395                 400
Lys Lys Tyr Pro Cys Asp Lys Asn Met Pro Leu Gln His Leu Leu Glu
                405                 410                 415
Gln Ile Lys Glu Leu Glu Lys Glu Arg Glu Lys Ile Leu Glu Tyr Lys
            420                 425                 430
Arg Gln Val Gln Asn Leu Val Asn Lys Ser Lys Lys Ile Val Gln Leu
```

-continued

```
                435                 440                 445
Lys Pro Arg Asn Pro Asp Tyr Arg Ser Asn Lys Pro Ile Ile Leu Arg
450                 455                 460

Ala Leu Cys Asp Tyr Lys Gln Asp Gln Lys Ile Val His Lys Gly Asp
465                 470                 475                 480

Glu Cys Ile Leu Lys Asp Asn Asn Glu Arg Ser Lys Trp Tyr Val Thr
                485                 490                 495

Gly Pro Gly Gly Val Asp Met Leu Val Pro Ser Val Gly Leu Ile Ile
                500                 505                 510

Pro Pro Pro Asn Pro Leu Ala Val Asp Leu Ser Cys Lys Ile Glu Gln
                515                 520                 525

Tyr Tyr Glu Ala Ile Leu Ala Leu Trp Asn Gln Leu Tyr Ile Asn Met
530                 535                 540

Lys Ser Leu Val Ser Trp His Tyr Cys Met Ile Asp Ile Glu Lys Ile
545                 550                 555                 560

Arg Ala Met Thr Ile Ala Lys Leu Lys Thr Met Arg Gln Glu Asp Tyr
                565                 570                 575

Met Lys Thr Ile Ala Asp Leu Glu Leu His Tyr Gln Glu Phe Ile Arg
                580                 585                 590

Asn Ser Gln Gly Ser Glu Met Phe Gly Asp Asp Lys Arg Lys Ile
                595                 600                 605

Gln Ser Gln Phe Thr Asp Ala Gln Lys His Tyr Gln Thr Leu Val Ile
610                 615                 620

Gln Leu Pro Gly Tyr Pro Gln His Gln Thr Val Thr Thr Thr Glu Ile
625                 630                 635                 640

Thr His His Gly Thr Cys Gln Asp Val Asn His Asn Lys Val Ile Glu
                645                 650                 655

Thr Asn Arg Glu Asn Asp Lys Gln Glu Thr Trp Met Leu Met Glu Leu
                660                 665                 670

Gln Lys Ile Arg Arg Gln Ile Glu His Cys Glu Gly Arg Met Thr Leu
                675                 680                 685

Lys Asn Leu Pro Leu Ala Asp Gln Gly Ser Ser His His Ile Thr Val
690                 695                 700

Lys Ile Asn Glu Leu Lys Ser Val Gln Asn Asp Ser Gln Ala Ile Ala
705                 710                 715                 720

Glu Val Leu Asn Gln Leu Lys Asp Met Leu Ala Asn Phe Arg Gly Ser
                725                 730                 735

Glu Lys Tyr Cys Tyr Leu Gln Asn Glu Val Phe Gly Leu Phe Gln Lys
                740                 745                 750

Leu Glu Asn Ile Asn Gly Val Thr Asp Gly Tyr Leu Asn Ser Leu Cys
                755                 760                 765

Thr Val Arg Ala Leu Leu Gln Ala Ile Leu Gln Thr Glu Asp Met Leu
770                 775                 780

Lys Val Tyr Glu Ala Arg Leu Thr Glu Glu Thr Val Cys Leu Asp
785                 790                 795                 800

Leu Asp Lys Val Glu Ala Tyr Arg Cys Gly Leu Lys Lys Ile Lys Asn
                805                 810                 815

Asp Leu Asn Leu Lys Lys Ser Leu Ala Thr Met Lys Thr Glu Leu
                820                 825                 830

Gln Lys Ala Gln Gln Ile His Ser Gln Thr Ser Gln Gln Tyr Pro Leu
                835                 840                 845

Tyr Asp Leu Asp Leu Gly Lys Phe Gly Glu Lys Val Thr Gln Leu Thr
850                 855                 860
```

-continued

```
Asp Arg Trp Gln Arg Ile Asp Lys Gln Ile Asp Phe Arg Leu Trp Asp
865                 870                 875                 880

Leu Glu Lys Gln Ile Lys Gln Leu Arg Asn Tyr Arg Asp Asn Tyr Gln
            885                 890                 895

Ala Phe Cys Lys Trp Leu Tyr Asp Ala Lys Arg Arg Gln Asp Ser Leu
        900                 905                 910

Glu Ser Met Lys Phe Gly Asp Ser Asn Thr Val Met Arg Phe Leu Asn
            915                 920                 925

Glu Gln Lys Asn Leu His Ser Glu Ile Ser Gly Lys Arg Asp Lys Ser
        930                 935                 940

Glu Glu Val Gln Lys Ile Ala Glu Leu Cys Ala Asn Ser Ile Lys Asp
945                 950                 955                 960

Tyr Glu Leu Gln Leu Ala Ser Tyr Thr Ser Gly Leu Glu Thr Leu Leu
            965                 970                 975

Asn Ile Pro Ile Lys Arg Thr Met Ile Gln Ser Pro Ser Gly Val Ile
        980                 985                 990

Leu Gln Glu Ala Ala Asp Val His Ala Arg Tyr Ile Glu Leu Leu Thr
            995                1000                1005

Arg Ser Gly Asp Tyr Tyr Arg Phe Leu Ser Glu Met Leu Lys Ser
    1010                1015                1020

Leu Glu Asp Leu Lys Leu Lys Asn Thr Lys Ile Glu Val Leu Glu
    1025                1030                1035

Glu Glu Leu Arg Leu Ala Arg Asp Ala Asn Ser Glu Asn Cys Asn
    1040                1045                1050

Lys Asn Lys Phe Leu Asp Gln Asn Leu Gln Lys Tyr Gln Ala Glu
    1055                1060                1065

Cys Ser Gln Phe Lys Ala Lys Leu Ala Ser Leu Glu Glu Leu Lys
    1070                1075                1080

Arg Gln Ala Glu Leu Asp Gly Lys Ser Ala Lys Gln Asn Leu Asp
    1085                1090                1095

Lys Cys Tyr Gly Gln Ile Lys Glu Leu Asn Glu Lys Ile Thr Arg
    1100                1105                1110

Leu Thr Tyr Glu Ile Glu Asp Glu Lys Arg Arg Lys Ser Val
    1115                1120                1125

Glu Asp Arg Phe Asp Gln Lys Asn Asp Tyr Asp Gln Leu Gln
    1130                1135                1140

Lys Ala Arg Gln Cys Glu Lys Glu Asn Leu Gly Trp Gln Lys Leu
    1145                1150                1155

Glu Ser Glu Lys Ala Ile Lys Glu Lys Glu Tyr Glu Ile Glu Arg
    1160                1165                1170

Leu Arg Val Leu Leu Gln Glu Glu Gly Thr Arg Lys Arg Glu Tyr
    1175                1180                1185

Glu Asn Glu Leu Ala Lys Val Arg Asn His Tyr Asn Glu Glu Met
    1190                1195                1200

Ser Asn Leu Arg Asn Lys Tyr Glu Thr Glu Ile Asn Ile Thr Lys
    1205                1210                1215

Thr Thr Ile Lys Glu Ile Ser Met Gln Lys Glu Asp Asp Ser Lys
    1220                1225                1230

Asn Leu Arg Asn Gln Leu Asp Arg Leu Ser Arg Glu Asn Arg Asp
    1235                1240                1245

Leu Lys Asp Glu Ile Val Arg Leu Asn Asp Ser Ile Leu Gln Ala
    1250                1255                1260
```

```
Thr Glu Gln Arg Arg Arg Ala Glu Glu Asn Ala Leu Gln Gln Lys
    1265                1270                1275
Ala Cys Gly Ser Glu Ile Met Gln Lys Lys Gln His Leu Glu Ile
    1280                1285                1290
Glu Leu Lys Gln Val Met Gln Arg Ser Glu Asp Asn Ala Arg
    1295                1300                1305
His Lys Gln Ser Leu Glu Glu Ala Ala Lys Thr Ile Gln Asp Lys
    1310                1315                1320
Asn Lys Glu Ile Glu Arg Leu Lys Ala Glu Phe Gln Glu Ala
    1325                1330                1335
Lys Arg Arg Trp Glu Tyr Glu Asn Glu Leu Ser Lys Val Arg Asn
    1340                1345                1350
Asn Tyr Asp Glu Glu Ile Ile Ser Leu Lys Asn Gln Phe Glu Thr
    1355                1360                1365
Glu Ile Asn Ile Thr Lys Thr Thr Ile His Gln Leu Thr Met Gln
    1370                1375                1380
Lys Glu Glu Asp Thr Ser Gly Tyr Arg Ala Gln Ile Asp Asn Leu
    1385                1390                1395
Thr Arg Glu Asn Arg Ser Leu Ser Glu Glu Ile Lys Arg Leu Lys
    1400                1405                1410
Asn Thr Leu Thr Gln Thr Thr Glu Asn Leu Arg Arg Val Glu Glu
    1415                1420                1425
Asp Ile Gln Gln Gln Lys Ala Thr Gly Ser Glu Val Ser Gln Arg
    1430                1435                1440
Lys Gln Gln Leu Glu Val Glu Leu Arg Gln Val Thr Gln Met Arg
    1445                1450                1455
Thr Glu Glu Ser Val Arg Tyr Lys Gln Ser Leu Asp Asp Ala Ala
    1460                1465                1470
Lys Thr Ile Gln Asp Lys Asn Lys Glu Ile Glu Arg Leu Lys Gln
    1475                1480                1485
Leu Ile Asp Lys Glu Thr Asn Asp Arg Lys Cys Leu Glu Asp Glu
    1490                1495                1500
Asn Ala Arg Leu Gln Arg Val Gln Tyr Asp Leu Gln Lys Ala Asn
    1505                1510                1515
Ser Ser Ala Thr Glu Thr Ile Asn Lys Leu Lys Val Gln Glu Gln
    1520                1525                1530
Glu Leu Thr Arg Leu Arg Ile Asp Tyr Glu Arg Val Ser Gln Glu
    1535                1540                1545
Arg Thr Val Lys Asp Gln Asp Ile Thr Arg Phe Gln Asn Ser Leu
    1550                1555                1560
Lys Glu Leu Gln Leu Gln Lys Gln Lys Val Glu Glu Leu Asn
    1565                1570                1575
Arg Leu Lys Arg Thr Ala Ser Glu Asp Ser Cys Lys Arg Lys Lys
    1580                1585                1590
Leu Glu Glu Glu Leu Glu Gly Met Arg Arg Ser Leu Lys Glu Gln
    1595                1600                1605
Ala Ile Lys Ile Thr Asn Leu Thr Gln Gln Leu Glu Gln Ala Ser
    1610                1615                1620
Ile Val Lys Lys Arg Ser Glu Asp Asp Leu Arg Gln Gln Arg Asp
    1625                1630                1635
Val Leu Asp Gly His Leu Arg Glu Lys Gln Arg Thr Gln Glu Glu
    1640                1645                1650
Leu Arg Arg Leu Ser Ser Glu Val Glu Ala Leu Arg Arg Gln Leu
```

```
            1655                1660                1665

Leu Gln Glu Gln Glu Ser Val Lys Gln Ala His Leu Arg Asn Glu
    1670                1675                1680

His Phe Gln Lys Ala Ile Glu Asp Lys Ser Arg Ser Leu Asn Glu
    1685                1690                1695

Ser Lys Ile Glu Ile Glu Arg Leu Gln Ser Leu Thr Glu Asn Leu
    1700                1705                1710

Thr Lys Glu His Leu Met Leu Glu Glu Leu Arg Asn Leu Arg
    1715                1720                1725

Leu Glu Tyr Asp Asp Leu Arg Arg Gly Arg Ser Glu Ala Asp Ser
    1730                1735                1740

Asp Lys Asn Ala Thr Ile Leu Glu Leu Arg Ser Gln Leu Gln Ile
    1745                1750                1755

Ser Asn Asn Arg Thr Leu Glu Leu Gln Gly Leu Ile Asn Asp Leu
    1760                1765                1770

Gln Arg Glu Arg Glu Asn Leu Arg Gln Glu Ile Glu Lys Phe Gln
    1775                1780                1785

Lys Gln Ala Leu Glu Ala Ser Asn Arg Ile Gln Glu Ser Lys Asn
    1790                1795                1800

Gln Cys Thr Gln Val Val Gln Glu Arg Glu Ser Leu Leu Val Lys
    1805                1810                1815

Ile Lys Val Leu Glu Gln Asp Lys Ala Arg Leu Gln Arg Leu Glu
    1820                1825                1830

Asp Glu Leu Asn Arg Ala Lys Ser Thr Leu Glu Ala Glu Thr Arg
    1835                1840                1845

Val Lys Gln Arg Leu Glu Cys Glu Lys Gln Gln Ile Gln Asn Asp
    1850                1855                1860

Leu Asn Gln Trp Lys Thr Gln Tyr Ser Arg Lys Glu Glu Ala Ile
    1865                1870                1875

Arg Lys Ile Glu Ser Glu Arg Glu Lys Ser Glu Arg Glu Lys Asn
    1880                1885                1890

Ser Leu Arg Ser Glu Ile Glu Arg Leu Gln Ala Glu Ile Lys Arg
    1895                1900                1905

Ile Glu Glu Arg Cys Arg Arg Lys Leu Glu Asp Ser Thr Arg Glu
    1910                1915                1920

Thr Gln Ser Gln Leu Glu Thr Glu Arg Ser Arg Tyr Gln Arg Glu
    1925                1930                1935

Ile Asp Lys Leu Arg Gln Arg Pro Tyr Gly Ser His Arg Glu Thr
    1940                1945                1950

Gln Thr Glu Cys Glu Trp Thr Val Asp Thr Ser Lys Leu Val Phe
    1955                1960                1965

Asp Gly Leu Arg Lys Lys Val Thr Ala Met Gln Leu Tyr Glu Cys
    1970                1975                1980

Gln Leu Ile Asp Lys Thr Thr Leu Asp Lys Leu Leu Lys Gly Lys
    1985                1990                1995

Lys Ser Val Glu Glu Val Ala Ser Glu Ile Gln Pro Phe Leu Arg
    2000                2005                2010

Gly Ala Gly Ser Ile Ala Gly Ala Ser Ala Ser Pro Lys Glu Lys
    2015                2020                2025

Tyr Ser Leu Val Glu Ala Lys Arg Lys Lys Leu Ile Ser Pro Glu
    2030                2035                2040

Ser Thr Val Met Leu Leu Glu Ala Gln Ala Ala Thr Gly Gly Ile
    2045                2050                2055
```

```
Ile Asp Pro His Arg Asn Glu Lys Leu Thr Val Asp Ser Ala Ile
    2060            2065                2070

Ala Arg Asp Leu Ile Asp Phe Asp Asp Arg Gln Gln Ile Tyr Ala
    2075            2080                2085

Ala Glu Lys Ala Ile Thr Gly Phe Asp Asp Pro Phe Ser Gly Lys
    2090            2095                2100

Thr Val Ser Val Ser Glu Ala Ile Lys Lys Asn Leu Ile Asp Arg
    2105            2110                2115

Glu Thr Gly Met Arg Leu Leu Glu Ala Gln Ile Ala Ser Gly Gly
    2120            2125                2130

Val Val Asp Pro Val Asn Ser Val Phe Leu Pro Lys Asp Val Ala
    2135            2140                2145

Leu Ala Arg Gly Leu Ile Asp Arg Asp Leu Tyr Arg Ser Leu Asn
    2150            2155                2160

Asp Pro Arg Asp Ser Gln Lys Asn Phe Val Asp Pro Val Thr Lys
    2165            2170                2175

Lys Lys Val Ser Tyr Val Gln Leu Lys Glu Arg Cys Arg Ile Glu
    2180            2185                2190

Pro His Thr Gly Leu Leu Leu Ser Val Gln Lys Arg Ser Met
    2195            2200                2205

Ser Phe Gln Gly Ile Arg Gln Pro Val Thr Val Thr Glu Leu Val
    2210            2215                2220

Asp Ser Gly Ile Leu Arg Pro Ser Thr Val Asn Glu Leu Glu Ser
    2225            2230                2235

Gly Gln Ile Ser Tyr Asp Glu Val Gly Glu Arg Ile Lys Asp Phe
    2240            2245                2250

Leu Gln Gly Ser Ser Cys Ile Ala Gly Ile Tyr Asn Glu Thr Thr
    2255            2260                2265

Lys Gln Lys Leu Gly Ile Tyr Glu Ala Met Lys Ile Gly Leu Val
    2270            2275                2280

Arg Pro Gly Thr Ala Leu Glu Leu Leu Glu Ala Gln Ala Ala Thr
    2285            2290                2295

Gly Phe Ile Val Asp Pro Val Ser Asn Leu Arg Leu Pro Val Glu
    2300            2305                2310

Glu Ala Tyr Lys Arg Gly Leu Val Gly Ile Glu Phe Lys Glu Lys
    2315            2320                2325

Leu Leu Ser Ala Glu Arg Ala Val Thr Gly Tyr Asn Asp Pro Glu
    2330            2335                2340

Thr Gly Asn Ile Ile Ser Leu Phe Gln Ala Met Asn Lys Glu Leu
    2345            2350                2355

Ile Glu Lys Gly His Gly Ile Arg Leu Leu Glu Ala Gln Ile Ala
    2360            2365                2370

Thr Gly Gly Ile Ile Asp Pro Lys Glu Ser His Arg Leu Pro Val
    2375            2380                2385

Asp Ile Ala Tyr Lys Arg Gly Tyr Phe Asn Glu Glu Leu Ser Glu
    2390            2395                2400

Ile Leu Ser Asp Pro Ser Asp Asp Thr Lys Gly Phe Phe Asp Pro
    2405            2410                2415

Asn Thr Glu Glu Asn Leu Thr Tyr Leu Gln Leu Lys Glu Arg Cys
    2420            2425                2430

Ile Lys Asp Glu Glu Thr Gly Leu Cys Leu Leu Pro Leu Lys Glu
    2435            2440                2445
```

```
Lys Lys Lys Gln Val Gln Thr Ser Gln Lys Asn Thr Leu Arg Lys
2450                2455            2460

Arg Arg Val Val Ile Val Asp Pro Glu Thr Asn Lys Glu Met Ser
2465                2470            2475

Val Gln Glu Ala Tyr Lys Lys Gly Leu Ile Asp Tyr Glu Thr Phe
2480                2485            2490

Lys Glu Leu Cys Glu Gln Glu Cys Glu Trp Glu Glu Ile Thr Ile
2495                2500            2505

Thr Gly Ser Asp Gly Ser Thr Arg Val Val Leu Val Asp Arg Lys
2510                2515            2520

Thr Gly Ser Gln Tyr Asp Ile Gln Asp Ala Ile Asp Lys Gly Leu
2525                2530            2535

Val Asp Arg Lys Phe Phe Asp Gln Tyr Arg Ser Gly Ser Leu Ser
2540                2545            2550

Leu Thr Gln Phe Ala Asp Met Ile Ser Leu Lys Asn Gly Val Gly
2555                2560            2565

Thr Ser Ser Ser Met Gly Ser Gly Val Ser Asp Asp Val Phe Ser
2570                2575            2580

Ser Ser Arg His Glu Ser Val Ser Lys Ile Ser Thr Ile Ser Ser
2585                2590            2595

Val Arg Asn Leu Thr Ile Arg Ser Ser Ser Phe Ser Asp Thr Leu
2600                2605            2610

Glu Glu Ser Ser Pro Ile Ala Ala Ile Phe Asp Thr Glu Asn Leu
2615                2620            2625

Glu Lys Ile Ser Ile Thr Glu Gly Ile Glu Arg Gly Ile Val Asp
2630                2635            2640

Ser Ile Thr Gly Gln Arg Leu Leu Glu Ala Gln Ala Cys Thr Gly
2645                2650            2655

Gly Ile Ile His Pro Thr Thr Gly Gln Lys Leu Ser Leu Gln Asp
2660                2665            2670

Ala Val Ser Gln Gly Val Ile Asp Gln Asp Met Ala Thr Arg Leu
2675                2680            2685

Lys Pro Ala Gln Lys Ala Phe Ile Gly Phe Glu Gly Val Lys Gly
2690                2695            2700

Lys Lys Lys Met Ser Ala Ala Glu Ala Val Lys Glu Lys Trp Leu
2705                2710            2715

Pro Tyr Glu Ala Gly Gln Arg Phe Leu Glu Phe Gln Tyr Leu Thr
2720                2725            2730

Gly Gly Leu Val Asp Pro Glu Val His Gly Arg Ile Ser Thr Glu
2735                2740            2745

Glu Ala Ile Arg Lys Gly Phe Ile Asp Gly Arg Ala Ala Gln Arg
2750                2755            2760

Leu Gln Asp Thr Ser Ser Tyr Ala Lys Ile Leu Thr Cys Pro Lys
2765                2770            2775

Thr Lys Leu Lys Ile Ser Tyr Lys Asp Ala Ile Asn Arg Ser Met
2780                2785            2790

Val Glu Asp Ile Thr Gly Leu Arg Leu Leu Glu Ala Ala Ser Val
2795                2800            2805

Ser Ser Lys Gly Leu Pro Ser Pro Tyr Asn Met Ser Ser Ala Pro
2810                2815            2820

Gly Ser Arg Ser Gly Ser Arg Ser Gly Ser Arg Ser Gly Ser Arg
2825                2830            2835

Ser Gly Ser Arg Ser Gly Ser Arg Arg Gly Ser Phe Asp Ala Thr
```

-continued

```
                2840                2845                2850
Gly Asn Ser Ser Tyr Ser Tyr Ser Tyr Ser Phe Ser Ser Ser Ser
        2855                2860                2865
Ile Gly His
    2870

<210> SEQ ID NO 2
<211> LENGTH: 2272
<212> TYPE: PRT
<213> ORGANISM: homo sapiens
<220> FEATURE:
<221> NAME/KEY: misc_feature
<223> OTHER INFORMATION: Desmoplakin isoform 2

<400> SEQUENCE: 2

Met Ser Cys Asn Gly Gly Ser His Pro Arg Ile Asn Thr Leu Gly Arg
1               5                   10                  15
Met Ile Arg Ala Glu Ser Gly Pro Asp Leu Arg Tyr Glu Val Thr Ser
            20                  25                  30
Gly Gly Gly Gly Thr Ser Arg Met Tyr Tyr Ser Arg Arg Gly Val Ile
        35                  40                  45
Thr Asp Gln Asn Ser Asp Gly Tyr Cys Gln Thr Gly Thr Met Ser Arg
    50                  55                  60
His Gln Asn Gln Asn Thr Ile Gln Glu Leu Leu Gln Asn Cys Ser Asp
65                  70                  75                  80
Cys Leu Met Arg Ala Glu Leu Ile Val Gln Pro Glu Leu Lys Tyr Gly
                85                  90                  95
Asp Gly Ile Gln Leu Thr Arg Ser Arg Glu Leu Asp Glu Cys Phe Ala
            100                 105                 110
Gln Ala Asn Asp Gln Met Glu Ile Leu Asp Ser Leu Ile Arg Glu Met
        115                 120                 125
Arg Gln Met Gly Gln Pro Cys Asp Ala Tyr Gln Lys Arg Leu Leu Gln
    130                 135                 140
Leu Gln Glu Gln Met Arg Ala Leu Tyr Lys Ala Ile Ser Val Pro Arg
145                 150                 155                 160
Val Arg Arg Ala Ser Ser Lys Gly Gly Gly Tyr Thr Cys Gln Ser
                165                 170                 175
Gly Ser Gly Trp Asp Glu Phe Thr Lys His Val Thr Ser Glu Cys Leu
            180                 185                 190
Gly Trp Met Arg Gln Gln Arg Ala Glu Met Asp Met Val Ala Trp Gly
        195                 200                 205
Val Asp Leu Ala Ser Val Glu Gln His Ile Asn Ser His Arg Gly Ile
    210                 215                 220
His Asn Ser Ile Gly Asp Tyr Arg Trp Gln Leu Asp Lys Ile Lys Ala
225                 230                 235                 240
Asp Leu Arg Glu Lys Ser Ala Ile Tyr Gln Leu Glu Glu Tyr Glu
                245                 250                 255
Asn Leu Leu Lys Ala Ser Phe Glu Arg Met Asp His Leu Arg Gln Leu
            260                 265                 270
Gln Asn Ile Ile Gln Ala Thr Ser Arg Glu Ile Met Trp Ile Asn Asp
        275                 280                 285
Cys Glu Glu Glu Glu Leu Leu Tyr Asp Trp Ser Asp Lys Asn Thr Asn
    290                 295                 300
Ile Ala Gln Lys Gln Glu Ala Phe Ser Ile Arg Met Ser Gln Leu Glu
305                 310                 315                 320
```

-continued

```
Val Lys Glu Lys Glu Leu Asn Lys Leu Lys Gln Glu Ser Asp Gln Leu
                325                 330                 335

Val Leu Asn Gln His Pro Ala Ser Asp Lys Ile Glu Ala Tyr Met Asp
            340                 345                 350

Thr Leu Gln Thr Gln Trp Ser Trp Ile Leu Gln Ile Thr Lys Cys Ile
        355                 360                 365

Asp Val His Leu Lys Glu Asn Ala Ala Tyr Phe Gln Phe Phe Glu Glu
    370                 375                 380

Ala Gln Ser Thr Glu Ala Tyr Leu Lys Gly Leu Gln Asp Ser Ile Arg
385                 390                 395                 400

Lys Lys Tyr Pro Cys Asp Lys Asn Met Pro Leu Gln His Leu Leu Glu
                405                 410                 415

Gln Ile Lys Glu Leu Glu Lys Glu Arg Glu Lys Ile Leu Glu Tyr Lys
            420                 425                 430

Arg Gln Val Gln Asn Leu Val Asn Lys Ser Lys Lys Ile Val Gln Leu
        435                 440                 445

Lys Pro Arg Asn Pro Asp Tyr Arg Ser Asn Lys Pro Ile Ile Leu Arg
    450                 455                 460

Ala Leu Cys Asp Tyr Lys Gln Asp Gln Lys Ile Val His Lys Gly Asp
465                 470                 475                 480

Glu Cys Ile Leu Lys Asp Asn Asn Glu Arg Ser Lys Trp Tyr Val Thr
                485                 490                 495

Gly Pro Gly Gly Val Asp Met Leu Val Pro Ser Val Gly Leu Ile Ile
            500                 505                 510

Pro Pro Pro Asn Pro Leu Ala Val Asp Leu Ser Cys Lys Ile Glu Gln
        515                 520                 525

Tyr Tyr Glu Ala Ile Leu Ala Leu Trp Asn Gln Leu Tyr Ile Asn Met
    530                 535                 540

Lys Ser Leu Val Ser Trp His Tyr Cys Met Ile Asp Ile Glu Lys Ile
545                 550                 555                 560

Arg Ala Met Thr Ile Ala Lys Leu Lys Thr Met Arg Gln Glu Asp Tyr
                565                 570                 575

Met Lys Thr Ile Ala Asp Leu Glu Leu His Tyr Gln Glu Phe Ile Arg
            580                 585                 590

Asn Ser Gln Gly Ser Glu Met Phe Gly Asp Asp Lys Arg Lys Ile
        595                 600                 605

Gln Ser Gln Phe Thr Asp Ala Gln Lys His Tyr Gln Thr Leu Val Ile
    610                 615                 620

Gln Leu Pro Gly Tyr Pro Gln His Gln Thr Val Thr Thr Glu Ile
625                 630                 635                 640

Thr His His Gly Thr Cys Gln Asp Val Asn His Asn Lys Val Ile Glu
                645                 650                 655

Thr Asn Arg Glu Asn Asp Lys Gln Glu Thr Trp Met Leu Met Glu Leu
            660                 665                 670

Gln Lys Ile Arg Arg Gln Ile Glu His Cys Glu Gly Arg Met Thr Leu
        675                 680                 685

Lys Asn Leu Pro Leu Ala Asp Gln Gly Ser Ser His Ile Thr Val
    690                 695                 700

Lys Ile Asn Glu Leu Lys Ser Val Gln Asn Asp Ser Gln Ala Ile Ala
705                 710                 715                 720

Glu Val Leu Asn Gln Leu Lys Asp Met Leu Ala Asn Phe Arg Gly Ser
                725                 730                 735

Glu Lys Tyr Cys Tyr Leu Gln Asn Glu Val Phe Gly Leu Phe Gln Lys
```

-continued

```
                740                 745                 750
Leu Glu Asn Ile Asn Gly Val Thr Asp Gly Tyr Leu Asn Ser Leu Cys
                755                 760                 765

Thr Val Arg Ala Leu Leu Gln Ala Ile Leu Gln Thr Glu Asp Met Leu
            770                 775                 780

Lys Val Tyr Glu Ala Arg Leu Thr Glu Glu Thr Val Cys Leu Asp
785                 790                 795                 800

Leu Asp Lys Val Glu Ala Tyr Arg Cys Gly Leu Lys Lys Ile Lys Asn
                805                 810                 815

Asp Leu Asn Leu Lys Lys Ser Leu Leu Ala Thr Met Lys Thr Glu Leu
            820                 825                 830

Gln Lys Ala Gln Gln Ile His Ser Gln Thr Ser Gln Gln Tyr Pro Leu
        835                 840                 845

Tyr Asp Leu Asp Leu Gly Lys Phe Gly Glu Lys Val Thr Gln Leu Thr
        850                 855                 860

Asp Arg Trp Gln Arg Ile Asp Lys Gln Ile Asp Phe Arg Leu Trp Asp
865                 870                 875                 880

Leu Glu Lys Gln Ile Lys Gln Leu Arg Asn Tyr Arg Asp Asn Tyr Gln
                885                 890                 895

Ala Phe Cys Lys Trp Leu Tyr Asp Ala Lys Arg Arg Gln Asp Ser Leu
                900                 905                 910

Glu Ser Met Lys Phe Gly Asp Ser Asn Thr Val Met Arg Phe Leu Asn
            915                 920                 925

Glu Gln Lys Asn Leu His Ser Glu Ile Ser Gly Lys Arg Asp Lys Ser
        930                 935                 940

Glu Glu Val Gln Lys Ile Ala Glu Leu Cys Ala Asn Ser Ile Lys Asp
945                 950                 955                 960

Tyr Glu Leu Gln Leu Ala Ser Tyr Thr Ser Gly Leu Glu Thr Leu Leu
                965                 970                 975

Asn Ile Pro Ile Lys Arg Thr Met Ile Gln Ser Pro Ser Gly Val Ile
            980                 985                 990

Leu Gln Glu Ala Ala Asp Val His Ala Arg Tyr Ile Glu Leu Leu Thr
        995                 1000                1005

Arg Ser Gly Asp Tyr Tyr Arg Phe Leu Ser Glu Met Leu Lys Ser
    1010                1015                1020

Leu Glu Asp Leu Lys Leu Lys Asn Thr Lys Ile Glu Val Leu Glu
    1025                1030                1035

Glu Glu Leu Arg Leu Ala Arg Asp Ala Asn Ser Glu Asn Cys Asn
    1040                1045                1050

Lys Asn Lys Phe Leu Asp Gln Asn Leu Gln Lys Tyr Gln Ala Glu
    1055                1060                1065

Cys Ser Gln Phe Lys Ala Lys Leu Ala Ser Leu Glu Glu Leu Lys
    1070                1075                1080

Arg Gln Ala Glu Leu Asp Gly Lys Ser Ala Lys Gln Asn Leu Asp
    1085                1090                1095

Lys Cys Tyr Gly Gln Ile Lys Glu Leu Asn Glu Lys Ile Thr Arg
    1100                1105                1110

Leu Thr Tyr Glu Ile Glu Asp Glu Lys Arg Arg Arg Lys Ser Val
    1115                1120                1125

Glu Asp Arg Phe Asp Gln Gln Lys Asn Asp Tyr Asp Gln Leu Gln
    1130                1135                1140

Lys Ala Arg Gln Cys Glu Lys Glu Asn Leu Gly Trp Gln Lys Leu
    1145                1150                1155
```

```
Glu Ser Glu Lys Ala Ile Lys Glu Lys Glu Tyr Glu Ile Glu Arg
    1160                1165                1170

Leu Arg Val Leu Leu Gln Glu Glu Gly Thr Arg Lys Arg Glu Tyr
    1175                1180                1185

Glu Asn Glu Leu Ala Lys Ala Ser Asn Arg Ile Gln Glu Ser Lys
    1190                1195                1200

Asn Gln Cys Thr Gln Val Val Gln Glu Arg Glu Ser Leu Leu Val
    1205                1210                1215

Lys Ile Lys Val Leu Glu Gln Asp Lys Ala Arg Leu Gln Arg Leu
    1220                1225                1230

Glu Asp Glu Leu Asn Arg Ala Lys Ser Thr Leu Glu Ala Glu Thr
    1235                1240                1245

Arg Val Lys Gln Arg Leu Glu Cys Glu Lys Gln Gln Ile Gln Asn
    1250                1255                1260

Asp Leu Asn Gln Trp Lys Thr Gln Tyr Ser Arg Lys Glu Glu Ala
    1265                1270                1275

Ile Arg Lys Ile Glu Ser Glu Arg Glu Lys Ser Glu Arg Glu Lys
    1280                1285                1290

Asn Ser Leu Arg Ser Glu Ile Glu Arg Leu Gln Ala Glu Ile Lys
    1295                1300                1305

Arg Ile Glu Glu Arg Cys Arg Arg Lys Leu Glu Asp Ser Thr Arg
    1310                1315                1320

Glu Thr Gln Ser Gln Leu Glu Thr Glu Arg Ser Arg Tyr Gln Arg
    1325                1330                1335

Glu Ile Asp Lys Leu Arg Gln Arg Pro Tyr Gly Ser His Arg Glu
    1340                1345                1350

Thr Gln Thr Glu Cys Glu Trp Thr Val Asp Thr Ser Lys Leu Val
    1355                1360                1365

Phe Asp Gly Leu Arg Lys Lys Val Thr Ala Met Gln Leu Tyr Glu
    1370                1375                1380

Cys Gln Leu Ile Asp Lys Thr Thr Leu Asp Lys Leu Leu Lys Gly
    1385                1390                1395

Lys Lys Ser Val Glu Glu Val Ala Ser Glu Ile Gln Pro Phe Leu
    1400                1405                1410

Arg Gly Ala Gly Ser Ile Ala Gly Ala Ser Ala Ser Pro Lys Glu
    1415                1420                1425

Lys Tyr Ser Leu Val Glu Ala Lys Arg Lys Lys Leu Ile Ser Pro
    1430                1435                1440

Glu Ser Thr Val Met Leu Leu Glu Ala Gln Ala Ala Thr Gly Gly
    1445                1450                1455

Ile Ile Asp Pro His Arg Asn Glu Lys Leu Thr Val Asp Ser Ala
    1460                1465                1470

Ile Ala Arg Asp Leu Ile Asp Phe Asp Asp Arg Gln Gln Ile Tyr
    1475                1480                1485

Ala Ala Glu Lys Ala Ile Thr Gly Phe Asp Asp Pro Phe Ser Gly
    1490                1495                1500

Lys Thr Val Ser Val Ser Glu Ala Ile Lys Lys Asn Leu Ile Asp
    1505                1510                1515

Arg Glu Thr Gly Met Arg Leu Leu Glu Ala Gln Ile Ala Ser Gly
    1520                1525                1530

Gly Val Val Asp Pro Val Asn Ser Val Phe Leu Pro Lys Asp Val
    1535                1540                1545
```

```
Ala Leu Ala Arg Gly Leu Ile Asp Arg Asp Leu Tyr Arg Ser Leu
    1550                1555                1560

Asn Asp Pro Arg Asp Ser Gln Lys Asn Phe Val Asp Pro Val Thr
    1565                1570                1575

Lys Lys Lys Val Ser Tyr Val Gln Leu Lys Glu Arg Cys Arg Ile
    1580                1585                1590

Glu Pro His Thr Gly Leu Leu Leu Ser Val Gln Lys Arg Ser
    1595                1600                1605

Met Ser Phe Gln Gly Ile Arg Gln Pro Val Thr Val Thr Glu Leu
    1610                1615                1620

Val Asp Ser Gly Ile Leu Arg Pro Ser Thr Val Asn Glu Leu Glu
    1625                1630                1635

Ser Gly Gln Ile Ser Tyr Asp Glu Val Gly Glu Arg Ile Lys Asp
    1640                1645                1650

Phe Leu Gln Gly Ser Ser Cys Ile Ala Gly Ile Tyr Asn Glu Thr
    1655                1660                1665

Thr Lys Gln Lys Leu Gly Ile Tyr Glu Ala Met Lys Ile Gly Leu
    1670                1675                1680

Val Arg Pro Gly Thr Ala Leu Glu Leu Leu Glu Ala Gln Ala Ala
    1685                1690                1695

Thr Gly Phe Ile Val Asp Pro Val Ser Asn Leu Arg Leu Pro Val
    1700                1705                1710

Glu Glu Ala Tyr Lys Arg Gly Leu Val Gly Ile Glu Phe Lys Glu
    1715                1720                1725

Lys Leu Leu Ser Ala Glu Arg Ala Val Thr Gly Tyr Asn Asp Pro
    1730                1735                1740

Glu Thr Gly Asn Ile Ile Ser Leu Phe Gln Ala Met Asn Lys Glu
    1745                1750                1755

Leu Ile Glu Lys Gly His Gly Ile Arg Leu Leu Glu Ala Gln Ile
    1760                1765                1770

Ala Thr Gly Gly Ile Ile Asp Pro Lys Glu Ser His Arg Leu Pro
    1775                1780                1785

Val Asp Ile Ala Tyr Lys Arg Gly Tyr Phe Asn Glu Glu Leu Ser
    1790                1795                1800

Glu Ile Leu Ser Asp Pro Ser Asp Asp Thr Lys Gly Phe Phe Asp
    1805                1810                1815

Pro Asn Thr Glu Glu Asn Leu Thr Tyr Leu Gln Leu Lys Glu Arg
    1820                1825                1830

Cys Ile Lys Asp Glu Glu Thr Gly Leu Cys Leu Leu Pro Leu Lys
    1835                1840                1845

Glu Lys Lys Lys Gln Val Gln Thr Ser Gln Lys Asn Thr Leu Arg
    1850                1855                1860

Lys Arg Arg Val Val Ile Val Asp Pro Glu Thr Asn Lys Glu Met
    1865                1870                1875

Ser Val Gln Glu Ala Tyr Lys Lys Gly Leu Ile Asp Tyr Glu Thr
    1880                1885                1890

Phe Lys Glu Leu Cys Glu Gln Glu Cys Glu Trp Glu Glu Ile Thr
    1895                1900                1905

Ile Thr Gly Ser Asp Gly Ser Thr Arg Val Val Leu Val Asp Arg
    1910                1915                1920

Lys Thr Gly Ser Gln Tyr Asp Ile Gln Asp Ala Ile Asp Lys Gly
    1925                1930                1935

Leu Val Asp Arg Lys Phe Phe Asp Gln Tyr Arg Ser Gly Ser Leu
```

```
                    1940                1945                1950

Ser Leu Thr Gln Phe Ala Asp Met Ile Ser Leu Lys Asn Gly Val
    1955                1960                1965

Gly Thr Ser Ser Ser Met Gly Ser Gly Val Ser Asp Asp Val Phe
    1970                1975                1980

Ser Ser Ser Arg His Glu Ser Val Ser Lys Ile Ser Thr Ile Ser
    1985                1990                1995

Ser Val Arg Asn Leu Thr Ile Arg Ser Ser Phe Ser Asp Thr
    2000                2005                2010

Leu Glu Glu Ser Ser Pro Ile Ala Ala Ile Phe Asp Thr Glu Asn
    2015                2020                2025

Leu Glu Lys Ile Ser Ile Thr Glu Gly Ile Glu Arg Gly Ile Val
    2030                2035                2040

Asp Ser Ile Thr Gly Gln Arg Leu Leu Glu Ala Gln Ala Cys Thr
    2045                2050                2055

Gly Gly Ile Ile His Pro Thr Thr Gly Gln Lys Leu Ser Leu Gln
    2060                2065                2070

Asp Ala Val Ser Gln Gly Val Ile Asp Gln Asp Met Ala Thr Arg
    2075                2080                2085

Leu Lys Pro Ala Gln Lys Ala Phe Ile Gly Phe Glu Gly Val Lys
    2090                2095                2100

Gly Lys Lys Lys Met Ser Ala Ala Glu Ala Val Lys Glu Lys Trp
    2105                2110                2115

Leu Pro Tyr Glu Ala Gly Gln Arg Phe Leu Glu Phe Gln Tyr Leu
    2120                2125                2130

Thr Gly Gly Leu Val Asp Pro Glu Val His Gly Arg Ile Ser Thr
    2135                2140                2145

Glu Glu Ala Ile Arg Lys Gly Phe Ile Asp Gly Arg Ala Ala Gln
    2150                2155                2160

Arg Leu Gln Asp Thr Ser Ser Tyr Ala Lys Ile Leu Thr Cys Pro
    2165                2170                2175

Lys Thr Lys Leu Lys Ile Ser Tyr Lys Asp Ala Ile Asn Arg Ser
    2180                2185                2190

Met Val Glu Asp Ile Thr Gly Leu Arg Leu Leu Glu Ala Ala Ser
    2195                2200                2205

Val Ser Ser Lys Gly Leu Pro Ser Pro Tyr Asn Met Ser Ser Ala
    2210                2215                2220

Pro Gly Ser Arg Ser Gly Ser Arg Ser Gly Ser Arg Ser Gly Ser
    2225                2230                2235

Arg Ser Gly Ser Arg Ser Gly Ser Arg Arg Gly Ser Phe Asp Ala
    2240                2245                2250

Thr Gly Asn Ser Ser Tyr Ser Tyr Ser Tyr Ser Phe Ser Ser Ser
    2255                2260                2265

Ser Ile Gly His
    2270

<210> SEQ ID NO 3
<211> LENGTH: 439
<212> TYPE: PRT
<213> ORGANISM: homo sapiens
<220> FEATURE:
<221> NAME/KEY: misc_feature
<223> OTHER INFORMATION: Rho GTPase-activating protein 1

<400> SEQUENCE: 3
```

-continued

```
Met Asp Pro Leu Ser Glu Leu Gln Asp Asp Leu Thr Leu Asp Asp Thr
1               5                   10                  15

Ser Glu Ala Leu Asn Gln Leu Lys Leu Ala Ser Ile Asp Glu Lys Asn
            20                  25                  30

Trp Pro Ser Asp Glu Met Pro Asp Phe Pro Lys Ser Asp Asp Ser Lys
        35                  40                  45

Ser Ser Ser Pro Glu Leu Val Thr His Leu Lys Trp Asp Asp Pro Tyr
    50                  55                  60

Tyr Asp Ile Ala Arg His Gln Ile Val Glu Val Ala Gly Asp Asp Lys
65                  70                  75                  80

Tyr Gly Arg Lys Ile Ile Val Phe Ser Ala Cys Arg Met Pro Pro Ser
                85                  90                  95

His Gln Leu Asp His Ser Lys Leu Leu Gly Tyr Leu Lys His Thr Leu
            100                 105                 110

Asp Gln Tyr Val Glu Ser Asp Tyr Thr Leu Leu Tyr Leu His His Gly
            115                 120                 125

Leu Thr Ser Asp Asn Lys Pro Ser Leu Ser Trp Leu Arg Asp Ala Tyr
        130                 135                 140

Arg Glu Phe Asp Arg Lys Tyr Lys Lys Asn Ile Lys Ala Leu Tyr Ile
145                 150                 155                 160

Val His Pro Thr Met Phe Ile Lys Thr Leu Leu Ile Leu Phe Lys Pro
                165                 170                 175

Leu Ile Ser Phe Lys Phe Gly Gln Lys Ile Phe Tyr Val Asn Tyr Leu
            180                 185                 190

Ser Glu Leu Ser Glu His Val Lys Leu Glu Gln Leu Gly Ile Pro Arg
        195                 200                 205

Gln Val Leu Lys Tyr Asp Asp Phe Leu Lys Ser Thr Gln Lys Ser Pro
210                 215                 220

Ala Thr Ala Pro Lys Pro Met Pro Pro Arg Pro Pro Leu Pro Asn Gln
225                 230                 235                 240

Gln Phe Gly Val Ser Leu Gln His Leu Gln Glu Lys Asn Pro Glu Gln
            245                 250                 255

Glu Pro Ile Pro Ile Val Leu Arg Glu Thr Val Ala Tyr Leu Gln Ala
        260                 265                 270

His Ala Leu Thr Thr Glu Gly Ile Phe Arg Arg Ser Ala Asn Thr Gln
    275                 280                 285

Val Val Arg Glu Val Gln Gln Lys Tyr Asn Met Gly Leu Pro Val Asp
        290                 295                 300

Phe Asp Gln Tyr Asn Glu Leu His Leu Pro Ala Val Ile Leu Lys Thr
305                 310                 315                 320

Phe Leu Arg Glu Leu Pro Glu Pro Leu Leu Thr Phe Asp Leu Tyr Pro
                325                 330                 335

His Val Val Gly Phe Leu Asn Ile Asp Glu Ser Gln Arg Val Pro Ala
            340                 345                 350

Thr Leu Gln Val Leu Gln Thr Leu Pro Glu Glu Asn Tyr Gln Val Leu
        355                 360                 365

Arg Phe Leu Thr Ala Phe Leu Val Gln Ile Ser Ala His Ser Asp Gln
370                 375                 380

Asn Lys Met Thr Asn Thr Asn Leu Ala Val Val Phe Gly Pro Asn Leu
385                 390                 395                 400

Leu Trp Ala Lys Asp Ala Ala Ile Thr Leu Lys Ala Ile Asn Pro Ile
                405                 410                 415

Asn Thr Phe Thr Lys Phe Leu Leu Asp His Gln Gly Glu Leu Phe Pro
```

Ser Pro Asp Pro Ser Gly Leu
              435

<210> SEQ ID NO 4
<211> LENGTH: 5090
<212> TYPE: PRT
<213> ORGANISM: homo sapiens
<220> FEATURE:
<221> NAME/KEY: misc_feature
<223> OTHER INFORMATION: Epiplakin

<400> SEQUENCE: 4

Met Ser Gly His Thr Leu Pro Pro Leu Pro Val Pro Gly Thr Asn Ser
1               5                   10                  15

Thr Glu Gln Ala Ser Val Pro Arg Ala Met Ala Thr Leu Gly Ala
            20                  25                  30

Gly Thr Pro Pro Arg Pro Gln Ala Arg Ser Ile Ala Gly Val Tyr Val
            35                  40                  45

Glu Ala Ser Gly Gln Ala Gln Ser Val Tyr Ala Ala Met Glu Gln Gly
        50                  55                  60

Leu Leu Pro Ala Gly Leu Gly Gln Ala Leu Leu Glu Ala Gln Ala Ala
65                  70                  75                  80

Thr Gly Gly Leu Val Asp Leu Ala Arg Gly Gln Leu Leu Pro Val Ser
                    85                  90                  95

Lys Ala Leu Gln Gln Gly Leu Val Gly Leu Glu Leu Lys Glu Lys Leu
                100                 105                 110

Leu Ala Ala Glu Arg Ala Thr Thr Gly Tyr Pro Asp Pro Tyr Gly Gly
            115                 120                 125

Glu Lys Leu Ala Leu Phe Gln Ala Ile Gly Lys Glu Val Val Asp Arg
        130                 135                 140

Ala Leu Gly Gln Ser Trp Leu Glu Val Gln Leu Ala Thr Gly Gly Leu
145                 150                 155                 160

Val Asp Pro Ala Gln Gly Val Leu Val Ala Pro Glu Pro Ala Cys His
                    165                 170                 175

Gln Gly Leu Leu Asp Arg Glu Thr Trp His Lys Leu Ser Glu Leu Glu
                180                 185                 190

Pro Gly Thr Gly Asp Leu Arg Phe Leu Asn Pro Asn Thr Leu Glu Arg
            195                 200                 205

Leu Thr Tyr His Gln Leu Leu Glu Arg Cys Val Arg Ala Pro Gly Ser
        210                 215                 220

Gly Leu Ala Leu Leu Pro Leu Lys Ile Thr Phe Arg Ser Met Gly Gly
225                 230                 235                 240

Ala Val Ser Ala Ala Glu Leu Leu Glu Val Gly Ile Leu Asp Glu Gln
                    245                 250                 255

Ala Val Gln Gly Leu Arg Glu Gly Arg Leu Ala Ala Val Asp Val Ser
                260                 265                 270

Ala Arg Ala Glu Val Arg Arg Tyr Leu Glu Gly Thr Gly Ser Val Ala
            275                 280                 285

Gly Val Val Leu Leu Pro Glu Gly His Lys Lys Ser Phe Phe Gln Ala
        290                 295                 300

Ala Thr Glu His Leu Leu Pro Met Gly Thr Ala Leu Pro Leu Leu Glu
305                 310                 315                 320

Ala Gln Ala Ala Thr His Thr Leu Val Asp Pro Ile Thr Gly Gln Arg
                    325                 330                 335

```
Leu Trp Val Asp Glu Ala Val Arg Ala Gly Leu Val Ser Pro Glu Leu
                340                 345                 350

His Glu Gln Leu Leu Val Ala Glu Gln Ala Val Thr Gly His His Asp
            355                 360                 365

Pro Phe Ser Gly Ser Gln Ile Pro Leu Phe Gln Ala Met Lys Lys Gly
        370                 375                 380

Leu Val Asp Arg Pro Leu Ala Leu Arg Leu Leu Asp Ala Gln Leu Ala
385                 390                 395                 400

Thr Gly Gly Leu Val Cys Pro Ala Arg Arg Leu Arg Leu Pro Leu Glu
                405                 410                 415

Ala Ala Leu Arg Cys Gly Cys Leu Asp Glu Asp Thr Gln Arg Gln Leu
            420                 425                 430

Ser Gln Ala Gly Ser Phe Ser Asp Gly Thr His Gly Gly Leu Arg Tyr
        435                 440                 445

Glu Gln Leu Leu Ala Leu Cys Val Thr Asp Pro Glu Thr Gly Leu Ala
        450                 455                 460

Phe Leu Pro Leu Ser Gly Gly Pro Arg Gly Glu Pro Gln Gly Pro
465                 470                 475                 480

Pro Phe Ile Lys Tyr Ser Thr Arg Gln Ala Leu Ser Thr Ala Thr Ala
                485                 490                 495

Thr Val Ser Val Gly Lys Phe Arg Gly Arg Pro Val Ser Leu Trp Glu
            500                 505                 510

Leu Leu Phe Ser Glu Ala Ile Ser Ser Glu Gln Arg Ala Met Leu Ala
        515                 520                 525

Gln Gln Tyr Gln Glu Gly Thr Leu Ser Val Glu Lys Leu Ala Ala Glu
530                 535                 540

Leu Ser Ala Thr Leu Glu Gln Ala Ala Ala Thr Ala Arg Val Thr Phe
545                 550                 555                 560

Ser Gly Leu Arg Asp Thr Val Thr Pro Gly Glu Leu Leu Lys Ala Glu
                565                 570                 575

Ile Ile Asp Gln Asp Leu Tyr Glu Arg Leu Glu His Gly Gln Ala Thr
            580                 585                 590

Ala Lys Asp Val Gly Ser Leu Ala Ser Ala Gln Arg Tyr Leu Gln Gly
        595                 600                 605

Thr Gly Cys Ile Ala Gly Leu Leu Pro Gly Ser Gln Glu Arg Leu
610                 615                 620

Ser Ile Tyr Glu Ala Arg Cys Lys Gly Leu Leu Arg Pro Gly Thr Ala
625                 630                 635                 640

Leu Ile Leu Leu Glu Ala Gln Ala Ala Thr Gly Phe Ile Ile Asp Pro
                645                 650                 655

Lys Ala Asn Lys Gly His Ser Val Glu Glu Ala Leu Arg Ala Ala Val
            660                 665                 670

Ile Gly Pro Asp Val Phe Ala Lys Leu Leu Ser Ala Glu Arg Ala Val
        675                 680                 685

Thr Gly Tyr Thr Asp Pro Tyr Thr Gly Gln Gln Ile Ser Leu Phe Gln
        690                 695                 700

Ala Met Gln Lys Gly Leu Ile Val Arg Glu His Gly Ile Arg Leu Leu
705                 710                 715                 720

Glu Ala Gln Ile Ala Thr Gly Gly Val Ile Asp Pro Val His Ser His
                725                 730                 735

Arg Val Pro Val Asp Val Ala Tyr Arg Arg Gly Tyr Phe Asp Gln Met
            740                 745                 750

Leu Asn Leu Ile Leu Leu Asp Pro Ser Asp Asp Thr Lys Gly Phe Phe
```

-continued

```
            755                 760                 765
Asp Pro Asn Thr His Glu Asn Leu Thr Tyr Leu Gln Leu Leu Glu Arg
770                 775                 780
Cys Val Arg Asp Pro Glu Thr Gly Leu Tyr Leu Leu Pro Leu Ser Ser
785                 790                 795                 800
Thr Gln Ser Pro Leu Val Asp Ser Ala Thr Gln Ala Phe Gln Asn
            805                 810                 815
Leu Leu Leu Ser Val Lys Tyr Gly Arg Phe Gln Gly Gln Arg Val Ser
            820                 825                 830
Ala Trp Glu Leu Ile Asn Ser Glu Tyr Phe Ser Glu Gly Arg Arg Arg
            835                 840                 845
Gln Leu Leu Arg Arg Tyr Arg Gln Arg Glu Val Thr Leu Gly Gln Val
            850                 855                 860
Ala Lys Leu Leu Glu Ala Glu Thr Gln Arg Gln Ala Asp Ile Met Leu
865                 870                 875                 880
Pro Ala Leu Arg Ser Arg Val Thr Val His Gln Leu Leu Glu Ala Gly
            885                 890                 895
Ile Ile Asp Gln Gln Leu Leu Asp Gln Val Leu Ala Gly Thr Ile Ser
            900                 905                 910
Pro Glu Ala Leu Leu Leu Met Asp Gly Val Arg Arg Tyr Leu Cys Gly
            915                 920                 925
Leu Gly Ala Val Gly Gly Val Arg Leu Leu Pro Ser Gly Gln Arg Leu
930                 935                 940
Ser Leu Tyr Gln Ala Met Arg Gln Lys Leu Leu Gly Pro Arg Val Ala
945                 950                 955                 960
Leu Ala Leu Leu Glu Ala Gln Ala Ala Thr Gly Thr Ile Met Asp Pro
            965                 970                 975
His Ser Pro Glu Ser Leu Ser Val Asp Glu Ala Val Arg Arg Gly Val
            980                 985                 990
Val Gly Pro Glu Leu Tyr Gly Arg Leu Lys Arg Ala Glu Gly Ala Ile
            995                 1000                1005
Ala Gly Phe Arg Asp Pro Phe Ser Gly Lys Gln Val Ser Val Phe
            1010                1015                1020
Gln Ala Met Lys Lys Gly Leu Ile Pro Trp Glu Gln Ala Ala Arg
            1025                1030                1035
Leu Leu Glu Ala Gln Val Ala Thr Gly Gly Ile Ile Asp Pro Thr
            1040                1045                1050
Ser His His His Leu Pro Met Pro Val Ala Ile Gln Arg Gly Tyr
            1055                1060                1065
Val Asp Gln Glu Met Glu Thr Ala Leu Ser Ser Ser Glu Thr
            1070                1075                1080
Phe Pro Thr Pro Asp Gly Gln Gly Arg Thr Ser Tyr Ala Gln Leu
            1085                1090                1095
Leu Glu Glu Cys Pro Arg Asp Glu Thr Ser Gly Leu His Leu Leu
            1100                1105                1110
Pro Leu Pro Glu Ser Ala Pro Ala Leu Pro Thr Glu Glu Gln Val
            1115                1120                1125
Gln Arg Ser Leu Gln Ala Val Pro Gly Ala Lys Asp Gly Thr Ser
            1130                1135                1140
Leu Trp Asp Leu Leu Ser Ser Cys His Phe Thr Glu Glu Gln Arg
            1145                1150                1155
Arg Gly Leu Leu Glu Asp Val Gln Glu Gly Arg Thr Thr Val Pro
            1160                1165                1170
```

-continued

Gln Leu Leu Ala Ser Val Gln Arg Trp Val Gln Glu Thr Lys Leu
    1175                1180                1185

Leu Ala Gln Ala Arg Val Met Val Pro Gly Pro Arg Gly Glu Val
    1190                1195                1200

Pro Ala Val Trp Leu Leu Asp Ala Gly Ile Ile Thr Gln Glu Thr
    1205                1210                1215

Leu Glu Ala Leu Ala Gln Gly Thr Gln Ser Pro Ala Gln Val Ala
    1220                1225                1230

Glu Gln Pro Ala Val Lys Ala Cys Leu Trp Gly Thr Gly Cys Val
    1235                1240                1245

Ala Gly Val Leu Leu Gln Pro Ser Gly Ala Lys Ala Ser Ile Ala
    1250                1255                1260

Gln Ala Val Arg Asp Gly Leu Leu Pro Thr Gly Leu Gly Gln Arg
    1265                1270                1275

Leu Leu Glu Ala Gln Val Ala Ser Gly Phe Leu Val Asp Pro Leu
    1280                1285                1290

Asn Asn Gln Arg Leu Ser Val Glu Asp Ala Val Lys Val Gly Leu
    1295                1300                1305

Val Gly Arg Glu Leu Ser Glu Gln Leu Gly Gln Ala Glu Arg Ala
    1310                1315                1320

Ala Ala Gly Tyr Pro Asp Pro Tyr Ser Arg Ala Ser Leu Ser Leu
    1325                1330                1335

Trp Gln Ala Met Glu Lys Gly Leu Val Pro Gln Asn Glu Gly Leu
    1340                1345                1350

Pro Leu Leu Gln Val Gln Leu Ala Thr Gly Gly Val Val Asp Pro
    1355                1360                1365

Val His Gly Val His Leu Pro Gln Ala Ala Ala Cys Arg Leu Gly
    1370                1375                1380

Leu Leu Asp Thr Gln Thr Ser Gln Val Leu Thr Ala Val Asp Lys
    1385                1390                1395

Asp Asn Lys Phe Phe Phe Asp Pro Ser Ala Arg Asp Gln Val Thr
    1400                1405                1410

Tyr Gln Gln Leu Arg Glu Arg Cys Val Cys Asp Ser Glu Thr Gly
    1415                1420                1425

Leu Leu Leu Leu Pro Leu Pro Ser Asp Thr Val Leu Glu Val Asp
    1430                1435                1440

Asp His Thr Ala Val Ala Leu Arg Ala Met Lys Val Pro Val Ser
    1445                1450                1455

Thr Gly Arg Phe Lys Gly Cys Ser Val Ser Leu Trp Asp Leu Leu
    1460                1465                1470

Leu Ser Glu Tyr Val Gly Ala Asp Lys Arg Arg Glu Leu Val Ala
    1475                1480                1485

Leu Cys Arg Ser Gly Arg Ala Ala Ala Leu Arg Gln Val Val Ser
    1490                1495                1500

Ala Val Thr Ala Leu Val Glu Ala Ala Glu Arg Gln Pro Leu Gln
    1505                1510                1515

Ala Thr Phe Arg Gly Leu Arg Lys Gln Val Ser Ala Arg Asp Leu
    1520                1525                1530

Phe Arg Ala Gln Leu Ile Ser Arg Lys Thr Leu Asp Glu Leu Ser
    1535                1540                1545

Gln Gly Thr Thr Thr Val Lys Glu Val Ala Glu Met Asp Ser Val
    1550                1555                1560

```
Lys Arg Ser Leu Glu Gly Gly Asn Phe Ile Ala Gly Val Leu Ile
    1565                1570                1575

Gln Gly Thr Gln Glu Arg Met Ser Ile Pro Glu Ala Leu Arg Arg
    1580                1585                1590

His Ile Leu Arg Pro Gly Thr Ala Leu Val Leu Leu Glu Ala Gln
    1595                1600                1605

Ala Ala Thr Gly Phe Ile Ile Asp Pro Ala Glu Asn Arg Lys Leu
    1610                1615                1620

Thr Val Glu Glu Ala Phe Lys Ala Gly Met Phe Gly Lys Glu Thr
    1625                1630                1635

Tyr Val Lys Leu Leu Ser Ala Glu Arg Ala Val Thr Gly Tyr Thr
    1640                1645                1650

Asp Pro Tyr Thr Gly Gln Gln Ile Ser Leu Phe Gln Ala Met Gln
    1655                1660                1665

Lys Asp Leu Ile Val Arg Glu His Gly Ile Arg Leu Leu Glu Ala
    1670                1675                1680

Gln Ile Ala Thr Gly Gly Ile Ile Asp Pro Val His Ser His Arg
    1685                1690                1695

Val Pro Val Asp Val Ala Tyr Arg Cys Gly Tyr Phe Asp Glu Glu
    1700                1705                1710

Met Asn Arg Ile Leu Ala Asp Pro Ser Asp Asp Thr Lys Gly Phe
    1715                1720                1725

Phe Asp Pro Asn Thr His Glu Asn Leu Thr Tyr Leu Gln Leu Leu
    1730                1735                1740

Glu Arg Cys Val Glu Asp Pro Glu Thr Gly Leu Tyr Leu Leu Gln
    1745                1750                1755

Ile Ile Lys Lys Gly Glu Asn Tyr Val Tyr Ile Asn Glu Ala Thr
    1760                1765                1770

Arg His Val Leu Gln Ser Arg Thr Ala Lys Met Arg Val Gly Arg
    1775                1780                1785

Phe Ala Asp Gln Val Val Ser Phe Trp Asp Leu Leu Ser Ser Pro
    1790                1795                1800

Tyr Phe Thr Glu Asp Arg Lys Arg Glu Leu Ile Gln Glu Tyr Gly
    1805                1810                1815

Ala Gln Ser Gly Gly Leu Glu Lys Leu Leu Glu Ile Ile Thr Thr
    1820                1825                1830

Thr Ile Glu Glu Thr Glu Thr Gln Asn Gln Gly Ile Lys Val Ala
    1835                1840                1845

Ala Ile Arg Gly Glu Val Thr Ala Ala Asp Leu Phe Asn Ser Arg
    1850                1855                1860

Val Ile Asp Gln Lys Thr Leu His Thr Leu Arg Val Gly Arg Thr
    1865                1870                1875

Gly Gly Gln Ala Leu Ser Thr Leu Glu Cys Val Lys Pro Tyr Leu
    1880                1885                1890

Glu Gly Ser Asp Cys Ile Ala Gly Val Thr Val Pro Ser Thr Arg
    1895                1900                1905

Glu Val Met Ser Leu His Glu Ala Ser Arg Lys Glu Leu Ile Pro
    1910                1915                1920

Ala Ala Phe Ala Thr Trp Leu Leu Glu Ala Gln Ala Ala Thr Gly
    1925                1930                1935

Phe Leu Leu Asp Pro Cys Thr Arg Gln Lys Leu Ser Val Asp Glu
    1940                1945                1950

Ala Val Asp Val Gly Leu Val Asn Glu Glu Leu Arg Glu Arg Leu
```

-continued

```
            1955                1960                1965
Leu Lys Ala Glu Arg Ala Ala Thr Gly Tyr Arg Asp Pro Ala Thr
        1970                1975                1980
Gly Asp Thr Ile Pro Leu Phe Gln Ala Met Gln Lys Gln Leu Ile
        1985                1990                1995
Glu Lys Ala Glu Ala Leu Arg Leu Leu Glu Val Gln Val Ala Thr
        2000                2005                2010
Gly Gly Val Ile Asp Pro Gln His His His Arg Leu Pro Leu Glu
        2015                2020                2025
Thr Ala Tyr Arg Arg Gly Cys Leu His Lys Asp Ile Tyr Ala Leu
        2030                2035                2040
Ile Ser Asp Gln Lys His Met Arg Lys Arg Phe Val Asp Pro Asn
        2045                2050                2055
Thr Gln Glu Lys Val Ser Tyr Arg Glu Leu Gln Glu Arg Cys Arg
        2060                2065                2070
Pro Gln Glu Asp Thr Gly Trp Val Leu Phe Pro Val Asn Lys Ala
        2075                2080                2085
Ala Arg Asp Ser Glu His Ile Asp Asp Glu Thr Arg Arg Ala Leu
        2090                2095                2100
Glu Ala Glu Gln Val Glu Ile Thr Val Gly Arg Phe Arg Gly Gln
        2105                2110                2115
Lys Pro Thr Leu Trp Ala Leu Leu Asn Ser Glu Tyr Val Thr Glu
        2120                2125                2130
Glu Lys Lys Leu Gln Leu Val Arg Met Tyr Arg Thr His Thr Arg
        2135                2140                2145
Arg Ala Leu Gln Thr Val Ala Gln Leu Ile Leu Glu Leu Ile Glu
        2150                2155                2160
Lys Gln Glu Thr Ser Asn Lys His Leu Trp Phe Gln Gly Ile Arg
        2165                2170                2175
Arg Gln Ile Thr Ala Ser Glu Leu Leu Ser Ser Ala Ile Ile Thr
        2180                2185                2190
Glu Glu Met Leu Gln Asp Leu Glu Thr Gly Arg Ser Thr Thr Gln
        2195                2200                2205
Glu Leu Met Glu Asp Asp Arg Val Lys Arg Tyr Leu Glu Gly Thr
        2210                2215                2220
Ser Cys Ile Ala Gly Val Leu Val Pro Ala Lys Asp Gln Pro Gly
        2225                2230                2235
Arg Gln Glu Lys Met Ser Ile Tyr Gln Ala Met Trp Lys Gly Val
        2240                2245                2250
Leu Arg Pro Gly Thr Ala Leu Val Leu Leu Glu Ala Gln Ala Ala
        2255                2260                2265
Thr Gly Phe Val Ile Asp Pro Val Arg Asn Leu Arg Leu Ser Val
        2270                2275                2280
Glu Glu Pro Val Pro Ala Gly Val Val Gly Ser Glu Ile Gln Glu
        2285                2290                2295
Lys Leu Leu Ser Ala Glu Arg Ala Val Thr Gly Tyr Thr Asp Pro
        2300                2305                2310
Tyr Thr Gly Gln Gln Ile Ser Leu Phe Gln Ala Met Gln Lys Asp
        2315                2320                2325
Leu Ile Val Arg Glu His Gly Ile Arg Leu Leu Glu Ala Gln Ile
        2330                2335                2340
Ala Thr Gly Gly Val Ile Asp Pro Val His Ser His Arg Val Pro
        2345                2350                2355
```

```
Val Asp Val Ala Tyr Arg Arg Gly Tyr Phe Asp Glu Glu Met Asn
    2360            2365                2370
Arg Val Leu Ala Asp Pro Ser Asp Asp Thr Lys Gly Phe Phe Asp
    2375            2380                2385
Pro Asn Thr His Glu Asn Leu Thr Tyr Val Gln Leu Leu Arg Arg
    2390            2395                2400
Cys Val Pro Asp Pro Asp Thr Gly Leu Tyr Met Leu Gln Leu Ala
    2405            2410                2415
Gly Arg Gly Ser Ala Val His Gln Leu Ser Glu Glu Leu Arg Cys
    2420            2425                2430
Ala Leu Arg Asp Ala Arg Val Thr Pro Gly Ser Gly Ala Leu Gln
    2435            2440                2445
Gly Gln Ser Val Ser Val Trp Glu Leu Leu Phe Tyr Arg Glu Val
    2450            2455                2460
Ser Glu Asp Arg Arg Gln Asp Leu Leu Ser Arg Tyr Arg Ala Gly
    2465            2470                2475
Thr Leu Thr Val Glu Glu Leu Gly Ala Thr Leu Thr Ser Leu Leu
    2480            2485                2490
Ala Gln Ala Gln Ala Gln Ala Arg Ala Glu Ala Glu Ala Gly Ser
    2495            2500                2505
Pro Arg Pro Asp Pro Arg Glu Ala Leu Arg Ala Ala Thr Met Glu
    2510            2515                2520
Val Lys Val Gly Arg Leu Arg Gly Arg Ala Val Pro Val Trp Asp
    2525            2530                2535
Val Leu Ala Ser Gly Tyr Val Ser Arg Ala Ala Arg Glu Glu Leu
    2540            2545                2550
Leu Ala Glu Phe Gly Ser Gly Thr Leu Asp Leu Pro Ala Leu Thr
    2555            2560                2565
Arg Arg Leu Thr Ala Ile Ile Glu Glu Ala Glu Ala Pro Gly
    2570            2575                2580
Ala Arg Pro Gln Leu Gln Asp Ala Arg Arg Gly Pro Arg Glu Pro
    2585            2590                2595
Gly Pro Ala Gly Arg Gly Asp Gly Asp Ser Gly Arg Ser Gln Arg
    2600            2605                2610
Glu Gly Gln Gly Glu Gly Glu Thr Gln Glu Ala Ala Ala Ala Ala
    2615            2620                2625
Ala Ala Ala Arg Arg Gln Glu Gln Thr Leu Arg Asp Ala Thr Met
    2630            2635                2640
Glu Val Gln Arg Gly Gln Phe Gln Gly Arg Pro Val Ser Val Trp
    2645            2650                2655
Asp Val Leu Phe Ser Ser Tyr Leu Ser Glu Ala Arg Arg Asp Glu
    2660            2665                2670
Leu Leu Ala Gln His Ala Ala Gly Ala Leu Gly Leu Pro Asp Leu
    2675            2680                2685
Val Ala Val Leu Thr Arg Val Ile Glu Glu Thr Glu Glu Arg Leu
    2690            2695                2700
Ser Lys Val Ser Phe Arg Gly Leu Arg Arg Gln Val Ser Ala Ser
    2705            2710                2715
Glu Leu His Thr Ser Gly Ile Leu Gly Pro Glu Thr Leu Arg Asp
    2720            2725                2730
Leu Ala Gln Gly Thr Lys Thr Leu Gln Glu Val Thr Glu Met Asp
    2735            2740                2745
```

```
Ser Val Lys Arg Tyr Leu Glu Gly Thr Ser Cys Ile Ala Gly Val
2750                2755                2760

Leu Val Pro Ala Lys Asp Gln Pro Gly Arg Gln Glu Lys Met Ser
2765                2770                2775

Ile Tyr Gln Ala Met Trp Lys Gly Val Leu Arg Pro Gly Thr Ala
2780                2785                2790

Leu Val Leu Leu Glu Ala Gln Ala Thr Gly Phe Val Ile Asp
2795                2800                2805

Pro Val Arg Asn Leu Arg Leu Ser Val Glu Glu Ala Val Ala Ala
2810                2815                2820

Gly Val Val Gly Gly Glu Ile Gln Glu Lys Leu Leu Ser Ala Glu
2825                2830                2835

Arg Ala Val Thr Gly Tyr Thr Asp Pro Tyr Thr Gly Gln Gln Ile
2840                2845                2850

Ser Leu Phe Gln Ala Met Gln Lys Asp Leu Ile Val Arg Glu His
2855                2860                2865

Gly Ile Arg Leu Leu Glu Ala Gln Ile Ala Thr Gly Gly Val Ile
2870                2875                2880

Asp Pro Val His Ser His Arg Val Pro Val Asp Val Ala Tyr Arg
2885                2890                2895

Arg Gly Tyr Phe Asp Glu Glu Met Asn Arg Val Leu Ala Asp Pro
2900                2905                2910

Ser Asp Asp Thr Lys Gly Phe Phe Asp Pro Asn Thr His Glu Asn
2915                2920                2925

Leu Thr Tyr Val Gln Leu Leu Arg Arg Cys Val Pro Asp Pro Asp
2930                2935                2940

Thr Gly Leu Tyr Met Leu Gln Leu Ala Gly Arg Gly Ser Ala Val
2945                2950                2955

His Gln Leu Ser Glu Glu Leu Arg Cys Ala Leu Arg Asp Ala Arg
2960                2965                2970

Val Thr Pro Gly Ser Gly Ala Leu Gln Gly Gln Ser Val Ser Val
2975                2980                2985

Trp Glu Leu Leu Phe Tyr Arg Glu Val Ser Glu Asp Arg Arg Gln
2990                2995                3000

Asp Leu Leu Ser Arg Tyr Arg Ala Gly Thr Leu Thr Val Glu Glu
3005                3010                3015

Leu Gly Ala Thr Leu Thr Ser Leu Leu Ala Gln Ala Gln Ala Gln
3020                3025                3030

Ala Arg Ala Glu Ala Glu Ala Gly Ser Pro Arg Pro Asp Pro Arg
3035                3040                3045

Glu Ala Leu Arg Ala Ala Thr Met Glu Val Lys Val Gly Arg Leu
3050                3055                3060

Arg Gly Arg Ala Val Pro Val Trp Asp Val Leu Ala Ser Gly Tyr
3065                3070                3075

Val Ser Gly Ala Ala Arg Glu Glu Leu Leu Ala Glu Phe Gly Ser
3080                3085                3090

Gly Thr Leu Asp Leu Pro Ala Leu Thr Arg Arg Leu Thr Ala Ile
3095                3100                3105

Ile Glu Glu Ala Glu Glu Ala Pro Gly Ala Arg Pro Gln Leu Gln
3110                3115                3120

Asp Ala Trp Arg Gly Pro Arg Glu Pro Gly Pro Ala Gly Arg Gly
3125                3130                3135

Asp Gly Asp Ser Gly Arg Ser Gln Arg Glu Gly Gln Gly Glu Gly
```

```
            3140              3145              3150
Glu Thr Gln Glu Ala Ala Ala Ala Ala Ala Arg Arg Gln
    3155             3160             3165
Glu Gln Thr Leu Arg Asp Ala Thr Met Glu Val Gln Arg Gly Gln
    3170             3175             3180
Phe Gln Gly Arg Pro Val Ser Val Trp Asp Val Leu Phe Ser Ser
    3185             3190             3195
Tyr Leu Ser Glu Ala Arg Arg Asp Glu Leu Leu Ala Gln His Ala
    3200             3205             3210
Ala Gly Ala Leu Gly Leu Pro Asp Leu Val Ala Val Leu Thr Arg
    3215             3220             3225
Val Ile Glu Glu Thr Glu Glu Arg Leu Ser Lys Val Ser Phe Arg
    3230             3235             3240
Gly Leu Arg Arg Gln Val Ser Ala Ser Glu Leu His Thr Ser Gly
    3245             3250             3255
Ile Leu Gly Pro Glu Thr Leu Arg Asp Leu Ala Gln Gly Thr Lys
    3260             3265             3270
Thr Leu Gln Glu Val Thr Glu Met Asp Ser Val Lys Arg Tyr Leu
    3275             3280             3285
Glu Gly Thr Ser Cys Ile Ala Gly Val Leu Val Pro Ala Lys Asp
    3290             3295             3300
Gln Pro Gly Arg Gln Glu Lys Met Ser Ile Tyr Gln Ala Met Trp
    3305             3310             3315
Lys Gly Val Leu Arg Pro Gly Thr Ala Leu Val Leu Leu Glu Ala
    3320             3325             3330
Gln Ala Ala Thr Gly Phe Val Ile Asp Pro Val Arg Asn Leu Arg
    3335             3340             3345
Leu Ser Val Glu Glu Ala Val Ala Ala Gly Val Val Gly Gly Glu
    3350             3355             3360
Ile Gln Glu Lys Leu Leu Ser Ala Glu Arg Ala Val Thr Gly Tyr
    3365             3370             3375
Thr Asp Pro Tyr Thr Gly Gln Gln Ile Ser Leu Phe Gln Ala Met
    3380             3385             3390
Gln Lys Asp Leu Ile Val Arg Glu His Gly Ile Arg Leu Leu Glu
    3395             3400             3405
Ala Gln Ile Ala Thr Gly Gly Val Ile Asp Pro Val His Ser His
    3410             3415             3420
Arg Val Pro Val Asp Val Ala Tyr Arg Arg Gly Tyr Phe Asp Glu
    3425             3430             3435
Glu Met Asn Arg Val Leu Ala Asp Pro Ser Asp Asp Thr Lys Gly
    3440             3445             3450
Phe Phe Asp Pro Asn Thr His Glu Asn Leu Thr Tyr Val Gln Leu
    3455             3460             3465
Leu Arg Arg Cys Val Pro Asp Pro Asp Thr Gly Leu Tyr Met Leu
    3470             3475             3480
Gln Leu Ala Gly Arg Gly Ser Ala Val His Gln Leu Ser Glu Glu
    3485             3490             3495
Leu Arg Cys Ala Leu Arg Asp Ala Arg Val Thr Pro Gly Ser Gly
    3500             3505             3510
Ala Leu Gln Gly Gln Ser Val Ser Val Trp Glu Leu Leu Phe Tyr
    3515             3520             3525
Arg Glu Val Ser Glu Asp Arg Arg Gln Asp Leu Leu Ser Arg Tyr
    3530             3535             3540
```

```
Arg Ala Gly Thr Leu Thr Val Glu Glu Leu Gly Ala Thr Leu Thr
3545                3550                3555

Ser Leu Leu Ala Gln Ala Gln Ala Gln Ala Arg Ala Glu Ala Glu
3560                3565                3570

Ala Gly Ser Pro Arg Pro Asp Pro Arg Glu Ala Leu Arg Ala Ala
3575                3580                3585

Thr Met Glu Val Lys Val Gly Arg Leu Arg Gly Arg Ala Val Pro
3590                3595                3600

Val Trp Asp Val Leu Ala Ser Gly Tyr Val Ser Gly Ala Ala Arg
3605                3610                3615

Glu Glu Leu Leu Ala Glu Phe Gly Ser Gly Thr Leu Asp Leu Pro
3620                3625                3630

Ala Leu Thr Arg Arg Leu Thr Ala Ile Ile Glu Ala Glu Glu
3635                3640                3645

Ala Pro Gly Ala Arg Pro Gln Leu Gln Asp Ala Trp Arg Gly Pro
3650                3655                3660

Arg Glu Pro Gly Pro Ala Gly Arg Gly Asp Gly Asp Ser Gly Arg
3665                3670                3675

Ser Gln Arg Glu Gly Gln Gly Glu Gly Glu Thr Gln Glu Ala Ala
3680                3685                3690

Ala Ala Ala Ala Ala Ala Arg Arg Gln Glu Gln Thr Leu Arg Asp
3695                3700                3705

Ala Thr Met Glu Val Gln Arg Gly Gln Phe Gln Gly Arg Pro Val
3710                3715                3720

Ser Val Trp Asp Val Leu Phe Ser Ser Tyr Leu Ser Glu Ala Arg
3725                3730                3735

Arg Asp Glu Leu Leu Ala Gln His Ala Ala Gly Ala Leu Gly Leu
3740                3745                3750

Pro Asp Leu Val Ala Val Leu Thr Arg Val Ile Glu Glu Thr Glu
3755                3760                3765

Glu Arg Leu Ser Lys Val Ser Phe Arg Gly Leu Arg Arg Gln Val
3770                3775                3780

Ser Ala Ser Glu Leu His Thr Ser Gly Ile Leu Gly Pro Glu Thr
3785                3790                3795

Leu Arg Asp Leu Ala Gln Gly Thr Lys Thr Leu Gln Glu Val Thr
3800                3805                3810

Glu Met Asp Ser Val Lys Arg Tyr Leu Glu Gly Thr Ser Cys Ile
3815                3820                3825

Ala Gly Val Leu Val Pro Ala Lys Asp Gln Pro Gly Arg Gln Glu
3830                3835                3840

Lys Met Ser Ile Tyr Gln Ala Met Trp Lys Gly Val Leu Arg Pro
3845                3850                3855

Gly Thr Ala Leu Val Leu Leu Glu Ala Gln Ala Ala Thr Gly Phe
3860                3865                3870

Val Ile Asp Pro Val Arg Asn Leu Arg Leu Ser Val Glu Glu Ala
3875                3880                3885

Val Ala Ala Gly Val Val Gly Gly Glu Ile Gln Glu Lys Leu Leu
3890                3895                3900

Ser Ala Glu Arg Ala Val Thr Gly Tyr Thr Asp Pro Tyr Thr Gly
3905                3910                3915

Gln Gln Ile Ser Leu Phe Gln Ala Met Gln Lys Asp Leu Ile Val
3920                3925                3930
```

Arg Glu His Gly Ile Arg Leu Leu Glu Ala Gln Ile Ala Thr Gly
3935                3940                3945

Gly Val Ile Asp Pro Val His Ser His Arg Val Pro Val Asp Val
3950                3955                3960

Ala Tyr Arg Arg Gly Tyr Phe Asp Glu Glu Met Asn Arg Val Leu
3965                3970                3975

Ala Asp Pro Ser Asp Asp Thr Lys Gly Phe Phe Asp Pro Asn Thr
3980                3985                3990

His Glu Asn Leu Thr Tyr Val Gln Leu Leu Arg Arg Cys Val Pro
3995                4000                4005

Asp Pro Asp Thr Gly Leu Tyr Met Leu Gln Leu Ala Gly Arg Gly
4010                4015                4020

Ser Ala Val His Gln Leu Ser Glu Glu Leu Arg Cys Ala Leu Arg
4025                4030                4035

Asp Ala Arg Val Thr Pro Gly Ser Gly Ala Leu Gln Gly Gln Ser
4040                4045                4050

Val Ser Val Trp Glu Leu Leu Phe Tyr Arg Glu Val Ser Glu Asp
4055                4060                4065

Arg Arg Gln Asp Leu Leu Ser Arg Tyr Arg Ala Ser Thr Leu Thr
4070                4075                4080

Val Glu Glu Leu Gly Ala Thr Leu Thr Ser Leu Leu Ala Gln Ala
4085                4090                4095

Gln Ala Gln Ala Arg Ala Glu Ala Glu Ala Gly Ser Pro Arg Pro
4100                4105                4110

Asp Pro Arg Glu Ala Leu Arg Ala Ala Thr Met Glu Val Lys Val
4115                4120                4125

Gly Arg Leu Arg Gly Arg Ala Val Pro Val Trp Asp Val Leu Ala
4130                4135                4140

Ser Gly Tyr Val Ser Arg Ala Ala Arg Glu Glu Leu Leu Ala Glu
4145                4150                4155

Phe Gly Ser Gly Thr Leu Asp Leu Pro Ala Leu Thr Arg Arg Leu
4160                4165                4170

Thr Ala Ile Ile Glu Glu Ala Glu Glu Ala Pro Gly Ala Arg Pro
4175                4180                4185

Gln Leu Gln Asp Ala Trp Arg Gly Pro Arg Glu Pro Gly Pro Ala
4190                4195                4200

Gly Arg Gly Asp Gly Asp Ser Gly Arg Ser Gln Arg Glu Gly Gln
4205                4210                4215

Gly Glu Gly Glu Thr Gln Glu Ala Ala Ala Ala Thr Ala Ala Ala
4220                4225                4230

Arg Arg Gln Glu Gln Thr Leu Arg Asp Ala Thr Met Glu Val Gln
4235                4240                4245

Arg Gly Gln Phe Gln Gly Arg Pro Val Ser Val Trp Asp Val Leu
4250                4255                4260

Phe Ser Ser Tyr Leu Ser Glu Ala Arg Arg Asp Glu Leu Leu Ala
4265                4270                4275

Gln His Ala Ala Gly Ala Leu Gly Leu Pro Asp Leu Val Ala Val
4280                4285                4290

Leu Thr Arg Val Ile Glu Glu Thr Glu Glu Arg Leu Ser Lys Val
4295                4300                4305

Ser Phe Arg Gly Leu Arg Arg Gln Val Ser Ala Ser Glu Leu His
4310                4315                4320

Thr Ser Gly Ile Leu Gly Pro Glu Thr Leu Arg Asp Leu Ala Gln

```
         4325                4330                4335
Gly Thr Lys Thr Leu Gln Glu Val Thr Glu Met Asp Ser Val Lys
         4340                4345                4350
Arg Tyr Leu Glu Gly Thr Ser Cys Ile Ala Gly Val Leu Val Pro
         4355                4360                4365
Ala Lys Asp Gln Pro Gly Arg Gln Glu Lys Met Ser Ile Tyr Gln
         4370                4375                4380
Ala Met Trp Lys Gly Val Leu Arg Pro Gly Thr Ala Leu Val Leu
         4385                4390                4395
Leu Glu Ala Gln Ala Ala Thr Gly Phe Val Ile Asp Pro Val Arg
         4400                4405                4410
Asn Leu Arg Leu Ser Val Glu Glu Ala Val Ala Ala Gly Val Val
         4415                4420                4425
Gly Gly Glu Ile Gln Glu Lys Leu Leu Ser Ala Glu Arg Ala Val
         4430                4435                4440
Thr Gly Tyr Thr Asp Pro Tyr Thr Gly Gln Gln Ile Ser Leu Phe
         4445                4450                4455
Gln Ala Met Gln Lys Asp Leu Ile Val Arg Glu His Gly Ile Arg
         4460                4465                4470
Leu Leu Glu Ala Gln Ile Ala Thr Gly Gly Val Ile Asp Pro Val
         4475                4480                4485
His Ser His Arg Val Pro Val Asp Val Ala Tyr Arg Arg Gly Tyr
         4490                4495                4500
Phe Asp Glu Glu Met Asn Arg Val Leu Ala Asp Pro Ser Asp Asp
         4505                4510                4515
Thr Lys Gly Phe Phe Asp Pro Asn Thr His Glu Asn Leu Thr Tyr
         4520                4525                4530
Val Gln Leu Leu Arg Arg Cys Val Pro Asp Pro Asp Thr Gly Leu
         4535                4540                4545
Tyr Met Leu Gln Leu Ala Gly Arg Gly Ser Ala Val His Gln Leu
         4550                4555                4560
Ser Glu Glu Leu Arg Cys Ala Leu Arg Asp Ala Arg Val Thr Pro
         4565                4570                4575
Gly Ser Gly Ala Leu Gln Gly Gln Ser Val Ser Val Trp Glu Leu
         4580                4585                4590
Leu Phe Tyr Arg Glu Val Ser Glu Asp Arg Arg Gln Asp Leu Leu
         4595                4600                4605
Ser Arg Tyr Arg Ala Gly Thr Leu Thr Val Glu Glu Leu Gly Ala
         4610                4615                4620
Thr Leu Thr Ser Leu Leu Ala Gln Ala Gln Ala Gln Ala Arg Ala
         4625                4630                4635
Glu Ala Glu Ala Gly Ser Pro Arg Pro Asp Pro Arg Glu Ala Leu
         4640                4645                4650
Arg Ala Ala Thr Met Glu Val Lys Val Gly Arg Leu Arg Gly Arg
         4655                4660                4665
Ala Val Pro Val Trp Asp Val Leu Ala Ser Gly Tyr Val Ser Gly
         4670                4675                4680
Ala Ala Arg Glu Glu Leu Leu Ala Glu Phe Gly Ser Gly Thr Leu
         4685                4690                4695
Asp Leu Pro Ala Leu Thr Arg Leu Thr Ala Ile Ile Glu Glu
         4700                4705                4710
Ala Glu Glu Ala Pro Gly Ala Arg Pro Gln Leu Gln Asp Ala Trp
         4715                4720                4725
```

Arg Gly Pro Arg Glu Pro Gly Pro Ala Gly Arg Gly Asp Gly Asp
4730            4735                4740

Ser Gly Arg Ser Gln Arg Glu Gly Gln Gly Glu Gly Glu Thr Gln
4745            4750                4755

Glu Ala Ala Ala Ala Ala Ala Ala Arg Arg Gln Glu Gln Thr
4760            4765                4770

Leu Arg Asp Ala Thr Met Glu Val Gln Arg Gly Gln Phe Gln Gly
4775            4780                4785

Arg Pro Val Ser Val Trp Asp Val Leu Phe Ser Ser Tyr Leu Ser
4790            4795                4800

Glu Ala Arg Arg Asp Glu Leu Leu Ala Gln His Ala Ala Gly Ala
4805            4810                4815

Leu Gly Leu Pro Asp Leu Val Ala Val Leu Thr Arg Val Ile Glu
4820            4825                4830

Glu Thr Glu Glu Arg Leu Ser Lys Val Ser Phe Arg Gly Leu Arg
4835            4840                4845

Arg Gln Val Ser Ala Ser Glu Leu His Thr Ser Gly Ile Leu Gly
4850            4855                4860

Pro Glu Thr Leu Arg Asp Leu Ala Gln Gly Thr Lys Thr Leu Gln
4865            4870                4875

Glu Val Thr Glu Met Asp Ser Val Lys Arg Tyr Leu Glu Gly Thr
4880            4885                4890

Ser Cys Ile Ala Gly Val Leu Val Pro Ala Lys Asp Gln Pro Gly
4895            4900                4905

Arg Gln Glu Lys Met Ser Ile Tyr Gln Ala Met Trp Lys Gly Val
4910            4915                4920

Leu Arg Pro Gly Thr Ala Leu Val Leu Leu Glu Ala Gln Ala Ala
4925            4930                4935

Thr Gly Phe Val Ile Asp Pro Val Arg Asn Leu Arg Leu Ser Val
4940            4945                4950

Glu Glu Ala Val Ala Ala Gly Val Val Gly Gly Glu Ile Gln Glu
4955            4960                4965

Lys Leu Leu Ser Ala Glu Arg Ala Val Thr Gly Tyr Thr Asp Pro
4970            4975                4980

Tyr Thr Gly Gln Gln Ile Ser Leu Phe Gln Ala Met Gln Lys Asp
4985            4990                4995

Leu Ile Val Arg Glu His Gly Ile Arg Leu Leu Glu Ala Gln Ile
5000            5005                5010

Ala Thr Gly Gly Val Ile Asp Pro Val His Ser His Arg Val Pro
5015            5020                5025

Val Asp Val Ala Tyr Arg Arg Gly Tyr Phe Asp Glu Glu Met Asn
5030            5035                5040

Arg Val Leu Ala Asp Pro Ser Asp Asp Thr Lys Gly Phe Phe Asp
5045            5050                5055

Pro Asn Thr His Glu Asn Leu Thr Tyr Leu Gln Leu Leu Gln Arg
5060            5065                5070

Ala Thr Leu Asp Pro Glu Thr Gly Leu Leu Phe Leu Ser Leu Ser
5075            5080                5085

Leu Gln
5090

<210> SEQ ID NO 5
<211> LENGTH: 515

```
<212> TYPE: PRT
<213> ORGANISM: homo sapiens
<220> FEATURE:
<221> NAME/KEY: misc_feature
<223> OTHER INFORMATION: Glucose-6-phosphate 1-dehydrogenase  short
      isoform 1

<400> SEQUENCE: 5

Met Ala Glu Gln Val Ala Leu Ser Arg Thr Gln Val Cys Gly Ile Leu
1               5                   10                  15

Arg Glu Glu Leu Phe Gln Gly Asp Ala Phe His Gln Ser Asp Thr His
            20                  25                  30

Ile Phe Ile Ile Met Gly Ala Ser Gly Asp Leu Ala Lys Lys Lys Ile
        35                  40                  45

Tyr Pro Thr Ile Trp Trp Leu Phe Arg Asp Gly Leu Leu Pro Glu Asn
50                  55                  60

Thr Phe Ile Val Gly Tyr Ala Arg Ser Arg Leu Thr Val Ala Asp Ile
65                  70                  75                  80

Arg Lys Gln Ser Glu Pro Phe Phe Lys Ala Thr Pro Glu Glu Lys Leu
                85                  90                  95

Lys Leu Glu Asp Phe Phe Ala Arg Asn Ser Tyr Val Ala Gly Gln Tyr
            100                 105                 110

Asp Asp Ala Ala Ser Tyr Gln Arg Leu Asn Ser His Met Asn Ala Leu
        115                 120                 125

His Leu Gly Ser Gln Ala Asn Arg Leu Phe Tyr Leu Ala Leu Pro Pro
    130                 135                 140

Thr Val Tyr Glu Ala Val Thr Lys Asn Ile His Glu Ser Cys Met Ser
145                 150                 155                 160

Gln Ile Gly Trp Asn Arg Ile Ile Val Glu Lys Pro Phe Gly Arg Asp
                165                 170                 175

Leu Gln Ser Ser Asp Arg Leu Ser Asn His Ile Ser Ser Leu Phe Arg
            180                 185                 190

Glu Asp Gln Ile Tyr Arg Ile Asp His Tyr Leu Gly Lys Glu Met Val
        195                 200                 205

Gln Asn Leu Met Val Leu Arg Phe Ala Asn Arg Ile Phe Gly Pro Ile
    210                 215                 220

Trp Asn Arg Asp Asn Ile Ala Cys Val Ile Leu Thr Phe Lys Glu Pro
225                 230                 235                 240

Phe Gly Thr Glu Gly Arg Gly Gly Tyr Phe Asp Glu Phe Gly Ile Ile
                245                 250                 255

Arg Asp Val Met Gln Asn His Leu Leu Gln Met Leu Cys Leu Val Ala
            260                 265                 270

Met Glu Lys Pro Ala Ser Thr Asn Ser Asp Asp Val Arg Asp Glu Lys
        275                 280                 285

Val Lys Val Leu Lys Cys Ile Ser Glu Val Gln Ala Asn Asn Val Val
    290                 295                 300

Leu Gly Gln Tyr Val Gly Asn Pro Asp Gly Glu Gly Glu Ala Thr Lys
305                 310                 315                 320

Gly Tyr Leu Asp Asp Pro Thr Val Pro Arg Gly Ser Thr Thr Ala Thr
                325                 330                 335

Phe Ala Ala Val Val Leu Tyr Val Glu Asn Glu Arg Trp Asp Gly Val
            340                 345                 350

Pro Phe Ile Leu Arg Cys Gly Lys Ala Leu Asn Glu Arg Lys Ala Glu
        355                 360                 365

Val Arg Leu Gln Phe His Asp Val Ala Gly Asp Ile Phe His Gln Gln
```

-continued

```
                370                 375                 380
Cys Lys Arg Asn Glu Leu Val Ile Arg Val Gln Pro Asn Glu Ala Val
385                 390                 395                 400

Tyr Thr Lys Met Met Thr Lys Lys Pro Gly Met Phe Phe Asn Pro Glu
                405                 410                 415

Glu Ser Glu Leu Asp Leu Thr Tyr Gly Asn Arg Tyr Lys Asn Val Lys
                420                 425                 430

Leu Pro Asp Ala Tyr Glu Arg Leu Ile Leu Asp Val Phe Cys Gly Ser
                435                 440                 445

Gln Met His Phe Val Arg Ser Asp Glu Leu Arg Glu Ala Trp Arg Ile
                450                 455                 460

Phe Thr Pro Leu Leu His Gln Ile Glu Leu Glu Lys Pro Lys Pro Ile
465                 470                 475                 480

Pro Tyr Ile Tyr Gly Ser Arg Gly Pro Thr Glu Ala Asp Glu Leu Met
                485                 490                 495

Lys Arg Val Gly Phe Gln Tyr Glu Gly Thr Tyr Lys Trp Val Asn Pro
                500                 505                 510

His Lys Leu
        515

<210> SEQ ID NO 6
<211> LENGTH: 561
<212> TYPE: PRT
<213> ORGANISM: homo sapiens
<220> FEATURE:
<221> NAME/KEY: misc_feature
<223> OTHER INFORMATION: Glucose-6-phosphate 1-dehydrogenase  long
      isoform 2

<400> SEQUENCE: 6

Met Ala Glu Gln Val Ala Leu Ser Arg Thr Gln Val Cys Gly Ile Leu
1               5                   10                  15

Arg Glu Glu Leu Phe Gln Gly Asp Ala Phe His Gln Ser Asp Thr His
                20                  25                  30

Ile Phe Ile Ile Met Gly Ala Ser Gly Asp Leu Ala Lys Lys Lys Ile
                35                  40                  45

Tyr Pro Thr Ile Trp Trp Leu Phe Arg Asp Gly Leu Leu Pro Glu Asn
50                  55                  60

Thr Phe Ile Val Gly Tyr Ala Arg Ser Arg Leu Thr Val Ala Asp Ile
65                  70                  75                  80

Arg Lys Gln Ser Glu Pro Phe Phe Lys Ala Thr Pro Glu Glu Lys Leu
                85                  90                  95

Lys Leu Glu Asp Phe Phe Ala Arg Asn Ser Tyr Val Ala Gly Gln Tyr
                100                 105                 110

Asp Asp Ala Ala Ser Tyr Gln Arg Leu Asn Ser His Met Asn Ala Leu
                115                 120                 125

His Leu Gly Ser Gln Ala Asn Arg Leu Phe Tyr Leu Ala Leu Pro Pro
                130                 135                 140

Thr Val Tyr Glu Ala Val Thr Lys Asn Ile His Glu Ser Cys Met Ser
145                 150                 155                 160

Gln Ile Gly Trp Asn Arg Ile Ile Val Glu Lys Pro Phe Gly Arg Asp
                165                 170                 175

Leu Gln Ser Ser Asp Arg Leu Ser Asn His Ile Ser Ser Leu Phe Arg
                180                 185                 190

Glu Asp Gln Ile Tyr Arg Ile Asp His Tyr Leu Gly Lys Glu Met Val
                195                 200                 205
```

Gln Asn Leu Met Val Leu Arg Phe Ala Asn Arg Ile Phe Gly Pro Ile
    210                 215                 220

Trp Asn Arg Asp Asn Ile Ala Cys Val Ile Leu Thr Phe Lys Glu Pro
225                 230                 235                 240

Phe Gly Thr Glu Gly Arg Gly Gly Tyr Phe Asp Glu Phe Gly Ile Ile
                245                 250                 255

Arg Gly Pro Gly Arg Gln Gly Gly Ser Gly Ser Glu Ser Cys Ser Leu
            260                 265                 270

Ser Leu Gly Ser Leu Val Trp Gly Pro His Ala Leu Glu Pro Gly Glu
        275                 280                 285

Gln Gly Gly Glu Leu Arg Arg Ala Leu Ala Ser Ser Val Pro Arg Asp
    290                 295                 300

Val Met Gln Asn His Leu Leu Gln Met Leu Cys Leu Val Ala Met Glu
305                 310                 315                 320

Lys Pro Ala Ser Thr Asn Ser Asp Asp Val Arg Asp Glu Lys Val Lys
                325                 330                 335

Val Leu Lys Cys Ile Ser Glu Val Gln Ala Asn Asn Val Val Leu Gly
            340                 345                 350

Gln Tyr Val Gly Asn Pro Asp Gly Glu Gly Glu Ala Thr Lys Gly Tyr
    355                 360                 365

Leu Asp Asp Pro Thr Val Pro Arg Gly Ser Thr Thr Ala Thr Phe Ala
370                 375                 380

Ala Val Val Leu Tyr Val Glu Asn Glu Arg Trp Asp Gly Val Pro Phe
385                 390                 395                 400

Ile Leu Arg Cys Gly Lys Ala Leu Asn Glu Arg Lys Ala Glu Val Arg
                405                 410                 415

Leu Gln Phe His Asp Val Ala Gly Asp Ile Phe His Gln Gln Cys Lys
            420                 425                 430

Arg Asn Glu Leu Val Ile Arg Val Gln Pro Asn Glu Ala Val Tyr Thr
    435                 440                 445

Lys Met Met Thr Lys Lys Pro Gly Met Phe Phe Asn Pro Glu Glu Ser
450                 455                 460

Glu Leu Asp Leu Thr Tyr Gly Asn Arg Tyr Lys Asn Val Lys Leu Pro
465                 470                 475                 480

Asp Ala Tyr Glu Arg Leu Ile Leu Asp Val Phe Cys Gly Ser Gln Met
                485                 490                 495

His Phe Val Arg Ser Asp Glu Leu Arg Glu Ala Trp Arg Ile Phe Thr
            500                 505                 510

Pro Leu Leu His Gln Ile Glu Leu Glu Lys Pro Lys Pro Ile Pro Tyr
    515                 520                 525

Ile Tyr Gly Ser Arg Gly Pro Thr Glu Ala Asp Glu Leu Met Lys Arg
530                 535                 540

Val Gly Phe Gln Tyr Glu Gly Thr Tyr Lys Trp Val Asn Pro His Lys
545                 550                 555                 560

Leu

<210> SEQ ID NO 7
<211> LENGTH: 545
<212> TYPE: PRT
<213> ORGANISM: homo sapiens
<220> FEATURE:
<221> NAME/KEY: misc_feature
<223> OTHER INFORMATION: Glucose-6-phosphate 1-dehydrogenase short
      isoform 3

```
<400> SEQUENCE: 7

Met Gly Arg Arg Gly Ser Ala Pro Gly Asn Gly Arg Thr Leu Arg Gly
1               5                   10                  15

Cys Glu Arg Gly Gly Arg Arg Arg Ser Ala Asp Ser Val Met Ala
            20                  25                  30

Glu Gln Val Ala Leu Ser Arg Thr Gln Val Cys Gly Ile Leu Arg Glu
            35                  40                  45

Glu Leu Phe Gln Gly Asp Ala Phe His Gln Ser Asp Thr His Ile Phe
    50                  55                  60

Ile Ile Met Gly Ala Ser Gly Asp Leu Ala Lys Lys Ile Tyr Pro
65                  70                  75                  80

Thr Ile Trp Trp Leu Phe Arg Asp Gly Leu Leu Pro Glu Asn Thr Phe
                85                  90                  95

Ile Val Gly Tyr Ala Arg Ser Arg Leu Thr Val Ala Asp Ile Arg Lys
                100                 105                 110

Gln Ser Glu Pro Phe Phe Lys Ala Thr Pro Glu Glu Lys Leu Lys Leu
            115                 120                 125

Glu Asp Phe Phe Ala Arg Asn Ser Tyr Val Ala Gly Gln Tyr Asp Asp
    130                 135                 140

Ala Ala Ser Tyr Gln Arg Leu Asn Ser His Met Asn Ala Leu His Leu
145                 150                 155                 160

Gly Ser Gln Ala Asn Arg Leu Phe Tyr Leu Ala Leu Pro Pro Thr Val
                165                 170                 175

Tyr Glu Ala Val Thr Lys Asn Ile His Glu Ser Cys Met Ser Gln Ile
                180                 185                 190

Gly Trp Asn Arg Ile Ile Val Glu Lys Pro Phe Gly Arg Asp Leu Gln
            195                 200                 205

Ser Ser Asp Arg Leu Ser Asn His Ile Ser Ser Leu Phe Arg Glu Asp
    210                 215                 220

Gln Ile Tyr Arg Ile Asp His Tyr Leu Gly Lys Glu Met Val Gln Asn
225                 230                 235                 240

Leu Met Val Leu Arg Phe Ala Asn Arg Ile Phe Gly Pro Ile Trp Asn
                245                 250                 255

Arg Asp Asn Ile Ala Cys Val Ile Leu Thr Phe Lys Glu Pro Phe Gly
            260                 265                 270

Thr Glu Gly Arg Gly Gly Tyr Phe Asp Glu Phe Gly Ile Ile Arg Asp
            275                 280                 285

Val Met Gln Asn His Leu Leu Gln Met Leu Cys Leu Val Ala Met Glu
    290                 295                 300

Lys Pro Ala Ser Thr Asn Ser Asp Asp Val Arg Asp Glu Lys Val Lys
305                 310                 315                 320

Val Leu Lys Cys Ile Ser Glu Val Gln Ala Asn Asn Val Val Leu Gly
                325                 330                 335

Gln Tyr Val Gly Asn Pro Asp Gly Glu Gly Glu Ala Thr Lys Gly Tyr
            340                 345                 350

Leu Asp Asp Pro Thr Val Pro Arg Gly Ser Thr Thr Ala Thr Phe Ala
    355                 360                 365

Ala Val Val Leu Tyr Val Glu Asn Glu Arg Trp Asp Gly Val Pro Phe
    370                 375                 380

Ile Leu Arg Cys Gly Lys Ala Leu Asn Glu Arg Lys Ala Glu Val Arg
385                 390                 395                 400

Leu Gln Phe His Asp Val Ala Gly Asp Ile Phe His Gln Gln Cys Lys
                405                 410                 415
```

```
Arg Asn Glu Leu Val Ile Arg Val Gln Pro Asn Glu Ala Val Tyr Thr
            420                 425                 430

Lys Met Met Thr Lys Lys Pro Gly Met Phe Phe Asn Pro Glu Glu Ser
            435                 440                 445

Glu Leu Asp Leu Thr Tyr Gly Asn Arg Tyr Lys Asn Val Lys Leu Pro
            450                 455                 460

Asp Ala Tyr Glu Arg Leu Ile Leu Asp Val Phe Cys Gly Ser Gln Met
465                 470                 475                 480

His Phe Val Arg Ser Asp Glu Leu Arg Glu Ala Trp Arg Ile Phe Thr
                485                 490                 495

Pro Leu Leu His Gln Ile Glu Leu Glu Lys Pro Lys Pro Ile Pro Tyr
                500                 505                 510

Ile Tyr Gly Ser Arg Gly Pro Thr Glu Ala Asp Glu Leu Met Lys Arg
                515                 520                 525

Val Gly Phe Gln Tyr Glu Gly Thr Tyr Lys Trp Val Asn Pro His Lys
            530                 535                 540

Leu
545

<210> SEQ ID NO 8
<211> LENGTH: 452
<212> TYPE: PRT
<213> ORGANISM: homo sapiens
<220> FEATURE:
<221> NAME/KEY: misc_feature
<223> OTHER INFORMATION: Isocitrate dehydrogenase [NADP]

<400> SEQUENCE: 8

Met Ala Gly Tyr Leu Arg Val Val Arg Ser Leu Cys Arg Ala Ser Gly
1               5                   10                  15

Ser Arg Pro Ala Trp Ala Pro Ala Ala Leu Thr Ala Pro Thr Ser Gln
            20                  25                  30

Glu Gln Pro Arg Arg His Tyr Ala Asp Lys Arg Ile Lys Val Ala Lys
        35                  40                  45

Pro Val Val Glu Met Asp Gly Asp Glu Met Thr Arg Ile Ile Trp Gln
    50                  55                  60

Phe Ile Lys Glu Lys Leu Ile Leu Pro His Val Asp Ile Gln Leu Lys
65                  70                  75                  80

Tyr Phe Asp Leu Gly Leu Pro Asn Arg Asp Gln Thr Asp Asp Gln Val
                85                  90                  95

Thr Ile Asp Ser Ala Leu Ala Thr Gln Lys Tyr Ser Val Ala Val Lys
            100                 105                 110

Cys Ala Thr Ile Thr Pro Asp Glu Ala Arg Val Glu Glu Phe Lys Leu
        115                 120                 125

Lys Lys Met Trp Lys Ser Pro Asn Gly Thr Ile Arg Asn Ile Leu Gly
    130                 135                 140

Gly Thr Val Phe Arg Glu Pro Ile Ile Cys Lys Asn Ile Pro Arg Leu
145                 150                 155                 160

Val Pro Gly Trp Thr Lys Pro Ile Thr Ile Gly Arg His Ala His Gly
                165                 170                 175

Asp Gln Tyr Lys Ala Thr Asp Phe Val Ala Asp Arg Ala Gly Thr Phe
            180                 185                 190

Lys Met Val Phe Thr Pro Lys Asp Gly Ser Gly Val Lys Glu Trp Glu
        195                 200                 205

Val Tyr Asn Phe Pro Ala Gly Gly Val Gly Met Gly Met Tyr Asn Thr
```

Asp Glu Ser Ile Ser Gly Phe Ala His Ser Cys Phe Gln Tyr Ala Ile
225                 230                 235                 240

Gln Lys Lys Trp Pro Leu Tyr Met Ser Thr Lys Asn Thr Ile Leu Lys
            245                 250                 255

Ala Tyr Asp Gly Arg Phe Lys Asp Ile Phe Gln Glu Ile Phe Asp Lys
                260                 265                 270

His Tyr Lys Thr Asp Phe Asp Lys Asn Lys Ile Trp Tyr Glu His Arg
            275                 280                 285

Leu Ile Asp Asp Met Val Ala Gln Val Leu Lys Ser Ser Gly Gly Phe
        290                 295                 300

Val Trp Ala Cys Lys Asn Tyr Asp Gly Asp Val Gln Ser Asp Ile Leu
305                 310                 315                 320

Ala Gln Gly Phe Gly Ser Leu Gly Leu Met Thr Ser Val Leu Val Cys
                325                 330                 335

Pro Asp Gly Lys Thr Ile Glu Ala Glu Ala Ala His Gly Thr Val Thr
                340                 345                 350

Arg His Tyr Arg Glu His Gln Lys Gly Arg Pro Thr Ser Thr Asn Pro
            355                 360                 365

Ile Ala Ser Ile Phe Ala Trp Thr Arg Gly Leu Glu His Arg Gly Lys
        370                 375                 380

Leu Asp Gly Asn Gln Asp Leu Ile Arg Phe Ala Gln Met Leu Glu Lys
385                 390                 395                 400

Val Cys Val Glu Thr Val Glu Ser Gly Ala Met Thr Lys Asp Leu Ala
                405                 410                 415

Gly Cys Ile His Gly Leu Ser Asn Val Lys Leu Asn Glu His Phe Leu
            420                 425                 430

Asn Thr Thr Asp Phe Leu Asp Thr Ile Lys Ser Asn Leu Asp Arg Ala
            435                 440                 445

Leu Gly Arg Gln
    450

<210> SEQ ID NO 9
<211> LENGTH: 400
<212> TYPE: PRT
<213> ORGANISM: homo sapiens
<220> FEATURE:
<221> NAME/KEY: misc_feature
<223> OTHER INFORMATION: Keratin type I cytoskeletal 19

<400> SEQUENCE: 9

Met Thr Ser Tyr Ser Tyr Arg Gln Ser Ser Ala Thr Ser Ser Phe Gly
1               5                   10                  15

Gly Leu Gly Gly Gly Ser Val Arg Phe Gly Pro Gly Val Ala Phe Arg
            20                  25                  30

Ala Pro Ser Ile His Gly Gly Ser Gly Gly Arg Gly Val Ser Val Ser
        35                  40                  45

Ser Ala Arg Phe Val Ser Ser Ser Ser Gly Ala Tyr Gly Gly Gly
    50                  55                  60

Tyr Gly Gly Val Leu Thr Ala Ser Asp Gly Leu Leu Ala Gly Asn Glu
65                  70                  75                  80

Lys Leu Thr Met Gln Asn Leu Asn Asp Arg Leu Ala Ser Tyr Leu Asp
                85                  90                  95

Lys Val Arg Ala Leu Glu Ala Ala Asn Gly Glu Leu Glu Val Lys Ile
            100                 105                 110

```
Arg Asp Trp Tyr Gln Lys Gln Gly Pro Gly Pro Ser Arg Asp Tyr Ser
            115                 120                 125

His Tyr Tyr Thr Thr Ile Gln Asp Leu Arg Asp Lys Ile Leu Gly Ala
        130                 135                 140

Thr Ile Glu Asn Ser Arg Ile Val Leu Gln Ile Asp Asn Ala Arg Leu
145                 150                 155                 160

Ala Ala Asp Asp Phe Arg Thr Lys Phe Glu Thr Gln Ala Leu Arg
                165                 170                 175

Met Ser Val Glu Ala Asp Ile Asn Gly Leu Arg Arg Val Leu Asp Glu
            180                 185                 190

Leu Thr Leu Ala Arg Thr Asp Leu Glu Met Gln Ile Glu Gly Leu Lys
            195                 200                 205

Glu Glu Leu Ala Tyr Leu Lys Lys Asn His Glu Glu Ile Ser Thr
            210                 215                 220

Leu Arg Gly Gln Val Gly Gly Gln Val Ser Val Glu Val Asp Ser Ala
225                 230                 235                 240

Pro Gly Thr Asp Leu Ala Lys Ile Leu Ser Asp Met Arg Ser Gln Tyr
                245                 250                 255

Glu Val Met Ala Glu Gln Asn Arg Lys Asp Ala Glu Ala Trp Phe Thr
            260                 265                 270

Ser Arg Thr Glu Glu Leu Asn Arg Glu Val Ala Gly His Thr Glu Gln
            275                 280                 285

Leu Gln Met Ser Arg Ser Glu Val Thr Asp Leu Arg Arg Thr Leu Gln
            290                 295                 300

Gly Leu Glu Ile Glu Leu Gln Ser Gln Leu Ser Met Lys Ala Ala Leu
305                 310                 315                 320

Glu Asp Thr Leu Ala Glu Thr Glu Ala Arg Phe Gly Ala Gln Leu Ala
                325                 330                 335

His Ile Gln Ala Leu Ile Ser Gly Ile Glu Ala Gln Leu Gly Asp Val
            340                 345                 350

Arg Ala Asp Ser Glu Arg Gln Asn Gln Glu Tyr Gln Arg Leu Met Asp
            355                 360                 365

Ile Lys Ser Arg Leu Glu Gln Glu Ile Ala Thr Tyr Arg Ser Leu Leu
            370                 375                 380

Glu Gly Gln Glu Asp His Tyr Asn Asn Leu Ser Ala Ser Lys Val Leu
385                 390                 395                 400

<210> SEQ ID NO 10
<211> LENGTH: 483
<212> TYPE: PRT
<213> ORGANISM: homo sapiens
<220> FEATURE:
<221> NAME/KEY: misc_feature
<223> OTHER INFORMATION: Keratin type I cytoskeletal 8 Isoform 1

<400> SEQUENCE: 10

Met Ser Ile Arg Val Thr Gln Lys Ser Tyr Lys Val Ser Thr Ser Gly
1               5                   10                  15

Pro Arg Ala Phe Ser Ser Arg Ser Tyr Thr Ser Gly Pro Gly Ser Arg
            20                  25                  30

Ile Ser Ser Ser Ser Phe Ser Arg Val Gly Ser Ser Asn Phe Arg Gly
        35                  40                  45

Gly Leu Gly Gly Gly Tyr Gly Gly Ala Ser Gly Met Gly Gly Ile Thr
    50                  55                  60

Ala Val Thr Val Asn Gln Ser Leu Leu Ser Pro Leu Val Leu Glu Val
65                  70                  75                  80
```

```
Asp Pro Asn Ile Gln Ala Val Arg Thr Gln Glu Lys Glu Gln Ile Lys
            85                  90                  95

Thr Leu Asn Asn Lys Phe Ala Ser Phe Ile Asp Lys Val Arg Phe Leu
            100                 105                 110

Glu Gln Gln Asn Lys Met Leu Glu Thr Lys Trp Ser Leu Leu Gln Gln
            115                 120                 125

Gln Lys Thr Ala Arg Ser Asn Met Asp Asn Met Phe Glu Ser Tyr Ile
130                 135                 140

Asn Asn Leu Arg Arg Gln Leu Glu Thr Leu Gly Gln Glu Lys Leu Lys
145                 150                 155                 160

Leu Glu Ala Glu Leu Gly Asn Met Gln Gly Leu Val Glu Asp Phe Lys
            165                 170                 175

Asn Lys Tyr Glu Asp Glu Ile Asn Lys Arg Thr Glu Met Glu Asn Glu
            180                 185                 190

Phe Val Leu Ile Lys Lys Asp Val Asp Glu Ala Tyr Met Asn Lys Val
            195                 200                 205

Glu Leu Glu Ser Arg Leu Glu Gly Leu Thr Asp Glu Ile Asn Phe Leu
            210                 215                 220

Arg Gln Leu Tyr Glu Glu Ile Arg Glu Leu Gln Ser Gln Ile Ser
225                 230                 235                 240

Asp Thr Ser Val Val Leu Ser Met Asp Asn Ser Arg Ser Leu Asp Met
            245                 250                 255

Asp Ser Ile Ile Ala Glu Val Lys Ala Gln Tyr Glu Asp Ile Ala Asn
            260                 265                 270

Arg Ser Arg Ala Glu Ala Glu Ser Met Tyr Gln Ile Lys Tyr Glu Glu
            275                 280                 285

Leu Gln Ser Leu Ala Gly Lys His Gly Asp Asp Leu Arg Arg Thr Lys
            290                 295                 300

Thr Glu Ile Ser Glu Met Asn Arg Asn Ile Ser Arg Leu Gln Ala Glu
305                 310                 315                 320

Ile Glu Gly Leu Lys Gly Gln Arg Ala Ser Leu Glu Ala Ala Ile Ala
            325                 330                 335

Asp Ala Glu Gln Arg Gly Glu Leu Ala Ile Lys Asp Ala Asn Ala Lys
            340                 345                 350

Leu Ser Glu Leu Glu Ala Ala Leu Gln Arg Ala Lys Gln Asp Met Ala
            355                 360                 365

Arg Gln Leu Arg Glu Tyr Gln Glu Leu Met Asn Val Lys Leu Ala Leu
            370                 375                 380

Asp Ile Glu Ile Ala Thr Tyr Arg Lys Leu Leu Glu Gly Glu Glu Ser
385                 390                 395                 400

Arg Leu Glu Ser Gly Met Gln Asn Met Ser Ile His Thr Lys Thr Thr
            405                 410                 415

Ser Gly Tyr Ala Gly Gly Leu Ser Ser Ala Tyr Gly Gly Leu Thr Ser
            420                 425                 430

Pro Gly Leu Ser Tyr Ser Leu Gly Ser Ser Phe Gly Ser Gly Ala Gly
            435                 440                 445

Ser Ser Ser Phe Ser Arg Thr Ser Ser Arg Ala Val Val Val Lys
            450                 455                 460

Lys Ile Glu Thr Arg Asp Gly Lys Leu Val Ser Glu Ser Ser Asp Val
465                 470                 475                 480

Leu Pro Lys
```

```
<210> SEQ ID NO 11
<211> LENGTH: 511
<212> TYPE: PRT
<213> ORGANISM: homo sapiens
<220> FEATURE:
<221> NAME/KEY: misc_feature
<223> OTHER INFORMATION: Keratin type I cytoskeletal 8 Isoform 2

<400> SEQUENCE: 11

Met Asn Gly Val Ser Trp Ser Gln Asp Leu Gln Glu Gly Ile Ser Ala
1               5                   10                  15

Trp Phe Gly Pro Pro Ala Ser Thr Pro Ala Ser Thr Met Ser Ile Arg
            20                  25                  30

Val Thr Gln Lys Ser Tyr Lys Val Ser Thr Ser Gly Pro Arg Ala Phe
        35                  40                  45

Ser Ser Arg Ser Tyr Thr Ser Gly Pro Gly Ser Arg Ile Ser Ser Ser
    50                  55                  60

Ser Phe Ser Arg Val Gly Ser Ser Asn Phe Arg Gly Gly Leu Gly Gly
65                  70                  75                  80

Gly Tyr Gly Gly Ala Ser Gly Met Gly Gly Ile Thr Ala Val Thr Val
                85                  90                  95

Asn Gln Ser Leu Leu Ser Pro Leu Val Leu Glu Val Asp Pro Asn Ile
            100                 105                 110

Gln Ala Val Arg Thr Gln Glu Lys Glu Gln Ile Lys Thr Leu Asn Asn
        115                 120                 125

Lys Phe Ala Ser Phe Ile Asp Lys Val Arg Phe Leu Glu Gln Gln Asn
    130                 135                 140

Lys Met Leu Glu Thr Lys Trp Ser Leu Leu Gln Gln Gln Lys Thr Ala
145                 150                 155                 160

Arg Ser Asn Met Asp Asn Met Phe Glu Ser Tyr Ile Asn Asn Leu Arg
                165                 170                 175

Arg Gln Leu Glu Thr Leu Gly Gln Glu Lys Leu Lys Leu Glu Ala Glu
            180                 185                 190

Leu Gly Asn Met Gln Gly Leu Val Glu Asp Phe Lys Asn Lys Tyr Glu
        195                 200                 205

Asp Glu Ile Asn Lys Arg Thr Glu Met Glu Asn Glu Phe Val Leu Ile
    210                 215                 220

Lys Lys Asp Val Asp Glu Ala Tyr Met Asn Lys Val Glu Leu Glu Ser
225                 230                 235                 240

Arg Leu Glu Gly Leu Thr Asp Glu Ile Asn Phe Leu Arg Gln Leu Tyr
                245                 250                 255

Glu Glu Glu Ile Arg Glu Leu Gln Ser Gln Ile Ser Asp Thr Ser Val
            260                 265                 270

Val Leu Ser Met Asp Asn Ser Arg Ser Leu Asp Met Asp Ser Ile Ile
        275                 280                 285

Ala Glu Val Lys Ala Gln Tyr Glu Asp Ile Ala Asn Arg Ser Arg Ala
    290                 295                 300

Glu Ala Glu Ser Met Tyr Gln Ile Lys Tyr Glu Glu Leu Gln Ser Leu
305                 310                 315                 320

Ala Gly Lys His Gly Asp Asp Leu Arg Arg Thr Lys Thr Glu Ile Ser
                325                 330                 335

Glu Met Asn Arg Asn Ile Ser Arg Leu Gln Ala Glu Ile Glu Gly Leu
            340                 345                 350

Lys Gly Gln Arg Ala Ser Leu Glu Ala Ala Ile Ala Asp Ala Glu Gln
        355                 360                 365
```

Arg Gly Glu Leu Ala Ile Lys Asp Ala Asn Ala Lys Leu Ser Glu Leu
    370                 375                 380

Glu Ala Ala Leu Gln Arg Ala Lys Gln Asp Met Ala Arg Gln Leu Arg
385                 390                 395                 400

Glu Tyr Gln Glu Leu Met Asn Val Lys Leu Ala Leu Asp Ile Glu Ile
                405                 410                 415

Ala Thr Tyr Arg Lys Leu Leu Glu Gly Glu Ser Arg Leu Glu Ser
            420                 425                 430

Gly Met Gln Asn Met Ser Ile His Thr Lys Thr Thr Ser Gly Tyr Ala
                435                 440                 445

Gly Gly Leu Ser Ser Ala Tyr Gly Gly Leu Thr Ser Pro Gly Leu Ser
    450                 455                 460

Tyr Ser Leu Gly Ser Ser Phe Gly Ser Gly Ala Gly Ser Ser Ser Phe
465                 470                 475                 480

Ser Arg Thr Ser Ser Ser Arg Ala Val Val Val Lys Lys Ile Glu Thr
                485                 490                 495

Arg Asp Gly Lys Leu Val Ser Gly Ser Ser Asp Val Leu Pro Lys
            500                 505                 510

<210> SEQ ID NO 12
<211> LENGTH: 570
<212> TYPE: PRT
<213> ORGANISM: homo sapiens
<220> FEATURE:
<221> NAME/KEY: misc_feature
<223> OTHER INFORMATION: Dihydropyrimidinase-related protein 3 Isoform 1

<400> SEQUENCE: 12

Met Ser Tyr Gln Gly Lys Lys Asn Ile Pro Arg Ile Thr Ser Asp Arg
1               5                   10                  15

Leu Leu Ile Lys Gly Gly Arg Ile Val Asn Asp Asp Gln Ser Phe Tyr
            20                  25                  30

Ala Asp Ile Tyr Met Glu Asp Gly Leu Ile Lys Gln Ile Gly Asp Asn
        35                  40                  45

Leu Ile Val Pro Gly Gly Val Lys Thr Ile Glu Ala Asn Gly Lys Met
    50                  55                  60

Val Ile Pro Gly Gly Ile Asp Val His Thr His Phe Gln Met Pro Tyr
65                  70                  75                  80

Lys Gly Met Thr Thr Val Asp Asp Phe Phe Gln Gly Thr Lys Ala Ala
                85                  90                  95

Leu Ala Gly Gly Thr Thr Met Ile Ile Asp His Val Val Pro Glu Pro
            100                 105                 110

Glu Ser Ser Leu Thr Glu Ala Tyr Glu Lys Trp Arg Glu Trp Ala Asp
        115                 120                 125

Gly Lys Ser Cys Cys Asp Tyr Ala Leu His Val Asp Ile Thr His Trp
130                 135                 140

Asn Asp Ser Val Lys Gln Glu Val Gln Asn Leu Ile Lys Asp Lys Gly
145                 150                 155                 160

Val Asn Ser Phe Met Val Tyr Met Ala Tyr Lys Asp Leu Tyr Gln Val
                165                 170                 175

Ser Asn Thr Glu Leu Tyr Glu Ile Phe Thr Cys Leu Gly Glu Leu Gly
            180                 185                 190

Ala Ile Ala Gln Val His Ala Glu Asn Gly Asp Ile Ile Ala Gln Glu
        195                 200                 205

Gln Thr Arg Met Leu Glu Met Gly Ile Thr Gly Pro Glu Gly His Val
    210                 215                 220

Leu Ser Arg Pro Glu Glu Leu Glu Ala Glu Ala Val Phe Arg Ala Ile
225                 230                 235                 240

Thr Ile Ala Ser Gln Thr Asn Cys Pro Leu Tyr Val Thr Lys Val Met
            245                 250                 255

Ser Lys Ser Ala Ala Asp Leu Ile Ser Gln Ala Arg Lys Lys Gly Asn
        260                 265                 270

Val Val Phe Gly Glu Pro Ile Thr Ala Ser Leu Gly Ile Asp Gly Thr
    275                 280                 285

His Tyr Trp Ser Lys Asn Trp Ala Lys Ala Ala Phe Val Thr Ser
290                 295                 300

Pro Pro Leu Ser Pro Asp Pro Thr Thr Pro Asp Tyr Ile Asn Ser Leu
305                 310                 315                 320

Leu Ala Ser Gly Asp Leu Gln Leu Ser Gly Ser Ala His Cys Thr Phe
            325                 330                 335

Ser Thr Ala Gln Lys Ala Ile Gly Lys Asp Asn Phe Thr Ala Ile Pro
        340                 345                 350

Glu Gly Thr Asn Gly Val Glu Glu Arg Met Ser Val Ile Trp Asp Lys
    355                 360                 365

Ala Val Ala Thr Gly Lys Met Asp Glu Asn Gln Phe Val Ala Val Thr
370                 375                 380

Ser Thr Asn Ala Ala Lys Ile Phe Asn Leu Tyr Pro Arg Lys Gly Arg
385                 390                 395                 400

Ile Ser Val Gly Ser Asp Ser Asp Leu Val Ile Trp Asp Pro Asp Ala
            405                 410                 415

Val Lys Ile Val Ser Ala Lys Asn His Gln Ser Ala Ala Glu Tyr Asn
        420                 425                 430

Ile Phe Glu Gly Met Glu Leu Arg Gly Ala Pro Leu Val Val Ile Cys
    435                 440                 445

Gln Gly Lys Ile Met Leu Glu Asp Gly Asn Leu His Val Thr Gln Gly
450                 455                 460

Ala Gly Arg Phe Ile Pro Cys Ser Pro Phe Ser Asp Tyr Val Tyr Lys
465                 470                 475                 480

Arg Ile Lys Ala Arg Arg Lys Met Ala Asp Leu His Ala Val Pro Arg
            485                 490                 495

Gly Met Tyr Asp Gly Pro Val Phe Asp Leu Thr Thr Thr Pro Lys Gly
        500                 505                 510

Gly Thr Pro Ala Gly Ser Ala Arg Gly Ser Pro Thr Arg Pro Asn Pro
    515                 520                 525

Pro Val Arg Asn Leu His Gln Ser Gly Phe Ser Leu Ser Gly Thr Gln
530                 535                 540

Val Asp Glu Gly Val Arg Ser Ala Ser Lys Arg Ile Val Ala Pro Pro
545                 550                 555                 560

Gly Gly Arg Ser Asn Ile Thr Ser Leu Ser
            565                 570

<210> SEQ ID NO 13
<211> LENGTH: 684
<212> TYPE: PRT
<213> ORGANISM: homo sapiens
<220> FEATURE:
<221> NAME/KEY: misc_feature
<223> OTHER INFORMATION: Dihydropyrimidinase-related protein 3 Isoform
      LCRMP-4

<400> SEQUENCE: 13

```
Met Ala Ser Gly Arg Gly Trp Asp Ser His Glu Asp Leu
 1               5                  10                  15

Pro Val Tyr Leu Ala Arg Pro Gly Thr Thr Asp Gln Val Pro Arg Gln
                20                  25                  30

Lys Tyr Gly Gly Met Phe Cys Asn Val Glu Gly Ala Phe Glu Ser Lys
                35                  40                  45

Thr Leu Asp Phe Asp Ala Leu Ser Val Gly Gln Arg Gly Ala Lys Thr
        50                  55                  60

Pro Arg Ser Gly Gln Gly Ser Asp Arg Gly Ser Gly Ser Arg Pro Gly
65                  70                  75                  80

Ile Glu Gly Asp Thr Pro Arg Arg Gly Gln Gly Arg Glu Glu Ser Arg
                85                  90                  95

Glu Pro Ala Pro Ala Ser Pro Ala Pro Ala Gly Val Glu Ile Arg Ser
                100                 105                 110

Ala Thr Gly Lys Glu Val Leu Gln Asn Leu Gly Pro Lys Asp Lys Ser
            115                 120                 125

Asp Arg Leu Leu Ile Lys Gly Gly Arg Ile Val Asn Asp Asp Gln Ser
        130                 135                 140

Phe Tyr Ala Asp Ile Tyr Met Glu Asp Gly Leu Ile Lys Gln Ile Gly
145                 150                 155                 160

Asp Asn Leu Ile Val Pro Gly Gly Val Lys Thr Ile Glu Ala Asn Gly
                165                 170                 175

Lys Met Val Ile Pro Gly Gly Ile Asp Val His Thr His Phe Gln Met
                180                 185                 190

Pro Tyr Lys Gly Met Thr Thr Val Asp Asp Phe Phe Gln Gly Thr Lys
            195                 200                 205

Ala Ala Leu Ala Gly Gly Thr Thr Met Ile Ile Asp His Val Val Pro
        210                 215                 220

Glu Pro Glu Ser Ser Leu Thr Glu Ala Tyr Glu Lys Trp Arg Glu Trp
225                 230                 235                 240

Ala Asp Gly Lys Ser Cys Cys Asp Tyr Ala Leu His Val Asp Ile Thr
                245                 250                 255

His Trp Asn Asp Ser Val Lys Gln Glu Val Gln Asn Leu Ile Lys Asp
                260                 265                 270

Lys Gly Val Asn Ser Phe Met Val Tyr Met Ala Tyr Lys Asp Leu Tyr
            275                 280                 285

Gln Val Ser Asn Thr Glu Leu Tyr Glu Ile Phe Thr Cys Leu Gly Glu
        290                 295                 300

Leu Gly Ala Ile Ala Gln Val His Ala Glu Asn Gly Asp Ile Ile Ala
305                 310                 315                 320

Gln Glu Gln Thr Arg Met Leu Glu Met Gly Ile Thr Gly Pro Glu Gly
                325                 330                 335

His Val Leu Ser Arg Pro Glu Glu Leu Glu Ala Glu Ala Val Phe Arg
                340                 345                 350

Ala Ile Thr Ile Ala Ser Gln Thr Asn Cys Pro Leu Tyr Val Thr Lys
            355                 360                 365

Val Met Ser Lys Ser Ala Ala Asp Leu Ile Ser Gln Ala Arg Lys Lys
        370                 375                 380

Gly Asn Val Val Phe Gly Glu Pro Ile Thr Ala Ser Leu Gly Ile Asp
385                 390                 395                 400

Gly Thr His Tyr Trp Ser Lys Asn Trp Ala Lys Ala Ala Ala Phe Val
                405                 410                 415

Thr Ser Pro Pro Leu Ser Pro Asp Pro Thr Thr Pro Asp Tyr Ile Asn
```

```
                420             425             430
     Ser Leu Leu Ala Ser Gly Asp Leu Gln Leu Ser Gly Ser Ala His Cys
                 435                 440                 445

Thr Phe Ser Thr Ala Gln Lys Ala Ile Gly Lys Asp Asn Phe Thr Ala
             450                 455                 460

Ile Pro Glu Gly Thr Asn Gly Val Glu Arg Met Ser Val Ile Trp
     465                 470                 475                 480

Asp Lys Ala Val Ala Thr Gly Lys Met Asp Glu Asn Gln Phe Val Ala
                     485                 490                 495

Val Thr Ser Thr Asn Ala Ala Lys Ile Phe Asn Leu Tyr Pro Arg Lys
                 500                 505                 510

Gly Arg Ile Ser Val Gly Ser Asp Ser Asp Leu Val Ile Trp Asp Pro
                 515                 520                 525

Asp Ala Val Lys Ile Val Ser Ala Lys Asn His Gln Ser Ala Ala Glu
                 530                 535                 540

Tyr Asn Ile Phe Glu Gly Met Glu Leu Arg Gly Ala Pro Leu Val Val
     545                 550                 555                 560

Ile Cys Gln Gly Lys Ile Met Leu Glu Asp Gly Asn Leu His Val Thr
                     565                 570                 575

Gln Gly Ala Gly Arg Phe Ile Pro Cys Ser Pro Phe Ser Asp Tyr Val
                     580                 585                 590

Tyr Lys Arg Ile Lys Ala Arg Arg Lys Met Ala Asp Leu His Ala Val
     595                 600                 605

Pro Arg Gly Met Tyr Asp Gly Pro Val Phe Asp Leu Thr Thr Thr Pro
                 610                 615                 620

Lys Gly Gly Thr Pro Ala Gly Ser Ala Arg Gly Ser Pro Thr Arg Pro
     625                 630                 635                 640

Asn Pro Pro Val Arg Asn Leu His Gln Ser Gly Phe Ser Leu Ser Gly
                     645                 650                 655

Thr Gln Val Asp Glu Gly Val Arg Ser Ala Ser Lys Arg Ile Val Ala
                 660                 665                 670

Pro Pro Gly Gly Arg Ser Asn Ile Thr Ser Leu Ser
                 675                 680

<210> SEQ ID NO 14
<211> LENGTH: 1170
<212> TYPE: PRT
<213> ORGANISM: homo sapiens
<220> FEATURE:
<221> NAME/KEY: misc_feature
<223> OTHER INFORMATION: Thrombospondin-1

<400> SEQUENCE: 14

Met Gly Leu Ala Trp Gly Leu Gly Val Leu Phe Leu Met His Val Cys
     1               5                   10                  15

Gly Thr Asn Arg Ile Pro Glu Ser Gly Gly Asp Asn Ser Val Phe Asp
                 20                  25                  30

Ile Phe Glu Leu Thr Gly Ala Ala Arg Lys Gly Ser Gly Arg Arg Leu
             35                  40                  45

Val Lys Gly Pro Asp Pro Ser Ser Pro Ala Phe Arg Ile Glu Asp Ala
         50                  55                  60

Asn Leu Ile Pro Pro Val Pro Asp Asp Lys Phe Gln Asp Leu Val Asp
     65                  70                  75                  80

Ala Val Arg Ala Glu Lys Gly Phe Leu Leu Leu Ala Ser Leu Arg Gln
                     85                  90                  95
```

```
Met Lys Lys Thr Arg Gly Thr Leu Leu Ala Leu Glu Arg Lys Asp His
                100                 105                 110

Ser Gly Gln Val Phe Ser Val Val Ser Asn Gly Lys Ala Gly Thr Leu
            115                 120                 125

Asp Leu Ser Leu Thr Val Gln Gly Lys Gln His Val Val Ser Val Glu
        130                 135                 140

Glu Ala Leu Leu Ala Thr Gly Gln Trp Lys Ser Ile Thr Leu Phe Val
145                 150                 155                 160

Gln Glu Asp Arg Ala Gln Leu Tyr Ile Asp Cys Glu Lys Met Glu Asn
                165                 170                 175

Ala Glu Leu Asp Val Pro Ile Gln Ser Val Phe Thr Arg Asp Leu Ala
            180                 185                 190

Ser Ile Ala Arg Leu Arg Ile Ala Lys Gly Gly Val Asn Asp Asn Phe
        195                 200                 205

Gln Gly Val Leu Gln Asn Val Arg Phe Val Phe Gly Thr Thr Pro Glu
            210                 215                 220

Asp Ile Leu Arg Asn Lys Gly Cys Ser Ser Thr Ser Val Leu Leu
225                 230                 235                 240

Thr Leu Asp Asn Asn Val Val Asn Gly Ser Ser Pro Ala Ile Arg Thr
                245                 250                 255

Asn Tyr Ile Gly His Lys Thr Lys Asp Leu Gln Ala Ile Cys Gly Ile
            260                 265                 270

Ser Cys Asp Glu Leu Ser Ser Met Val Leu Glu Leu Arg Gly Leu Arg
        275                 280                 285

Thr Ile Val Thr Thr Leu Gln Asp Ser Ile Arg Lys Val Thr Glu Glu
    290                 295                 300

Asn Lys Glu Leu Ala Asn Glu Leu Arg Arg Pro Pro Leu Cys Tyr His
305                 310                 315                 320

Asn Gly Val Gln Tyr Arg Asn Asn Glu Glu Trp Thr Val Asp Ser Cys
                325                 330                 335

Thr Glu Cys His Cys Gln Asn Ser Val Thr Ile Cys Lys Lys Val Ser
            340                 345                 350

Cys Pro Ile Met Pro Cys Ser Asn Ala Thr Val Pro Asp Gly Glu Cys
        355                 360                 365

Cys Pro Arg Cys Trp Pro Ser Asp Ser Ala Asp Asp Gly Trp Ser Pro
    370                 375                 380

Trp Ser Glu Trp Thr Ser Cys Ser Thr Ser Cys Gly Asn Gly Ile Gln
385                 390                 395                 400

Gln Arg Gly Arg Ser Cys Asp Ser Leu Asn Asn Arg Cys Glu Gly Ser
                405                 410                 415

Ser Val Gln Thr Arg Thr Cys His Ile Gln Glu Cys Asp Lys Arg Phe
            420                 425                 430

Lys Gln Asp Gly Gly Trp Ser His Trp Ser Pro Trp Ser Ser Cys Ser
        435                 440                 445

Val Thr Cys Gly Asp Gly Val Ile Thr Arg Ile Arg Leu Cys Asn Ser
    450                 455                 460

Pro Ser Pro Gln Met Asn Gly Lys Pro Cys Glu Gly Glu Ala Arg Glu
465                 470                 475                 480

Thr Lys Ala Cys Lys Lys Asp Ala Cys Pro Ile Asn Gly Gly Trp Gly
                485                 490                 495

Pro Trp Ser Pro Trp Asp Ile Cys Ser Val Thr Cys Gly Gly Gly Val
            500                 505                 510

Gln Lys Arg Ser Arg Leu Cys Asn Asn Pro Thr Pro Gln Phe Gly Gly
```

```
                515                 520                 525
Lys Asp Cys Val Gly Asp Val Thr Glu Asn Gln Ile Cys Asn Lys Gln
530                 535                 540

Asp Cys Pro Ile Asp Gly Cys Leu Ser Asn Pro Cys Phe Ala Gly Val
545                 550                 555                 560

Lys Cys Thr Ser Tyr Pro Asp Gly Ser Trp Lys Cys Gly Ala Cys Pro
                565                 570                 575

Pro Gly Tyr Ser Gly Asn Gly Ile Gln Cys Thr Asp Val Asp Glu Cys
                580                 585                 590

Lys Glu Val Pro Asp Ala Cys Phe Asn His Asn Gly Glu His Arg Cys
                595                 600                 605

Glu Asn Thr Asp Pro Gly Tyr Asn Cys Leu Pro Cys Pro Pro Arg Phe
                610                 615                 620

Thr Gly Ser Gln Pro Phe Gly Gln Gly Val Glu His Ala Thr Ala Asn
625                 630                 635                 640

Lys Gln Val Cys Lys Pro Arg Asn Pro Cys Thr Asp Gly Thr His Asp
                645                 650                 655

Cys Asn Lys Asn Ala Lys Cys Asn Tyr Leu Gly His Tyr Ser Asp Pro
                660                 665                 670

Met Tyr Arg Cys Glu Cys Lys Pro Gly Tyr Ala Gly Asn Gly Ile Ile
                675                 680                 685

Cys Gly Glu Asp Thr Asp Leu Asp Gly Trp Pro Asn Glu Asn Leu Val
690                 695                 700

Cys Val Ala Asn Ala Thr Tyr His Cys Lys Lys Asp Asn Cys Pro Asn
705                 710                 715                 720

Leu Pro Asn Ser Gly Gln Glu Asp Tyr Asp Lys Asp Gly Ile Gly Asp
                725                 730                 735

Ala Cys Asp Asp Asp Asp Asp Asn Asp Lys Ile Pro Asp Asp Arg Asp
                740                 745                 750

Asn Cys Pro Phe His Tyr Asn Pro Ala Gln Tyr Asp Tyr Asp Arg Asp
                755                 760                 765

Asp Val Gly Asp Arg Cys Asp Asn Cys Pro Tyr Asn His Asn Pro Asp
                770                 775                 780

Gln Ala Asp Thr Asp Asn Asn Gly Glu Gly Asp Ala Cys Ala Ala Asp
785                 790                 795                 800

Ile Asp Gly Asp Gly Ile Leu Asn Glu Arg Asp Asn Cys Gln Tyr Val
                805                 810                 815

Tyr Asn Val Asp Gln Arg Asp Thr Asp Met Asp Gly Val Gly Asp Gln
                820                 825                 830

Cys Asp Asn Cys Pro Leu Glu His Asn Pro Asp Gln Leu Asp Ser Asp
                835                 840                 845

Ser Asp Arg Ile Gly Asp Thr Cys Asp Asn Asn Gln Asp Ile Asp Glu
                850                 855                 860

Asp Gly His Gln Asn Asn Leu Asp Asn Cys Pro Tyr Val Pro Asn Ala
865                 870                 875                 880

Asn Gln Ala Asp His Asp Lys Asp Gly Lys Gly Asp Ala Cys Asp His
                885                 890                 895

Asp Asp Asp Asn Asp Gly Ile Pro Asp Asp Lys Asp Asn Cys Arg Leu
                900                 905                 910

Val Pro Asn Pro Asp Gln Lys Asp Ser Asp Gly Asp Gly Arg Gly Asp
                915                 920                 925

Ala Cys Lys Asp Asp Phe Asp His Asp Ser Val Pro Asp Ile Asp Asp
                930                 935                 940
```

Ile Cys Pro Glu Asn Val Asp Ile Ser Glu Thr Asp Phe Arg Arg Phe
945                 950                 955                 960

Gln Met Ile Pro Leu Asp Pro Lys Gly Thr Ser Gln Asn Asp Pro Asn
            965                 970                 975

Trp Val Val Arg His Gln Gly Lys Glu Leu Val Gln Thr Val Asn Cys
        980                 985                 990

Asp Pro Gly Leu Ala Val Gly Tyr Asp Glu Phe Asn Ala Val Asp Phe
            995                 1000                1005

Ser Gly Thr Phe Phe Ile Asn Thr Glu Arg Asp Asp Asp Tyr Ala
        1010                1015                1020

Gly Phe Val Phe Gly Tyr Gln Ser Ser Ser Arg Phe Tyr Val Val
        1025                1030                1035

Met Trp Lys Gln Val Thr Gln Ser Tyr Trp Asp Thr Asn Pro Thr
        1040                1045                1050

Arg Ala Gln Gly Tyr Ser Gly Leu Ser Val Lys Val Val Asn Ser
        1055                1060                1065

Thr Thr Gly Pro Gly Glu His Leu Arg Asn Ala Leu Trp His Thr
        1070                1075                1080

Gly Asn Thr Pro Gly Gln Val Arg Thr Leu Trp His Asp Pro Arg
        1085                1090                1095

His Ile Gly Trp Lys Asp Phe Thr Ala Tyr Arg Trp Arg Leu Ser
        1100                1105                1110

His Arg Pro Lys Thr Gly Phe Ile Arg Val Val Met Tyr Glu Gly
        1115                1120                1125

Lys Lys Ile Met Ala Asp Ser Gly Pro Ile Tyr Asp Lys Thr Tyr
        1130                1135                1140

Ala Gly Gly Arg Leu Gly Leu Phe Val Phe Ser Gln Glu Met Val
        1145                1150                1155

Phe Phe Ser Asp Leu Lys Tyr Glu Cys Arg Asp Pro
        1160                1165                1170

<210> SEQ ID NO 15
<211> LENGTH: 471
<212> TYPE: PRT
<213> ORGANISM: homo sapiens
<220> FEATURE:
<221> NAME/KEY: misc_feature
<223> OTHER INFORMATION: Tryptophanyl-tRNA synthetase Isoform 1

<400> SEQUENCE: 15

Met Pro Asn Ser Glu Pro Ala Ser Leu Leu Glu Leu Phe Asn Ser Ile
1               5                   10                  15

Ala Thr Gln Gly Glu Leu Val Arg Ser Leu Lys Ala Gly Asn Ala Ser
            20                  25                  30

Lys Asp Glu Ile Asp Ser Ala Val Lys Met Leu Val Ser Leu Lys Met
        35                  40                  45

Ser Tyr Lys Ala Ala Ala Gly Glu Asp Tyr Lys Ala Asp Cys Pro Pro
    50                  55                  60

Gly Asn Pro Ala Pro Thr Ser Asn His Gly Pro Asp Ala Thr Glu Ala
65                  70                  75                  80

Glu Glu Asp Phe Val Asp Pro Trp Thr Val Gln Thr Ser Ser Ala Lys
                85                  90                  95

Gly Ile Asp Tyr Asp Lys Leu Ile Val Arg Phe Gly Ser Ser Lys Ile
            100                 105                 110

Asp Lys Glu Leu Ile Asn Arg Ile Glu Arg Ala Thr Gly Gln Arg Pro

```
                 115                 120                 125
        His His Phe Leu Arg Arg Gly Ile Phe Phe Ser His Arg Asp Met Asn
            130                 135                 140

Gln Val Leu Asp Ala Tyr Glu Asn Lys Lys Pro Phe Tyr Leu Tyr Thr
        145                 150                 155                 160

Gly Arg Gly Pro Ser Ser Glu Ala Met His Val Gly His Leu Ile Pro
                            165                 170                 175

Phe Ile Phe Thr Lys Trp Leu Gln Asp Val Phe Asn Val Pro Leu Val
                        180                 185                 190

Ile Gln Met Thr Asp Asp Glu Lys Tyr Leu Trp Lys Asp Leu Thr Leu
                    195                 200                 205

Asp Gln Ala Tyr Ser Tyr Ala Val Glu Asn Ala Lys Asp Ile Ile Ala
                210                 215                 220

Cys Gly Phe Asp Ile Asn Lys Thr Phe Ile Phe Ser Asp Leu Asp Tyr
        225                 230                 235                 240

Met Gly Met Ser Ser Gly Phe Tyr Lys Asn Val Val Lys Ile Gln Lys
                            245                 250                 255

His Val Thr Phe Asn Gln Val Lys Gly Ile Phe Gly Phe Thr Asp Ser
                        260                 265                 270

Asp Cys Ile Gly Lys Ile Ser Phe Pro Ala Ile Gln Ala Ala Pro Ser
                    275                 280                 285

Phe Ser Asn Ser Phe Pro Gln Ile Phe Arg Asp Arg Thr Asp Ile Gln
                290                 295                 300

Cys Leu Ile Pro Cys Ala Ile Asp Gln Asp Pro Tyr Phe Arg Met Thr
        305                 310                 315                 320

Arg Asp Val Ala Pro Arg Ile Gly Tyr Pro Lys Pro Ala Leu Leu His
                            325                 330                 335

Ser Thr Phe Phe Pro Ala Leu Gln Gly Ala Gln Thr Lys Met Ser Ala
                        340                 345                 350

Ser Asp Pro Asn Ser Ser Ile Phe Leu Thr Asp Thr Ala Lys Gln Ile
                    355                 360                 365

Lys Thr Lys Val Asn Lys His Ala Phe Ser Gly Gly Arg Asp Thr Ile
                370                 375                 380

Glu Glu His Arg Gln Phe Gly Gly Asn Cys Asp Val Asp Val Ser Phe
        385                 390                 395                 400

Met Tyr Leu Thr Phe Phe Leu Glu Asp Asp Lys Leu Glu Gln Ile
                            405                 410                 415

Arg Lys Asp Tyr Thr Ser Gly Ala Met Leu Thr Gly Glu Leu Lys Lys
                        420                 425                 430

Ala Leu Ile Glu Val Leu Gln Pro Leu Ile Ala Glu His Gln Ala Arg
                    435                 440                 445

Arg Lys Glu Val Thr Asp Glu Ile Val Lys Glu Phe Met Thr Pro Arg
                450                 455                 460

Lys Leu Ser Phe Asp Phe Gln
        465                 470

<210> SEQ ID NO 16
<211> LENGTH: 424
<212> TYPE: PRT
<213> ORGANISM: homo sapiens
<220> FEATURE:
<221> NAME/KEY: misc_feature
<223> OTHER INFORMATION: Tryptophanyl-tRNA synthetase Isoform 2

<400> SEQUENCE: 16
```

```
Met Ser Tyr Lys Ala Ala Gly Glu Asp Tyr Lys Ala Asp Cys Pro
1               5                   10                  15

Pro Gly Asn Pro Ala Pro Thr Ser Asn His Gly Pro Asp Ala Thr Glu
            20                  25                  30

Ala Glu Glu Asp Phe Val Asp Pro Trp Thr Val Gln Thr Ser Ser Ala
        35                  40                  45

Lys Gly Ile Asp Tyr Asp Lys Leu Ile Val Arg Phe Gly Ser Ser Lys
    50                  55                  60

Ile Asp Lys Glu Leu Ile Asn Arg Ile Glu Arg Ala Thr Gly Gln Arg
65                  70                  75                  80

Pro His His Phe Leu Arg Arg Gly Ile Phe Phe Ser His Arg Asp Met
                85                  90                  95

Asn Gln Val Leu Asp Ala Tyr Glu Asn Lys Lys Pro Phe Tyr Leu Tyr
            100                 105                 110

Thr Gly Arg Gly Pro Ser Ser Glu Ala Met His Val Gly His Leu Ile
        115                 120                 125

Pro Phe Ile Phe Thr Lys Trp Leu Gln Asp Val Phe Asn Val Pro Leu
    130                 135                 140

Val Ile Gln Met Thr Asp Asp Glu Lys Tyr Leu Trp Lys Asp Leu Thr
145                 150                 155                 160

Leu Asp Gln Ala Tyr Ser Tyr Ala Val Glu Asn Ala Lys Asp Ile Ile
                165                 170                 175

Ala Cys Gly Phe Asp Ile Asn Lys Thr Phe Ile Phe Ser Asp Leu Asp
            180                 185                 190

Tyr Met Gly Met Ser Ser Gly Phe Tyr Lys Asn Val Val Lys Ile Gln
        195                 200                 205

Lys His Val Thr Phe Asn Gln Val Lys Gly Ile Phe Gly Phe Thr Asp
    210                 215                 220

Ser Asp Cys Ile Gly Lys Ile Ser Phe Pro Ala Ile Gln Ala Ala Pro
225                 230                 235                 240

Ser Phe Ser Asn Ser Phe Pro Gln Ile Phe Arg Asp Arg Thr Asp Ile
                245                 250                 255

Gln Cys Leu Ile Pro Cys Ala Ile Asp Gln Asp Pro Tyr Phe Arg Met
            260                 265                 270

Thr Arg Asp Val Ala Pro Arg Ile Gly Tyr Pro Lys Pro Ala Leu Leu
        275                 280                 285

His Ser Thr Phe Phe Pro Ala Leu Gln Gly Ala Gln Thr Lys Met Ser
    290                 295                 300

Ala Ser Asp Pro Asn Ser Ser Ile Phe Leu Thr Asp Thr Ala Lys Gln
305                 310                 315                 320

Ile Lys Thr Lys Val Asn Lys His Ala Phe Ser Gly Gly Arg Asp Thr
                325                 330                 335

Ile Glu Glu His Arg Gln Phe Gly Gly Asn Cys Asp Val Asp Val Ser
            340                 345                 350

Phe Met Tyr Leu Thr Phe Phe Leu Glu Asp Asp Lys Leu Glu Gln
        355                 360                 365

Ile Arg Lys Asp Tyr Thr Ser Gly Ala Met Leu Thr Gly Glu Leu Lys
    370                 375                 380

Lys Ala Leu Ile Glu Val Leu Gln Pro Leu Ile Ala Glu His Gln Ala
385                 390                 395                 400

Arg Arg Lys Glu Val Thr Asp Glu Ile Val Lys Glu Phe Met Thr Pro
                405                 410                 415

Arg Lys Leu Ser Phe Asp Phe Gln
```

<210> SEQ ID NO 17
<211> LENGTH: 626
<212> TYPE: PRT
<213> ORGANISM: homo sapiens
<220> FEATURE:
<221> NAME/KEY: misc_feature
<223> OTHER INFORMATION: SAM domain and HD domain-containing protein 1
      Isoform 1

<400> SEQUENCE: 17

```
Met Gln Arg Ala Asp Ser Glu Gln Pro Ser Lys Arg Pro Arg Cys Asp
1               5                   10                  15

Asp Ser Pro Arg Thr Pro Ser Asn Thr Pro Ser Ala Glu Ala Asp Trp
            20                  25                  30

Ser Pro Gly Leu Glu Leu His Pro Asp Tyr Lys Thr Trp Gly Pro Glu
        35                  40                  45

Gln Val Cys Ser Phe Leu Arg Arg Gly Gly Phe Glu Glu Pro Val Leu
    50                  55                  60

Leu Lys Asn Ile Arg Glu Asn Glu Ile Thr Gly Ala Leu Leu Pro Cys
65                  70                  75                  80

Leu Asp Glu Ser Arg Phe Glu Asn Leu Gly Val Ser Ser Leu Gly Glu
                85                  90                  95

Arg Lys Lys Leu Leu Ser Tyr Ile Gln Arg Leu Val Gln Ile His Val
            100                 105                 110

Asp Thr Met Lys Val Ile Asn Asp Pro Ile His Gly His Ile Glu Leu
        115                 120                 125

His Pro Leu Leu Val Arg Ile Ile Asp Thr Pro Gln Phe Gln Arg Leu
    130                 135                 140

Arg Tyr Ile Lys Gln Leu Gly Gly Gly Tyr Tyr Val Phe Pro Gly Ala
145                 150                 155                 160

Ser His Asn Arg Phe Glu His Ser Leu Gly Val Gly Tyr Leu Ala Gly
                165                 170                 175

Cys Leu Val His Ala Leu Gly Glu Lys Gln Pro Glu Leu Gln Ile Ser
            180                 185                 190

Glu Arg Asp Val Leu Cys Val Gln Ile Ala Gly Leu Cys His Asp Leu
        195                 200                 205

Gly His Gly Pro Phe Ser His Met Phe Asp Gly Arg Phe Ile Pro Leu
    210                 215                 220

Ala Arg Pro Glu Val Lys Trp Thr His Glu Gln Gly Ser Val Met Met
225                 230                 235                 240

Phe Glu His Leu Ile Asn Ser Asn Gly Ile Lys Pro Val Met Glu Gln
                245                 250                 255

Tyr Gly Leu Ile Pro Glu Glu Asp Ile Cys Phe Ile Lys Glu Gln Ile
            260                 265                 270

Val Gly Pro Leu Glu Ser Pro Val Glu Asp Ser Leu Trp Pro Tyr Lys
        275                 280                 285

Gly Arg Pro Glu Asn Lys Ser Phe Leu Tyr Glu Ile Val Ser Asn Lys
    290                 295                 300

Arg Asn Gly Ile Asp Val Asp Lys Trp Asp Tyr Phe Ala Arg Asp Cys
305                 310                 315                 320

His His Leu Gly Ile Gln Asn Asn Phe Asp Tyr Lys Arg Phe Ile Lys
                325                 330                 335

Phe Ala Arg Val Cys Glu Val Asp Asn Glu Leu Arg Ile Cys Ala Arg
            340                 345                 350
```

-continued

Asp Lys Glu Val Gly Asn Leu Tyr Asp Met Phe His Thr Arg Asn Ser
        355                 360                 365

Leu His Arg Arg Ala Tyr Gln His Lys Val Gly Asn Ile Ile Asp Thr
        370                 375                 380

Met Ile Thr Asp Ala Phe Leu Lys Ala Asp Tyr Ile Glu Ile Thr
385                 390                 395                 400

Gly Ala Gly Gly Lys Lys Tyr Arg Ile Ser Thr Ala Ile Asp Asp Met
                405                 410                 415

Glu Ala Tyr Thr Lys Leu Thr Asp Asn Ile Phe Leu Glu Ile Leu Tyr
        420                 425                 430

Ser Thr Asp Pro Lys Leu Lys Asp Ala Arg Glu Ile Leu Lys Gln Ile
        435                 440                 445

Glu Tyr Arg Asn Leu Phe Lys Tyr Val Gly Glu Thr Gln Pro Thr Gly
        450                 455                 460

Gln Ile Lys Ile Lys Arg Glu Asp Tyr Glu Ser Leu Pro Lys Glu Val
465                 470                 475                 480

Ala Ser Ala Lys Pro Lys Val Leu Leu Asp Val Lys Leu Lys Ala Glu
                485                 490                 495

Asp Phe Ile Val Asp Val Ile Asn Met Asp Tyr Gly Met Gln Glu Lys
        500                 505                 510

Asn Pro Ile Asp His Val Ser Phe Tyr Cys Lys Thr Ala Pro Asn Arg
        515                 520                 525

Ala Ile Arg Ile Thr Lys Asn Gln Val Ser Gln Leu Leu Pro Glu Lys
        530                 535                 540

Phe Ala Glu Gln Leu Ile Arg Val Tyr Cys Lys Lys Val Asp Arg Lys
545                 550                 555                 560

Ser Leu Tyr Ala Ala Arg Gln Tyr Phe Val Gln Trp Cys Ala Asp Arg
                565                 570                 575

Asn Phe Thr Lys Pro Gln Asp Gly Asp Val Ile Ala Pro Leu Ile Thr
        580                 585                 590

Pro Gln Lys Lys Glu Trp Asn Asp Ser Thr Ser Val Gln Asn Pro Thr
        595                 600                 605

Arg Leu Arg Glu Ala Ser Lys Ser Arg Val Gln Leu Phe Lys Asp Asp
        610                 615                 620

Pro Met
625

<210> SEQ ID NO 18
<211> LENGTH: 602
<212> TYPE: PRT
<213> ORGANISM: homo sapiens
<220> FEATURE:
<221> NAME/KEY: misc_feature
<223> OTHER INFORMATION: SAM domain and HD domain-containing protein 1
      Isoform 2

<400> SEQUENCE: 18

Met Gln Arg Ala Asp Ser Glu Gln Pro Ser Lys Arg Pro Arg Cys Asp
1               5                   10                  15

Asp Ser Pro Arg Thr Pro Ser Asn Thr Pro Ser Ala Glu Ala Asp Trp
                20                  25                  30

Ser Pro Gly Leu Glu Leu His Pro Asp Tyr Lys Thr Trp Gly Pro Glu
        35                  40                  45

Gln Val Cys Ser Phe Leu Arg Arg Gly Gly Phe Glu Glu Pro Val Leu
        50                  55                  60

-continued

Leu Lys Asn Ile Arg Glu Asn Glu Ile Thr Gly Ala Leu Leu Pro Cys
65                  70                  75                  80

Leu Asp Glu Ser Arg Phe Glu Asn Leu Gly Val Ser Ser Leu Gly Glu
            85                  90                  95

Arg Lys Lys Leu Leu Ser Tyr Ile Gln Arg Leu Val Gln Ile His Val
        100                 105                 110

Asp Thr Pro Gln Phe Gln Arg Leu Arg Tyr Ile Lys Gln Leu Gly Gly
        115                 120                 125

Gly Tyr Tyr Val Phe Pro Gly Ala Ser His Asn Arg Phe Glu His Ser
        130                 135                 140

Leu Gly Val Gly Tyr Leu Ala Gly Cys Leu Val His Ala Leu Gly Glu
145                 150                 155                 160

Lys Gln Pro Glu Leu Gln Ile Ser Glu Arg Asp Val Leu Cys Val Gln
            165                 170                 175

Ile Ala Gly Leu Cys His Asp Leu Gly His Gly Pro Phe Ser His Met
            180                 185                 190

Phe Asp Gly Arg Phe Ile Pro Leu Ala Arg Pro Glu Val Lys Trp Thr
        195                 200                 205

His Glu Gln Gly Ser Val Met Met Phe Glu His Leu Ile Asn Ser Asn
210                 215                 220

Gly Ile Lys Pro Val Met Glu Gln Tyr Gly Leu Ile Pro Glu Glu Asp
225                 230                 235                 240

Ile Cys Phe Ile Lys Glu Gln Ile Val Gly Pro Leu Glu Ser Pro Val
            245                 250                 255

Glu Asp Ser Leu Trp Pro Tyr Lys Gly Arg Pro Glu Asn Lys Ser Phe
        260                 265                 270

Leu Tyr Glu Ile Val Ser Asn Lys Arg Asn Gly Ile Asp Val Asp Lys
        275                 280                 285

Trp Asp Tyr Phe Ala Arg Asp Cys His His Leu Gly Ile Gln Asn Asn
        290                 295                 300

Phe Asp Tyr Lys Arg Phe Ile Lys Phe Ala Arg Val Cys Glu Val Asp
305                 310                 315                 320

Asn Glu Leu Arg Ile Cys Ala Arg Asp Lys Glu Val Gly Asn Leu Tyr
            325                 330                 335

Asp Met Phe His Thr Arg Asn Ser Leu His Arg Arg Ala Tyr Gln His
            340                 345                 350

Lys Val Gly Asn Ile Ile Asp Thr Met Ile Thr Asp Ala Phe Leu Lys
        355                 360                 365

Ala Asp Asp Tyr Ile Glu Ile Thr Gly Ala Gly Gly Lys Lys Tyr Arg
        370                 375                 380

Ile Ser Thr Ala Ile Asp Asp Met Glu Ala Tyr Thr Lys Leu Thr Asp
385                 390                 395                 400

Asn Ile Phe Leu Glu Ile Leu Tyr Ser Thr Asp Pro Lys Leu Lys Asp
            405                 410                 415

Ala Arg Glu Ile Leu Lys Gln Ile Glu Tyr Arg Asn Leu Phe Lys Tyr
            420                 425                 430

Val Gly Glu Thr Gln Pro Thr Gly Gln Ile Lys Ile Lys Arg Glu Asp
        435                 440                 445

Tyr Glu Ser Leu Pro Lys Glu Val Ala Ser Ala Lys Pro Lys Val Leu
        450                 455                 460

Leu Asp Val Lys Leu Lys Ala Glu Asp Phe Ile Val Asp Val Ile Asn
465                 470                 475                 480

Met Asp Tyr Gly Met Gln Glu Lys Asn Pro Ile Asp His Val Ser Phe

```
                    485                 490                 495
Tyr Cys Lys Thr Ala Pro Asn Arg Ala Ile Arg Ile Thr Lys Asn Gln
                500                 505                 510

Val Ser Gln Leu Leu Pro Glu Lys Phe Ala Glu Gln Leu Ile Arg Val
                515                 520                 525

Tyr Cys Lys Lys Val Asp Arg Lys Ser Leu Tyr Ala Ala Arg Gln Tyr
                530                 535                 540

Phe Val Gln Trp Cys Ala Asp Arg Asn Phe Thr Lys Pro Gln Asp Gly
545                 550                 555                 560

Asp Val Ile Ala Pro Leu Ile Thr Pro Gln Lys Lys Glu Trp Asn Asp
                565                 570                 575

Ser Thr Ser Val Gln Asn Pro Thr Arg Leu Arg Glu Ala Ser Lys Ser
                580                 585                 590

Arg Val Gln Leu Phe Lys Asp Asp Pro Met
                595                 600

<210> SEQ ID NO 19
<211> LENGTH: 102
<212> TYPE: PRT
<213> ORGANISM: homo sapiens
<220> FEATURE:
<221> NAME/KEY: misc_feature
<223> OTHER INFORMATION: 10 kDa heat shock protein, mitochondrial

<400> SEQUENCE: 19

Met Ala Gly Gln Ala Phe Arg Lys Phe Leu Pro Leu Phe Asp Arg Val
1               5                   10                  15

Leu Val Glu Arg Ser Ala Ala Glu Thr Val Thr Lys Gly Gly Ile Met
                20                  25                  30

Leu Pro Glu Lys Ser Gln Gly Lys Val Leu Gln Ala Thr Val Val Ala
                35                  40                  45

Val Gly Ser Gly Ser Lys Gly Lys Gly Gly Glu Ile Gln Pro Val Ser
                50                  55                  60

Val Lys Val Gly Asp Lys Val Leu Leu Pro Glu Tyr Gly Gly Thr Lys
65                  70                  75                  80

Val Val Leu Asp Asp Lys Asp Tyr Phe Leu Phe Arg Asp Gly Asp Ile
                85                  90                  95

Leu Gly Lys Tyr Val Asp
                100

<210> SEQ ID NO 20
<211> LENGTH: 330
<212> TYPE: PRT
<213> ORGANISM: homo sapiens
<220> FEATURE:
<221> NAME/KEY: misc_feature
<223> OTHER INFORMATION: Ig gamma-1 chain C region

<400> SEQUENCE: 20

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
                35                  40                  45

Gly Val His Thr Phe Pro Ala Val Leu Gln Ser Ser Gly Leu Tyr Ser
                50                  55                  60

Leu Ser Ser Val Val Thr Val Pro Ser Ser Ser Leu Gly Thr Gln Thr
```

```
                65                  70                  75                  80
Tyr Ile Cys Asn Val Asn His Lys Pro Ser Asn Thr Lys Val Asp Lys
                    85                  90                  95

Lys Val Glu Pro Lys Ser Cys Asp Lys Thr His Thr Cys Pro Pro Cys
                100                 105                 110

Pro Ala Pro Glu Leu Leu Gly Gly Pro Ser Val Phe Leu Phe Pro Pro
                115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
                180                 185                 190

His Gln Asp Trp Leu Asn Gly Lys Glu Tyr Lys Cys Lys Val Ser Asn
                195                 200                 205

Lys Ala Leu Pro Ala Pro Ile Glu Lys Thr Ile Ser Lys Ala Lys Gly
                210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
                275                 280                 285

Leu Tyr Ser Lys Leu Thr Val Asp Lys Ser Arg Trp Gln Gln Gly Asn
                290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 21
<211> LENGTH: 917
<212> TYPE: PRT
<213> ORGANISM: homo sapiens
<220> FEATURE:
<221> NAME/KEY: misc_feature
<223> OTHER INFORMATION: Hexokinase-1 Isoform 1

<400> SEQUENCE: 21

Met Ile Ala Ala Gln Leu Leu Ala Tyr Tyr Phe Thr Glu Leu Lys Asp
1               5                   10                  15

Asp Gln Val Lys Lys Ile Asp Lys Tyr Leu Tyr Ala Met Arg Leu Ser
                20                  25                  30

Asp Glu Thr Leu Ile Asp Ile Met Thr Arg Phe Arg Lys Glu Met Lys
                35                  40                  45

Asn Gly Leu Ser Arg Asp Phe Asn Pro Thr Ala Thr Val Lys Met Leu
                50                  55                  60

Pro Thr Phe Val Arg Ser Ile Pro Asp Gly Ser Glu Lys Gly Asp Phe
65                  70                  75                  80

Ile Ala Leu Asp Leu Gly Gly Ser Ser Phe Arg Ile Leu Arg Val Gln
                85                  90                  95
```

```
Val Asn His Glu Lys Asn Gln Asn Val His Met Glu Ser Glu Val Tyr
            100                 105                 110

Asp Thr Pro Glu Asn Ile Val His Gly Ser Gly Ser Gln Leu Phe Asp
            115                 120                 125

His Val Ala Glu Cys Leu Gly Asp Phe Met Glu Lys Arg Lys Ile Lys
            130                 135                 140

Asp Lys Lys Leu Pro Val Gly Phe Thr Phe Ser Phe Pro Cys Gln Gln
145                 150                 155                 160

Ser Lys Ile Asp Glu Ala Ile Leu Ile Thr Trp Thr Lys Arg Phe Lys
                165                 170                 175

Ala Ser Gly Val Glu Gly Ala Asp Val Val Lys Leu Leu Asn Lys Ala
            180                 185                 190

Ile Lys Lys Arg Gly Asp Tyr Asp Ala Asn Ile Val Ala Val Val Asn
            195                 200                 205

Asp Thr Val Gly Thr Met Met Thr Cys Gly Tyr Asp Asp Gln His Cys
            210                 215                 220

Glu Val Gly Leu Ile Ile Gly Thr Gly Thr Asn Ala Cys Tyr Met Glu
225                 230                 235                 240

Glu Leu Arg His Ile Asp Leu Val Glu Gly Asp Glu Gly Arg Met Cys
                245                 250                 255

Ile Asn Thr Glu Trp Gly Ala Phe Gly Asp Asp Gly Ser Leu Glu Asp
            260                 265                 270

Ile Arg Thr Glu Phe Asp Arg Glu Ile Asp Arg Gly Ser Leu Asn Pro
            275                 280                 285

Gly Lys Gln Leu Phe Glu Lys Met Val Ser Gly Met Tyr Leu Gly Glu
290                 295                 300

Leu Val Arg Leu Ile Leu Val Lys Met Ala Lys Glu Gly Leu Leu Phe
305                 310                 315                 320

Glu Gly Arg Ile Thr Pro Glu Leu Leu Thr Arg Gly Lys Phe Asn Thr
                325                 330                 335

Ser Asp Val Ser Ala Ile Glu Lys Asn Lys Glu Gly Leu His Asn Ala
            340                 345                 350

Lys Glu Ile Leu Thr Arg Leu Gly Val Glu Pro Ser Asp Asp Asp Cys
            355                 360                 365

Val Ser Val Gln His Val Cys Thr Ile Val Ser Phe Arg Ser Ala Asn
370                 375                 380

Leu Val Ala Ala Thr Leu Gly Ala Ile Leu Asn Arg Leu Arg Asp Asn
385                 390                 395                 400

Lys Gly Thr Pro Arg Leu Arg Thr Thr Val Gly Val Asp Gly Ser Leu
                405                 410                 415

Tyr Lys Thr His Pro Gln Tyr Ser Arg Arg Phe His Lys Thr Leu Arg
            420                 425                 430

Arg Leu Val Pro Asp Ser Asp Val Arg Phe Leu Leu Ser Glu Ser Gly
            435                 440                 445

Ser Gly Lys Gly Ala Ala Met Val Thr Ala Val Ala Tyr Arg Leu Ala
450                 455                 460

Glu Gln His Arg Gln Ile Glu Glu Thr Leu Ala His Phe His Leu Thr
465                 470                 475                 480

Lys Asp Met Leu Leu Glu Val Lys Lys Arg Met Arg Ala Glu Met Glu
                485                 490                 495

Leu Gly Leu Arg Lys Gln Thr His Asn Asn Ala Val Val Lys Met Leu
            500                 505                 510

Pro Ser Phe Val Arg Arg Thr Pro Asp Gly Thr Glu Asn Gly Asp Phe
```

```
            515                 520                 525
Leu Ala Leu Asp Leu Gly Gly Thr Asn Phe Arg Val Leu Leu Val Lys
    530                 535                 540

Ile Arg Ser Gly Lys Lys Arg Thr Val Glu Met His Asn Lys Ile Tyr
545                 550                 555                 560

Ala Ile Pro Ile Glu Ile Met Gln Gly Thr Gly Glu Glu Leu Phe Asp
                565                 570                 575

His Ile Val Ser Cys Ile Ser Asp Phe Leu Asp Tyr Met Gly Ile Lys
            580                 585                 590

Gly Pro Arg Met Pro Leu Gly Phe Thr Phe Ser Phe Pro Cys Gln Gln
        595                 600                 605

Thr Ser Leu Asp Ala Gly Ile Leu Ile Thr Trp Thr Lys Gly Phe Lys
    610                 615                 620

Ala Thr Asp Cys Val Gly His Asp Val Val Thr Leu Leu Arg Asp Ala
625                 630                 635                 640

Ile Lys Arg Arg Glu Glu Phe Asp Leu Asp Val Val Ala Val Val Asn
                645                 650                 655

Asp Thr Val Gly Thr Met Met Thr Cys Ala Tyr Glu Glu Pro Thr Cys
            660                 665                 670

Glu Val Gly Leu Ile Val Gly Thr Gly Ser Asn Ala Cys Tyr Met Glu
        675                 680                 685

Glu Met Lys Asn Val Glu Met Val Glu Gly Asp Gln Gly Gln Met Cys
    690                 695                 700

Ile Asn Met Glu Trp Gly Ala Phe Gly Asp Asn Gly Cys Leu Asp Asp
705                 710                 715                 720

Ile Arg Thr His Tyr Asp Arg Leu Val Asp Glu Tyr Ser Leu Asn Ala
                725                 730                 735

Gly Lys Gln Arg Tyr Glu Lys Met Ile Ser Gly Met Tyr Leu Gly Glu
            740                 745                 750

Ile Val Arg Asn Ile Leu Ile Asp Phe Thr Lys Lys Gly Phe Leu Phe
        755                 760                 765

Arg Gly Gln Ile Ser Glu Thr Leu Lys Thr Arg Gly Ile Phe Glu Thr
    770                 775                 780

Lys Phe Leu Ser Gln Ile Glu Ser Asp Arg Leu Ala Leu Leu Gln Val
785                 790                 795                 800

Arg Ala Ile Leu Gln Gln Leu Gly Leu Asn Ser Thr Cys Asp Asp Ser
                805                 810                 815

Ile Leu Val Lys Thr Val Cys Gly Val Val Ser Arg Arg Ala Ala Gln
            820                 825                 830

Leu Cys Gly Ala Gly Met Ala Ala Val Val Asp Lys Ile Arg Glu Asn
        835                 840                 845

Arg Gly Leu Asp Arg Leu Asn Val Thr Val Gly Val Asp Gly Thr Leu
    850                 855                 860

Tyr Lys Leu His Pro His Phe Ser Arg Ile Met His Gln Thr Val Lys
865                 870                 875                 880

Glu Leu Ser Pro Lys Cys Asn Val Ser Phe Leu Leu Ser Glu Asp Gly
                885                 890                 895

Ser Gly Lys Gly Ala Ala Leu Ile Thr Ala Val Gly Val Arg Leu Arg
            900                 905                 910

Thr Glu Ala Ser Ser
            915

<210> SEQ ID NO 22
```

<211> LENGTH: 916
<212> TYPE: PRT
<213> ORGANISM: homo sapiens
<220> FEATURE:
<221> NAME/KEY: misc_feature
<223> OTHER INFORMATION: Hexokinase-1 Isoform 2

<400> SEQUENCE: 22

```
Met Asp Cys Glu His Ser Leu Ser Leu Pro Cys Arg Gly Ala Glu Ala
1               5                   10                  15

Trp Glu Ile Gly Ile Asp Lys Tyr Leu Tyr Ala Met Arg Leu Ser Asp
            20                  25                  30

Glu Thr Leu Ile Asp Ile Met Thr Arg Phe Arg Lys Glu Met Lys Asn
        35                  40                  45

Gly Leu Ser Arg Asp Phe Asn Pro Thr Ala Thr Val Lys Met Leu Pro
    50                  55                  60

Thr Phe Val Arg Ser Ile Pro Asp Gly Ser Glu Lys Gly Asp Phe Ile
65                  70                  75                  80

Ala Leu Asp Leu Gly Gly Ser Ser Phe Arg Ile Leu Arg Val Gln Val
                85                  90                  95

Asn His Glu Lys Asn Gln Asn Val His Met Glu Ser Glu Val Tyr Asp
            100                 105                 110

Thr Pro Glu Asn Ile Val His Gly Ser Gly Ser Gln Leu Phe Asp His
        115                 120                 125

Val Ala Glu Cys Leu Gly Asp Phe Met Glu Lys Arg Lys Ile Lys Asp
    130                 135                 140

Lys Lys Leu Pro Val Gly Phe Thr Phe Ser Phe Pro Cys Gln Gln Ser
145                 150                 155                 160

Lys Ile Asp Glu Ala Ile Leu Ile Thr Trp Thr Lys Arg Phe Lys Ala
                165                 170                 175

Ser Gly Val Glu Gly Ala Asp Val Val Lys Leu Leu Asn Lys Ala Ile
            180                 185                 190

Lys Lys Arg Gly Asp Tyr Asp Ala Asn Ile Val Ala Val Val Asn Asp
        195                 200                 205

Thr Val Gly Thr Met Met Thr Cys Gly Tyr Asp Asp Gln His Cys Glu
    210                 215                 220

Val Gly Leu Ile Ile Gly Thr Gly Thr Asn Ala Cys Tyr Met Glu Glu
225                 230                 235                 240

Leu Arg His Ile Asp Leu Val Glu Gly Asp Glu Gly Arg Met Cys Ile
                245                 250                 255

Asn Thr Glu Trp Gly Ala Phe Gly Asp Asp Gly Ser Leu Glu Asp Ile
            260                 265                 270

Arg Thr Glu Phe Asp Arg Glu Ile Asp Arg Gly Ser Leu Asn Pro Gly
        275                 280                 285

Lys Gln Leu Phe Glu Lys Met Val Ser Gly Met Tyr Leu Gly Glu Leu
    290                 295                 300

Val Arg Leu Ile Leu Val Lys Met Ala Lys Glu Gly Leu Leu Phe Glu
305                 310                 315                 320

Gly Arg Ile Thr Pro Glu Leu Leu Thr Arg Gly Lys Phe Asn Thr Ser
                325                 330                 335

Asp Val Ser Ala Ile Glu Lys Asn Lys Glu Gly Leu His Asn Ala Lys
            340                 345                 350

Glu Ile Leu Thr Arg Leu Gly Val Glu Pro Ser Asp Asp Cys Val
        355                 360                 365

Ser Val Gln His Val Cys Thr Ile Val Ser Phe Arg Ser Ala Asn Leu
```

-continued

```
            370                 375                 380
Val Ala Ala Thr Leu Gly Ala Ile Leu Asn Arg Leu Arg Asp Asn Lys
385                 390                 395                 400

Gly Thr Pro Arg Leu Arg Thr Val Gly Val Asp Gly Ser Leu Tyr
                405                 410                 415

Lys Thr His Pro Gln Tyr Ser Arg Arg Phe His Lys Thr Leu Arg Arg
                420                 425                 430

Leu Val Pro Asp Ser Asp Val Arg Phe Leu Leu Ser Glu Ser Gly Ser
                435                 440                 445

Gly Lys Gly Ala Ala Met Val Thr Ala Val Ala Tyr Arg Leu Ala Glu
            450                 455                 460

Gln His Arg Gln Ile Glu Glu Thr Leu Ala His Phe His Leu Thr Lys
465                 470                 475                 480

Asp Met Leu Leu Glu Val Lys Lys Arg Met Arg Ala Glu Met Glu Leu
                485                 490                 495

Gly Leu Arg Lys Gln Thr His Asn Asn Ala Val Val Lys Met Leu Pro
                500                 505                 510

Ser Phe Val Arg Arg Thr Pro Asp Gly Thr Glu Asn Gly Asp Phe Leu
                515                 520                 525

Ala Leu Asp Leu Gly Gly Thr Asn Phe Arg Val Leu Leu Val Lys Ile
                530                 535                 540

Arg Ser Gly Lys Lys Arg Thr Val Glu Met His Asn Lys Ile Tyr Ala
545                 550                 555                 560

Ile Pro Ile Glu Ile Met Gln Gly Thr Gly Glu Glu Leu Phe Asp His
                565                 570                 575

Ile Val Ser Cys Ile Ser Asp Phe Leu Asp Tyr Met Gly Ile Lys Gly
                580                 585                 590

Pro Arg Met Pro Leu Gly Phe Thr Phe Ser Phe Pro Cys Gln Gln Thr
                595                 600                 605

Ser Leu Asp Ala Gly Ile Leu Ile Thr Trp Thr Lys Gly Phe Lys Ala
                610                 615                 620

Thr Asp Cys Val Gly His Asp Val Val Thr Leu Leu Arg Asp Ala Ile
625                 630                 635                 640

Lys Arg Arg Glu Glu Phe Asp Leu Asp Val Val Ala Val Val Asn Asp
                645                 650                 655

Thr Val Gly Thr Met Met Thr Cys Ala Tyr Glu Glu Pro Thr Cys Glu
                660                 665                 670

Val Gly Leu Ile Val Gly Thr Gly Ser Asn Ala Cys Tyr Met Glu Glu
                675                 680                 685

Met Lys Asn Val Glu Met Val Glu Gly Asp Gln Gly Gln Met Cys Ile
                690                 695                 700

Asn Met Glu Trp Gly Ala Phe Gly Asp Asn Gly Cys Leu Asp Asp Ile
705                 710                 715                 720

Arg Thr His Tyr Asp Arg Leu Val Asp Glu Tyr Ser Leu Asn Ala Gly
                725                 730                 735

Lys Gln Arg Tyr Glu Lys Met Ile Ser Gly Met Tyr Leu Gly Glu Ile
                740                 745                 750

Val Arg Asn Ile Leu Ile Asp Phe Thr Lys Lys Gly Phe Leu Phe Arg
                755                 760                 765

Gly Gln Ile Ser Glu Thr Leu Lys Thr Arg Gly Ile Phe Glu Thr Lys
                770                 775                 780

Phe Leu Ser Gln Ile Glu Ser Asp Arg Leu Ala Leu Leu Gln Val Arg
785                 790                 795                 800
```

-continued

```
Ala Ile Leu Gln Gln Leu Gly Leu Asn Ser Thr Cys Asp Asp Ser Ile
            805                 810                 815

Leu Val Lys Thr Val Cys Gly Val Val Ser Arg Arg Ala Ala Gln Leu
        820                 825                 830

Cys Gly Ala Gly Met Ala Ala Val Val Asp Lys Ile Arg Glu Asn Arg
            835                 840                 845

Gly Leu Asp Arg Leu Asn Val Thr Val Gly Val Asp Gly Thr Leu Tyr
        850                 855                 860

Lys Leu His Pro His Phe Ser Arg Ile Met His Gln Thr Val Lys Glu
865                 870                 875                 880

Leu Ser Pro Lys Cys Asn Val Ser Phe Leu Leu Ser Glu Asp Gly Ser
            885                 890                 895

Gly Lys Gly Ala Ala Leu Ile Thr Ala Val Gly Val Arg Leu Arg Thr
        900                 905                 910

Glu Ala Ser Ser
        915
```

<210> SEQ ID NO 23
<211> LENGTH: 921
<212> TYPE: PRT
<213> ORGANISM: homo sapiens
<220> FEATURE:
<221> NAME/KEY: misc_feature
<223> OTHER INFORMATION: Hexokinase-1 Isoform 3

<400> SEQUENCE: 23

```
Met Gly Gln Ile Cys Gln Arg Glu Ser Ala Thr Ala Ala Glu Lys Pro
1               5                   10                  15

Lys Leu His Leu Leu Ala Glu Ser Glu Ile Asp Lys Tyr Leu Tyr Ala
            20                  25                  30

Met Arg Leu Ser Asp Glu Thr Leu Ile Asp Ile Met Thr Arg Phe Arg
        35                  40                  45

Lys Glu Met Lys Asn Gly Leu Ser Arg Asp Phe Asn Pro Thr Ala Thr
    50                  55                  60

Val Lys Met Leu Pro Thr Phe Val Arg Ser Ile Pro Asp Gly Ser Glu
65                  70                  75                  80

Lys Gly Asp Phe Ile Ala Leu Asp Leu Gly Gly Ser Ser Phe Arg Ile
                85                  90                  95

Leu Arg Val Gln Val Asn His Glu Lys Asn Gln Asn Val His Met Glu
            100                 105                 110

Ser Glu Val Tyr Asp Thr Pro Glu Asn Ile Val His Gly Ser Gly Ser
        115                 120                 125

Gln Leu Phe Asp His Val Ala Glu Cys Leu Gly Asp Phe Met Glu Lys
    130                 135                 140

Arg Lys Ile Lys Asp Lys Lys Leu Pro Val Gly Phe Thr Phe Ser Phe
145                 150                 155                 160

Pro Cys Gln Gln Ser Lys Ile Asp Glu Ala Ile Leu Ile Thr Trp Thr
                165                 170                 175

Lys Arg Phe Lys Ala Ser Gly Val Glu Gly Ala Asp Val Val Lys Leu
            180                 185                 190

Leu Asn Lys Ala Ile Lys Lys Arg Gly Asp Tyr Asp Ala Asn Ile Val
        195                 200                 205

Ala Val Val Asn Asp Thr Val Gly Thr Met Met Thr Cys Gly Tyr Asp
    210                 215                 220

Asp Gln His Cys Glu Val Gly Leu Ile Ile Gly Thr Gly Thr Asn Ala
```

```
                225                 230                 235                 240
Cys Tyr Met Glu Glu Leu Arg His Ile Asp Leu Val Glu Gly Asp Glu
                245                 250                 255
Gly Arg Met Cys Ile Asn Thr Glu Trp Gly Ala Phe Gly Asp Asp Gly
                260                 265                 270
Ser Leu Glu Asp Ile Arg Thr Glu Phe Asp Arg Glu Ile Asp Arg Gly
                275                 280                 285
Ser Leu Asn Pro Gly Lys Gln Leu Phe Glu Lys Met Val Ser Gly Met
290                 295                 300
Tyr Leu Gly Glu Leu Val Arg Leu Ile Leu Val Lys Met Ala Lys Glu
305                 310                 315                 320
Gly Leu Leu Phe Glu Gly Arg Ile Thr Pro Glu Leu Leu Thr Arg Gly
                325                 330                 335
Lys Phe Asn Thr Ser Asp Val Ser Ala Ile Glu Lys Asn Lys Glu Gly
                340                 345                 350
Leu His Asn Ala Lys Glu Ile Leu Thr Arg Leu Gly Val Glu Pro Ser
                355                 360                 365
Asp Asp Asp Cys Val Ser Val Gln His Val Cys Thr Ile Val Ser Phe
370                 375                 380
Arg Ser Ala Asn Leu Val Ala Ala Thr Leu Gly Ala Ile Leu Asn Arg
385                 390                 395                 400
Leu Arg Asp Asn Lys Gly Thr Pro Arg Leu Arg Thr Val Gly Val
                405                 410                 415
Asp Gly Ser Leu Tyr Lys Thr His Pro Gln Tyr Ser Arg Arg Phe His
                420                 425                 430
Lys Thr Leu Arg Arg Leu Val Pro Asp Ser Asp Val Arg Phe Leu Leu
                435                 440                 445
Ser Glu Ser Gly Ser Gly Lys Gly Ala Ala Met Val Thr Ala Val Ala
                450                 455                 460
Tyr Arg Leu Ala Glu Gln His Arg Gln Ile Glu Glu Thr Leu Ala His
465                 470                 475                 480
Phe His Leu Thr Lys Asp Met Leu Leu Glu Val Lys Lys Arg Met Arg
                485                 490                 495
Ala Glu Met Glu Leu Gly Leu Arg Lys Gln Thr His Asn Asn Ala Val
                500                 505                 510
Val Lys Met Leu Pro Ser Phe Val Arg Arg Thr Pro Asp Gly Thr Glu
                515                 520                 525
Asn Gly Asp Phe Leu Ala Leu Asp Leu Gly Gly Thr Asn Phe Arg Val
                530                 535                 540
Leu Leu Val Lys Ile Arg Ser Gly Lys Lys Arg Thr Val Glu Met His
545                 550                 555                 560
Asn Lys Ile Tyr Ala Ile Pro Ile Glu Ile Met Gln Gly Thr Gly Glu
                565                 570                 575
Glu Leu Phe Asp His Ile Val Ser Cys Ile Ser Asp Phe Leu Asp Tyr
                580                 585                 590
Met Gly Ile Lys Gly Pro Arg Met Pro Leu Gly Phe Thr Phe Ser Phe
                595                 600                 605
Pro Cys Gln Gln Thr Ser Leu Asp Ala Gly Ile Leu Ile Thr Trp Thr
                610                 615                 620
Lys Gly Phe Lys Ala Thr Asp Cys Val Gly His Asp Val Val Thr Leu
625                 630                 635                 640
Leu Arg Asp Ala Ile Lys Arg Arg Glu Glu Phe Asp Leu Asp Val Val
                645                 650                 655
```

```
Ala Val Val Asn Asp Thr Val Gly Thr Met Met Thr Cys Ala Tyr Glu
            660                 665                 670

Glu Pro Thr Cys Glu Val Gly Leu Ile Val Gly Thr Gly Ser Asn Ala
            675                 680                 685

Cys Tyr Met Glu Glu Met Lys Asn Val Glu Met Val Glu Gly Asp Gln
            690                 695                 700

Gly Gln Met Cys Ile Asn Met Glu Trp Gly Ala Phe Gly Asp Asn Gly
705                 710                 715                 720

Cys Leu Asp Asp Ile Arg Thr His Tyr Asp Arg Leu Val Asp Glu Tyr
                725                 730                 735

Ser Leu Asn Ala Gly Lys Gln Arg Tyr Glu Lys Met Ile Ser Gly Met
            740                 745                 750

Tyr Leu Gly Glu Ile Val Arg Asn Ile Leu Ile Asp Phe Thr Lys Lys
            755                 760                 765

Gly Phe Leu Phe Arg Gly Gln Ile Ser Glu Thr Leu Lys Thr Arg Gly
            770                 775                 780

Ile Phe Glu Thr Lys Phe Leu Ser Gln Ile Glu Ser Asp Arg Leu Ala
785                 790                 795                 800

Leu Leu Gln Val Arg Ala Ile Leu Gln Gln Leu Gly Leu Asn Ser Thr
                805                 810                 815

Cys Asp Asp Ser Ile Leu Val Lys Thr Val Cys Gly Val Val Ser Arg
            820                 825                 830

Arg Ala Ala Gln Leu Cys Gly Ala Gly Met Ala Ala Val Val Asp Lys
            835                 840                 845

Ile Arg Glu Asn Arg Gly Leu Asp Arg Leu Asn Val Thr Val Gly Val
850                 855                 860

Asp Gly Thr Leu Tyr Lys Leu His Pro His Phe Ser Arg Ile Met His
865                 870                 875                 880

Gln Thr Val Lys Glu Leu Ser Pro Lys Cys Asn Val Ser Phe Leu Leu
                885                 890                 895

Ser Glu Asp Gly Ser Gly Lys Gly Ala Ala Leu Ile Thr Ala Val Gly
            900                 905                 910

Val Arg Leu Arg Thr Glu Ala Ser Ser
            915                 920

<210> SEQ ID NO 24
<211> LENGTH: 905
<212> TYPE: PRT
<213> ORGANISM: homo sapiens
<220> FEATURE:
<221> NAME/KEY: misc_feature
<223> OTHER INFORMATION: Hexokinase-1 Isoform 4

<400> SEQUENCE: 24

Met Ala Lys Arg Ala Leu His Asp Phe Ile Asp Lys Tyr Leu Tyr Ala
1               5                   10                  15

Met Arg Leu Ser Asp Glu Thr Leu Ile Asp Ile Met Thr Arg Phe Arg
            20                  25                  30

Lys Glu Met Lys Asn Gly Leu Ser Arg Asp Phe Asn Pro Thr Ala Thr
        35                  40                  45

Val Lys Met Leu Pro Thr Phe Val Arg Ser Ile Pro Asp Gly Ser Glu
    50                  55                  60

Lys Gly Asp Phe Ile Ala Leu Asp Leu Gly Gly Ser Ser Phe Arg Ile
65                  70                  75                  80

Leu Arg Val Gln Val Asn His Glu Lys Asn Gln Asn Val His Met Glu
```

```
                85                  90                  95
Ser Glu Val Tyr Asp Thr Pro Glu Asn Ile Val His Gly Ser Gly Ser
                100                 105                 110

Gln Leu Phe Asp His Val Ala Glu Cys Leu Gly Asp Phe Met Glu Lys
            115                 120                 125

Arg Lys Ile Lys Asp Lys Lys Leu Pro Val Gly Phe Thr Phe Ser Phe
        130                 135                 140

Pro Cys Gln Gln Ser Lys Ile Asp Glu Ala Ile Leu Ile Thr Trp Thr
145                 150                 155                 160

Lys Arg Phe Lys Ala Ser Gly Val Glu Gly Ala Asp Val Val Lys Leu
                165                 170                 175

Leu Asn Lys Ala Ile Lys Lys Arg Gly Asp Tyr Asp Ala Asn Ile Val
            180                 185                 190

Ala Val Val Asn Asp Thr Val Gly Thr Met Met Thr Cys Gly Tyr Asp
        195                 200                 205

Asp Gln His Cys Glu Val Gly Leu Ile Ile Gly Thr Gly Thr Asn Ala
210                 215                 220

Cys Tyr Met Glu Glu Leu Arg His Ile Asp Leu Val Glu Gly Asp Glu
225                 230                 235                 240

Gly Arg Met Cys Ile Asn Thr Glu Trp Gly Ala Phe Gly Asp Asp Gly
                245                 250                 255

Ser Leu Glu Asp Ile Arg Thr Glu Phe Asp Arg Glu Ile Asp Arg Gly
            260                 265                 270

Ser Leu Asn Pro Gly Lys Gln Leu Phe Glu Lys Met Val Ser Gly Met
        275                 280                 285

Tyr Leu Gly Glu Leu Val Arg Leu Ile Leu Val Lys Met Ala Lys Glu
290                 295                 300

Gly Leu Leu Phe Glu Gly Arg Ile Thr Pro Glu Leu Leu Thr Arg Gly
305                 310                 315                 320

Lys Phe Asn Thr Ser Asp Val Ser Ala Ile Glu Lys Asn Lys Glu Gly
                325                 330                 335

Leu His Asn Ala Lys Glu Ile Leu Thr Arg Leu Gly Val Glu Pro Ser
            340                 345                 350

Asp Asp Asp Cys Val Ser Val Gln His Val Cys Thr Ile Val Ser Phe
        355                 360                 365

Arg Ser Ala Asn Leu Val Ala Ala Thr Leu Gly Ala Ile Leu Asn Arg
370                 375                 380

Leu Arg Asp Asn Lys Gly Thr Pro Arg Leu Arg Thr Thr Val Gly Val
385                 390                 395                 400

Asp Gly Ser Leu Tyr Lys Thr His Pro Gln Tyr Ser Arg Arg Phe His
                405                 410                 415

Lys Thr Leu Arg Arg Leu Val Pro Asp Ser Asp Val Arg Phe Leu Leu
            420                 425                 430

Ser Glu Ser Gly Ser Gly Lys Gly Ala Ala Met Val Thr Ala Val Ala
        435                 440                 445

Tyr Arg Leu Ala Glu Gln His Arg Gln Ile Glu Glu Thr Leu Ala His
450                 455                 460

Phe His Leu Thr Lys Asp Met Leu Leu Glu Val Lys Lys Arg Met Arg
465                 470                 475                 480

Ala Glu Met Glu Leu Gly Leu Arg Lys Gln Thr His Asn Asn Ala Val
                485                 490                 495

Val Lys Met Leu Pro Ser Phe Val Arg Arg Thr Pro Asp Gly Thr Glu
            500                 505                 510
```

```
Asn Gly Asp Phe Leu Ala Leu Asp Leu Gly Gly Thr Asn Phe Arg Val
        515                 520                 525

Leu Leu Val Lys Ile Arg Ser Gly Lys Lys Arg Thr Val Glu Met His
    530                 535                 540

Asn Lys Ile Tyr Ala Ile Pro Ile Glu Ile Met Gln Gly Thr Gly Glu
545                 550                 555                 560

Glu Leu Phe Asp His Ile Val Ser Cys Ile Ser Asp Phe Leu Asp Tyr
                565                 570                 575

Met Gly Ile Lys Gly Pro Arg Met Pro Leu Gly Phe Thr Phe Ser Phe
                580                 585                 590

Pro Cys Gln Gln Thr Ser Leu Asp Ala Gly Ile Leu Ile Thr Trp Thr
        595                 600                 605

Lys Gly Phe Lys Ala Thr Asp Cys Val Gly His Asp Val Val Thr Leu
    610                 615                 620

Leu Arg Asp Ala Ile Lys Arg Glu Glu Phe Asp Leu Asp Val Val
625                 630                 635                 640

Ala Val Val Asn Asp Thr Val Gly Thr Met Met Thr Cys Ala Tyr Glu
                645                 650                 655

Glu Pro Thr Cys Glu Val Gly Leu Ile Val Gly Thr Gly Ser Asn Ala
                660                 665                 670

Cys Tyr Met Glu Glu Met Lys Asn Val Glu Met Val Glu Gly Asp Gln
        675                 680                 685

Gly Gln Met Cys Ile Asn Met Glu Trp Gly Ala Phe Gly Asp Asn Gly
    690                 695                 700

Cys Leu Asp Asp Ile Arg Thr His Tyr Asp Arg Leu Val Asp Glu Tyr
705                 710                 715                 720

Ser Leu Asn Ala Gly Lys Gln Arg Tyr Glu Lys Met Ile Ser Gly Met
                725                 730                 735

Tyr Leu Gly Glu Ile Val Arg Asn Ile Leu Ile Asp Phe Thr Lys Lys
                740                 745                 750

Gly Phe Leu Phe Arg Gly Gln Ile Ser Glu Thr Leu Lys Thr Arg Gly
        755                 760                 765

Ile Phe Glu Thr Lys Phe Leu Ser Gln Ile Glu Ser Asp Arg Leu Ala
    770                 775                 780

Leu Leu Gln Val Arg Ala Ile Leu Gln Gln Leu Gly Leu Asn Ser Thr
785                 790                 795                 800

Cys Asp Asp Ser Ile Leu Val Lys Thr Val Cys Gly Val Val Ser Arg
                805                 810                 815

Arg Ala Ala Gln Leu Cys Gly Ala Gly Met Ala Ala Val Val Asp Lys
                820                 825                 830

Ile Arg Glu Asn Arg Gly Leu Asp Arg Leu Asn Val Thr Val Gly Val
        835                 840                 845

Asp Gly Thr Leu Tyr Lys Leu His Pro His Phe Ser Arg Ile Met His
    850                 855                 860

Gln Thr Val Lys Glu Leu Ser Pro Lys Cys Asn Val Ser Phe Leu Leu
865                 870                 875                 880

Ser Glu Asp Gly Ser Gly Lys Gly Ala Ala Leu Ile Thr Ala Val Gly
                885                 890                 895

Val Arg Leu Arg Thr Glu Ala Ser Ser
                900                 905
```

METHOD FOR IN VITRO DIAGNOSING AND PROGNOSING OF TRIPLE NEGATIVE BREAST CANCER RECURRENCE

RELATED APPLICATIONS

This application is a National Stage Application under 35 U.S.C. 371 of co-pending PCT application PCT/EP2014/075424, filed Nov. 24, 2014 and EP application no. 13306603.5, filed Nov. 22, 2013 each of which are hereby incorporated by reference in their entireties.

INTRODUCTION

The present invention is in the technical field of breast cancer management, and more particularly relates to the diagnosis and/or prognosing of triple-negative breast cancer (TNBC). The invention is more particularly based on the finding that specific biomarkers are abberantly expressed in patients suffering from a triple-negative breast cancer recurrence, and are highly related to the aggressiveness of this disease, and thus to survival of said patient.

With over 1.3 million cases of invasive breast cancers diagnosed annually, and more than 450,000 deaths reported per year, breast cancer is the most common malignancy diagnosed in women and one of the leading causes of cancer-related death in females.

Breast cancer represents a heterogeneous disease, as it encompasses a plethora of tumor subtypes which not only have distinct morphological features but also clinical behaviors. These subtypes have thus different implications in prognosis and response to therapy. Determination of hormone receptor status (estrogen (ER) and progesterone receptor (PR)) has become standard practice in the management of invasive breast cancers: ER positivity can predict response to endocrine therapy such as anti-estrogen administration or ovarian suppression, while human epithelial growth factor receptor 2 (HER2, c-erbB-2) positivity is useful for selecting targeted therapy with the monoclonal antibody against HER2.

Despite the decreased incidence and mortality linked to this pathology due to screening and improved therapy, breast cancer remains nevertheless a major cause of deaths. It has thus become crucial to diagnose more accurately breast cancer subtypes, and select appropriate treatments, not only for the patients, but also for health economic reasons.

Among breast cancer subtypes, triple-negative breast cancer (TNBC) is responsible for a relatively large proportion of deaths, due notably to its generally aggressive clinical outcome. Triple-negative breast cancer is defined by a lack of expression of estrogen, progesterone, and HER2/neu receptors, which accounts for about 10 to 15% of all breast cancers. The term "triple-negative breast cancer" has been described for the first time in 2005 (Brenton et al., 2005), and has since appeared in over a 1000 publications. While it is frequently presumed to affect predominantly young women (i.e. below 50 years old), its distribution is actually similar in all age groups (Hudis et al., 2011). This cancer subtype is usually more frequent in African-American women, present as interval cancers, highly chemo-sensitive, and shows a weak association between tumor size and lymph node metastases. Most importantly, it is, as mentioned above, associated with an aggressive phenotype, and has generally a poor outcome compared to other breast cancer subtypes. Unfortunately, due to its negativity for the three molecular markers ER, PR, and HER2/neu, triple-negative breast cancer is unresponsive to usual endocrine therapy or therapy targeted to human epidermal growth factor receptor type 2 (HER2). In addition, triple-negative breast cancer exhibits a very particular relapse pattern that differs from hormone-positive breast cancers, as about 30% of patient relapse in the first 3 to 5 years. This risk of relapse nevertheless decreases after about 5 years from the initial diagnosis.

Due to the absence of specific treatment guidelines for patients affected by this particular cancer, triple-negative breast cancers are nowadays managed with standard adjuvant chemotherapy. Such treatment is however less effective than for other breast cancer subtypes and remains associated with a high rate of local and systemic relapse. It is therefore critical to identify relapsing patients as early as possible, in order to adapt accordingly their treatment.

Most studies described in the literature were conducted to identify biomarkers characterizing triple-negative breast cancer, without discriminating relapsing from non-relapsing patients. Besides, these studies were mainly focused on genotypic-phenotypic correlations, such as genetic polymorphisms or gene expression variations, but not on the actual functional entities, proteins, that are differentially expressed in breast cancer cells. However, the behavior of these functional entities can not be predicted from their encoding genes. Once transcribed, a protein expression may indeed still be regulated at the translation level, and corresponding proteins can be subjected to posttranslational modifications, varying half-lives, and compartmentalization.

Given that the diagnostic and prognostic of triple-negative breast cancer and targeted therapy are today ill-defined, there is an urgent need to identify and characterize reliable biomarkers allowing to accurately identify the different subsets of TNBC patients, especially those developing a local or distant cancer recurrence, in order to design and adapt accordingly their therapy.

This need is addressed by the present invention, which reports herein the results of an investigation conducted on a large cohort of relapsing and non-relapsing triple-negative breast cancer patients, by a quantitative proteomic approach using iTRAQ labeling, peptide OFFGEL Fractionation and mass spectrometry analysis (Ernoult et al., 2008 and 2010). By contrast to genomic biomarkers, proteomic biomarkers are indeed particularly advantageous as they are more reflective of a tumor microenvironment and can undergo cancer specific posttranslational modifications. To the best of Applicant's knowledge, this is the first study investigating proteomic biomarkers in a comprehensive panel of breast cancer patients to diagnose and prognose TNBC recurrence.

By combining both a multivariate and an univariate analysis, the inventors have identified key biomarkers of triple-negative breast cancer recurrence and non-recurrence. In particular, the inventors have identified, on one hand, Desmoplakin, Rho GTPase-activating protein 1, Epiplakin, Glucose-6-phosphate 1-dehydrogenase, Isocitrate dehydroge-nase [NADP], Keratin type I cytoskeletal 19, Keratin type I cytoskeletal 8, Dihydropyrimidinase-related protein 3, and/or Thrombospondin-1 as biomarkers associated with TNBC recurrence and a poor clinical outcome, and, on the other hand, Hexokinase-1, 10 kDa heat shock protein, Ig gamma-1 chain C region, SAM domain and HD domain-containing protein 1, and/or Tryptophanyl-tRNA synthetase as biomarkers associated with TNBC non-recurrence and a good clinical outcome.

All the biomarkers disclosed herein can thus be used to monitor disease progression or regression, to assess the susceptibility or prediction of response to treatment, but also to evaluate the efficacy of a treatment. They can also be used as therapeutic targets to design novel drugs.

Therefore, based on the findings disclosed herein, the present invention provides for the first time accurate and reliable diagnostic, prognostic and therapeutic methods for triple-negative breast cancer recurrence, which are based, at least in part, on determination of the expression level of the above-mentioned biomarkers. The invention further provides a screening method for identifying drugs, a method for determining a drug-responding or non-responding phenotype, as well as a method for designing or adapting a treatment regimen. Kits and protein microarrays for carrying out the methods of the invention are also provided herein.

DETAILED DESCRIPTION OF THE INVENTION

Unless stated otherwise, scientific and technical terms used in connection with the present invention shall have the meanings that are commonly understood by those of ordinary skill in the art. Further, unless otherwise required by context, nomenclatures used herein, and techniques of molecular biology and cell culture are those well-known and commonly used in the art.

Nevertheless, with respect to the use of different terms throughout the current specification, the following definitions more particularly apply.

According to the different aspects and embodiments of the invention, the term "comprising" or "containing" means the inclusion of the referent and does not exclude the presence of any other element. By contrast to the term "comprising", the term "consisting of" means the sole inclusion of the referent and thus excludes the presence of any other element.

By "triple-negative breast cancer" or "TNBC", it is meant herein, as indicated above, any breast cancer that does not express the estrogen receptor (ER), the progesterone receptor (PR) and Her2/neu (HER2). A triple-negative breast cancer can thus be alternatively referred as an estrogen receptor negative (ER−), progesterone receptor negative (PR−) and Her2/neu negative (HER2−) breast cancer. Triple-negative breast cancer (TNBC) encompasses several common histologic subtypes, including notably medullary, metaplastic, secretory, myoepithelial and adenoid cystic carcinomas, as well as less common histologic subtypes such as apocrine carcinoma, pleomorphic lobular carcinoma, and duct-lobular cancer. Further information about triple-negative breast cancer (TNBC) may be found in Rakha et al. (2008).

By "recurrence", "recurring", "relapse or "relapsing", it is meant herein, in the context of potential clinical outcomes of cancer and as defined by the National Cancer Institute, that the cancer has recurred (come back), usually after a period of time during which the cancer could not be detected. A recurring cancer may refer to a cancer that comes back to the same place as the original (primary) tumor or to another place in the body (also known as metastasis).

By contrast, the term "non-recurrence", "non-relapse", "absence of recurrence", "absence of relapse", means that the cancer has not recurred (i.e. not come back), usually after a period of time during which the cancer could not be detected.

The term "subject" or "patient" is used herein to describe any member of the animal kingdom, preferably a human being, more preferably a woman.

The term "diagnosing" or "diagnosis", as used in the context of the present invention, include the act or process of identifying the existence (or non-existence) and/or type of disease from which an individual may be suffering.

The term "prognosis", "prognosing" or "clinical outcome" as used herein refers to the likely outcome or course of a disease; the chance of recovery or non-recovery. A prognosis may indicate whether a cancer patient will likely have a cancer-attributable death or progression, and/or a short-term or long-term survival. A clinical outcome can be assessed for example in the context of an individual's outcome relative to an outcome of a population of patients having a comparable clinical diagnosis, using various endpoints well-known in the art, such as Overall Survival (OS), Disease-Free Survival (DFS), Hazard Ratios (HR) and the like. Such parameters are well-known by the skilled person, who may refer to the definitions provided by the National Cancer Institute.

The term "positive clinical outcome" or "good prognosis" means a desired clinical outcome. In the context of the present invention, a positive clinical outcome may be an expectation or low probability of TNBC-attributable death or progression. Preferably, a positive clinical outcome means that said subject has a risk of TNBC-attributable death or progression inferior to 25%, within 5 years from the initial diagnosis of triple-negative breast cancer.

By contrast, the terms "negative clinical outcome" or "poor prognosis" are used herein interchangeably to mean an undesired clinical outcome. In the context of the present invention, a negative clinical outcome may be an expectation or high probability of TNBC-attributable death or progression. Preferably, a negative clinical outcome means that said subject has a risk of TNBC-attributable death or progression superior to 75%, within 5 years from the initial diagnosis of triple-negative breast cancer.

A "biological sample" according to the invention can be any sample that may be isolated from a subject, including, without limitation, a biological fluid such as blood or a fractional component thereof (serum, plasma, cellular extract), lymph, tumor interstitial fluid, saliva, mucus, sputum, sweat, urine, as well as a tissue biopsy such as a tumor biopsy. Furthermore, in the case of a local or a distant cancer recurrence, a biological sample can further include circulating tumoral cells (CTCs) that may be isolated from a biological fluid as defined above, preferably from blood, by techniques well-known in the art. An example of a technique allowing the isolation of circulating tumoral cells (CTCs) is Dean Flow Fractionation (DFF), as established by Hou et al., 2013. More preferably, the biological sample according to the invention is a tumor biopsy, such as the biopsy of a breast tumor or of a metastasis thereof.

The term biomarker according to the invention preferably refers to a polypeptide or protein, fragment thereof, or epitope that is differentially present in a subject as compared to healthy subjects, including differentially modified (e.g. differentially glycosylated) and/or expressed biomarkers. Examples of biomarkers according to the invention are listed in Tables 1, 2, 6A and 8A, and can be referred herein as "biomarkers of the disclosure". It should be noted that the term "biomarker" includes soluble biomarkers, i.e. biomarkers which are differentially cleaved, secreted, released or shed from a tumor cell in a subject, and are thus detectable in a biological fluid as defined above. For example, in the context of the present invention, a soluble form of the plasma membrane protein Desmoplakin, as further described below, can be detected from a mere blood sample or a fractional component thereof (Lopez-Farré et al., 2012). "Soluble biomarkers" can be released into a biological fluid through several possible mechanisms, such as local tissue destruction during disease progression. For example, soluble biomarkers may be released into the blood circulation through aberrant shedding and secretion from tumor cells or through destruction of tissue architecture and angiogenesis as the tumor invades. Proteins can also be cleaved from the extracellular surface of tumor cells by proteases and subsequently make their way into the blood circulation. In light of the above, one skilled in the art would readily understand that, if the expression level of a soluble biomarker of interest is to be assessed from a biological sample, said sample is preferably selected from at least one of the biological fluids described above, thereby preventing any invasive act on the patient. A soluble biomarker remains nevertheless detectable within its site of expression, i.e. in the context of the present invention, within a breast tumor or a metastasis thereof.

The term "expression level", as applied to a biomarker such as a protein, refers herein to the amount or level of a biomarker of interest expressed in a cell, tissue, biological fluid, or organ(s). The term "level" as used herein refers to an amount (e.g. relative amount or concentration) of a biomarker that is detectable or measurable in a sample. For example, the level can be a concentration such as µg/L or a relative amount by comparison to a reference expression level. The act of actually "determining the expression level" of a biomarker in a biological sample refers to the act of actively detecting whether a biomarker is expressed in said sample or not, and notably allows to detect whether the biomarker expression is upregulated, downregulated or substantially unchanged when compared to a reference expression level.

By "reference expression level" or "control expression level" of a biomarker, it is meant a predetermined expression level of said biomarker, which can be used as a reference in any method of the invention. For example, a reference expression level can be the expression level of a biomarker in a biological sample of a healthy subject, or the average or median expression level in a biological sample of a population of healthy subjects.

Additional definitions are provided throughout the specification.

The present invention may be understood more readily by reference to the following detailed description, including preferred embodiments of the invention, and examples included herein.

The inventors have surprisingly discovered key biomarkers associated with recurrence and non-recurrence of triple-negative breast cancer (TNBC). In particular, the inventors have discovered that the expression level of specific biomarkers correlate with disease status and progression. These specific biomarkers can thus allow for a reliable and rapid detection of a TNBC recurrence, and provide a good indication of the clinical outcome.

Accordingly, in a first aspect, the present invention relates to an in vitro method for diagnosing and/or prognosing a triple-negative breast cancer (TNBC) recurrence or non-recurrence in a subject, comprising the steps of:
  a) determining from a biological sample of a subject the expression level of at least two biomarkers selected from the group consisting of Desmoplakin, Rho GTPase-activating protein 1, Epiplakin, Glucose-6-phosphate 1-dehydrogenase, Isocitrate dehydroge-nase [NADP], Keratin type I cytoskeletal 19, Keratin type I cytoskeletal 8, Dihydropyrimidinase-related protein 3, and Thrombospondin-1; and
  b) comparing said expression level with a reference expression level of sais biomarkers.

The above method may optionally further comprise the step c) of determining whether said subject is suffering or not from a triple-negative breast cancer (TNBC) recurrence, and/or determining or predicting the clinical outcome in said subject, based upon the comparison in step b).

It shall be understood that said subject has previously been suffering from a primary triple-negative breast cancer (TNBC), and may have been diagnosed as such and/or been treated for it.

As illustrated in the experimental results of the present application, the inventors have discovered that the above mentioned biomarkers are associated with TNBC recurrence, as well as with a poor prognosis.

Particularly preferred biomarkers associated with TNBC recurrence according to the invention are listed in the following Table 1.

TABLE 1

Biomarkers of TNBC recurrence

| Symbol | Full name | Accession number UniprotKB/Swiss-Prot (SEQ ID number) |
|---|---|---|
| DSP or DP | Desmoplakin: Isoforms 1 and 2<br>Alternative name(s):<br>250/210 kDA paraneoplastic pemphigus antigen | P15924-1 (Isoform 1: SEQ ID NO: 1)<br>P15924-2 (Isoform 2: SEQ ID NO: 2) |
| ARHGAP1 | Rho GTPase-activating protein 1<br>Alternative name(s):<br>CDC42 GTPase-activating protein (CDC42GAP)<br>GTPase-activating protein rhoOGAP<br>Rho-related small GTPase protein activator<br>Rho-type GTPase-activating protein 1 (RHOGAP1)<br>p50-RhoGAP | Q07960 (SEQ ID NO: 3) |
| EPPK1 | Epiplakin<br>Alternative name(s):<br>450 kDa epidermal antigen | P58107 (SEQ ID NO: 4) |
| G6PD | Glucose-6-phosphate dehydrogenase<br>(enzyme EC 1.1.1.49):<br>Isoform short, Isoform long and isoform 3 | P11413-1<br>(Isoform short: SEQ ID NO: 5)<br>P11413-2<br>(Isoform long: SEQ ID NO: 6)<br>P11413-3<br>(Isoform 3: SEQ ID NO: 7) |
| IDH2 | Isocitrate dehydrogenase [NADP]<br>(enzyme EC 1.1.1.42)<br>Alternative names(s): | P48735 (SEQ ID NO: 8) |

TABLE 1-continued

Biomarkers of TNBC recurrence

| Symbol | Full name | Accession number UniprotKB/Swiss-Prot (SEQ ID number) |
|---|---|---|
| | ICD-M<br>IDP<br>NADP(+)-specific ICDH<br>Oxalosuccinate decarboxylase | |
| KRT19 | Keratin type I cytoskeletal 19<br>Alternative name(s):<br>Cytokeratin-19 (CK-19)<br>Keratin-19 (K19) | P08727 (SEQ ID NO: 9) |
| KRT8 | Keratin type II cytoskeletal 8: Isoforms 1 and 2<br>Alternative name(s):<br>Cytokeratin-8 (CK-8)<br>Keratin-8 (K8)<br>Type-II keratin Kb8 | P05787-1 (Isoform 1: SEQ ID NO: 10)<br>P05787-2 (Isoform 2: SEQ ID NO: 11) |
| DPYSL3 | Dihydropyrimidinase-related protein 3:<br>Isoform 1 and Isoform LCRMP-4<br>Alternative name(s):<br>Collapsin response mediator protein 4 (CRMP-4)<br>Unc-33-like phosphoprotein 1 (ULIP-1) | Q14195-1 (Isoform 1: SEQ ID NO: 12)<br>Q14195-2 (Isoform LCRMP-4: SEQ ID NO: 13) |
| THBS1 | Thrombospondin-1 | P07996 (SEQ ID NO: 14) |

In a preferred embodiment, an expression level of said at least two biomarkers associated with TNBC recurrence as described above, superior to a reference expression level obtained from a biological sample of at least one healthy subject, is indicative that the subject is suffering from a triple-negative breast cancer (TNBC) recurrence, and/or is indicative of a negative clinical outcome.

By superior to a reference expression level, it is preferably meant that the ratio between the expression level of said biomarkers and the reference expression level is above 1.

Notably, with regard to clinical outcome, the inventors have discovered that a higher expression of said biomarkers, compared to a reference expression level, correlates with a low Disease Free Survival rate (DSF), a low Overall Survival rate (OS), an increased risk of death and/or an increased risk of disease progression, as demonstrated in the experimental results.

According to a further preferred embodiment, the above method further comprises the step of determining from the biological sample of said subject the expression level of at least two biomarkers selected from the group consisting of Hexokinase-1, 10 kDa heat shock protein, Ig gamma-1 chain C region, SAM domain and HD domain-containing protein 1, and Tryptophanyl-tRNA synthetase. One skilled in the art will readily understand that a comparison to the expression level of said biomarkers with a reference expression level of said biomarkers is also carried out.

As illustrated in the experimental results of the present application, the inventors have indeed discovered that the above-mentioned biomarkers are associated with TNBC non-recurrence, as well as with a good prognosis.

Particularly preferred biomarkers associated with TNBC non-recurrence according to the invention are listed in the following Table 2.

TABLE 2

Biomarkers of TNBC non-recurrence

| Symbol | Full name | Accession number UniprotKB/Swiss-Prot (SEQ ID number) |
|---|---|---|
| WARS | Tryptophanyl-tRNA synthetase<br>(enzyme EC 6.1.1.2): Isoforms 1 and 2<br>Alternative name(s):<br>Interferon-induced protein 53 (IFP53)<br>Tryptophanyl-tRNA ligase, cytoplasmique | P23381-1 (Isoform 1: SEQ ID NO: 15)<br>P23381-2 (Isoform 2: SEQ ID NO: 16) |
| SAMHD1 | SAM domain and HD domain-containing protein 1<br>(enzyme EC 3.1.4.—): Isoforms 1 and 2<br>Alternative name(s):<br>Dendritic cell-derived IFNG-induced protein (DCIP)<br>Monocyte protein 5 (MOP-5) | Q9Y3Z3-1 (Isoform 1: SEQ ID NO: 17)<br>Q9Y3Z3-2 (Isoform 1: SEQ ID NO: 18) |
| HSPE1 | 10 kDa heat shock protein, mitochondrial<br>Alternative name(s):<br>10 kDa chaperonin<br>Chaperonin 10 (CPN10)<br>Early-pregnancy factor (EPF) | P61604 (SEQ ID NO: 19) |
| IGHG1 | Ig gamma-1 chain C region | P01857 (SEQ ID NO: 20) |
| HK1 | Hexokinase-1 (enzyme EC 2.7.1.1):<br>Isoforms 1, 2, 3 and 4<br>Alternative name(s):<br>Brain form hexokinase<br>Hexokinase type I (HK I) | P19367-1 (SEQ ID NO: 21)<br>P19367-2 (SEQ ID NO: 22)<br>P19367-3 (SEQ ID NO: 23)<br>P19367-4 (SEQ ID NO: 24) |

In a preferred embodiment, an expression level of said at least two biomarkers selected from the group consisting of:
Hexokinase-1, 10 kDa heat shock protein, SAM domain and HD domain-containing protein 1, and Tryptophanyl-tRNA synthetase, superior to a reference expression level obtained from a biological sample of at least one healthy subject, and
Ig gamma-1 chain C region, inferior to a reference expression level obtained from a biological sample of at least one healthy subject,
is indicative that the subject is not suffering from a triple-negative breast cancer (TNBC) recurrence, and/or is indicative of a positive clinical outcome.

By inferior to a reference expression level, it is preferably meant that the ratio between the expression level of said biomarkers and the reference expression level is below 1.

In particular, with regard to clinical outcome, the inventors have discovered that a higher expression of Hexokinase-1, 10 kDa heat shock protein, SAM domain and HD domain-containing protein 1, and/or Tryptophanyl-tRNA synthetase, and/or a lower expression of Ig gamma-1 chain C region, compared to a reference expression level, correlates with a high Disease Free Survival rate (DSF), a high Overall Survival rate (OS), a low risk of death and/or a low risk of disease progression.

The skilled person in the art will readily understand that more than two biomarkers of TNBC recurrence or non-recurrence may be combined as a panel of biomarkers, each of which contributing to the final diagnosis and/or prognosis of the invention. It is within the skill of ordinary person in the art to select the biomarkers to be combined in the present method, as well as in other methods of the invention. Most preferably, the skilled person will combine the nine biomarkers associated with TNBC recurrence and/or the five biomarkers associated with TNBC non-recurrence as described above.

Even though the above listed biomarkers are sufficient to carry out a diagnosis and/or a prognosis, it shall be understood that the information obtained using the methods of the invention as described herein may be used in combination with other information, such as, but not limited to, expression levels of additional biomarkers which may be standard biomarkers, clinical chemical parameters, histopathological parameters, or age, gender and/or weight of the subject.

Thus in a preferred embodiment, the above method further comprises the step of determining from the biological sample of said subject the expression level of at least one additional biomarker of Tables 7A and/or 8A as described below, and any combination thereof. One skilled in the art would readily understand from the data provided herein that the biomarkers listed in Tables 7A and/or 8A may aid in the diagnosis and/or prognosis of the invention. Besides, it should be noted that the numerical values indicated in those tables are provided as a representative example of the expression level of each biomarker; those values are therefore not limiting to the invention, and do not preclude slightly larger and/or slightly smaller values. It is within the skill of ordinary person in the art to select the biomarkers of Tables 7A and/or 8A to be combined in the present method, as well as in other methods of the invention.

In the context of the present invention, the expression level is preferably measured at the protein level. Methods for measuring protein expression levels are well-known in the art and are notably reviewed by Reeves et al. (2000) and Schena (2005). Those methods generally involve contacting a biological sample of interest with one or more detectable reagents that is or are suitable for measuring protein expression level, such as an antibody, and subsequently determining protein expression level based on the level of detected reagent, preferably after normalization. Examples of methods which generally involve the use of an antibody include, without limitation, Western blot, immunoblot, enzyme-linked immunosorbant assay (ELISA), enzyme-linked immunospot (ELISPOT), radioimmunoassay (RIA), immunohistochemistry and immunoprecipitation. Other methods suitable for measuring a protein expression level, which do not necessarily involve the use of an antibody, may be used, including, without limitation, fluorescence activated cell sorting (FACS), microscopy such as atomic force microscopy, flow cytometry, microcytometry, protein binding assay, ligand binding assay, microarray, polyacrylamide gel electrophoresis such as SDS-PAGE, surface plasmon resonance (SPR), Förster resonance energy transfer (FRET), Bioluminescence resonance energy transfer (BRET), chemiluminescence, fluorescent polarization, phosphorescence, mass spectrometry such as liquid chromatography mass spectrometry (LC-MS) or liquid chromatography/mass spectrometry/mass spectrometry (LC-MS-MS), matrix-assisted laser desorption/ionization time-of-flight (MALDI-TOF), surface-enhanced laser desorption/ionization time-of-flight (SELDI-TOF), and magnetic resonance imaging (MRI).

According to the different aspect and preferred embodiments of the present invention, the step of determining the expression level of a biomarker of interest preferably further comprises a substep of normalizing the expression level of said biomarker. The method for normalizing expression level can be selected based upon the method used for measuring expression level. For example, if a Western-blot is performed, the expression level of a biomarker of interest in a biological sample may be normalized by assessing in parallel in said sample the expression level of a protein which is usually constitutively expressed in any cell of a living organism, preferably at the same expression level whether the cell is healthy or not (e.g. cancerous or not). An example of constitutively expressed protein is a housekeeping protein, which may be selected, without limitation, among actin, beta-tubulin, and Glyceraldehyde 3-phosphate dehydrogenase (GAPDH), to name a few. Alternatively, if an ELISA is performed, involving for example a colorimetric detection method, protein expression level can be normalized by total cell number. Yet, still alternatively, if a microarray is performed, protein expression level can be normalized, for example, by loess-regression. For a detailed review of normalization methods of protein expression level in an antibody microarray, one skilled in the art may refer to Hamelinck et al. (2005).

All these methods for measuring and normalizing protein expression level are well-known to the skilled person, and thus do need not to be further detailed herein. Should the skilled person wish to use any of the above methods involving the use of an antibody to measure a biomarker protein expression level, one may use any appropriate commercial antibody specific for said biomarker. Alternatively, based on the knowledge of the amino-acid sequence of a biomarker of interest, it is easy to the skilled person to design suitable reagent(s) to measure expression level in any biological sample. For example, an antibody directed against a specific biomarker may be prepared by any conventional method, e.g. by immunizing an animal, such as a mouse, with an immunogenic form of said biomarker which elicits an antibody response in said animal. Methods for producing polyclonal and monoclonal antibodies are well described in the literature (see notably Kohler and Milstein, 1975; Kozbor et al., 1983; Roder et al., 1986; and Huse et al., 1986), and therefore need not be further detailed herein.

The comparison of a determined or tested expression level with a reference expression level can be done by merely calculating the ratio between the expression level of a biomarker of interest in the tested biological sample and in at least one reference sample, preferably after normalization as described above. Accordingly, a ratio above 1 is indicative that the biomarker is overexpressed, while a ratio below 1 is indicative that the biomarker is underexpressed (i.e. downregulated).

In another aspect of the present invention, the biomarkers disclosed herein can be used to determine if a patient will respond or not to a cancer therapy. Associating a patient's response to treatment with such biomarker(s) can indeed elucidate new opportunities for treatment in non-responding patients or indicate one treatment over other treatment choices.

Therefore, the present invention further provides an in vitro method for determining a drug-responding or non-responding phenotype in a subject suffering from a triple-negative breast cancer recurrence, comprising the steps of:
  a) determining from a biological sample of said subject the expression level of at least two biomarkers selected from the group consisting of Desmoplakin, Rho GTPase-activating protein 1, Epiplakin, Glucose-6-phosphate 1-dehydrogenase, Isocitrate dehydroge-nase [NADP], Keratin type I cytoskeletal 19, Keratin type I cytoskeletal 8, Dihydropyrimidinase-related protein 3, and Thrombospondin-1;
  b) comparing the expression level in step a) to a reference expression level of said biomarkers; and
  c) determining from said comparison the drug-responding or non-responding phenotype.

According to the present invention, a "drug-responding phenotype" refers to a response state of a subject to the administration of a drug. A "response state" means that said subject responds to the treatment, i.e. that said treatment is efficacious in said subject. A responding phenotype is thus characterized by an improvement in clinical signs, i.e. in the context of the present invention, a responding phenotype is characterized for example by a regression or disappearance of triple-negative breast cancer cells and metastases thereof, if any. A regression or disappearance of cancer cells may be primarily assessed by determining a tumor volume, such as by computed tomography (CT) imaging or magnetic resonance imaging (MRI). By contrast, a "drug-non responding phenotype" refers to the absence in said subject of a state response, meaning that said subject is refractory to the treatment.

In a preferred embodiment, the method as described above further comprises the step of determining from said sample the expression level of at least two biomarkers associated with TNBC non-recurrence as described above.

The skilled person would understand that more than two of the above mentioned biomarkers may be used as a panel of biomarkers, in order to contribute to the determination of a drug-responding or non-responding phenotype according to the method of the invention.

One skilled person would also understand from the data provided herein that the biomarkers listed in Tables 7A and/or 8A may further aid in this determination.

Accordingly, in a preferred embodiment, the method as described above further comprises the step of determining from said sample the expression level of at least one additional biomarker of Tables 7A and/or 8A, as described below.

In a further aspect of the present invention, the biomarkers disclosed herein can be used to design or adapt treatment against a triple-negative breast cancer (TNBC) recurrence. In particular, such treatment may be designed or adapted once a subject has been diagnosed as having a TNBC recurrence, according to the method of the invention.

Accordingly, the present invention provides herein a method for designing or adapting a treatment regimen for a subject suffering from a triple-negative breast cancer (TNBC) recurrence, comprising the steps of:
  a) determining from a biological sample of said subject a drug-responding or non-responding phenotype, according to the method described above; and
  b) designing or adapting a treatment regimen for said subject based upon said responding or non-responding phenotype.

The present method is particularly useful for offering a therapy tailored to each patient affected by a TNBC recurrence.

The term "treatment regimen" refers herein to a treatment plan that specifies the type of treatment (i.e. type of drug or combination of drugs and mode of administration of said drug(s)), dosage, schedule and/or duration of a treatment provided to a subject in need thereof. A dosage, schedule and/or duration of treatment can vary, depending on the progression of disease and the selected type of treatment. In this regard, in addition to the drugs that can be identified according to the screening method of the invention, therapeutic agents that may be used in the treatment regimen according to the invention include, without limitation, chemotherapeutic agents, vascular endothelial growth factor receptor (VEGFR) inhibitors such as bevacizumab, epidermal growth factor receptor (EGFR) inhibitors such as cetuximab and panitumumab, tyrosine kinase inhibitors, poly (ADP-ribose) polymerase (PARP) inhibitors, transmembrane glycoprotein NMB (GPNMB) inhibitors such as glembatumumab vedotin (CDX-011), and any combination thereof.

Standard chemotherapeutic drugs for treating breast cancer include, without limitation, platinum-based agents such as oxaliplatin, cisplatin, carboplatin, spiroplatin, iproplatin, and satraplatin; alkylating agents such as cyclophosphamide, ifosfamide, chlorambucil, busulfan, melphalan, mechlorethamine, uramustine, thiotepa, and nitrosoureas; anti-metabolites such as 5-fluorouracil, azathioprine, 6-mercaptopurine, methotrexate, leucovorin, capecitabine, cytarabine, floxuridine, fludarabine, gemcitabine, pemetrexed, or raltitrexed; plant alkaloids such as vincristine, vinblastine, vinorelbine, vindesine, podophyllotoxin, or taxanes such as paclitaxel and docetaxel; topoisomerase inhibitors such as irinotecan, topotecan, amsacrine, etoposide (VP16), etoposide phosphate, or teniposide; antitumor antibiotics such as anthracyclines (e.g. doxorubicin, daunorubicin, epirubicin, mitoxantrone), actinomycin, bleomycin, mitomycin, or plicamycin; and any combination thereof.

Examples of tyrosine kinase inhibitors that can be used in the treatment regimen according to the invention include, without limitation, dasatinib, gefitinib, sunitinib, erlotinib, lapatinib, canertinib, semaxinib, vatalanib, sorafenib, imatinib mesylate, leflunomide, vandetanib, pelitinib, CP-654577, CP-724714, HKI-272, PKI-166, AEE788, BMS-599626, HKI-357, BIBW 2992, ARRY-334543, JNJ-26483327, JNJ-26483327, and any combination thereof.

Examples of poly (ADP-ribose) polymerase (PARP) inhibitors that can be used in the treatment regimen according to the invention include, without limitation, olaparid (AZD-2281), iniparib (BSI-201), rucaparib (AG014699, PF-01367338), veliparib (ABT-888), CEP 9722, MK 4827, BMN-673, 3-aminobenzamide, and any combination thereof.

Particularly preferred treatment regimen according to the invention consists in the combination of three agents ("triplet therapy" or "triplet treatment regimen"). For example, three therapeutic agents of distinct categories may be combined, said agents being selected from a chemotherapeutic agent, a vascular endothelial growth factor receptor (VEGFR) inhibitor, an epidermal growth factor receptor (EGFR) inhibitor, a tyrosine kinase inhibitor, a poly (ADP-ribose) polymerase (PARP) inhibitor, and/or a transmembrane glycoprotein NMB (GPNMB) inhibitor, as defined above. Another example of a triplet therapy can include an inhibitor of a biomarker associated with TNBC recurrence along with two therapeutic agents of distinct categories as described above.

In the above method, the treatment regimen that is designed or adapted and optionally administered to the subject depends on the responding or non-responding phenotype. In particular, a treatment regimen may be selected for the first time, continued, adjusted or stopped based upon said phenotype. For example, a treatment regimen may be adjusted by increasing the dose to be administered, or stopped and switched to an alternative treatment regimen, if the subject is non-responding. Still, alternatively, a treatment regimen may be selected for the first time or continued if a subject is responding. One skilled in the art would nevertheless easily design or adjust the type of treatment with the dosage, schedule and duration of treatment, depending upon the phenotype of the subject.

Furthermore, based upon said phenotype, the selected treatment regimen can be an aggressive one which is expected to result in the best clinical outcome (e.g., regression and/or disappearance of triple-negative breast cancer cells and metastases thereof, if any) and which may be associated with some discomfort to the subject or adverse side effects (e.g., damage to healthy cells or tissue). An example of aggressive treatment regimen include a treatment regimen as described above combined with surgical intervention to remove tumoral cells, tissue or organs and/or an exposure to radiation therapy. An aggressive treatment regimen may also include a higher dosage of the therapeutic agent(s), a more frequent administration of said agent(s), and/or a longer duration of treatment.

Thus, once a treatment regimen has been determined in accordance with the teachings of the invention, the subject may receive the appropriate treatment.

Therefore, in another aspect, the invention relates to a method for treating a triple-negative breast cancer recurrence in a subject in need thereof, comprising the steps of:
 a) determining from a biological sample of said subject a drug-responding or non-responding phenotype, according to the method described above; and
 b) administering to said subject said drug if the phenotype is a responding phenotype.

The term "administering" as used herein means that the drug(s) of interest is delivered or dispensed to a subject orally, or parenterally such as by subcutaneous, intravenous, intramuscular, intrathecal or intraperitoneal injection.

In another aspect of the present invention, the biomarkers disclosed herein may be used for drug screening purposes. In particular, novel drug assays may be provided, which identify therapeutics efficiently interfering with the proliferation of triple-negative breast cancer cells that aberrantly express those biomarkers. Current treatment of triple-negative breast cancer (TNBC) mainly relies on chemotherapy and/or antiangiogenic drugs, which may be combined, if need be, with surgery. However, with chemotherapy alone, the residual risk of recurrence remains high, between 30 to 40%. Furthermore, as indicated above, endocrine and anti-HER2 therapy are usually not indicated for TNBC patients, as those are negative for the estrogen receptor (ER), progesterone receptor (PR) and human epidermal growth factor receptor 2 (HER2). The present invention thus provides a novel screening assay to identify candidate drugs that are targeted to triple-negative breast cancer recurrence.

In this aspect, the present invention more particularly relates to a screening method for identifying a drug or combination of drugs suitable for treating a triple-negative breast cancer recurrence, comprising the steps of:
 a) contacting isolated breast cancer cells or cell line displaying a triple-negative breast cancer recurrence phenotype with a candidate drug or combination of candidate drugs;
 b) determining, from said cells or cell line contacted with said drug or combination of drugs, the expression level of at least two biomarkers selected from the group consisting of Desmoplakin, Rho GTPase-activating protein 1, Epiplakin, Glucose-6-phosphate 1-dehydrogenase, Isocitrate dehydroge-nase [NADP], Keratin type I cytoskeletal 19, Keratin type I cytoskeletal 8, Dihydropyrimidinase-related protein 3, and Thrombospondin-1; and
 c) comparing the expression level of said biomarkers in step b) to their expression level in the absence of said drug or combination of drugs.

By "drug" or "agent", it is meant herein a compound such as chemical or a biological molecule that can be administered or tested according to the invention. A chemical can be of any composition such as inorganic or organic. A biological molecule can be a molecule of any biological origin that can be found in or produced by, at least in part, a cell, such as, without limitation, peptides or proteins such as antibodies or affibodies, lipids, nucleic acids such as RNAi or aptamers, carbohydrates, and any combination thereof.

By "drug suitable for treating a TNBC recurrence", it is meant herein a drug that can slow or stop the growth of triple-negative breast cancer cells and metastases thereof, if any, either by killing said cells, or by slowing or stopping their uncontrolled division.

Furthermore, it shall be understood that by "breast cancer cells or cell line displaying a TNBC recurrence phenotype" according to the invention, it is meant breast cancer cells or cell line that exhibit(s) the same expression profile of the biomarker(s) associated with triple-negative breast cancer recurrence as the one described above, such as the expression profile described in Table 7A. Preferably, the cells or cell line used in the present screening method are breast cancer cells or cell line isolated from a subject suffering from a triple-negative breast cancer recurrence.

The screening method described above is preferably an in vitro screening method. For example, the cells or cell line used in the present method can be cultured in a three-dimensional (3D) culture system, so as to mimic a TNBC tumor micro-environment. To do so, said cells can be embedded in an extracellular matrix (ECM) as described by Weigelt et al. (2008), Kenny et al. (2007) and Li et al. (2010).

In order to assess the efficacy of the candidate anti-cancer agent, said cells or cell line may, as an alternative or as a validation test, be grafted to an animal, such as a mouse. This procedure, also known as a xenograft, has successfully been used to assess the efficacy of metformin on TNBC mice xenografts (Liu et al., 2009). Should such xenograft be carried out, the screening method described above preferably further comprises the step of killing said animal.

In a preferred embodiment of the above method, an expression level of said biomarkers in step b) inferior to their expression level in the absence of said drug or combination of drugs is indicative that said drug or combination of drugs is suitable for treating a TNBC recurrence.

Preferably, an expression level of the nine biomarkers in step b) inferior to their expression level in the absence of said drug or combination of drugs is indicative that said drug or combination of drugs is suitable for treating a TNBC recurrence.

Yet, in a preferred embodiment, the screening method of the invention further comprises the step of determining, from said cells or cell line, the expression level of at least one additional biomarker of Table 7A as described below. One skilled in the art would readily understand from the data provided herein that the biomarkers listed in Table 7A may aid in the identification of a drug or combination of drugs suitable for treating a TNBC recurrence.

In another aspect, the present invention provides kits that can be employed in the methods described herein. In this regard, the invention relates to a kit for use in any method described above, comprising or consisting of:
a) a reagent capable of specifically determining the expression level of at least two biomarkers selected from the group consisting of Desmoplakin, Rho GTPase-activating protein 1, Epiplakin, Glucose-6-phosphate 1-dehydrogenase, Isocitrate dehydroge-nase [NADP], Keratin type I cytoskeletal 19, Keratin type I cytoskeletal 8, Dihydropyrimidinase-related protein 3, and Thrombospondin-1; and
b) instructions for performing said method.

As used herein, the term "instructions" refers to a publication, a recording, a diagram, or any other medium which can be used to communicate how to perform a method of the invention. Said instructions can, for example, be affixed to a container which contains said kit. Preferably, the instructions for using said kit include a reference expression level of said biomarkers.

The term "reagent capable of specifically determining the expression level" designates a reagent or a set of reagents which specifically recognizes given biomarker(s) and allows for the quantification for the expression level of said biomarker(s). These reagents can be for example antibodies, aptamers or affibodies specifically recognizing a biomarker. In the context of the present invention, such reagent is said to be "specific" for its target (i.e. biomarker) or "recognizes specifically" its target if it 1) exhibits a threshold level of binding activity, and/or 2) does not significantly cross-react with target molecules known to be related to the biomarker of interest. The binding affinity of such reagent can be easily determined by one skilled in the art, for example, by Scatchard analysis. Cross-reactivity of a reagent can as well be easily determined by one skilled in the art, and thus need to be further detailed herein. Examples of reagents capable of specifically determining the expression level of a biomarker include, without limitation, antibodies.

In a preferred embodiment, the kit of the invention may further comprise:
c) a reagent capable of specifically determining the expression level of at least two biomarkers associated with TNBC non-recurrence as described above.

Yet, in a further preferred embodiment, the kit of the invention further comprises a reagent capable of specifically determining the expression level of at least one additional biomarker of Table 7A and/or 8A, as further described below, and any combination thereof.

In order to normalize protein expression level, the kit of the invention may also optionally comprise a reagent capable of specifically determining the expression level of a housekeeping protein, such as actin, beta-tubulin, or Glyceraldehyde 3-phosphate dehydrogenase (GAPDH).

In yet another aspect, the methods of the invention can be practiced using a microarray, so as to notably determine the expression level of biomarkers of interest in the present invention.

The term "microarray" refers herein to a spatially defined and separated collection of individual biological molecules which are immobilized on a solid surface, and to which one or several biomarkers of interest specifically bind(s). Those biological molecules allow for the determination of the expression level of said biomarker(s), and may be antibodies, affibodies or aptamers if the microarray is a protein microarray, which is a preferred type of microarray according to the invention. Protein microarrays technologies are well-known to the skilled person, and are notably described in Mitchell (2002), Haab (2005), and Eckel-Passow et al. (2005), and in U.S. Pat. Nos. 6,087,102, 6,139,831, and 6,087,103. For determination of protein expression level of one or several biomarkers by using such array, two technologies can typically be used: 1) direct labeling, and 2) indirect labeling, as described for example by Kingsmore et al. (2006). In the "direct labeling" method, the protein of interest (i.e. biomarker of the invention, or target) obtained from a sample, such as a biological sample, is labeled with a specific marker (e.g. a fluorescent or a radioisotope marker), and subsequently hybridized to the microarray by specifically binding to a reagent recognizing said biomarker, said reagent being conjugated to the surface of the protein microarray. If the expression level of several biomarkers is to be assessed, each biomarker is labeled with a distinct marker. In the "indirect labeling" method, the sample containing the biomarker of interest is hybridized to the microarray by specifically binding to an unlabeled reagent recognizing said biomarker, said reagent being conjugated to the surface of the protein microarray, and a secondary labeled reagent, specifically recognizing as well said biomarker, is then added. The specificity and sensitivity of such indirect labeling method can further be enhanced by using a third labeled reagent, recognizing the secondary reagent (sandwich assay). Similarly, if the expression level of several biomarkers is to be assessed in the indirect labeling method, each secondary or third reagent is labeled with a distinct marker. Label-free systems may also be used to determine the expression level of a biomarker on a protein microarray; in such system, detection of the biomarker, and hence of its expression level, may be done by surface plasmon resonance (SPR), microcantilever biosensing, SELDI-TOF-MS, or atomic force microscopy (Chandra et al., 2011).

Therefore, the invention further relates herein to a protein microarray for use in any method described above, comprising or consisting of:
a) a reagent capable of specifically determining the expression level of at least two biomarkers selected from the group consisting of Desmoplakin, Rho GTPase-activating protein 1, Epiplakin, Glucose-6-phosphate 1-dehydrogenase, Isocitrate dehydroge-nase [NADP], Keratin type I cytoskeletal 19, Keratin type I cytoskeletal 8, Dihydropyrimidinase-related protein 3, and Thrombospondin-1.

In a preferred embodiment, the protein microarray of the invention may further comprise:

b) a reagent capable of specifically determining the expression level of at least two biomarkers associated with triple-negative breast cancer (TNBC) non-recurrence as described above.

Yet, in a further preferred embodiment, the microarray of the invention further comprises a reagent capable of specifically determining the expression level of at least one additional biomarker of Table 7A and/or 8A, as further described below, and any combination thereof.

In order to normalize protein expression level, the microarray of the invention may also optionally comprise a reagent capable of specifically determining the expression level of a housekeeping protein, such as actin, beta-tubulin, or Glyceraldehyde 3-phosphate dehydrogenase (GAPDH).

The present invention will be better understood in the light of the following detailed description of experiments, including examples. Nevertheless, the skilled artisan will appreciate that this detailed description is not limitative and that various modifications, substitutions, omissions, and changes may be made without departing from the scope of the invention.

EXAMPLES

Figure 1:
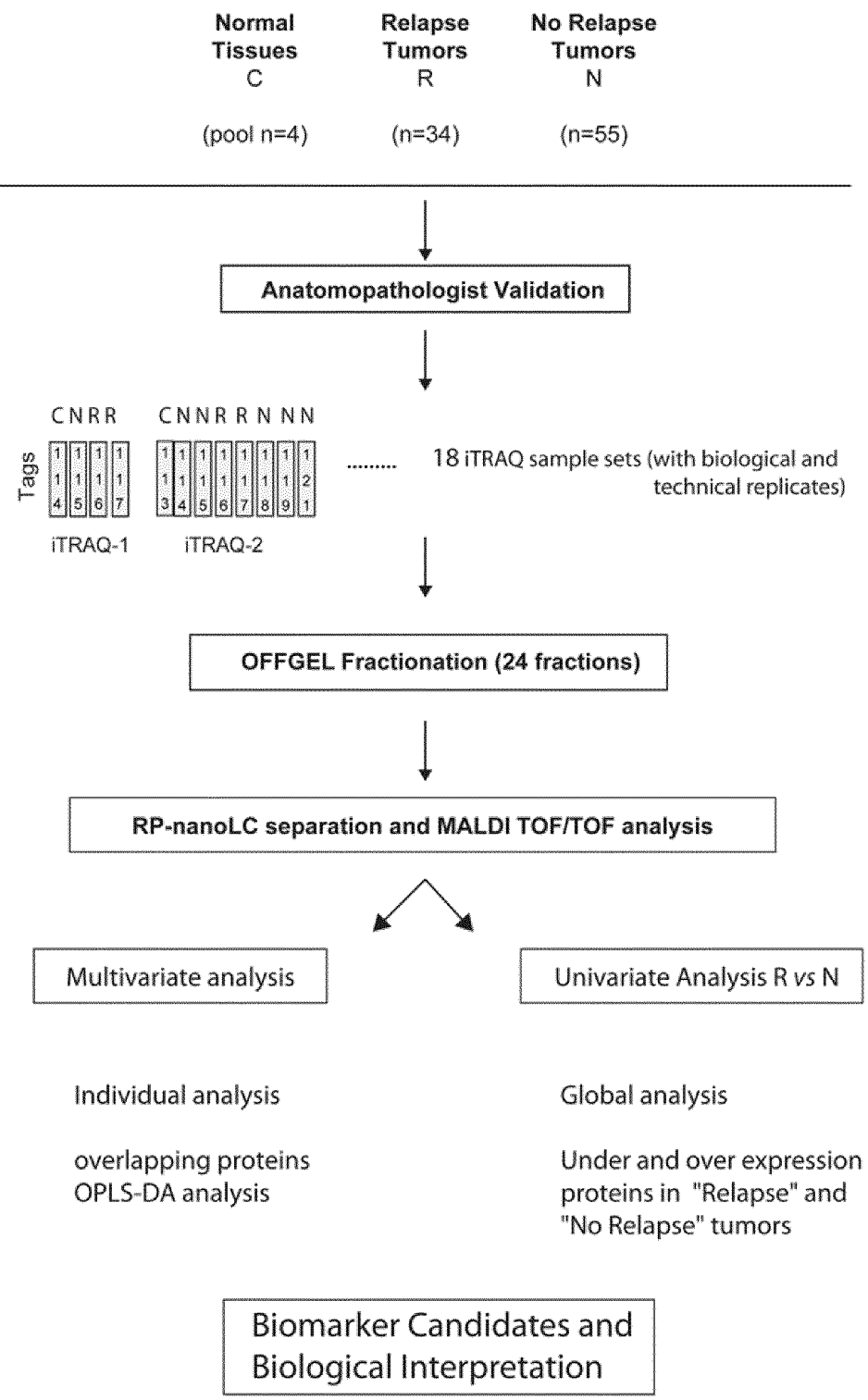
FIG. 1. Schematic workflow of experimental design and data analysis of the present invention.

1. Materials and Methods 1.1. Sample Collection

The inventors selected cases of triple negative breast tumors (TNBC) that were surgically resected with curative intent in the West Cancer Institute tumor bank. All patients provided informed consent for participation and this project was approved by the Institutional Review Board. All specimens were collected immediately after surgery, snap frozen and stored in liquid nitrogen until the time of analysis. We also selected 4 normal macroscopically areas for our control pool. Frozen sections (12 μm thick) of either TNBC or normal areas were cut on a cryostat (Bright Instrument Co Ltd, St Margarets Way, UK). Specific sections were stained with toluidine blue for visual reference and each tissue sections from all specimens were evaluated by experienced pathologists for cancer cell proportion determination. Samples containing less than 80% of tumor cells were removed. Clinical features of tissue candidates are summarized in Table 3 below.

TABLE 3

Clinico-pathological characteristics of patients for tissue proteomic studies

|  | Total (n = 80) | Non recurrence (n = 45) | Recurrence (n = 35) |
|---|---|---|---|
| Age |  |  |  |
| Median (range) | 56 (28-78) | 55 (28-78) | 58 (37-76) |
| Grade |  |  |  |
| 1 | 1 | 0 | 1 |
| 2 | 6 | 6 | 0 |
| 3 | 73 | 39 | 34 |
| pT |  |  |  |
| 08-11 | 6 | 5 | 1 |
| 12-15 | 23 | 16 | 7 |
| 16-19 | 11 | 7 | 4 |
| 20-23 | 15 | 10 | 5 |
| 24-27 | 6 | 4 | 2 |
| 28-31 | 5 | 2 | 3 |
| 32-35 | 6 | 4 | 2 |
| 36-70 | 7 | 3 | 4 |
| Adjuvant chemotherapy | 3 | 2 | 1 |
| Radiotherapy | 77 | 49 | 28 |

1.2. Protein Extraction from Frozen Tissues

Frozen sections (12 μm thick) of TNBC or normal breast area were cut on a cryostat (Bright Instrument Co Ltd, St Margarets Way, UK). Specific sections were stained with toluidine blue for visual reference. Ten frozen sections per tumor were lysed in a buffer consisting of 0.1 M Tris-HCl, pH 8.0, 0.1 M DTT, and 4% SDS at 95° C. for 90 min. Detergent was removed from the lysates and the proteins were digested with trypsin using the FASP protocol (Wisniewski et al., 2009) using spin ultrafiltration units of nominal molecular weight cut of 30 000. To YM-30 microcon filter units (Cat No. MRCF0R030, Millipore) containing protein concentrates, 200 μL of 8 M urea in 0.1 M Tris/HCl, pH 8.5 (UA), was added and samples were centrifuged at 14 000 g at 20 C for 8 min. This step was performed thrice. Then 6 μL of 200 mM MMTS in 8 M urea was added to the filters and the samples were incubated for 20 min. Filters were washed thrice with 200 μL of 8 M UA followed by six washes with 100 μL 0.5M TEAB. Finally, trypsin (AB sciex) was added in 100 μL 0.5M TEAB to each filter. The protein to enzyme ratio was 100:1. Samples were incubated overnight at 37° C. and released peptides were collected by centrifugation. Samples were then dried completely using a Speed-Vac and re-suspended in 100 μl of 0.5% trifluoroacetic acid (TFA) in 5% acetonitrile, and were desalted via PepClean C-18 spin columns (Pierce Biotechnology, Rockford, Ill.). Peptide content was determined using Micro BCA Protein Assay Kit (Pierce-Thermo Scientific, Rockford, Ill.).

1.3. Peptide Labelling with iTRAQ Reagents

Each peptide solution was labelled at room temperature for 2 h with one iTRAQ reagent vial previously reconstituted with 70 μl of ethanol for 4plex iTRAQ reagent and reconstituted with 50 μl of isopropanol for 8plex iTRAQ reagent. A mixture containing small aliquots from each labeled sample was analyzed by MS/MS to determine a proper mixing ratio to correct for unevenness in peptide yield from Liquid Tissues procedures. Labeled peptides were then mixed in 1:1:1:1 (or 1:1:1:1:1:1:1:1) ratio. Peptide mixture was then dried completely using a Speed-Vac.

1.4. Peptide OFFGEL Fractionation

For pI-based peptide separation, the inventors used the 3100 OFFGEL Fractionator (Agilent Technologies, Böblingen, Germany) with a 24-well set-up according to the protocol described by Ernoult et al. (2008). Briefly, prior to electrofocusing, samples were desalted onto a Sep-Pak C18 cartridge (Waters). For 24-well set-up, peptide samples were diluted to a final volume of respectively 3.6 mL using OFFGEL peptide sample solution. To start, the IPG gel strip of 24 cm-long (GE Healthcare, Munchen, Germany) with a 3-10 linear pH range was rehydrated with the Peptide IPG Strip Rehydradation Solution according to the protocol of the manufacturer for 15 min. Then, 150 µL of sample was loaded in each well. Electrofocusing of the peptides was performed at 20° C. and 50 µA until the 50 kVh level was reached. After focusing, the 24 peptide fractions were withdrawn and the wells were washed with 200 µL of a solution of water/methanol/formic acid (49/50/1). After 15 min, the washing solutions were pooled with their corresponding peptide fraction. All fractions were evaporated by centrifugation under vacuum and maintained at −20° C. Just prior nano-LC, the fractions were resuspended in 20 µL of $H_2O$ with 0.1% (v/v) TFA.

1.5. Capillary LC Separation

The samples were separated on an Ultimate 3,000 nano-LC system (Dionex, Sunnyvale, USA) using a C18 column (PepMap100, 3 µm, 100 A, 75 µm id×15 cm, Dionex) at 300 nL/min a flow rate. Buffer A was 2% ACN in water with 0.05% TFA and buffer B was 80% ACN in water with 0.04% TFA. Peptides were desalted for 3 min. using only buffer A on the precolumn, followed by a separation for 105 min. using the following gradient: 0 to 20% B in 10 min, 20% to 45% B in 85 min and 45% to 100% B in 10 min. Chromatograms were recorded at the wavelength of 214 nm. Peptide fractions were collected using a Probot microfraction collector (Dionex). We used CHCA (LaserBioLabs, Sophia-Antipolis, France) as MALDI matrix. The matrix (concentration of 2 mg/mL in 70% ACN in water with 0.1% TFA) was continuously added to the column effluent via a micro "T" mixing piece at 1.2 µL/min flow rate. After 12 min run, a start signal was sent to the Probot to initiate fractionation. Fractions were collected for 10 s and spotted on a MALDI sample plate (1,664 spots per plate, Applied Biosystems, Foster City, Calif.).

1.6. MALDI-MS/MS

MS and MS/MS analyses of off-line spotted peptide samples were performed using the 5800 MALDI-TOF/TOF Analyser (ABsciex) and 4000 Series Explorer software, version 4.0. The instrument was operated in a positive ion mode and externally calibrated using a mass calibration standard kit (ABsciex). The laser power was set between 2800 and 3400 for MS and between 3600 and 4200 for MS/MS acquisition. After screening all LC-MALDI sample positions in MS-positive reflector mode using 1500 laser shots, the fragmentation of automatically-selected precursors was performed at a collision energy of 1 kV using air as collision gas (pressure of ~2×10-6 Torr) with an accumulation of 2000 shots for each spectrum. MS spectra were acquired between m/z 1000 and 4000. For internal calibration, we used the parent ion of Glu1-fibrinopeptide at m/z 1570.677 diluted in the matrix (30 femtomoles per spot). Up to 12 of the most intense ion signals per spot position having a S/N>12 were selected as precursors for MS/MS acquisition. Peptide and protein identification were performed by the ProteinPilot™ Software V 4.0 (AB Sciex) using the Paragon algorithm as the search engine (Shilov et al., 2007).

Each MS/MS spectrum was searched for *Homo sapiens* specie against the Uniprot/swissprot database (UniProtKB/Sprot 20110208 release 01, with 525997 sequence entries). The searches were run using with the fixed modification of methylmethanethiosulfate labeled cysteine parameter enabled. Other parameters such as tryptic cleavage specificity, precursor ion mass accuracy and fragment ion mass accuracy are MALDI 5800 built-in functions of ProteinPilot software. The detected protein threshold (unused protscore (confidence)) in the software was set to 1.3 to achieve 95% confidence, and identified proteins were grouped by the ProGroup algorithm (ABsciex) to minimize redundancy. The bias correction option was executed.

A decoy database search strategy was also used to estimate the false discovery rate (FDR), defined as the percentage of decoy proteins identified against the total protein identification. The FDR was calculated by searching the spectral against the Uniprot *Homo sapiens* decoy database. The estimated low FDR of 0.9% indicated a high reliability in the identified proteins.

1.7. Quantification of Relative Protein Expression.

The inventors employed a customized software package, iQuantitator (Schwacke et al., 2009; Grant et al., 2009; and Besson et al., 2011) to infer the magnitude of change in protein expression. The software infers treatment-dependent changes in expression using Bayesian statistical methods. Basically, this approach was used to generate means, medians, and 95% credible intervals (upper and lower) for each treatment-dependent change in protein expression by using peptide-level data for each component peptide, and integrating data across the two experiments. For proteins whose iTRAQ ratios were downregulated in tissues, the extent of downregulation was considered further if the higher limit of the credible interval had a value lower than 1. Conversely, for proteins whose iTRAQ ratios were up-regulated in tumors, the extent of upregulation was considered further if the lower limit of the credible interval had a value greater than 1. The width of these credible intervals depends on the data available for a given protein. Since the number of peptides observed and the number of spectra used to quantify the change in expression for a given protein are taken into consideration, it is possible to detect small but significant changes in up- or downregulation when many peptides are available. For each protein, and each peptide associated with a given protein, the mean, median, and 95% credible intervals were computed for each of the protein- and peptide-level treatment effects.

The peptide selection criteria for relative quantification were performed as follows. Only peptides unique for a given protein were considered for relative quantification, excluding those common to other isoforms or proteins of the same family. Proteins were identified on the basis of having at least one peptide with an ion score above 95% confidence. The protein sequence coverage (95%) was estimated for specific proteins by the percentage of matching amino acids from the identified peptides having confidence greater than or equal to 95% divided by the total number of amino acids in the sequence.

1.8. Functional Annotation and Network Analysis

Gene ontology (GO) terms for identified proteins were extracted, and overrepresented functional categories for differentially abundant proteins were determined by the high throughput GOMiner tool (National Cancer Institute) (Zeeberg et al., 2005). All proteins that were subjected to iQuantitator analysis served as the background list, and GO terms with at least five proteins were used for statistical calculations. A p value for each term was calculated via the one-sided Fisher's exact test, and FDR was estimated by permutation analysis using 1000 randomly selected sets of proteins sampled from the background list. Statistically significant (FDR <25%) GO terms were clustered based on the correlation of associated proteins to minimize potential redundancy in significant GO terms.

1.9. Western Blot Analysis of Proteins in TNBC

Freezed tumors were mounted in OCT and cut with a cryostat (Starlet 2212). Forty 12 μm sections were then lysed in FASP buffer (4% SDS, 0.1 M Tris) for 90 min at 95° C., sonicated 3 times and centrifugated 10 min RT at 13200 rpm. Protein concentration was evaluated using Pierce BCA protein assay kit (Thermo scientific, #23225). Western blot on tumor lysates were performed as described previously (Besson et al., 2011). Briefly, 50 μg of tumor lysates were loaded on 12% polyacrylamide gel and then transferred onto PVDF membrane. After blocking with 5% BSA in TBS (0.1 M, pH 7.4), blots were incubated with the respective primary antibodies at 4° C. overnight (Thrombospondin-1: Abcam Ab1823 1/500, 10 kDa heat shock protein: Abcam Ab108600 1/10000, Tryptophanyl-tRNA synthetase: Abcam Ab 92733 1/10000). The protein abundance of Hsc70 was used as a control for protein loading and was determined with mouse anti Hsc from Santa Cruz sc-7278 1/500 2 h at room temperature. The membranes were incubated with the respective secondary antibody, horseradish peroxidase-conjugated rabbit anti-IgG (goat anti-rabbit IgG-HRP sc-2004, 1:4000; Santa Cruz Biotechnology Inc.) or horseradish peroxidase-conjugated mouse anti-IgG (goat anti-mouse IgG-HRP, sc-2005, 1:4000; Santa Cruz Biotechnology Inc.), for 45 min at room temperature. After each step, blots were washed three times with 0.05% Tween, TBS. The membrane was probed with the indicated antibodies and developed with the ECL on a Chemidoc System (Bio-Rad).

1.10. ELISA (Enzyme-Linked Immunosorbent Assay)

Commercially available ELISA kits from USCN Life Science Inc. or R&D were used to assay concentrations of Decorin, Asporin and Thrombospondin-1. The kits consisted of 96-well microtiter plates coated with antibody specific to each type of molecule, detection antibodies for identifying the antibody-protein in the plate by streptavidin-biotin labeling and TMB substrate which generated colored product. The sample was added and assay was conducted according to the manufacturer's instruction. The absorbance of the colored product developed at the end of the assay was quantified at wavelength 450 nm on ELISA reader (Tecan Magellan Sunrise). Dilutions of the serums are indicated in Table 4 below.

TABLE 4

| Proteins | Supplier | Reference | serum dilution |
| --- | --- | --- | --- |
| DECORIN | USCN Life Science Inc. | E92127Hu | 1/5 in PBS |
| ASPORIN | USCN Life Science Inc. | E92321Hu | 1/5 in PBS |
| THROMBOSPONDIN-1 | R&D Systems | Quantikine DTSP10 | 1/100 in RD5-33 1X (supplied by Manufacturer) |

2. Results 2.1. Identification of Expressed Proteins: Proteomic Coverage of 80 Triple-Negative Breast Tumors Using Protein Pilot and iQuantitator softwares, the inventors identified and quantified a total of 2805 non-redundant proteins with at least 2 peptides, according the schematic workflow of experimental design in FIG. 1. By taking into consideration both the peptide and spectra numbers, this approach allowed us to detect small but significant expression changes, provided that several peptides are detected (data not shown). Using this analysis, the inventors were able to obtain a list of quantified proteins from the twenty iTRAQ experiments. Examining these proteins with the function "Enrichment of protein function" of Metacore (Table 5A), the inventors characterized among all the proteins, 690 enzymes, 58 phosphatases, 122 proteases, 105 kinases, 73 ligands, 82 transcription factors and 83 receptors. This analysis showed that the best enrichment score and p-value were assigned to the GO Process "Metabolic Process" (Table 5B) and to the Pathway maps "Cytoskeleton Remodeling" (Table 5C).

TABLE 5A

Enrichment by protein function

| Protein class | Actual | n | R | N | Expected | Ratio | p-value | z-score | Percentage | | |
| --- | --- | --- | --- | --- | --- | --- | --- | --- | --- | --- | --- |
| | | | | | | | | | In data set | In protein function | Protein function in database |
| Enzymes | 690 | 3099 | 2724 | 23844 | 354 | 1.949 | 8.622E−78 | 20.34 | 22.27% | 25.33% | 11.42% |
| Phosphatases | 58 | 3099 | 230 | 23844 | 29.89 | 1.94 | 3.724E−07 | 5.538 | 1.87% | 25.22% | 0.96% |
| Proteases | 122 | 3099 | 559 | 23844 | 72.65 | 1.679 | 3.748E−09 | 6.281 | 3.94% | 21.82% | 2.34% |
| Kinases | 105 | 3099 | 654 | 23844 | 85 | 1.235 | 1.234E−02 | 2.358 | 3.39% | 16.06% | 2.74% |
| Ligands | 73 | 3099 | 514 | 23844 | 66.8 | 1.093 | 2.230E−01 | 0.8215 | 2.36% | 14.20% | 2.16% |
| Transcription factors | 82 | 3099 | 959 | 23844 | 124.6 | 0.6579 | 7.007E−06 | −4.18 | 2.65% | 8.55% | 4.02% |
| Receptors | 83 | 3099 | 1565 | 23844 | 203.4 | 0.4081 | 2.446E−25 | −9.363 | 2.68% | 5.30% | 6.56% |
| Other | 1891 | 3099 | 16691 | 23844 | 2169 | 0.8717 | 1.285E−30 | −11.7 | 61.02% | 11.33% | 70.00% |

Columns have the following meaning:
Protein class: a broadly defined protein function;
Actual: number of network objects from the activated dataset(s) for a given protein class;
n: number of network objects in the activated dataset(s);
R: number of network objects of a given protein class in the complete database or background list;
N: total number of network objects in the complete database or background list;
Expected: mean value for hypergeometric distribution (n*R/N);
Ratio: connectivity ratio (Actual/Expected);
z-score: z-score ((Actual-Expected)/sqrt(variance));
p-value: probability to have the given value of Actual or higher (or lower for negative z-score);
In data set: fraction of network objects with a selected function in the activated dataset;
In protein function: fraction of network with a selected function in the activated dataset among; network objects with this function in the complete database or background list;
Protein function in database: fraction of network objects with a selected function in the complete database or background list.

TABLE 5B

| Pathway maps | | |
|---|---|---|
| Pathway maps | p-Value | ratio |
| 1 Cytoskeleton remodeling_Cytoskeleton remodeling | 1.008e−20 | 55/102 |
| 2 Cytoskeleton remodeling_Keratin filaments | 5.196e−16 | 27/36 |
| 3 LRRK2 in neurons in Parkinson's disease | 4.337e−15 | 25/33 |
| 4 Cytoskeleton remodeling_TGF, WNT and cytoskeletal remodeling | 8.787e−15 | 50/111 |
| 5 Cytoskeleton remodeling_Regulation of actin cytoskeleton by Rho GTPases | 1.902e−14 | 20/23 |
| 6 Cell adhesion_Integrin-mediated cell adhesion and migration | 2.581e−12 | 28/48 |
| 7 Cell adhesion_Chemokines and adhesion | 9.170e−11 | 41/100 |
| 8 Apoptosis and survival_Granzyme A signaling | 1.152e−10 | 20/30 |
| 9 Transport_Clathrin-coated vesicle cycle | 1.174e−10 | 33/71 |
| 10 Immune response_Alternative complement pathway | 1.760e−10 | 23/39 |

TABLE 5C

| Gene Ontology (GO) process | | | |
|---|---|---|---|
| | Processes | p-Value | ratio |
| 1 | metabolic process | 7.084e−193 | 2305/10691 |
| 2 | cellular metabolic process | 4.692e−171 | 2079/9418 |
| 3 | primary metabolic process | 1.426e−158 | 2081/9619 |
| 4 | cellular process | 6.761e−152 | 2875/15962 |
| 5 | catabolic process | 5.562e−151 | 790/2270 |
| 6 | small molecule metabolic process | 1.146e−145 | 910/2880 |
| 7 | cellular catabolic process | 2.285e−142 | 695/1910 |
| 8 | cellular component organization or biogenesis | 1.902e−139 | 1255/4755 |
| 9 | cellular component organization or biogenesis at cellular level | 1.762e−131 | 1090/3947 |
| 10 | cellular component organization | 2.660e−129 | 1204/4596 |

Among these 2805 proteins, 219 proteins met the inventors' definition for differential expression in a comparison between tumor and normal tissues: 126 were overexpressed and 93 were underexpressed (Table 6A). The inventors subjected the 219 identified proteins that were differentially expressed in triple-negative breast tumors to Metacore analysis and categorized them, in a first time, according to molecular function and biological process. When the inventors analyzed the dysregulated proteins for molecular function, they found that the best enrichment score and p-Value were assigned to the GO terms Protein binding, MHC class I receptor activity and GTPase activity ($p=2.0 \cdot 10^{-13}$), which included 7 members RAS oncogen family (Table 6B). When the inventors grouped dysregulated proteins based on biological processes, they found that the best GO term score was obtained with cytoskeleton organization ($p=9.2 \cdot 10^{-16}$) (Table 6C). Finally, when the inventors analyzed the enrichment of protein function of these dysregulated proteins, they found that the first class with the best z-score was "ligands" with 14 proteins, indicating potentially biomarker candidates (Table 6D).

TABLE 6A

Proteins underexpressed and overexpressed in triple-negative breast cancer

| Gene | Protein | Mean | confidence intervals min | max | Peptide number |
|---|---|---|---|---|---|
| EEF1A1 | Elongation factor 1-alpha 1 | 3.325 | 2.191 | 5.243 | 12 |
| HLA-A | HLA class I histocompatibility antigen. A-33 alpha chain | 2.594 | 1.935 | 3.498 | 4 |
| KRT8 | Keratin type II cytoskeletal 8 | 2.698 | 1.747 | 4.278 | 14 |
| MAPK13 | Mitogen-activated protein kinase 13 | 2.9 | 1.601 | 5.366 | 2 |
| TUBA1C | Tubulin alpha-1C chain | 3.593 | 1.537 | 8.237 | 5 |
| NME1 | Nucleoside diphosphate kinase A | 2.045 | 1.462 | 2.906 | 6 |
| YBX1 | Nuclease-sensitive element-binding protein 1 | 1.955 | 1.395 | 2.714 | 6 |
| HSPA8 | Heat shock cognate 71 kDa protein | 5.889 | 1.372 | 31.395 | 27 |
| ITGAM | Integrin alpha-M | 2.086 | 1.357 | 3.218 | 5 |
| TPM3 | Tropomyosin alpha-3 chain | 1.886 | 1.345 | 2.686 | 8 |
| NAMPT | Nicotinamide phosphoribosyltransferase | 1.992 | 1.341 | 3.104 | 12 |
| NME2 | Nucleoside diphosphate kinase B | 1.791 | 1.326 | 2.442 | 11 |
| RAB5A | Ras-related protein Rab-5A | 2.095 | 1.312 | 3.464 | 4 |
| USP15 | Ubiquitin carboxyl-terminal hydrolase 15 | 1.887 | 1.31 | 2.744 | 5 |
| KHDRBS1 | KH domain-containing. RNA-binding. signal transduction-associated protein 1 | 2.265 | 1.288 | 4.013 | 3 |
| STK3 | Serine/threonine-protein kinase 3 | 1.725 | 1.264 | 2.336 | 3 |
| DPYSL3 | Dihydropyrimidinase-related protein 3 | 2.215 | 1.26 | 4.311 | 12 |
| HSP90AB1 | Heat shock protein HSP 90-beta | 1.878 | 1.259 | 2.76 | 26 |
| SDR16C5 | Epidermal retinol dehydrogenase 2 | 1.943 | 1.248 | 3.029 | 4 |
| DSP | Desmoplakin | 2.119 | 1.247 | 4.138 | 27 |
| THBS1 | Thrombospondin-1 | 1.682 | 1.243 | 2.342 | 25 |
| SNRPB | Small nuclear ribonucleoprotein-associated proteins B and B' | 1.748 | 1.236 | 2.519 | 10 |
| S100A8 | Protein S100-A8 | 1.652 | 1.222 | 2.268 | 10 |
| TUBA1B | Tubulin alpha-1B chain | 2.971 | 1.221 | 7.506 | 4 |
| AP1M1 | AP-1 complex subunit mu-1 | 1.869 | 1.215 | 2.927 | 3 |
| GSTM1 | Glutathione S-transferase Mu 1 | 2.161 | 1.214 | 3.872 | 2 |
| ACTG1 | Actin. cytoplasmic 2 | 1.666 | 1.206 | 2.342 | 8 |
| THBS2 | Thrombospondin-2 | 1.802 | 1.188 | 2.753 | 10 |
| XRCC6 | X-ray repair cross-complementing protein 6 | 1.605 | 1.186 | 2.166 | 22 |
| GGH | Gamma-glutamyl hydrolase | 2.392 | 1.186 | 5.251 | 3 |
| SORD | Sorbitol dehydrogenase | 1.763 | 1.182 | 2.657 | 7 |
| NA | Small nuclear ribonucleoprotein G-like protein | 1.759 | 1.181 | 2.659 | 2 |
| IGLC2 | Ig lambda-2 chain C regions | 1.601 | 1.177 | 2.151 | 5 |
| HLA-B | HLA class I histocompatibility antigen. B-14 alpha chain | 1.55 | 1.174 | 2.05 | 3 |
| MSN | Moesin | 1.514 | 1.172 | 1.974 | 36 |
| MYO6 | Myosin-VI | 1.62 | 1.17 | 2.26 | 9 |
| TNC | Tenascin | 1.616 | 1.164 | 2.242 | 44 |
| AP1B1 | AP-1 complex subunit beta-1 | 1.676 | 1.155 | 2.446 | 10 |
| XYLT2 | Xylosyltransferase 2 | 2.337 | 1.153 | 4.893 | 2 |
| H2AFV | Histone H2A.V | 1.987 | 1.15 | 3.472 | 2 |
| COTL1 | Coactosin-like protein | 1.703 | 1.147 | 2.54 | 6 |
| ENAH | Protein enabled homolog | 1.693 | 1.146 | 2.496 | 4 |
| AKR7A3 | Aflatoxin B1 aldehyde reductase member 3 | 1.832 | 1.146 | 2.934 | 2 |
| CAMK2D | Calcium/calmodulin-dependent protein kinase type II subunit delta | 1.793 | 1.144 | 2.84 | 4 |
| DBI | Acyl-CoA-binding protein | 1.606 | 1.143 | 2.29 | 7 |
| LRRC59 | Leucine-rich repeat-containing protein 59 | 1.717 | 1.141 | 2.559 | 7 |
| SMARCA5 | SWI/SNF-related matrix-associated actin-dependent regulator of chromatin subfamily A member 5 | 1.544 | 1.14 | 2.087 | 13 |
| CFL1 | Cofilin-1 | 1.569 | 1.136 | 2.194 | 18 |
| GUSB | Beta-glucuronidase | 1.59 | 1.135 | 2.215 | 21 |
| XRCC5 | X-ray repair cross-complementing protein 5 | 1.533 | 1.133 | 2.06 | 24 |
| PSME1 | Proteasome activator complex subunit 1 | 1.536 | 1.124 | 2.079 | 11 |
| CFL2 | Cofilin-2 | 1.713 | 1.124 | 2.63 | 2 |
| TUBB | Tubulin beta chain | 1.481 | 1.118 | 1.973 | 15 |
| NDRG1 | Protein NDRG1 | 1.554 | 1.117 | 2.159 | 6 |
| HYOU1 | Hypoxia up-regulated protein 1 | 2.287 | 1.117 | 5.424 | 21 |
| ARF4 | ADP-ribosylation factor 4 | 1.606 | 1.114 | 2.333 | 6 |
| TOP2B | DNA topoisomerase 2-beta | 1.566 | 1.11 | 2.232 | 6 |
| CRABP2 | Cellular retinoic acid-binding protein 2 | 1.617 | 1.11 | 2.408 | 8 |
| PPP4R1 | Serine/threonine-protein phosphatase 4 regulatory subunit 1 | 1.677 | 1.108 | 2.532 | 3 |
| FABP7 | Fatty acid-binding protein. brain | 2.98 | 1.106 | 10.019 | 6 |
| SET | Protein SET | 1.596 | 1.105 | 2.318 | 7 |
| TM9SF3 | Transmembrane 9 superfamily member 3 | 1.66 | 1.105 | 2.49 | 6 |
| SARS | Seryl-tRNA synthetase. cytoplasmic | 1.519 | 1.103 | 2.092 | 12 |
| DSTN | Destrin | 1.978 | 1.101 | 3.997 | 6 |
| COPA | Coatomer subunit alpha | 1.496 | 1.095 | 2.068 | 31 |
| PRKCSH | Glucosidase 2 subunit beta | 1.603 | 1.095 | 2.324 | 15 |

TABLE 6A-continued

Proteins underexpressed and overexpressed in triple-negative breast cancer

| Gene | Protein | Mean | confidence intervals min | max | Peptide number |
|---|---|---|---|---|---|
| UAP1L1 | UDP-N-acetylhexosamine pyrophosphorylase-like protein 1 | 1.461 | 1.094 | 1.946 | 4 |
| ARF1 | ADP-ribosylation factor 1 | 1.624 | 1.092 | 2.396 | 5 |
| EHD1 | EH domain-containing protein 1 | 1.883 | 1.091 | 3.34 | 6 |
| GBP1 | Interferon-induced guanylate-binding protein 1 | 1.753 | 1.089 | 2.823 | 8 |
| TPM1 | Tropomyosin alpha-1 chain | 1.516 | 1.086 | 2.14 | 14 |
| NA | Ig kappa chain V-III region HAH | 1.666 | 1.084 | 2.577 | 4 |
| PPP2R4 | Serine/threonine-protein phosphatase 2A activator | 1.64 | 1.08 | 2.468 | 3 |
| RAB1A | Ras-related protein Rab-1A | 1.418 | 1.078 | 1.872 | 6 |
| GSTO1 | Glutathione S-transferase omega-1 | 1.586 | 1.076 | 2.316 | 7 |
| EML4 | Echinoderm microtubule-associated protein-like 4 | 1.8 | 1.075 | 3.045 | 8 |
| PLIN2 | Perilipin-2 | 1.774 | 1.074 | 2.931 | 4 |
| DDT | D-dopachrome decarboxylase | 1.504 | 1.072 | 2.129 | 5 |
| RAB11A | Ras-related protein Rab-11A | 1.542 | 1.072 | 2.259 | 2 |
| ERH | Enhancer of rudimentary homolog | 1.828 | 1.072 | 3.166 | 2 |
| CLIC4 | Chloride intracellular channel protein 4 | 1.803 | 1.07 | 3.033 | 3 |
| MCM6 | DNA replication licensing factor MCM6 | 1.498 | 1.065 | 2.126 | 7 |
| MAPRE1 | Microtubule-associated protein RP/EB family member 1 | 1.575 | 1.06 | 2.362 | 5 |
| DLD | Dihydrolipoyl dehydrogenase. mitochondrial | 1.887 | 1.059 | 3.951 | 8 |
| NONO | Non-P | 1.5 | 1.057 | 2.099 | 24 |
| S100A11 | Protein S100-A11 | 1.613 | 1.057 | 2.465 | 4 |
| SAR1A | GTP-binding protein SAR1a | 1.529 | 1.054 | 2.235 | 6 |
| EPPK1 | Epiplakin | 1.423 | 1.052 | 1.921 | 14 |
| MYL12B | Myosin regulatory light chain 12B | 1.579 | 1.052 | 2.347 | 7 |
| FTL | Ferritin light chain | 1.743 | 1.051 | 3.054 | 9 |
| SEC14L2 | SEC14-like protein 2 | 1.603 | 1.048 | 2.499 | 5 |
| FKBP4 | Peptidyl-prolyl cis-trans isomerase FKBP4 | 1.46 | 1.045 | 2.025 | 18 |
| ACSL3 | Long-chain-fatty-acid--CoA ligase 3 | 1.38 | 1.044 | 1.838 | 12 |
| MACF1 | Microtubule-actin cross-linking factor 1. isoforms 1/2/3/5 | 1.539 | 1.044 | 2.276 | 5 |
| CALR | Calreticulin | 1.539 | 1.04 | 2.334 | 21 |
| C22 | UPF0027 protein C22orf28 | 1.336 | 1.036 | 1.72 | 10 |
| RAP1B | Ras-related protein Rap-1b | 1.496 | 1.035 | 2.158 | 7 |
| ALDOA | Fructose-bisphosphate aldolase A | 1.37 | 1.033 | 1.816 | 19 |
| PRCC | Proline-rich protein PRCC | 1.747 | 1.032 | 2.985 | 2 |
| NAPA | Alpha-soluble NSF attachment protein | 1.585 | 1.029 | 2.451 | 5 |
| PRKDC | DNA-dependent protein kinase catalytic subunit | 1.276 | 1.027 | 1.587 | 55 |
| ERO1L | ER | 1.571 | 1.027 | 2.441 | 6 |
| BAZ1B | Tyrosine-protein kinase BAZ1B | 1.558 | 1.026 | 2.371 | 5 |
| RAD23B | UV excision repair protein RAD23 homolog B | 1.389 | 1.025 | 1.88 | 7 |
| ISYNA1 | Inositol-3-phosphate synthase 1 | 1.631 | 1.025 | 2.6 | 3 |
| ACTN1 | Alpha-actinin-1 | 2.196 | 1.025 | 4.273 | 25 |
| FBL | rRNA 2'- | 1.365 | 1.023 | 1.846 | 12 |
| KRT18 | Keratin. type I cytoskeletal 18 | 2.377 | 1.023 | 5.583 | 5 |
| NCF4 | Neutrophil cytosol factor 4 | 1.687 | 1.021 | 2.871 | 4 |
| YWHAZ | 14-3-3 protein zeta/delta | 1.388 | 1.02 | 1.892 | 13 |
| ECM29 | Proteasome-associated protein ECM29 homolog | 1.477 | 1.02 | 2.169 | 5 |
| ACTR2 | Actin-related protein 2 | 1.439 | 1.019 | 2.037 | 13 |
| RPLP0 | 60S acidic ribosomal protein P0 | 1.527 | 1.018 | 2.353 | 7 |
| RANBP1 | Ran-specific GTPase-activating protein | 1.554 | 1.017 | 2.403 | 6 |
| GFPT1 | Glucosamine--fructose-6-phosphate aminotransferase [isomerizing] 1 | 1.526 | 1.016 | 2.308 | 9 |
| PAICS | Multifunctional protein ADE2 | 1.43 | 1.015 | 1.996 | 12 |
| RAN | GTP-binding nuclear protein Ran | 1.345 | 1.01 | 1.77 | 14 |
| CALD1 | Caldesmon | 1.434 | 1.009 | 2.039 | 13 |
| CTSB | Cathepsin B | 1.481 | 1.009 | 2.181 | 7 |
| IMPDH2 | Inosine-5'-monophosphate dehydrogenase 2 | 1.444 | 1.008 | 2.09 | 8 |
| KPNA2 | Importin subunit alpha-2 | 2.048 | 1.007 | 3.91 | 5 |
| RUVBL2 | RuvB-like 2 | 1.345 | 1.006 | 1.801 | 15 |
| CMPK1 | UMP-CMP kinase | 1.332 | 1.005 | 1.758 | 8 |
| KRT6A | Keratin. type II cytoskeletal 6A | 1.644 | 1.005 | 2.705 | 3 |
| HTATIP2 | Oxidoreductase HTATIP2 | 1.927 | 1.005 | 3.78 | 2 |
| KRT19 | Keratin type I cytoskeletal 19 | 2.235 | 1.005 | 4.978 | 8 |
| ALDH1A1 | Retinal dehydrogenase 1 | 0.717 | 0.53 | 0.971 | 11 |
| MYO1C | Myosin-Ic | 0.67 | 0.527 | 0.849 | 18 |
| UAP1 | UDP-N-acetylhexosamine pyrophosphorylase | 0.701 | 0.526 | 0.934 | 5 |
| CFH | Complement factor H | 0.693 | 0.518 | 0.935 | 23 |
| KIAA1967 | Protein KIAA1967 | 0.677 | 0.498 | 0.909 | 8 |
| KRT5 | Keratin. type II cytoskeletal 5 | 0.66 | 0.495 | 0.875 | 22 |
| CTNNB1 | Catenin beta-1 | 0.66 | 0.483 | 0.902 | 10 |
| ALDH6A1 | Methylmalonate-semialdehyde dehydrogenase [acylating]. mitochondrial | 0.686 | 0.48 | 0.977 | 7 |
| EIF2C1 | Protein argonaute-1 | 0.686 | 0.478 | 0.983 | 2 |

TABLE 6A-continued

Proteins underexpressed and overexpressed in triple-negative breast cancer

| Gene | Protein | Mean | confidence intervals min | max | Peptide number |
|---|---|---|---|---|---|
| PPP3CB | Serine/threonine-protein phosphatase 2B catalytic subunit beta isoform | 0.687 | 0.469 | 0.999 | 2 |
| KRT10 | Keratin. type I cytoskeletal 10 | 0.656 | 0.466 | 0.927 | 14 |
| S100A10 | Protein S100-A10 | 0.645 | 0.461 | 0.912 | 8 |
| AHNAK | Neuroblast differentiation-associated protein AHNAK | 0.606 | 0.453 | 0.817 | 96 |
| TINAGL1 | Tubulointerstitial nephritis antigen-like | 0.673 | 0.452 | 0.982 | 6 |
| ITGB4 | Integrin beta-4 | 0.594 | 0.45 | 0.781 | 17 |
| F2 | Prothrombin | 0.602 | 0.448 | 0.817 | 18 |
| APOA1 | Apolipoprotein A-I | 0.602 | 0.439 | 0.831 | 23 |
| HLA-C | HLA class I histocompatibility antigen. Cw-15 alpha chain | 0.571 | 0.424 | 0.77 | 5 |
| SERPINF1 | Pigment epithelium-derived factor | 0.563 | 0.41 | 0.772 | 8 |
| PCOLCE | Procollagen C-endopeptidase enhancer 1 | 0.597 | 0.408 | 0.86 | 7 |
| USP11 | Ubiquitin carboxyl-terminal hydrolase 11 | 0.593 | 0.406 | 0.857 | 5 |
| RAB5B | Ras-related protein Rab-5B | 0.618 | 0.398 | 0.949 | 4 |
| HDAC1 | Histone deacetylase 1 | 0.591 | 0.394 | 0.883 | 5 |
| CAV1 | Caveolin-1 | 0.623 | 0.392 | 0.991 | 3 |
| PYCRL | Pyrroline-5-carboxylate reductase 3 | 0.613 | 0.384 | 0.976 | 4 |
| EHD2 | EH domain-containing protein 2 | 0.613 | 0.384 | 0.985 | 9 |
| APOH | Beta-2-glycoprotein 1 | 0.602 | 0.382 | 0.951 | 9 |
| HIST1H2BK | Histone H2B type 1-K | 0.546 | 0.374 | 0.812 | 7 |
| GNB1 | Guanine nucleotide-binding protein G(I)/G(S)/G(T) subunit beta-1 | 0.603 | 0.373 | 0.952 | 2 |
| KRT16 | Keratin. type I cytoskeletal 16 | 0.566 | 0.372 | 0.855 | 3 |
| UROS | Uroporphyrinogen-III synthase | 0.568 | 0.37 | 0.865 | 4 |
| AMBP | Protein AMBP | 0.528 | 0.368 | 0.75 | 6 |
| LRG1 | Leucine-rich alpha-2-glycoprotein | 0.587 | 0.362 | 0.939 | 3 |
| CP | Ceruloplasmin | 0.493 | 0.36 | 0.69 | 13 |
| SERPINA4 | Kallistatin | 0.579 | 0.359 | 0.922 | 4 |
| LIPE | Hormone-sensitive lipase | 0.59 | 0.358 | 0.977 | 3 |
| METTL7B | Methyltransferase-like protein 7B | 0.587 | 0.357 | 0.959 | 3 |
| NES | Nestin | 0.508 | 0.354 | 0.73 | 14 |
| RAB5C | Ras-related protein Rab-5C | 0.527 | 0.354 | 0.781 | 5 |
| HLA-A | HLA class I histocompatibility antigen. A-2 alpha chain | 0.572 | 0.354 | 0.921 | 2 |
| LMO7 | LIM domain only protein 7 | 0.558 | 0.35 | 0.883 | 6 |
| CSNK1A1 | Casein kinase I isoform alpha | 0.596 | 0.35 | 0.989 | 2 |
| WDR36 | WD repeat-containing protein 36 | 0.581 | 0.344 | 0.963 | 3 |
| SFRP1 | Secreted frizzled-related protein 1 | 0.523 | 0.333 | 0.82 | 4 |
| CBX5 | Chromobox protein homolog 5 | 0.552 | 0.332 | 0.919 | 2 |
| AFM | Afamin | 0.532 | 0.33 | 0.863 | 5 |
| KNG1 | Kininogen-1 | 0.514 | 0.327 | 0.822 | 10 |
| APOA2 | Apolipoprotein A-II | 0.556 | 0.313 | 0.974 | 3 |
| GSTM3 | Glutathione S-transferase Mu 3 | 0.523 | 0.312 | 0.867 | 3 |
| PCCB | Propionyl-CoA carboxylase beta chain. mitochondrial | 0.528 | 0.309 | 0.904 | 2 |
| ACOT2 | Acyl-coenzyme A thioesterase 2. mitochondrial | 0.494 | 0.308 | 0.773 | 3 |
| LBP | Lipopolysaccharide-binding protein | 0.52 | 0.303 | 0.89 | 3 |
| APOA4 | Apolipoprotein A-IV | 0.458 | 0.302 | 0.687 | 9 |
| ABI3BP | Target of Nesh-SH3 | 0.508 | 0.295 | 0.869 | 4 |
| PLIN1 | Perilipin-1 | 0.437 | 0.293 | 0.659 | 8 |
| CAST | Calpastatin | 0.496 | 0.29 | 0.823 | 5 |
| TNXB | Tenascin-X | 0.448 | 0.286 | 0.696 | 8 |
| ORM1 | Alpha-1-acid glycoprotein 1 | 0.446 | 0.281 | 0.715 | 7 |
| HIST2H2AC | Histone H2A type 2-C | 0.391 | 0.279 | 0.546 | 4 |
| OLFML3 | Olfactomedin-like 3 | 0.437 | 0.278 | 0.68 | 4 |
| CLEC3B | Tetranectin | 0.462 | 0.27 | 0.799 | 4 |
| COL4A1 | Collagen alpha-1(IV) chain | 0.481 | 0.269 | 0.88 | 3 |
| IGLC1 | Ig lambda-1 chain C regions | 0.42 | 0.267 | 0.656 | 2 |
| GC | Vitamin D-binding protein | 0.462 | 0.265 | 0.804 | 12 |
| PIGR | Polymeric immunoglobulin receptor | 0.488 | 0.265 | 0.836 | 6 |
| KRT1 | Keratin. type II cytoskeletal 1 | 0.453 | 0.26 | 0.788 | 5 |
| PTRF | Polymerase I and transcript release factor | 0.441 | 0.253 | 0.749 | 6 |
| OLFML1 | Olfactomedin-like 1 | 0.45 | 0.249 | 0.82 | 2 |
| AGR2 | Anterior gradient protein 2 homolog | 0.413 | 0.241 | 0.699 | 6 |
| MYH11 | Myosin-11 | 0.354 | 0.234 | 0.526 | 13 |
| MFAP4 | Microfibril-associated glycoprotein 4 | 0.402 | 0.232 | 0.688 | 2 |
| CMA1 | Chymase | 0.363 | 0.229 | 0.591 | 8 |
| TTR | Transthyretin | 0.327 | 0.224 | 0.482 | 7 |
| CFD | Complement factor D | 0.38 | 0.214 | 0.663 | 2 |
| SOD3 | Extracellular superoxide dismutase [Cu—Zn] | 0.368 | 0.197 | 0.687 | 3 |
| HIST3H2A | Histone H2A type 3 | 0.289 | 0.193 | 0.433 | 2 |
| COL6A6 | Collagen alpha-6(VI) chain | 0.38 | 0.183 | 0.823 | 9 |
| AOC3 | Membrane primary amine oxidase | 0.335 | 0.179 | 0.616 | 11 |

TABLE 6A-continued

Proteins underexpressed and overexpressed in triple-negative breast cancer

| Gene | Protein | Mean | confidence intervals min | max | Peptide number |
|---|---|---|---|---|---|
| ATL2 | Atlastin-2 | 0.419 | 0.176 | 0.942 | 2 |
| SERPIND1 | Heparin cofactor 2 | 0.363 | 0.167 | 0.79 | 2 |
| DPT | Dermatopontin | 0.282 | 0.144 | 0.534 | 7 |
| TPSAB1 | Tryptase alpha-1 | 0.356 | 0.139 | 0.831 | 2 |
| ADH1C | Alcohol dehydrogenase 1C | 0.27 | 0.131 | 0.533 | 2 |
| AZGP1 | Zinc-alpha-2-glycoprotein | 0.172 | 0.123 | 0.239 | 16 |
| OGN | Mimecan | 0.144 | 0.104 | 0.196 | 15 |
| DCN | Decorin | 0.503 | 0.1 | 0.75 | 19 |
| ELN | Elastin | 0.141 | 0.074 | 0.271 | 4 |
| IGHA2 | Ig alpha-2 chain C region | 0.121 | 0.054 | 0.313 | 8 |
| APOD | Apolipoprotein D | 0.065 | 0.043 | 0.099 | 10 |
| LGALS4 | Galectin-4 | 0.077 | 0.035 | 0.174 | 3 |
| PIP | Prolactin-inducible protein | 0.096 | 0.031 | 0.289 | 5 |
| IGJ | Immunoglobulin J chain | 0.077 | 0.027 | 0.214 | 2 |
| DES | Desmin | 0.038 | 0.019 | 0.079 | 3 |

TABLE 6B

Gene ontology (GO) molecular function - triple-negative breast cancer

| | Molecular functions | pValue | Ratio |
|---|---|---|---|
| 1 | protein binding | 8.478e−25 | 193/8829 |
| 2 | MHC class I receptor activity | 3.771e−19 | 14/31 |
| 3 | binding | 9.638e−17 | 232/13778 |
| 4 | GTPase activity | 2.003e−13 | 23/257 |
| 5 | polysaccharide binding | 2.689e−11 | 20/239 |
| 6 | pattern binding | 2.689e−11 | 20/239 |
| 7 | glycosaminoglycan binding | 3.064e−11 | 19/214 |
| 8 | nucleoside-triphosphatase activity | 3.074e−11 | 37/840 |
| 9 | heparin binding | 3.601e−11 | 17/166 |
| 10 | small molecule binding | 4.286e−11 | 75/2773 |
| 11 | receptor binding | 6.439e−11 | 51/1506 |
| 12 | GTP binding | 7.220e−11 | 25/407 |
| 13 | carbohydrate binding | 8.160e−11 | 28/514 |
| 14 | pyrophosphatase activity | 1.081e−10 | 37/878 |
| 15 | hydrolase activity, acting on acid anhydrides, in phosphorus-containing anhydrides | 1.190e−10 | 37/881 |
| 16 | hydrolase activity, acting on acid anhydrides | 1.268e−10 | 37/883 |
| 17 | guanyl nucleotide binding | 1.631e−10 | 25/423 |
| 18 | guanyl ribonucleotide binding | 1.631e−10 | 25/423 |
| 19 | structural molecule activity | 2.884e−10 | 32/699 |
| 20 | purine ribonucleoside triphosphate binding | 1.339e−9 | 57/1960 |
| 21 | purine ribonucleotide binding | 2.570e−9 | 57/1995 |
| 22 | ribonucleotide binding | 2.617e−9 | 57/1996 |
| 23 | structural constituent of cytoskeleton | 2.943e−9 | 12/96 |
| 24 | nucleotide binding | 3.295e−9 | 67/2573 |
| 25 | nucleoside phosphate binding | 3.348e−9 | 67/2574 |
| 26 | purine nucleotide binding | 3.440e−9 | 57/2011 |
| 27 | actin binding | 1.710e−8 | 21/381 |
| 28 | cytoskeletal protein binding | 2.807e−7 | 27/703 |
| 29 | catalytic activity | 4.501e−7 | 114/6069 |
| 30 | hydrolase activity | 1.013e−6 | 62/2676 |
| 31 | protein complex binding | 5.122e−6 | 20/496 |
| 32 | phosphatidylcholine-sterol O-acyltransferase activator activity | 1.922e−5 | 03/05 |
| 33 | cholesterol binding | 2.334e−5 | 05/28 |
| 34 | glutathione transferase activity | 5.354e−5 | 05/33 |
| 35 | identical protein binding | 5.658e−5 | 28/992 |
| 36 | ATP binding | 9.852e−5 | 38/1592 |
| 37 | opsonin binding | 1.047e−4 | 03/08 |
| 38 | sterol binding | 1.076e−4 | 05/38 |
| 39 | collagen binding | 1.154e−4 | 06/61 |
| 40 | peptidase regulator activity | 1.202e−4 | 13/301 |
| 41 | adenyl ribonucleotide binding | 1.428e−4 | 38/1621 |
| 42 | transferase activity, transferring alkyl or aryl (other than methyl) groups | 1.510e−4 | 06/64 |
| 43 | intermediate filament binding | 1.556e−4 | 03/09 |

TABLE 6B-continued

Gene ontology (GO) molecular function - triple-negative breast cancer

| | Molecular functions | pValue | Ratio |
|---|---|---|---|
| 44 | rRNA primary transcript binding | 1.571e−4 | 02/02 |
| 45 | D-dopachrome decarboxylase activity | 1.571e−4 | 02/02 |
| 46 | adenyl nucleotide binding | 1.679e−4 | 38/1634 |
| 47 | microfilament motor activity | 2.120e−4 | 04/24 |
| 48 | steroid binding | 2.381e−4 | 07/98 |
| 49 | extracellular matrix binding | 2.438e−4 | 05/45 |
| 50 | cysteine-type endopeptidase inhibitor activity | 2.481e−4 | 06/70 |

TABLE 6C

Gene ontology (GO) process - triple-negative breast cancer

| | Process networks | pValue | Ratio |
|---|---|---|---|
| 1 | Cytoskeleton_Intermediate filaments | 9.295e−16 | 21/81 |
| 2 | Cell adhesion_Integrin-mediated cell-matrix adhesion | 8.568e−9 | 23/214 |
| 3 | Cell adhesion_Cell junctions | 4.510e−8 | 19/162 |
| 4 | Cytoskeleton_Regulation of cytoskeleton rearrangement | 6.496e−8 | 20/183 |
| 5 | Immune response_Phagosome in antigen presentation | 4.017e−7 | 22/243 |
| 6 | Protein folding_Protein folding nucleus | 2.395e−6 | 10/58 |
| 7 | Cytoskeleton_Actin filaments | 3.764e−6 | 17/176 |
| 8 | Protein folding_ER and cytoplasm | 1.997e−5 | 08/45 |
| 9 | Immune response_Antigen presentation | 6.401e−5 | 16/197 |
| 10 | Cell cycle_Mitosis | 7.642e−5 | 15/179 |

TABLE 6D

Enrichment by protein function - triple-negative breast cancer

| Protein class | Actual | n | R | N | Expected | Ratio | p-value | z-score | Percentage In data set | In protein function | Protein function in database |
|---|---|---|---|---|---|---|---|---|---|---|---|
| Ligands | 14 | 271 | 514 | 23844 | 5.842 | 2.396 | 2.400E−03 | 3.432 | 5.17% | 2.72% | 2.16% |
| Proteases | 10 | 271 | 559 | 23844 | 6.353 | 1.574 | 1.066E−01 | 1.472 | 3.69% | 1.79% | 2.34% |
| Enzymes | 48 | 271 | 2724 | 23844 | 30.96 | 1.55 | 1.353E−03 | 3.273 | 17.71% | 1.76% | 11.42% |
| Kinases | 10 | 271 | 654 | 23844 | 7.433 | 1.345 | 2.125E−01 | 0.9602 | 3.69% | 1.53% | 2.74% |
| Phosphatases | 3 | 271 | 230 | 23844 | 2.614 | 1.148 | 4.867E−01 | 0.2412 | 1.11% | 1.30% | 0.96% |
| Receptors | 18 | 271 | 1565 | 23844 | 17.79 | 1.012 | 5.143E−01 | 0.05253 | 6.64% | 1.15% | 6.56% |
| Transcription factors | 4 | 271 | 959 | 23844 | 10.9 | 0.367 | 1.428E−02 | −2.145 | 1.48% | 0.42% | 4.02% |
| Other | 164 | 271 | 16691 | 23844 | 189.7 | 0.8645 | 5.086E−04 | −3.427 | 60.52% | 0.98% | 70.00% |

2.2. A Proteomic Coverage of the Different Status

The inventors used the iQuantitator software to quantify protein expression between the different status "relapse" and "no relapse". For the "relapse" group, 295 proteins were significantly differentially expressed: 165 were overexpressed and 130 were underexpressed (Table 7A). The Metacore analysis of this list of proteins indicated a cytoskeleton remodeling with a pValue=9.2 10-12 for the Process Network "Regulation of Cytoskeleton Rearrangement" and a best enrichment score and p-value for "Binding" (p=9.4 10-26) in the GO Molecular Functions term. It should be noted that 26 ligands were found in this list characterizing the "Relapse" group (Table 7D).

TABLE 7A

Proteins underexpressed and overexpressed in recurrence of triple-negative breast cancer

| Gene | Protein | Mean | min | max | Peptide number |
|---|---|---|---|---|---|
| CYP2A6 | Cytochrome P450 2A6 | 5.532 | 3.695 | 8.322 | 7 |
| ALOX15B | Arachidonate 15-lipoxygenase B | 5.031 | 3.61 | 7.064 | 10 |
| SDR16C5 | Epidermal retinol dehydrogenase 2 | 5.394 | 3.079 | 9.449 | 4 |
| HLA-A | HLA class I histocompatibility antigen. A-33 alpha chain | 3.504 | 2.388 | 5.128 | 4 |
| GUSB | Beta-glucuronidase | 2.962 | 2.209 | 3.971 | 18 |
| S100A7 | Protein S100-A7 | 2.952 | 1.93 | 4.509 | 2 |
| HPGD | 15-hydroxyprostaglandin dehydrogenase [NAD+] | 2.917 | 1.896 | 4.542 | 5 |
| DHRS2 | Dehydrogenase/reductase SDR family member 2 | 3.134 | 1.885 | 5.283 | 7 |
| FKBP5 | Peptidyl-prolyl cis-trans isomerase FKBP5 | 3.329 | 1.822 | 6.087 | 6 |
| ACSL3 | Long-chain-fatty-acid--CoA ligase 3 | 2.536 | 1.803 | 3.581 | 12 |
| NAMPT | Nicotinamide phosphoribosyltransferase | 2.566 | 1.788 | 3.695 | 11 |
| KRT8 | Keratin type II cytoskeletal 8 | 2.782 | 1.678 | 4.622 | 14 |
| EEF1A1 | Elongation factor 1-alpha 1 | 2.348 | 1.674 | 3.317 | 12 |
| NA | Small nuclear ribonucleoprotein G-like protein | 2.505 | 1.669 | 3.818 | 2 |
| DBI | Acyl-CoA-binding protein | 2.266 | 1.595 | 3.249 | 6 |
| SCP2 | Non-specific lipid-transfer protein | 2.129 | 1.571 | 2.881 | 10 |
| MDH2 | Malate dehydrogenase. mitochondrial | 2.226 | 1.567 | 3.166 | 11 |
| CALR | Calreticulin | 1.998 | 1.564 | 2.531 | 21 |
| TM9SF3 | Transmembrane 9 superfamily member 3 | 2.576 | 1.538 | 4.319 | 5 |
| UAP1L1 | UDP-N-acetylhexosamine pyrophosphorylase-like protein 1 | 2.268 | 1.529 | 3.401 | 3 |
| SNRPB | Small nuclear ribonucleoprotein-associated proteins B and B' | 2.079 | 1.517 | 2.834 | 10 |
| SEC14L2 | SEC14-like protein 2 | 2.471 | 1.476 | 4.225 | 4 |
| YBX1 | Nuclease-sensitive element-binding protein 1 | 2.086 | 1.464 | 3.001 | 6 |
| IPO9 | Importin-9 | 2.527 | 1.42 | 4.424 | 3 |
| KPNB1 | Importin subunit beta-1 | 2.1 | 1.409 | 3.081 | 10 |
| HLA-B | HLA class I histocompatibility antigen. B-14 alpha chain | 2.154 | 1.386 | 3.375 | 3 |
| MCCC2 | Methylcrotonoyl-CoA carboxylase beta chain. mitochondrial | 1.905 | 1.377 | 2.66 | 12 |
| RAB5A | Ras-related protein Rab-5A | 2.185 | 1.366 | 3.557 | 3 |
| TPM3 | Tropomyosin alpha-3 chain | 2.182 | 1.344 | 3.648 | 7 |
| AKR1C2 | Aldo-keto reductase family 1 member C2 | 2.442 | 1.337 | 4.435 | 5 |
| IDI1 | Isopentenyl-diphosphate Delta-isomerase 1 | 2.071 | 1.335 | 3.198 | 6 |
| CNN2 | Calponin-2 | 2.131 | 1.335 | 3.388 | 4 |
| GOT1 | Aspartate aminotransferase. cytoplasmic | 1.983 | 1.33 | 2.99 | 7 |
| THBS1 | Thrombospondin-1 | 1.728 | 1.316 | 2.285 | 23 |
| DPYSL3 | Dihydropyrimidinase-related protein 3 | 1.892 | 1.313 | 2.712 | 12 |

TABLE 7A-continued

Proteins underexpressed and overexpressed in recurrence of triple-negative breast cancer

| Gene | Protein | Mean | min | max | Peptide number |
|---|---|---|---|---|---|
| DSP | Desmoplakin | 1.818 | 1.311 | 2.531 | 25 |
| CRABP2 | Cellular retinoic acid-binding protein 2 | 1.923 | 1.31 | 2.816 | 8 |
| HSP90AB1 | Heat shock protein HSP 90-beta | 1.927 | 1.309 | 2.921 | 25 |
| KPNA2 | Importin subunit alpha-2 | 2.158 | 1.308 | 3.501 | 5 |
| DDT | D-dopachrome decarboxylase | 2.116 | 1.301 | 3.485 | 5 |
| IDH2 | Isocitrate dehydrogenase [NADP]. mitochondrial | 1.733 | 1.299 | 2.304 | 20 |
| G6PD | Glucose-6-phosphate 1-dehydrogenase | 1.751 | 1.298 | 2.376 | 18 |
| S100A11 | Protein S100-A11 | 2.031 | 1.289 | 3.176 | 3 |
| PLIN2 | Perilipin-2 | 2.216 | 1.288 | 3.846 | 4 |
| GPI | Glucose-6-phosphate isomerase | 1.739 | 1.277 | 2.349 | 16 |
| NME2 | Nucleoside diphosphate kinase B | 1.678 | 1.268 | 2.215 | 11 |
| NDRG1 | Protein NDRG1 | 1.838 | 1.268 | 2.663 | 5 |
| ALCAM | CD166 antigen | 1.865 | 1.255 | 2.789 | 7 |
| ITGAM | Integrin alpha-M | 2.019 | 1.246 | 3.283 | 5 |
| FTL | Ferritin light chain | 1.892 | 1.24 | 3.011 | 9 |
| IPO5 | Importin-5 | 1.9 | 1.238 | 2.936 | 8 |
| TUBA1C | Tubulin alpha-1C chain | 1.752 | 1.236 | 2.503 | 4 |
| SORD | Sorbitol dehydrogenase | 2.005 | 1.227 | 3.329 | 4 |
| USP15 | Ubiquitin carboxyl-terminal hydrolase 15 | 1.931 | 1.209 | 3.115 | 3 |
| TOP2B | DNA topoisomerase 2-beta | 1.671 | 1.206 | 2.333 | 6 |
| FKBP4 | Peptidyl-prolyl cis-trans isomerase FKBP4 | 1.715 | 1.193 | 2.489 | 18 |
| AKR1B15 | Putative aldo-keto reductase family 1 member B15 | 1.969 | 1.193 | 3.263 | 3 |
| SAR1A | GTP-binding protein SAR1a | 1.725 | 1.184 | 2.498 | 5 |
| STK3 | Serine/threonine-protein kinase 3 | 1.746 | 1.184 | 2.563 | 2 |
| CFL2 | Cofilin-2 | 1.673 | 1.181 | 2.4 | 2 |
| PPA2 | Inorganic pyrophosphatase 2. mitochondrial | 2.403 | 1.179 | 4.955 | 2 |
| AP1M2 | AP-1 complex subunit mu-2 | 1.778 | 1.178 | 2.732 | 4 |
| KRT7 | Keratin. type II cytoskeletal 7 | 2.271 | 1.178 | 4.914 | 26 |
| SET | Protein SET | 1.678 | 1.175 | 2.438 | 6 |
| PPP2R4 | Serine/threonine-protein phosphatase 2A activator | 1.969 | 1.171 | 3.321 | 2 |
| PRKCSH | Glucosidase 2 subunit beta | 1.592 | 1.167 | 2.18 | 15 |
| XRCC5 | X-ray repair cross-complementing protein 5 | 1.502 | 1.164 | 1.936 | 23 |
| CALD1 | Caldesmon | 1.676 | 1.158 | 2.426 | 12 |
| ENAH | Protein enabled homolog | 1.911 | 1.158 | 3.183 | 3 |
| ACOX1 | Peroxisomal acyl-coenzyme A oxidase 1 | 1.774 | 1.156 | 2.804 | 7 |
| CRAT | Carnitine | 1.862 | 1.156 | 3.019 | 4 |
| THBS2 | Thrombospondin-2 | 1.628 | 1.148 | 2.323 | 10 |
| EEF1D | Elongation factor 1-delta | 1.631 | 1.147 | 2.356 | 10 |
| DHCR24 | 24-dehydrocholesterol reductase | 1.936 | 1.146 | 3.379 | 3 |
| MSN | Moesin | 1.412 | 1.145 | 1.724 | 35 |
| H2AFV | Histone H2A.V | 1.995 | 1.142 | 3.485 | 2 |
| PPP4R1 | Serine/threonine-protein phosphatase 4 regulatory subunit 1 | 1.888 | 1.14 | 3.209 | 2 |
| CRABP1 | Cellular retinoic acid-binding protein 1 | 1.677 | 1.137 | 2.467 | 7 |
| S100A8 | Protein S100-A8 | 1.522 | 1.134 | 2.046 | 9 |
| ATP6V1A | V-type proton ATPase catalytic subunit A | 1.551 | 1.133 | 2.128 | 10 |
| TMED7 | Transmembrane emp24 domain-containing protein 7 | 2.07 | 1.126 | 3.85 | 3 |
| ARF4 | ADP-ribosylation factor 4 | 1.692 | 1.123 | 2.576 | 6 |
| TKT | Transketolase | 1.584 | 1.122 | 2.208 | 21 |
| PSME1 | Proteasome activator complex subunit 1 | 1.519 | 1.118 | 2.057 | 11 |
| TNC | Tenascin | 1.574 | 1.116 | 2.269 | 44 |
| NQO1 | NAD(P)H dehydrogenase [quinone] 1 | 1.542 | 1.108 | 2.152 | 6 |
| SOD1 | Superoxide dismutase [Cu—Zn] | 1.615 | 1.108 | 2.347 | 6 |
| CAMK2D | Calcium/calmodulin-dependent protein kinase type II subunit delta | 1.739 | 1.108 | 2.769 | 4 |
| MAPK13 | Mitogen-activated protein kinase 13 | 1.942 | 1.107 | 3.547 | 2 |
| FASN | Fatty acid synthase | 1.563 | 1.106 | 2.223 | 56 |
| HSD17B11 | Estradiol 17-beta-dehydrogenase 11 | 2.016 | 1.106 | 3.671 | 4 |
| RAB1A | Ras-related protein Rab-1A | 1.551 | 1.099 | 2.203 | 5 |
| NAPA | Alpha-soluble NSF attachment protein | 1.752 | 1.099 | 2.864 | 5 |
| CDK1 | Cell division protein kinase 1 | 1.92 | 1.099 | 3.38 | 3 |
| C1S | Complement C1s subcomponent | 2.216 | 1.099 | 4.614 | 4 |
| TUBB | Tubulin beta chain | 1.463 | 1.098 | 1.942 | 15 |
| FAH | Fumarylacetoacetase | 1.953 | 1.097 | 3.452 | 3 |
| SEC23B | Protein transport protein Sec23B | 1.497 | 1.092 | 2.062 | 10 |
| IMPDH2 | Inosine-5'-monophosphate dehydrogenase 2 | 1.596 | 1.088 | 2.341 | 8 |
| RAP1B | Ras-related protein Rap-1b | 1.46 | 1.083 | 1.972 | 7 |
| ECM29 | Proteasome-associated protein ECM29 homolog | 1.611 | 1.081 | 2.401 | 5 |
| TUBA1B | Tubulin alpha-1B chain | 1.604 | 1.08 | 2.415 | 3 |
| SMARCA5 | SWI/SNF-related matrix-associated actin-dependent regulator of chromatin subfamily A member 5 | 1.458 | 1.077 | 1.981 | 12 |
| SQRDL | Sulfide:quinone oxidoreductase. mitochondrial | 1.415 | 1.076 | 1.861 | 14 |
| PMVK | Phosphomevalonate kinase | 1.549 | 1.075 | 2.239 | 8 |

TABLE 7A-continued

Proteins underexpressed and overexpressed in recurrence of triple-negative breast cancer

| Gene | Protein | Mean | Confidence intervals min | max | Peptide number |
|---|---|---|---|---|---|
| MYO6 | Myosin-VI | 1.634 | 1.074 | 2.472 | 9 |
| IARS | Isoleucyl-tRNA synthetase. cytoplasmic | 1.458 | 1.073 | 2.004 | 14 |
| NDUFS8 | NADH dehydrogenase [ubiquinone] iron-sulfur protein 8. mitochondrial | 1.671 | 1.072 | 2.652 | 2 |
| RBM25 | RNA-binding protein 25 | 1.627 | 1.07 | 2.479 | 3 |
| MCM6 | DNA replication licensing factor MCM6 | 1.488 | 1.069 | 2.085 | 7 |
| PTGES3 | Prostaglandin E synthase 3 | 1.56 | 1.067 | 2.304 | 5 |
| GGH | Gamma-glutamyl hydrolase | 1.775 | 1.067 | 2.933 | 3 |
| COPE | Coatomer subunit epsilon | 1.589 | 1.066 | 2.37 | 5 |
| PRKDC | DNA-dependent protein kinase catalytic subunit | 1.279 | 1.063 | 1.537 | 55 |
| GLO1 | Lactoylglutathione lyase | 1.477 | 1.062 | 2.062 | 6 |
| IDH1 | Isocitrate dehydrogenase [NADP] cytoplasmic | 1.483 | 1.06 | 2.085 | 11 |
| GSTO1 | Glutathione S-transferase omega-1 | 1.54 | 1.059 | 2.244 | 7 |
| CSE1L | Exportin-2 | 1.588 | 1.059 | 2.381 | 7 |
| PPA1 | Inorganic pyrophosphatase | 1.518 | 1.056 | 2.194 | 8 |
| SSBP1 | Single-stranded DNA-binding protein. mitochondrial | 1.467 | 1.055 | 2.041 | 8 |
| PTBP1 | Polypyrimidine tract-binding protein 1 | 1.472 | 1.052 | 2.1 | 14 |
| CCT7 | T-complex protein 1 subunit eta | 1.528 | 1.051 | 2.267 | 17 |
| RPL8 | 60S ribosomal protein L8 | 1.475 | 1.05 | 2.087 | 13 |
| GOLGB1 | Golgin subfamily B member 1 | 1.674 | 1.05 | 2.662 | 3 |
| PPP3CA | Serine/threonine-protein phosphatase 2B catalytic subunit alpha isoform | 1.672 | 1.05 | 2.685 | 2 |
| GFPT1 | Glucosamine--fructose-6-phosphate aminotransferase [isomerizing] 1 | 1.629 | 1.049 | 2.499 | 8 |
| SFRS1 | Splicing factor. arginine/serine-rich 1 | 1.569 | 1.047 | 2.373 | 8 |
| SOD2 | Superoxide dismutase [Mn]. mitochondrial | 1.545 | 1.046 | 2.277 | 5 |
| PGRMC1 | Membrane-associated progesterone receptor component 1 | 1.662 | 1.041 | 2.592 | 3 |
| DERL1 | Derlin-1 | 1.902 | 1.041 | 3.49 | 2 |
| SERBP1 | Plasminogen activator inhibitor 1 RNA-binding protein | 1.512 | 1.04 | 2.211 | 9 |
| CANX | Calnexin | 1.416 | 1.039 | 1.942 | 18 |
| PPIB | Peptidyl-prolyl cis-trans isomerase B | 1.499 | 1.038 | 2.186 | 17 |
| PEPD | Xaa-Pro dipeptidase | 1.842 | 1.038 | 3.357 | 2 |
| SARS | Seryl-tRNA synthetase. cytoplasmic | 1.405 | 1.037 | 1.914 | 11 |
| CALU | Calumenin | 1.45 | 1.035 | 2.015 | 8 |
| STAT3 | Signal transducer and activator of transcription 3 | 1.482 | 1.034 | 2.126 | 8 |
| UGDH | UDP-glucose 6-dehydrogenase | 1.358 | 1.033 | 1.779 | 17 |
| POR | NADPH--cytochrome P450 reductase | 1.392 | 1.033 | 1.859 | 9 |
| ISYNA1 | Inositol-3-phosphate synthase 1 | 1.739 | 1.032 | 2.962 | 3 |
| DNASE2 | Deoxyribonuclease-2-alpha | 2.018 | 1.03 | 3.973 | 2 |
| CLIC4 | Chloride intracellular channel protein 4 | 1.781 | 1.029 | 3.075 | 3 |
| PGAM1 | Phosphoglycerate mutase 1 | 1.374 | 1.026 | 1.866 | 15 |
| EIF2C2 | Protein argonaute-2 | 1.474 | 1.024 | 2.108 | 3 |
| KRT18 | Keratin. type I cytoskeletal 18 | 2.195 | 1.024 | 4.949 | 5 |
| DPP3 | Dipeptidyl peptidase 3 | 1.514 | 1.023 | 2.236 | 11 |
| RAP2B | Ras-related protein Rap-2b | 1.719 | 1.023 | 2.872 | 3 |
| PAICS | Multifunctional protein ADE2 | 1.366 | 1.021 | 1.825 | 12 |
| RAN | GTP-binding nuclear protein Ran | 1.304 | 1.02 | 1.678 | 14 |
| EPPK1 | Epiplakin | 1.44 | 1.015 | 2.047 | 13 |
| DDB1 | DNA damage-binding protein 1 | 1.487 | 1.015 | 2.203 | 10 |
| KRT19 | Keratin type I cytoskeletal 19 | 2.044 | 1.013 | 4.534 | 8 |
| NONO | Non-P | 1.259 | 1.012 | 1.584 | 23 |
| SERPINH1 | Serpin H1 | 1.272 | 1.011 | 1.59 | 20 |
| RPL35 | 60S ribosomal protein L35 | 1.521 | 1.01 | 2.291 | 6 |
| CALML5 | Calmodulin-like protein 5 | 1.554 | 1.009 | 2.377 | 7 |
| HIST1H1C | Histone H1.2 | 1.468 | 1.008 | 2.12 | 9 |
| NUDT3 | Diphosphoinositol polyphosphate phosphohydrolase 1 | 1.639 | 1.008 | 2.662 | 3 |
| TES | Testin | 1.669 | 1.008 | 2.833 | 5 |
| EIF4A1 | Eukaryotic initiation factor 4A-I | 1.366 | 1.007 | 1.83 | 14 |
| SLC25A6 | ADP/ATP translocase 3 | 1.65 | 1.006 | 2.667 | 4 |
| LRRC59 | Leucine-rich repeat-containing protein 59 | 1.489 | 1.003 | 2.217 | 7 |
| IL4I1 | L-amino-acid oxidase | 1.507 | 1 | 2.243 | 3 |
| ERH | Enhancer of rudimentary homolog | 1.863 | 1 | 3.455 | 2 |
| LMNA | Prelamin-A/C | 0.8 | 0.662 | 0.966 | 26 |
| AHNAK | Neuroblast differentiation-associated protein AHNAK | 0.671 | 0.578 | 0.779 | 96 |
| SPTAN1 | Spectrin alpha chain. brain | 0.711 | 0.577 | 0.874 | 58 |
| ACADVL | Very long-chain specific acyl-CoA dehydrogenase. mitochondrial | 0.736 | 0.546 | 0.992 | 12 |
| HSPG2 | Basement membrane-specific heparan sulfate proteoglycan core protein | 0.67 | 0.535 | 0.842 | 53 |
| UBC | Polyubiquitin-C | 0.696 | 0.524 | 0.923 | 5 |
| RBM39 | RNA-binding protein 39 | 0.7 | 0.516 | 0.949 | 7 |

TABLE 7A-continued

Proteins underexpressed and overexpressed in recurrence of triple-negative breast cancer

| Gene | Protein | Mean | Confidence intervals min | max | Peptide number |
|---|---|---|---|---|---|
| CFH | Complement factor H | 0.642 | 0.512 | 0.808 | 23 |
| SPTBN1 | Spectrin beta chain. brain 1 | 0.635 | 0.505 | 0.797 | 34 |
| HIST1H2BL | Histone H2B type 1-L | 0.669 | 0.501 | 0.911 | 8 |
| ITGB4 | Integrin beta-4 | 0.661 | 0.498 | 0.875 | 17 |
| KRT10 | Keratin. type I cytoskeletal 10 | 0.676 | 0.493 | 0.934 | 14 |
| RAB1B | Ras-related protein Rab-1B | 0.674 | 0.483 | 0.941 | 6 |
| SELENBP1 | Selenium-binding protein 1 | 0.639 | 0.479 | 0.853 | 12 |
| NA | Ras-related protein Rap-1b-like protein | 0.67 | 0.471 | 0.959 | 2 |
| KIAA1967 | Protein KIAA1967 | 0.664 | 0.47 | 0.941 | 7 |
| CAD | CAD protein | 0.666 | 0.467 | 0.966 | 12 |
| MAGOHB | Protein mago nashi homolog 2 | 0.669 | 0.463 | 0.973 | 4 |
| APCS | Serum amyloid P-component | 0.659 | 0.461 | 0.941 | 6 |
| UTRN | Utrophin | 0.677 | 0.46 | 0.987 | 6 |
| NES | Nestin | 0.589 | 0.457 | 0.753 | 14 |
| APOB | Apolipoprotein B-100 | 0.603 | 0.45 | 0.808 | 19 |
| ASPN | Asporin | 0.657 | 0.435 | 0.976 | 16 |
| CTNNB1 | Catenin beta-1 | 0.602 | 0.427 | 0.852 | 10 |
| LAMA5 | Laminin subunit alpha-5 | 0.605 | 0.424 | 0.87 | 7 |
| HRG | Histidine-rich glycoprotein | 0.637 | 0.424 | 0.977 | 11 |
| S100A10 | Protein S100-A10 | 0.592 | 0.423 | 0.818 | 7 |
| TST | Thiosulfate sulfurtransferase | 0.622 | 0.422 | 0.926 | 8 |
| CNN1 | Calponin-1 | 0.636 | 0.413 | 0.983 | 3 |
| CES1 | Liver carboxylesterase 1 | 0.625 | 0.409 | 0.943 | 6 |
| IGLC6 | Ig lambda-6 chain C region | 0.61 | 0.404 | 0.899 | 2 |
| LAMB2 | Laminin subunit beta-2 | 0.562 | 0.403 | 0.79 | 6 |
| LRG1 | Leucine-rich alpha-2-glycoprotein | 0.619 | 0.402 | 0.935 | 3 |
| EIF2C1 | Protein argonaute-1 | 0.609 | 0.401 | 0.93 | 2 |
| MYO1C | Myosin-Ic | 0.553 | 0.4 | 0.767 | 18 |
| F13A1 | Coagulation factor XIII A chain | 0.542 | 0.398 | 0.737 | 11 |
| APOH | Beta-2-glycoprotein 1 | 0.59 | 0.398 | 0.871 | 9 |
| CAST | Calpastatin | 0.607 | 0.396 | 0.935 | 5 |
| SLC4A1 | Band 3 anion transport protein | 0.618 | 0.395 | 0.964 | 5 |
| SUCLG2 | Succinyl-CoA ligase [GDP-forming] subunit beta. mitochondrial | 0.62 | 0.395 | 0.965 | 4 |
| F2 | Prothrombin | 0.512 | 0.391 | 0.667 | 17 |
| USP11 | Ubiquitin carboxyl-terminal hydrolase 11 | 0.597 | 0.391 | 0.906 | 3 |
| AMBP | Protein AMBP | 0.555 | 0.388 | 0.801 | 6 |
| NID1 | Nidogen-1 | 0.559 | 0.387 | 0.797 | 9 |
| CCDC22 | Coiled-coil domain-containing protein 22 | 0.618 | 0.387 | 0.975 | 4 |
| DDX60 | Probable ATP-dependent RNA helicase DDX60 | 0.617 | 0.382 | 0.976 | 2 |
| HDAC1 | Histone deacetylase 1 | 0.584 | 0.378 | 0.905 | 5 |
| FABP4 | Fatty acid-binding protein. adipocyte | 0.602 | 0.374 | 0.972 | 7 |
| ALG5 | Dolichyl-phosphate beta-glucosyltransferase | 0.604 | 0.369 | 0.976 | 3 |
| LMO7 | LIM domain only protein 7 | 0.568 | 0.368 | 0.877 | 6 |
| HPDL | 4-hydroxyphenylpyruvate dioxygenase-like protein | 0.595 | 0.364 | 0.966 | 5 |
| CAMK2B | Calcium/calmodulin-dependent protein kinase type II subunit beta | 0.596 | 0.364 | 0.981 | 2 |
| KRT15 | Keratin. type I cytoskeletal 15 | 0.558 | 0.363 | 0.855 | 8 |
| GSTM3 | Glutathione S-transferase Mu 3 | 0.593 | 0.362 | 0.963 | 3 |
| SERPING1 | Plasma protease C1 inhibitor | 0.525 | 0.359 | 0.766 | 7 |
| PCOLCE | Procollagen C-endopeptidase enhancer 1 | 0.551 | 0.355 | 0.867 | 7 |
| SERPINA4 | Kallistatin | 0.562 | 0.355 | 0.885 | 4 |
| SERPINF1 | Pigment epithelium-derived factor | 0.513 | 0.353 | 0.735 | 8 |
| OLFML3 | Olfactomedin-like 3 | 0.537 | 0.35 | 0.819 | 4 |
| CP | Ceruloplasmin | 0.473 | 0.346 | 0.643 | 13 |
| ACTB | Actin. cytoplasmic 1 | 0.481 | 0.343 | 0.675 | 8 |
| WDR36 | WD repeat-containing protein 36 | 0.565 | 0.336 | 0.947 | 2 |
| METTL7B | Methyltransferase-like protein 7B | 0.567 | 0.335 | 0.952 | 3 |
| LBP | Lipopolysaccharide-binding protein | 0.57 | 0.333 | 0.978 | 3 |
| MRPL13 | 39S ribosomal protein L13. mitochondrial | 0.559 | 0.332 | 0.928 | 2 |
| S100B | Protein S100-B | 0.562 | 0.331 | 0.95 | 2 |
| APOA1 | Apolipoprotein A-I | 0.422 | 0.327 | 0.549 | 23 |
| TINAGL1 | Tubulointerstitial nephritis antigen-like | 0.492 | 0.324 | 0.756 | 5 |
| ACOT2 | Acyl-coenzyme A thioesterase 2. mitochondrial | 0.518 | 0.324 | 0.818 | 3 |
| GNB1 | Guanine nucleotide-binding protein G(I)/G(S)/G(T) subunit beta-1 | 0.553 | 0.324 | 0.927 | 2 |
| PCCB | Propionyl-CoA carboxylase beta chain. mitochondrial | 0.558 | 0.324 | 0.95 | 2 |
| CTSG | Cathepsin G | 0.522 | 0.323 | 0.86 | 3 |
| CSNK1A1 | Casein kinase I isoform alpha | 0.561 | 0.322 | 0.963 | 2 |
| CFD | Complement factor D | 0.554 | 0.317 | 0.951 | 2 |
| SAP30BP | SAP30-binding protein | 0.567 | 0.317 | 0.996 | 2 |
| KNG1 | Kininogen-1 | 0.508 | 0.307 | 0.857 | 10 |
| APOA2 | Apolipoprotein A-II | 0.5 | 0.294 | 0.853 | 3 |

TABLE 7A-continued

Proteins underexpressed and overexpressed in recurrence of triple-negative breast cancer

| Gene | Protein | Mean | min | max | Peptide number |
|---|---|---|---|---|---|
| UAP1 | UDP-N-acetylhexosamine pyrophosphorylase | 0.435 | 0.288 | 0.654 | 4 |
| PLS1 | Plastin-1 | 0.517 | 0.285 | 0.911 | 2 |
| ARF3 | ADP-ribosylation factor 3 | 0.483 | 0.284 | 0.831 | 3 |
| MYO1G | Myosin-Ig | 0.519 | 0.281 | 0.937 | 3 |
| AFM | Afamin | 0.482 | 0.276 | 0.838 | 5 |
| RAB5C | Ras-related protein Rab-5C | 0.418 | 0.275 | 0.632 | 4 |
| APOA4 | Apolipoprotein A-IV | 0.387 | 0.271 | 0.55 | 9 |
| PTRF | Polymerase I and transcript release factor | 0.415 | 0.269 | 0.645 | 6 |
| CPB1 | Carboxypeptidase B | 0.391 | 0.268 | 0.571 | 5 |
| CD36 | Platelet glycoprotein 4 | 0.476 | 0.267 | 0.841 | 2 |
| ORM1 | Alpha-1-acid glycoprotein 1 | 0.405 | 0.265 | 0.625 | 7 |
| SFRP1 | Secreted frizzled-related protein 1 | 0.418 | 0.254 | 0.676 | 3 |
| CLEC3B | Tetranectin | 0.434 | 0.251 | 0.75 | 3 |
| TUBGCP2 | Gamma-tubulin complex component 2 | 0.497 | 0.25 | 0.976 | 2 |
| EHD2 | EH domain-containing protein 2 | 0.352 | 0.247 | 0.506 | 9 |
| HLA-C | HLA class I histocompatibility antigen. Cw-15 alpha chain | 0.387 | 0.247 | 0.601 | 5 |
| PLIN4 | Perilipin-4 | 0.45 | 0.244 | 0.84 | 3 |
| GC | Vitamin D-binding protein | 0.436 | 0.234 | 0.838 | 11 |
| AGR2 | Anterior gradient protein 2 homolog | 0.385 | 0.231 | 0.641 | 6 |
| CMA1 | Chymase | 0.312 | 0.221 | 0.446 | 8 |
| PIGR | Polymeric immunoglobulin receptor | 0.339 | 0.218 | 0.531 | 6 |
| PLIN1 | Perilipin-1 | 0.343 | 0.218 | 0.543 | 8 |
| OLFML1 | Olfactomedin-like 1 | 0.399 | 0.217 | 0.739 | 2 |
| ATL2 | Atlastin-2 | 0.455 | 0.215 | 0.89 | 2 |
| ABI3BP | Target of Nesh-SH3 | 0.404 | 0.212 | 0.75 | 3 |
| PRELP | Prolargin | 0.32 | 0.192 | 0.57 | 16 |
| HP | Haptoglobin | 0.275 | 0.191 | 0.396 | 16 |
| CPA3 | Mast cell carboxypeptidase A | 0.309 | 0.189 | 0.507 | 4 |
| MYH11 | Myosin-11 | 0.262 | 0.179 | 0.382 | 13 |
| TNXB | Tenascin-X | 0.301 | 0.179 | 0.497 | 6 |
| HIST2H2AC | Histone H2A type 2-C | 0.259 | 0.177 | 0.376 | 4 |
| LTF | Lactotransferrin | 0.243 | 0.164 | 0.359 | 41 |
| AOC3 | Membrane primary amine oxidase | 0.232 | 0.161 | 0.328 | 11 |
| DPT | Dermatopontin | 0.253 | 0.161 | 0.397 | 7 |
| TTR | Transthyretin | 0.271 | 0.159 | 0.466 | 6 |
| ORM2 | Alpha-1-acid glycoprotein 2 | 0.276 | 0.154 | 0.505 | 3 |
| TPSAB1 | Tryptase alpha-1 | 0.284 | 0.153 | 0.52 | 2 |
| HIST3H2A | Histone H2A type 3 | 0.241 | 0.149 | 0.386 | 2 |
| AZGP1 | Zinc-alpha-2-glycoprotein | 0.192 | 0.133 | 0.276 | 15 |
| SOD3 | Extracellular superoxide dismutase [Cu—Zn] | 0.227 | 0.132 | 0.391 | 3 |
| COL6A6 | Collagen alpha-6(VI) chain | 0.257 | 0.132 | 0.483 | 9 |
| IGHA2 | Ig alpha-2 chain C region | 0.23 | 0.128 | 0.415 | 8 |
| MFAP4 | Microfibril-associated glycoprotein 4 | 0.231 | 0.121 | 0.433 | 2 |
| OGN | Mimecan | 0.135 | 0.102 | 0.178 | 15 |
| IGHA1 | Ig alpha-1 chain C region | 0.112 | 0.081 | 0.152 | 14 |
| ELN | Elastin | 0.141 | 0.08 | 0.248 | 4 |
| APOD | Apolipoprotein D | 0.107 | 0.075 | 0.152 | 10 |
| DCN | Decorin | 0.103 | 0.07 | 0.153 | 19 |
| LGALS4 | Galectin-4 | 0.106 | 0.059 | 0.191 | 3 |
| IGJ | Immunoglobulin J chain | 0.122 | 0.049 | 0.291 | 2 |
| PIP | Prolactin-inducible protein | 0.077 | 0.039 | 0.152 | 5 |
| DES | Desmin | 0.03 | 0.017 | 0.051 | 3 |
| ARHGAP1 | Rho GTPase-activating protein 1 | 1.289 | 1.002 | 1.716 | 8 |

TABLE 7B

Gene Ontology (GO) molecular function - recurrence of triple-negative breast cancer

| | Molecular functions | pValue | Ratio |
|---|---|---|---|
| 1 | binding | 9.410e−26 | 324/13778 |
| 2 | protein binding | 5.514e−25 | 249/8829 |
| 3 | MHC class I receptor activity | 3.277e−17 | 14/31 |
| 4 | glycosaminoglycan binding | 4.145e−13 | 24/214 |
| 5 | polysaccharide binding | 6.496e−13 | 25/239 |
| 6 | pattern binding | 6.496e−13 | 25/239 |
| 7 | carbohydrate binding | 1.109e−12 | 36/514 |
| 8 | heparin binding | 1.190e−12 | 21/166 |
| 9 | structural molecule activity | 8.422e−12 | 41/699 |
| 10 | small molecule binding | 1.884e−11 | 95/2773 |
| 11 | catalytic activity | 2.085e−11 | 164/6069 |
| 12 | oxidoreductase activity, acting on the CH—OH group of donors, NAD or NADP as acceptor | 3.350e−11 | 18/139 |
| 13 | oxidoreductase activity, acting on CH—OH group of donors | 1.883e−10 | 18/154 |
| 14 | receptor binding | 3.434e−10 | 61/1506 |
| 15 | nucleotide binding | 4.193e−9 | 84/2573 |
| 16 | nucleoside phosphate binding | 4.270e−9 | 84/2574 |
| 17 | collagen binding | 6.695e−9 | 11/61 |
| 18 | isomerase activity | 1.890e−8 | 16/160 |
| 19 | hydrolase activity | 1.140e−7 | 82/2676 |
| 20 | GTPase activity | 1.211e−7 | 19/257 |
| 21 | actin binding | 2.305e−7 | 23/381 |
| 22 | superoxide dismutase activity | 4.297e−7 | 04/05 |
| 23 | oxidoreductase activity, acting on superoxide radicals as acceptor | 4.297e−7 | 04/05 |
| 24 | oxidoreductase activity | 5.270e−7 | 36/839 |
| 25 | GTP binding | 7.314e−7 | 23/407 |
| 26 | structural constituent of cytoskeleton | 8.242e−7 | 11/96 |
| 27 | guanyl nucleotide binding | 1.416e−6 | 23/423 |
| 28 | guanyl ribonucleotide binding | 1.416e−6 | 23/423 |
| 29 | pyrophosphatase activity | 1.521e−6 | 36/878 |
| 30 | hydrolase activity, acting on acid anhydrides, in phosphorus-containing anhydrides | 1.645e−6 | 36/881 |
| 31 | hydrolase activity, acting on acid anhydrides | 1.733e−6 | 36/883 |
| 32 | purine ribonucleoside triphosphate binding | 2.038e−6 | 62/1960 |
| 33 | calmodulin binding | 2.914e−6 | 14/179 |
| 34 | purine ribonucleotide binding | 3.624e−6 | 62/1995 |
| 35 | ribonucleotide binding | 3.683e−6 | 62/1996 |
| 36 | purine nucleotide binding | 4.683e−6 | 62/2011 |
| 37 | cytoskeletal protein binding | 5.434e−6 | 30/703 |
| 38 | monocarboxylic acid binding | 5.647e−6 | 09/75 |
| 39 | coenzyme binding | 6.287e−6 | 15/218 |
| 40 | high-density lipoprotein particle binding | 1.025e−5 | 04/09 |
| 41 | nucleoside-triphosphatase activity | 1.032e−5 | 33/840 |
| 42 | extracellular matrix binding | 1.108e−5 | 07/45 |
| 43 | cofactor binding | 2.797e−5 | 17/308 |
| 44 | intramolecular oxidoreductase activity | 2.944e−5 | 07/52 |
| 45 | phosphatidylcholine-sterol O-acyltransferase activator activity | 4.962e−5 | 03/05 |
| 46 | steroid binding | 4.998e−5 | 09/98 |
| 47 | carboxylic acid binding | 7.754e−5 | 13/210 |
| 48 | lipoprotein particle binding | 8.777e−5 | 05/27 |
| 49 | protein-lipid complex binding | 8.777e−5 | 05/27 |
| 50 | cholesterol transporter activity | 1.023e−4 | 04/15 |

TABLE 7C

Gene Ontology (GO) process - recurrence of triple-negative breast cancer

| | Networks | pValue | Ratio |
|---|---|---|---|
| 1 | Cytoskeleton_Intermediate filaments | 9.234e−12 | 19/81 |
| 2 | Cytoskeleton_Regulation of cytoskeleton rearrangement | 1.330e−7 | 22/183 |
| 3 | Cell adhesion_Integrin-mediated cell-matrix adhesion | 7.312e−6 | 21/214 |
| 4 | Immune response_Phagosome in antigen presentation | 1.609e−5 | 22/243 |
| 5 | Cytoskeleton_Actin filaments | 1.919e−5 | 18/176 |
| 6 | Cell cycle_Mitosis | 2.418e−5 | 18/179 |
| 7 | Cell adhesion_Cell-matrix interactions | 2.075e−4 | 18/211 |
| 8 | Immune response_Antigen presentation | 2.719e−4 | 17/197 |
| 9 | Cytoskeleton_Spindle microtubules | 9.227e−4 | 11/109 |
| 10 | Cell adhesion_Cell junctions | 9.275e−4 | 14/162 |

TABLE 7D

Enrichment by protein function - recurrence of triple-negative breast cancer

| Protein class | Actual | n | R | N | Expected | Ratio | p-value | z-score | In data set | In protein function | Protein function in database |
|---|---|---|---|---|---|---|---|---|---|---|---|
| Ligands | 26 | 382 | 514 | 23844 | 8.235 | 3.157 | 2.918E−07 | 6.309 | 6.81% | 5.06% | 2.16% |
| Phosphatases | 8 | 382 | 230 | 23844 | 3.685 | 2.171 | 3.259E−02 | 2.277 | 2.09% | 3.48% | 0.96% |
| Proteases | 17 | 382 | 559 | 23844 | 8.956 | 1.898 | 9.214E−03 | 2.742 | 4.45% | 3.04% | 2.34% |
| Enzymes | 80 | 382 | 2724 | 23844 | 43.64 | 1.833 | 5.155E−08 | 5.895 | 20.94% | 2.94% | 11.42% |
| Kinases | 12 | 382 | 654 | 23844 | 10.48 | 1.145 | 3.572E−01 | 0.4808 | 3.14% | 1.83% | 2.74% |
| Receptors | 22 | 382 | 1565 | 23844 | 25.07 | 0.8775 | 3.034E−01 | −0.6399 | 5.76% | 1.41% | 6.56% |
| Transcription factors | 3 | 382 | 959 | 23844 | 15.36 | 0.1953 | 1.170E−04 | −3.246 | 0.79% | 0.31% | 4.02% |
| Other | 215 | 382 | 16691 | 23844 | 267.4 | 0.804 | 7.684E−09 | −5.898 | 56.28% | 1.29% | 70.00% |

For the "no relapse" group, 189 proteins were significantly differentially expressed: 98 were overexpressed and 91 were underexpressed (Table 8A). For this group, the best score for the Process Network was obtained for "Cell adhesion_Integrin-mediated cell-matrix adhesion" ($p=7.5 \cdot 10^{-11}$) (Table 8C). The protein class "ligands" was found to have to best z-score in the module "Enrichment for Protein Function" with 15 proteins (Table 8D).

TABLE 8A

Proteins underexpressed and overexpressed in non-recurrence of triple-negative breast cancer

| Gene | Protein | Mean | min | max | Peptide number |
|---|---|---|---|---|---|
| APOD | Apolipoprotein D | 0.049 | 0.03 | 0.08 | 10 |
| PIP | Prolactin-inducible protein | 0.069 | 0.016 | 0.224 | 5 |
| IGHA2 | Ig alpha-2 chain C region | 0.07 | 0.044 | 0.112 | 8 |
| COL1A1 | Collagen alpha-1(I) chain | 0.087 | 0.054 | 0.128 | 21 |
| IGJ | Immunoglobulin J chain | 0.087 | 0.037 | 0.201 | 2 |
| AZGP1 | Zinc-alpha-2-glycoprotein | 0.1 | 0.068 | 0.147 | 15 |
| DCN | Decorin | 0.155 | 0.096 | 0.269 | 19 |
| OGN | Mimecan | 0.16 | 0.118 | 0.214 | 11 |
| TF | Serotransferrin | 0.165 | 0.132 | 0.206 | 41 |
| LTF | Lactotransferrin | 0.18 | 0.088 | 0.373 | 36 |
| COL6A6 | Collagen alpha-6(VI) chain | 0.187 | 0.078 | 0.42 | 3 |
| HMGCS2 | Hydroxymethylglutaryl-CoA synthase. mitochondrial | 0.215 | 0.119 | 0.391 | 4 |
| DES | Desmin | 0.22 | 0.111 | 0.428 | 2 |
| ADH1C | Alcohol dehydrogenase 1C | 0.299 | 0.12 | 0.681 | 2 |
| AKR1C1 | Aldo-keto reductase family 1 member C1 | 0.306 | 0.164 | 0.565 | 2 |
| TTR | Transthyretin | 0.327 | 0.222 | 0.484 | 6 |
| DPT | Dermatopontin | 0.333 | 0.2 | 0.562 | 4 |
| OLFML3 | Olfactomedin-like protein 3 | 0.35 | 0.197 | 0.617 | 4 |
| DHRS2 | Dehydrogenase/reductase SDR family member 2 | 0.353 | 0.186 | 0.668 | 7 |
| HIST3H2A | Histone H2A type 3 | 0.359 | 0.242 | 0.529 | 2 |
| PLIN1 | Perilipin-1 | 0.361 | 0.217 | 0.585 | 7 |
| CLEC3B | Tetranectin | 0.38 | 0.173 | 0.804 | 2 |
| BCCIP | BRCA2 and CDKN1A-interacting protein | 0.381 | 0.209 | 0.678 | 2 |
| IGHG1 | Ig gamma-1 chain C region | 0.398 | 0.275 | 0.571 | 12 |
| LBP | Lipopolysaccharide-binding protein | 0.407 | 0.24 | 0.686 | 3 |
| HPGD | 15-hydroxyprostaglandin dehydrogenase [NAD+] | 0.41 | 0.251 | 0.654 | 5 |
| OAT | Ornithine aminotransferase. mitochondrial | 0.416 | 0.301 | 0.565 | 20 |
| CFD | Complement factor D | 0.417 | 0.218 | 0.781 | 2 |
| HP | Haptoglobin | 0.421 | 0.302 | 0.58 | 13 |
| HPX | Hemopexin | 0.421 | 0.214 | 0.912 | 16 |
| GC | Vitamin D-binding protein | 0.423 | 0.291 | 0.605 | 9 |
| LRG1 | Leucine-rich alpha-2-glycoprotein | 0.426 | 0.247 | 0.723 | 3 |
| SERPINA4 | Kallistatin | 0.435 | 0.234 | 0.792 | 4 |
| AOC3 | Membrane primary amine oxidase | 0.436 | 0.3 | 0.633 | 10 |
| APOA4 | Apolipoprotein A-IV | 0.438 | 0.256 | 0.754 | 6 |
| PTRF | Polymerase I and transcript release factor | 0.443 | 0.26 | 0.738 | 5 |
| ALOX15B | Arachidonate 15-lipoxygenase B | 0.448 | 0.285 | 0.702 | 10 |
| MYH11 | Myosin-11 | 0.457 | 0.343 | 0.61 | 13 |
| MFAP4 | Microfibril-associated glycoprotein 4 | 0.459 | 0.259 | 0.807 | 2 |
| ORM1 | Alpha-1-acid glycoprotein 1 | 0.46 | 0.26 | 0.8 | 4 |
| IDI1 | Isopentenyl-diphosphate Delta-isomerase 1 | 0.463 | 0.263 | 0.798 | 5 |
| SFRP1 | Secreted frizzled-related protein 1 | 0.464 | 0.311 | 0.699 | 3 |
| NA | Ig kappa chain V-II region GM607 (Fragment) | 0.465 | 0.267 | 0.803 | 2 |
| MCCC1 | Methylcrotonoyl-CoA carboxylase subunit alpha. mitochondrial | 0.465 | 0.228 | 0.917 | 2 |
| CP | Ceruloplasmin | 0.467 | 0.349 | 0.624 | 11 |
| CYP2A6 | Cytochrome P450 2A6 | 0.469 | 0.3 | 0.726 | 7 |
| AHSG | Alpha-2-HS-glycoprotein | 0.471 | 0.191 | 0.997 | 4 |
| AACS | Acetoacetyl-CoA synthetase | 0.474 | 0.235 | 0.916 | 2 |
| AMBP | Protein AMBP | 0.475 | 0.334 | 0.674 | 5 |
| CMA1 | Chymase | 0.48 | 0.344 | 0.679 | 6 |
| IGLC6 | Ig lambda-6 chain C region | 0.482 | 0.333 | 0.697 | 2 |
| MCCC2 | Methylcrotonoyl-CoA carboxylase beta chain. mitochondrial | 0.482 | 0.322 | 0.712 | 11 |
| BGN | Biglycan | 0.483 | 0.365 | 0.631 | 19 |
| UROS | Uroporphyrinogen-III synthase | 0.483 | 0.281 | 0.808 | 3 |
| AKR1B15 | Putative aldo-keto reductase family 1 member B15 | 0.487 | 0.308 | 0.773 | 3 |
| HAAO | 3-hydroxyanthranilate 3.4-dioxygenase | 0.496 | 0.287 | 0.846 | 2 |
| ASPN | Asporin | 0.497 | 0.364 | 0.672 | 15 |
| IGHM | Ig mu chain C region | 0.498 | 0.369 | 0.682 | 15 |
| PIGR | Polymeric immunoglobulin receptor | 0.505 | 0.307 | 0.81 | 5 |
| HBA1 | Hemoglobin subunit alpha | 0.51 | 0.29 | 0.881 | 10 |
| F2 | Prothrombin | 0.516 | 0.397 | 0.673 | 14 |
| TNXB | Tenascin-X | 0.519 | 0.309 | 0.897 | 6 |
| SDCBP | Syntenin-1 | 0.522 | 0.337 | 0.812 | 5 |

TABLE 8A-continued

Proteins underexpressed and overexpressed in non-recurrence of triple-negative breast cancer

| Gene | Protein | Mean | Confidence intervals min | max | Peptide number |
|---|---|---|---|---|---|
| ACSS3 | Acyl-CoA synthetase short-chain family member 3. mitochondrial | 0.526 | 0.285 | 0.961 | 2 |
| LPP | Lipoma-preferred partner | 0.529 | 0.355 | 0.787 | 10 |
| SOD3 | Extracellular superoxide dismutase [Cu—Zn] | 0.54 | 0.314 | 0.886 | 3 |
| OPLAH | 5-oxoprolinase | 0.546 | 0.332 | 0.923 | 13 |
| DNAJA3 | DnaJ homolog subfamily A member 3. mitochondrial | 0.548 | 0.325 | 0.908 | 4 |
| APOH | Beta-2-glycoprotein 1 | 0.555 | 0.323 | 0.948 | 5 |
| PCOLCE | Procollagen C-endopeptidase enhancer 1 | 0.556 | 0.36 | 0.848 | 6 |
| ALDH6A1 | Methylmalonate-semialdehyde dehydrogenase [acylating]. mitochondrial | 0.559 | 0.356 | 0.862 | 7 |
| SLC9A3R1 | Na(+)/H(+) exchange regulatory cofactor NHE-RF1 | 0.567 | 0.368 | 0.865 | 4 |
| TWF1 | Twinfilin-1 | 0.579 | 0.375 | 0.886 | 4 |
| CTBP2 | C-terminal-binding protein 2 | 0.589 | 0.362 | 0.954 | 3 |
| CYB5A | Cytochrome b5 | 0.594 | 0.397 | 0.879 | 4 |
| AHNAK | Neuroblast differentiation-associated protein AHNAK | 0.597 | 0.48 | 0.739 | 61 |
| PLG | Plasminogen | 0.6 | 0.409 | 0.875 | 12 |
| CLU | Clusterin | 0.605 | 0.384 | 0.973 | 8 |
| ERLIN2 | Erlin-2 | 0.607 | 0.385 | 0.952 | 4 |
| EFEMP1 | EGF-containing fibulin-like extracellular matrix protein 1 | 0.608 | 0.391 | 0.937 | 3 |
| ERLIN2 | Erlin-2 | 0.609 | 0.383 | 0.959 | 4 |
| KRT1 | Keratin. type II cytoskeletal 1 | 0.612 | 0.408 | 0.955 | 13 |
| SERPING1 | Plasma protease C1 inhibitor | 0.616 | 0.397 | 0.961 | 6 |
| HIST1H2AC | Histone H2A type 1-C | 0.619 | 0.415 | 0.926 | 2 |
| ASS1 | Argininosuccinate synthase | 0.619 | 0.388 | 0.981 | 4 |
| HIST2H2AC | Histone H2A type 2-C | 0.62 | 0.429 | 0.898 | 4 |
| SCP2 | Non-specific lipid-transfer protein | 0.643 | 0.467 | 0.888 | 10 |
| HIST1H2BK | Histone H2B type 1-K | 0.646 | 0.466 | 0.874 | 6 |
| MGST1 | Microsomal glutathione S-transferase 1 | 0.648 | 0.421 | 0.999 | 4 |
| C4BPA | C4b-binding protein alpha chain | 0.669 | 0.448 | 0.997 | 4 |
| SELENBP1 | Selenium-binding protein 1 | 0.765 | 0.6 | 0.976 | 11 |
| ADAR | Double-stranded RNA-specific adenosine deaminase | 1.324 | 1.002 | 1.738 | 11 |
| CHD4 | Chromodomain-helicase-DNA-binding protein 4 | 1.344 | 1.029 | 1.757 | 11 |
| SAMHD1 | SAM domain and HD domain-containing protein 1 | 1.347 | 1.055 | 1.713 | 13 |
| PSME1 | Proteasome activator complex subunit 1 | 1.347 | 1.022 | 1.786 | 9 |
| NONO | Non-POU domain-containing octamer-binding protein | 1.366 | 1.073 | 1.731 | 19 |
| DDX5 | Probable ATP-dependent RNA helicase DDX5 | 1.372 | 1 | 1.864 | 7 |
| NCL | Nucleolin | 1.376 | 1.019 | 1.891 | 19 |
| GRB2 | Growth factor receptor-bound protein 2 | 1.409 | 1.036 | 1.941 | 8 |
| CCT2 | T-complex protein 1 subunit beta | 1.416 | 1.064 | 1.877 | 13 |
| HNRNPA2B1 | Heterogeneous nuclear ribonucleoproteins A2/B1 | 1.441 | 1.024 | 2.14 | 21 |
| FBL | rRNA 2'-O-methyltransferase fibrillarin | 1.444 | 1.047 | 1.99 | 9 |
| PRKAR2A | cAMP-dependent protein kinase type II-alpha regulatory subunit | 1.445 | 1.043 | 2.019 | 6 |
| TRIM28 | Transcription intermediary factor 1-beta | 1.449 | 1.13 | 1.857 | 17 |
| DYNLL1 | Dynein light chain 1. cytoplasmic | 1.46 | 1.042 | 2.066 | 4 |
| HK1 | Hexokinase-1 | 1.463 | 1.002 | 2.228 | 12 |
| DNM2 | Dynamin-2 | 1.481 | 1.071 | 2.035 | 9 |
| STIP1 | Stress-induced-phosphoprotein 1 | 1.49 | 1.076 | 2.102 | 11 |
| S100A8 | Protein S100-A8 | 1.5 | 1.106 | 2.024 | 9 |
| SNRPB | Small nuclear ribonucleoprotein-associated proteins B and B' | 1.505 | 1.071 | 2.146 | 10 |
| EZR | Ezrin | 1.522 | 1.05 | 2.208 | 9 |
| P4HB | Protein disulfide-isomerase | 1.522 | 1.033 | 2.274 | 28 |
| ATP6V1A | V-type proton ATPase catalytic subunit A | 1.529 | 1.073 | 2.203 | 9 |
| HSP90B1 | Endoplasmin | 1.53 | 1.212 | 1.954 | 32 |
| CALR | Calreticulin | 1.533 | 1.168 | 2.03 | 18 |
| HSP90B1 | Endoplasmin | 1.537 | 1.213 | 1.979 | 32 |
| PAICS | Multifunctional protein ADE2 | 1.538 | 1.108 | 2.14 | 10 |
| MAP2K2 | Dual specificity mitogen-activated protein kinase kinase 2 | 1.539 | 1.031 | 2.33 | 2 |
| H2AFY | Core histone macro-H2A.1 | 1.542 | 1.078 | 2.199 | 10 |
| DEK | Protein DEK | 1.545 | 1.13 | 2.127 | 8 |
| SET | Protein SET | 1.55 | 1.099 | 2.189 | 6 |
| ACTR3 | Actin-related protein 3 | 1.552 | 1.129 | 2.13 | 12 |
| ACTG1 | Actin. cytoplasmic 2 | 1.559 | 1.103 | 2.197 | 6 |
| GAA | Lysosomal alpha-glucosidase | 1.568 | 1.078 | 2.297 | 10 |
| LCP1 | Plastin-2 | 1.569 | 1.126 | 2.193 | 20 |

TABLE 8A-continued

Proteins underexpressed and overexpressed in non-recurrence of triple-negative breast cancer

| Gene | Protein | Mean | Confidence intervals min | max | Peptide number |
|---|---|---|---|---|---|
| XRCC5 | X-ray repair cross-complementing protein 5 | 1.583 | 1.103 | 2.286 | 16 |
| SSRP1 | FACT complex subunit SSRP1 | 1.588 | 1.067 | 2.356 | 8 |
| KRT14 | Keratin. type I cytoskeletal 14 | 1.588 | 1.011 | 2.549 | 5 |
| HSPE1 | 10 kDa heat shock protein. mitochondrial | 1.591 | 1.083 | 2.363 | 6 |
| TNC | Tenascin | 1.609 | 1.114 | 2.496 | 38 |
| EIF2S3 | Eukaryotic translation initiation factor 2 subunit 3 | 1.61 | 1.127 | 2.307 | 3 |
| WARS | Tryptophanyl-tRNA synthetase. cytoplasmic | 1.615 | 1.001 | 2.598 | 9 |
| HSPA5 | 78 kDa glucose-regulated protein | 1.623 | 1.177 | 2.298 | 30 |
| SSR1 | Translocon-associated protein subunit alpha | 1.626 | 1.016 | 2.583 | 3 |
| CAMK2D | Calcium/calmodulin-dependent protein kinase type II subunit delta | 1.631 | 1.07 | 2.574 | 3 |
| PPIA | Peptidyl-prolyl cis-trans isomerase A | 1.633 | 1.012 | 2.56 | 14 |
| MRPL19 | 39S ribosomal protein L19. mitochondrial | 1.635 | 1.087 | 2.459 | 4 |
| ERH | Enhancer of rudimentary homolog | 1.642 | 1.01 | 2.699 | 2 |
| CALU | Calumenin | 1.649 | 1.133 | 2.418 | 7 |
| LRRC59 | Leucine-rich repeat-containing protein 59 | 1.656 | 1.14 | 2.419 | 7 |
| ERH | Enhancer of rudimentary homolog | 1.657 | 1.017 | 2.724 | 2 |
| PAPSS1 | Bifunctional 3'-phosphoadenosine 5'-phosphosulfate synthase 1 | 1.677 | 1.113 | 2.551 | 13 |
| CFL1 | Cofilin-1 | 1.681 | 1.054 | 2.543 | 17 |
| MSN | Moesin | 1.695 | 1.349 | 2.133 | 32 |
| ISYNA1 | Inositol-3-phosphate synthase 1 | 1.698 | 1.016 | 2.853 | 3 |
| RBMX | Heterogeneous nuclear ribonucleoprotein G | 1.706 | 1.08 | 2.706 | 6 |
| MAT2B | Methionine adenosyltransferase 2 subunit beta | 1.711 | 1.002 | 2.923 | 3 |
| AKR7A3 | Aflatoxin B1 aldehyde reductase member 3 | 1.711 | 1 | 2.994 | 2 |
| RAN | GTP-binding nuclear protein Ran | 1.722 | 1.3 | 2.29 | 9 |
| ARF1 | ADP-ribosylation factor 1 | 1.722 | 1.176 | 2.553 | 5 |
| NME2 | Nucleoside diphosphate kinase B | 1.725 | 1.191 | 2.515 | 9 |
| RPS27A | Ubiquitin-40S ribosomal protein S27a | 1.733 | 1.192 | 2.533 | 4 |
| TUBB | Tubulin beta chain | 1.758 | 1.118 | 2.706 | 15 |
| SLC2A1 | Solute carrier family 2. facilitated glucose transporter member 1 | 1.782 | 1.081 | 3.003 | 3 |
| SMARCA5 | SWI/SNF-related matrix-associated actin-dependent regulator of chromatin subfamily A member 5 | 1.796 | 1.164 | 2.832 | 4 |
| YBX1 | Nuclease-sensitive element-binding protein 1 | 1.797 | 1.176 | 2.765 | 6 |
| PAK2 | Serine/threonine-protein kinase PAK 2 | 1.804 | 1.079 | 3.009 | 2 |
| CTNNBL1 | Beta-catenin-like protein 1 | 1.834 | 1.054 | 3.211 | 4 |
| MACF1 | Microtubule-actin cross-linking factor 1. isoforms 1/2/3/5 | 1.838 | 1.109 | 3.039 | 3 |
| USP15 | Ubiquitin carboxyl-terminal hydrolase 15 | 1.853 | 1.263 | 2.737 | 4 |
| RPS9 | 40S ribosomal protein S9 | 1.862 | 1.195 | 3.145 | 14 |
| AP1B1 | AP-1 complex subunit beta-1 | 1.877 | 1.2 | 2.947 | 10 |
| CPNE3 | Copine-3 | 1.914 | 1.221 | 3.052 | 4 |
| EIF4A1 | Eukaryotic initiation factor 4A-I | 1.921 | 1.446 | 2.559 | 13 |
| EIF4A1 | Eukaryotic initiation factor 4A-I | 1.927 | 1.457 | 2.614 | 13 |
| TUBA1B | Tubulin alpha-1B chain | 1.929 | 1.063 | 3.529 | 2 |
| CPNE1 | Copine-1 | 1.932 | 1.214 | 3.123 | 4 |
| MYL12B | Myosin regulatory light chain 12B | 1.943 | 1.43 | 2.651 | 7 |
| MAN2B1 | Lysosomal alpha-mannosidase | 1.952 | 1.22 | 3.123 | 5 |
| MAPRE1 | Microtubule-associated protein RP/EB family member 1 | 1.973 | 1.217 | 3.188 | 3 |
| CSDE1 | Cold shock domain-containing protein E1 | 1.975 | 1.057 | 3.613 | 4 |
| SOD2 | Superoxide dismutase [Mn]. mitochondrial | 1.991 | 1.332 | 2.986 | 5 |
| GSTM1 | Glutathione S-transferase Mu 1 | 1.993 | 1.1 | 3.682 | 2 |
| MRPL9 | 39S ribosomal protein L9. mitochondrial | 1.994 | 1.163 | 3.469 | 3 |
| AARS | Alanyl-tRNA synthetase. cytoplasmic | 2.001 | 1.33 | 3.056 | 9 |
| KRT6A | Keratin. type II cytoskeletal 6A | 2.004 | 1.09 | 3.811 | 3 |
| KRT15 | Keratin. type I cytoskeletal 15 | 2.049 | 1.271 | 3.401 | 8 |
| KDM1A | Lysine-specific histone demethylase 1A | 2.069 | 1.065 | 3.93 | 2 |
| LSP1 | Lymphocyte-specific protein 1 | 2.077 | 1.047 | 4.086 | 2 |
| TPM1 | Tropomyosin alpha-1 chain | 2.089 | 1.296 | 3.316 | 12 |
| NME1 | Nucleoside diphosphate kinase A | 2.162 | 1.395 | 3.349 | 4 |
| ACTN4 | Alpha-actinin-4 | 2.47 | 1.088 | 4.765 | 22 |
| AP1M1 | AP-1 complex subunit mu-1 | 2.492 | 1.437 | 4.336 | 3 |
| EEF1A1 | Elongation factor 1-alpha 1 | 2.508 | 1.538 | 4.473 | 11 |
| ACP2 | Lysosomal acid phosphatase | 2.543 | 1.451 | 4.436 | 3 |
| ITGAM | Integrin alpha-M | 2.555 | 1.486 | 4.406 | 3 |
| MAPK13 | Mitogen-activated protein kinase 13 | 2.761 | 1.514 | 5.106 | 2 |
| SSB | Lupus La protein | 2.884 | 1.705 | 4.803 | 5 |
| AGR2 | Anterior gradient protein 2 homolog | 6.456 | 3.28 | 12.577 | 3 |

TABLE 8B

Gene Ontology (GO) molecular function - non-recurrence of triple-negative breast cancer

| | Molecular functions | pValue | Ratio |
|---|---|---|---|
| 1 | protein binding | 1.134e−22 | 168/8829 |
| 2 | binding | 1.241e−21 | 210/13778 |
| 3 | small molecule binding | 5.986e−10 | 65/2773 |
| 4 | nucleotide binding | 2.893e−8 | 58/2573 |
| 5 | nucleoside phosphate binding | 2.933e−8 | 58/2574 |
| 6 | oxidoreductase activity, acting on the CH—OH group of donors, NAD or NADP as acceptor | 3.779e−8 | 12/139 |
| 7 | structural constituent of cytoskeleton | 8.925e−8 | 10/96 |
| 8 | oxidoreductase activity, acting on CH—OH group of donors | 1.177e−7 | 12/154 |
| 9 | structural molecule activity | 6.414e−7 | 24/699 |
| 10 | catalytic activity | 1.507e−6 | 99/6069 |
| 11 | purine ribonucleotide binding | 3.651e−6 | 44/1995 |
| 12 | ribonucleotide binding | 3.699e−6 | 44/1996 |
| 13 | aldo-keto reductase (NADP) activity | 4.047e−6 | 05/23 |
| 14 | alditol:NADP+ 1-oxidoreductase activity | 4.128e−6 | 04/11 |
| 15 | purine nucleotide binding | 4.489e−6 | 44/2011 |
| 16 | purine ribonucleoside triphosphate binding | 5.512e−6 | 43/1960 |
| 17 | cell surface binding | 5.773e−6 | 07/64 |
| 18 | identical protein binding | 1.006e−5 | 27/992 |
| 19 | enzyme binding | 1.157e−5 | 32/1302 |
| 20 | oxidoreductase activity | 1.449e−5 | 24/839 |
| 21 | actin binding | 1.843e−5 | 15/381 |
| 22 | alcohol dehydrogenase (NADP+) activity | 2.182e−5 | 04/16 |
| 23 | cytoskeletal protein binding | 2.724e−5 | 21/703 |
| 24 | receptor binding | 3.475e−5 | 34/1506 |
| 25 | heterocyclic compound binding | 3.705e−5 | 92/5912 |
| 26 | organic cyclic compound binding | 3.731e−5 | 92/5913 |
| 27 | adenyl ribonucleotide binding | 6.522e−5 | 35/1621 |
| 28 | serine-type endopeptidase activity | 7.581e−5 | 10/203 |
| 29 | adenyl nucleotide binding | 7.650e−5 | 35/1634 |
| 30 | ATP binding | 1.038e−4 | 34/1592 |
| 31 | methylcrotonoyl-CoA carboxylase activity | 1.162e−4 | 02/02 |
| 32 | androsterone dehydrogenase (B-specific) activity | 1.162e−4 | 02/02 |
| 33 | glycosaminoglycan binding | 1.173e−4 | 10/214 |
| 34 | unfolded protein binding | 1.445e−4 | 8/140 |
| 35 | carbohydrate binding | 1.586e−4 | 16/514 |
| 36 | serine-type peptidase activity | 2.261e−4 | 10/232 |
| 37 | serine hydrolase activity | 2.507e−4 | 10/235 |
| 38 | hydrolase activity | 2.554e−4 | 48/2676 |
| 39 | polysaccharide binding | 2.868e−4 | 10/239 |
| 40 | pattern binding | 2.868e−4 | 10/239 |
| 41 | chaperone binding | 3.159e−4 | 05/55 |
| 42 | nucleoside-triphosphatase activity | 3.259e−4 | 21/840 |
| 43 | actin filament binding | 4.356e−4 | 06/90 |
| 44 | heparin binding | 4.590e−4 | 8/166 |
| 45 | pyrophosphatase activity | 5.807e−4 | 21/878 |
| 46 | hydrolase activity, acting on acid anhydrides, in phosphorus-containing anhydrides | 6.067e−4 | 21/881 |
| 47 | hydrolase activity, acting on acid anhydrides | 6.246e−4 | 21/883 |
| 48 | complement binding | 6.284e−4 | 03/16 |
| 49 | ketosteroid monooxygenase activity | 6.876e−4 | 02/04 |
| 50 | 17-alpha,20-alpha-dihydroxypregn-4-en-3-one dehydrogenase activity | 6.876e−4 | 02/04 |

TABLE 8C

Gene Ontology (GO) process - non-recurrence of triple-negative breast cancer

| | Process networks | pValue | Ratio |
|---|---|---|---|
| 1 | Cell adhesion_Integrin-mediated cell-matrix adhesion | 7.479e−11 | 24/214 |
| 2 | Cytoskeleton_Intermediate filaments | 3.098e−9 | 14/81 |
| 3 | Cytoskeleton_Regulation of cytoskeleton rearrangement | 5.148e−9 | 20/183 |
| 4 | Cytoskeleton_Actin filaments | 4.775e−7 | 17/176 |
| 5 | Immune response_Phagosome in antigen presentation | 2.548e−6 | 19/243 |
| 6 | Immune response_Phagocytosis | 1.175e−5 | 17/222 |
| 7 | Inflammation_Amphoterin signaling | 7.625e−5 | 11/118 |
| 8 | Cell cycle_Mitosis | 2.233e−4 | 13/179 |
| 9 | Inflammation_Kallikrein-kinin system | 3.088e−4 | 13/185 |
| 10 | Inflammation_IL-6 signaling | 3.807e−4 | 10/119 |

TABLE 8D

Enrichment by protein function - non-recurrence of triple-negative breast cancer

| Protein class | Actual | n | R | N | Expected | Ratio | p-value | z-score | In data set | In protein function | Protein function in database |
|---|---|---|---|---|---|---|---|---|---|---|---|
| | | | | | | | | | | Percentage | |
| Ligands | 15 | 235 | 514 | 23844 | 5.066 | 2.961 | 1.925E−04 | 4.484 | 6.38% | 2.92% | 2.16% |
| Enzymes | 49 | 235 | 2724 | 23844 | 26.85 | 1.825 | 2.103E−05 | 4.565 | 20.85% | 1.80% | 11.42% |
| Kinases | 10 | 235 | 654 | 23844 | 6.446 | 1.551 | 1.139E−01 | 1.427 | 4.26% | 1.53% | 2.74% |
| Phosphatases | 3 | 235 | 230 | 23844 | 2.267 | 1.323 | 3.958E−01 | 0.4918 | 1.28% | 1.30% | 0.96% |
| Proteases | 7 | 235 | 559 | 23844 | 5.509 | 1.271 | 3.141E−01 | 0.6458 | 2.98% | 1.25% | 2.34% |
| Receptors | 5 | 235 | 1565 | 23844 | 15.42 | 0.3242 | 1.553E−03 | −2.759 | 2.13% | 0.32% | 6.56% |
| Transcription factors | 3 | 235 | 959 | 23844 | 9.452 | 0.3174 | 1.365E−02 | −2.153 | 1.28% | 0.31% | 4.02% |
| Other | 143 | 235 | 16691 | 23844 | 164.5 | 0.8693 | 1.631E−03 | −3.076 | 60.85% | 0.86% | 70.00% |

2.3. Classification Based on Relapse Status

Figure 2:
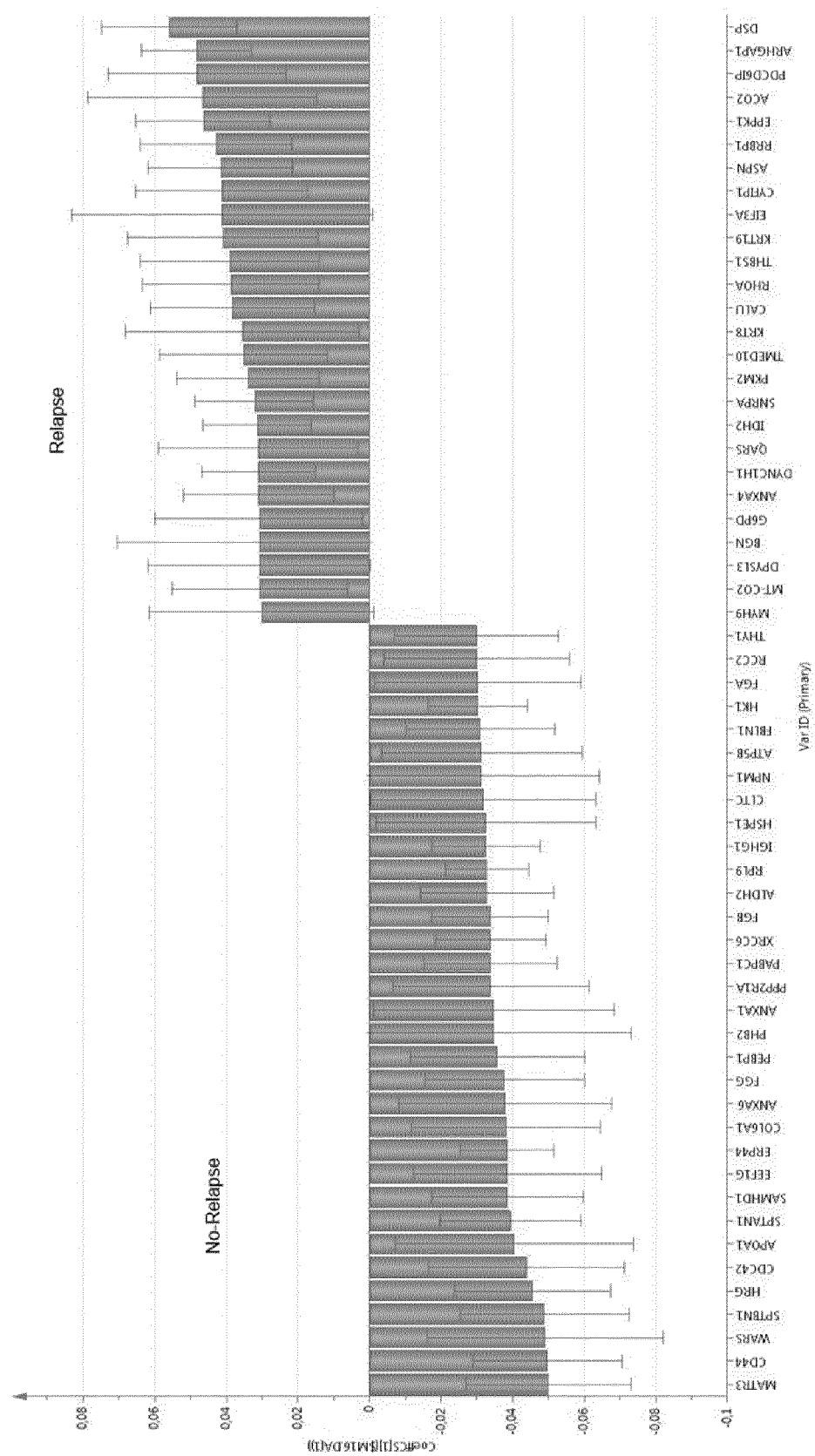
FIG. 2. Tumor classification by orthogonal partial least squares analysis (OPLS) in the global analysis.

The inventors investigated if they could detect differences between "relapse" and "no relapse" groups in terms of protein levels in the triple-negative tumors by OPLS analysis. This analysis was performed on 549 proteins for which quantitative informative was available in all the tumors. The OPLS model, initially based on all 549 proteins, was optimized by stepwise removal of proteins with small VIP (Variable Importance in the Projection) value. This was performed until the model did not improve anymore as judged by the CV-ANOVA p-value, indicative of the probability that the model is the result of chance alone. The optimized OPLS model included 58 proteins (p=2.1 $10^{-15}$) (FIG. 2). Among these proteins, 33 were assigned to the group without recurrence and 26 to the group with recurrence. These proteins were matched against a database consisting of known protein signaling pathways using Metacore. For the "No-Relapse" group, 2 significant pathways (p<0.05) were found: Blood coagulation (p=4.4 $10^{-6}$) and Chemotaxis_Lipoxin inhibitory action on fMLP-induced neutrophil chemotaxis (p=0.0003). The Relapse group was characterized by just one significant pathway: Cytoskeleton remodeling_Keratin filaments (p=7.9 $10^{-7}$) (Table 9).

TABLE 9

| | | Maps | pValue | Ratio | |
|---|---|---|---|---|---|
| No relapse | 1 | Blood coagulation_Blood coagulation | 4.471E−06 | 4 | 39 |
| | 2 | Chemotaxis_Lipoxin inhibitory action on fMLP-induced neutrophil chemotaxis | 3.141E−04 | 3 | 46 |
| relapse | 1 | Cytoskeleton remodeling_Keratin filaments | 7.957E−07 | 4 | 36 |

2.4. Proteomic Signature of "Relapse" Group Triple-Negative Breast Tumors

By combining protein lists obtained from the univariate (with iQuantitator) and the multivariate analyses (OPLS), two lists of proteins were generated that characterized the "Relapse" (9 proteins) and "No Relapse" (5 proteins) groups of triple negative breast tumors (Tables 10A and B). It is not possible to assign a significant pathway for the "No-Relapse" group with a FDR<0.05; on the other side, the pathway Cytoskeleton remodeling_Keratin filaments (p=1.9 $10^{-8}$) was found for the "Relapse" group, according our previous analyses for this group. Among these proteins, Thrombospondin-1 is known to be a secreted ligand. While the Desmoplakin is a plasma membrane protein, it has already been described as a protein detectable in serum (López-Farré A. J. et al, 2012).

TABLE 10A

Proteins characterizing the "no relapse" for triple-negative breast cancer

| Biomarkers for TNBC no Relapse | | GO uniprot | expression | iTRAQ ratio |
|---|---|---|---|---|
| WARS | Tryptophanyl-tRNA synthetase | mitochondria | over-expressed | 1.6 |
| SAMHD1 | SAM domain and HD domain-containing protein 1 | nucleus | over-expressed | 1.4 |
| HSPE1 | 10 kDa heat shock protein | mitochondria | over-expressed | 1.6 |
| IGHG1 | Ig gamma-1 chain C region | secreted | under-expressed | 0.4 |
| HK1 | Hexokinase-1 | cytosol | over-expressed | 1.5 |

TABLE 10B

Proteins characterizing the "relapse" for triple-negative breast cancer

| Biomarkers for TNBC Relapse | | GO uniprot | expression | iTRAQ ratio |
|---|---|---|---|---|
| DSP | Desmoplakin | plasma membrane | over-expressed | 1.8 |
| ARHGAP1 | Rho GTPase-activating protein 1 | cytosol | over-expressed | 1.3 |
| EPPK1 | Epiplakin | cytoplasm | over-expressed | 1.4 |
| KRT19 | Keratin type I cytoskeletal 19 | cell periphery | over-expressed | 2.1 |
| THBS1 | Thrombospondin-1 | secreted | over-expressed | 1.7 |
| KRT8 | Keratin type II cytoskeletal 8 | keratin filament | over-expressed | 2.7 |
| IDH2 | Isocitrate dehydrogenase [NADP] | mitochondria | over-expressed | 1.7 |
| G6PD | Glucose-6-phosphate 1-dehydrogenase | cytoplasm | over-expressed | 1.7 |
| DPYSL3 | Dihydropyrimidinase-related protein 3 | cytoplasm | over-expressed | 1.9 |

2.5. Pathways Analysis of Individual Tumor

Pathway analysis was also performed on each of the 80 tumor samples separately. By this, the inventors obtained a fingerprint of affected pathways for each tumor. All proteins with a level significantly differing from the mean protein level among all "Relapse group" tumors or "No-relapse group" tumors were included in the individual tumor analysis; in total 1078 proteins. The relative intensities of these tumor specific proteins were mapped to the pathway maps of the Metacore database. The analysis identified the pathways that were the most significant in each of the 80 individual tumors data sets, measured by Fisher's exact test. The inventors used the association ranks as input variables to the multivariate analysis for sample comparison, thus based on pathway enrichment. To detect pathway alterations connected to relapse risk, the inventors performed OLPLS analysis on the pathway association data. The OPLS model was optimized as described in the group analysis. The inventors performed stepwise removal of variables (i.e. pathways) with less influence on the separation performance of the model until the model did not improve anymore. The most significant pathway for "No-relapse group" is Glycolysis. The top-ranked pathways in relapse group were cytoskeleton Remodeling_Keratins-filaments and Gap junctions.

2.6. Validation of Dysregulated Protein Expression

Figure 3:
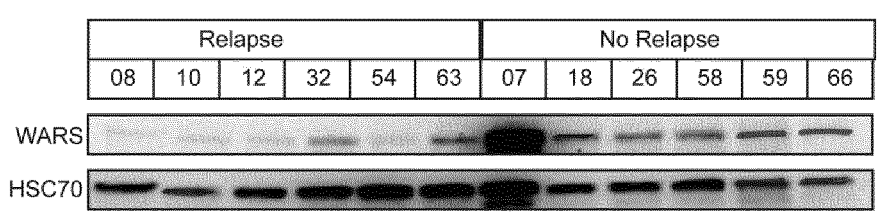
FIG. 3. Immunoblot analysis of the WARS and THBS1 biomarkers expression in relapsing and non-relapsing subject. Six and seven "Relapse" tumors and six and eight "No Relapse" tumors were immunoblotted. HSC70 was used as a control.
Figure 3:
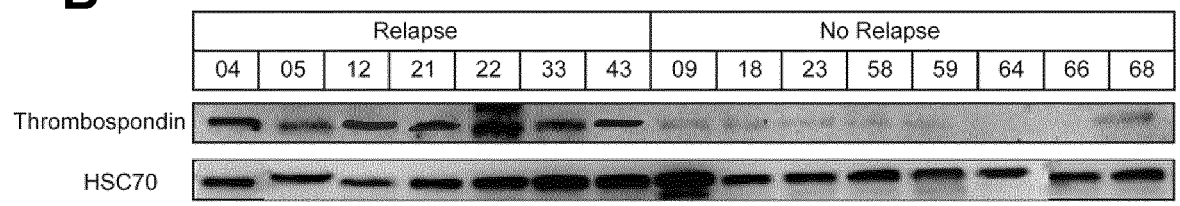

To proceed with the first steps in validating our MS analysis, the inventors confirmed the differential expression of two dysregulated proteins by Western-Blot analysis using samples from the same triple-negative breast tumors cohort. The proteins Thrombospondin-1 and Tryptophanyl-tRNA synthetase were selected for validation based on their potential significance in breast cancer tumorigenesis. The expression of Thrombospondin-1 was found to be elevated in primary breast tumors of the "recurrent" group when compared to the "non-recurrent" group tumors. Inversely, Tryptophanyl-tRNA synthetase was found to be elevated in the "No Relapse" group when compared to the "Relapse" group (FIG. 3).

2.7. Pronostic Value of the Markers

The prognostic value of the markers was evaluated through estimation of overall survival (OS) using Kaplan-Meier method. The patients were divided into two categories based on the median iTraq expression data for each marker: high versus low expression.

Figure 4:
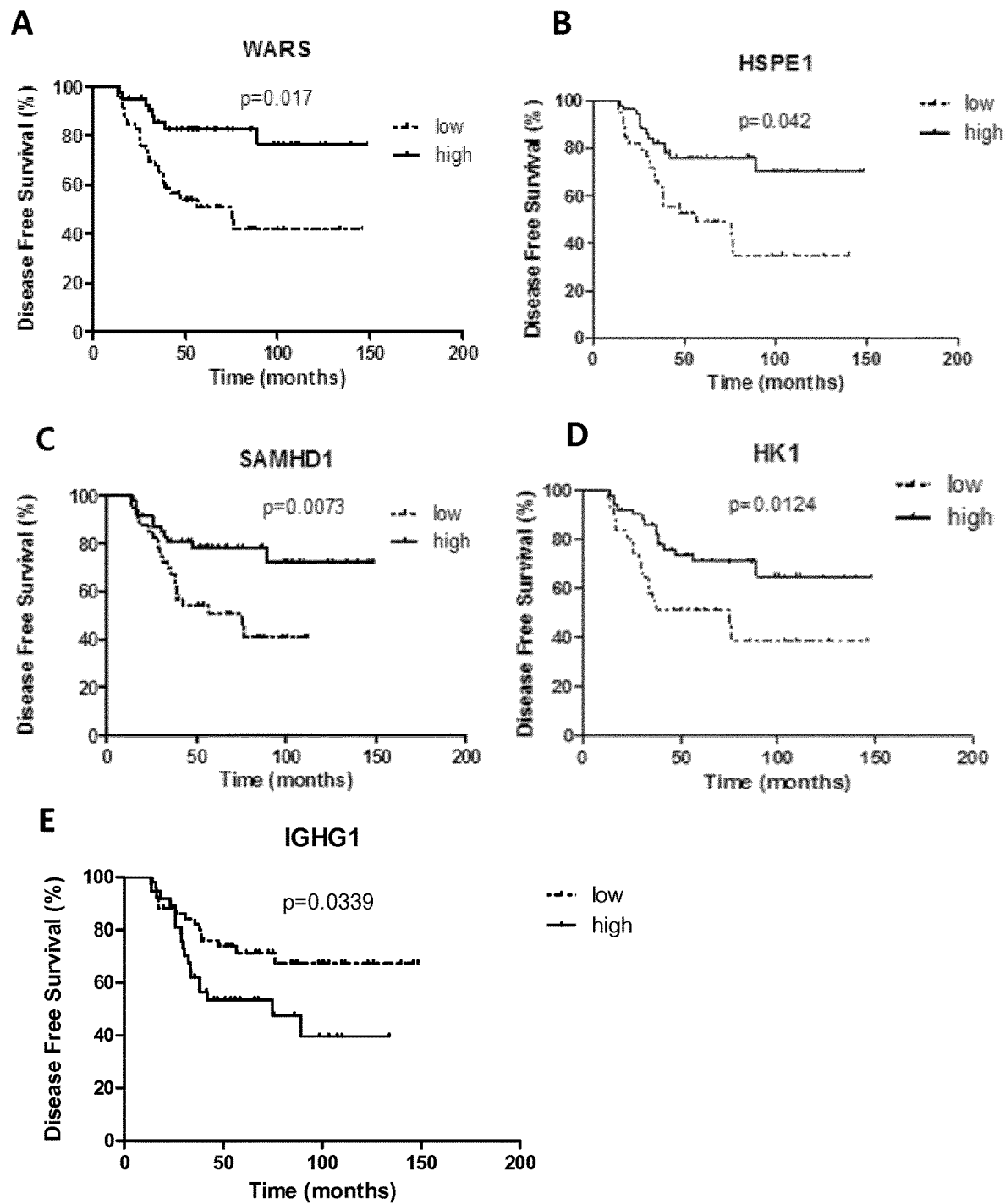
FIG. 4. Kaplan-Meier estimates of disease-free survival for WARS (A), HSPE1 (B), SAMHD1 (C), HK1 (D), and IGHG1 (E) expression.
Figure 5:
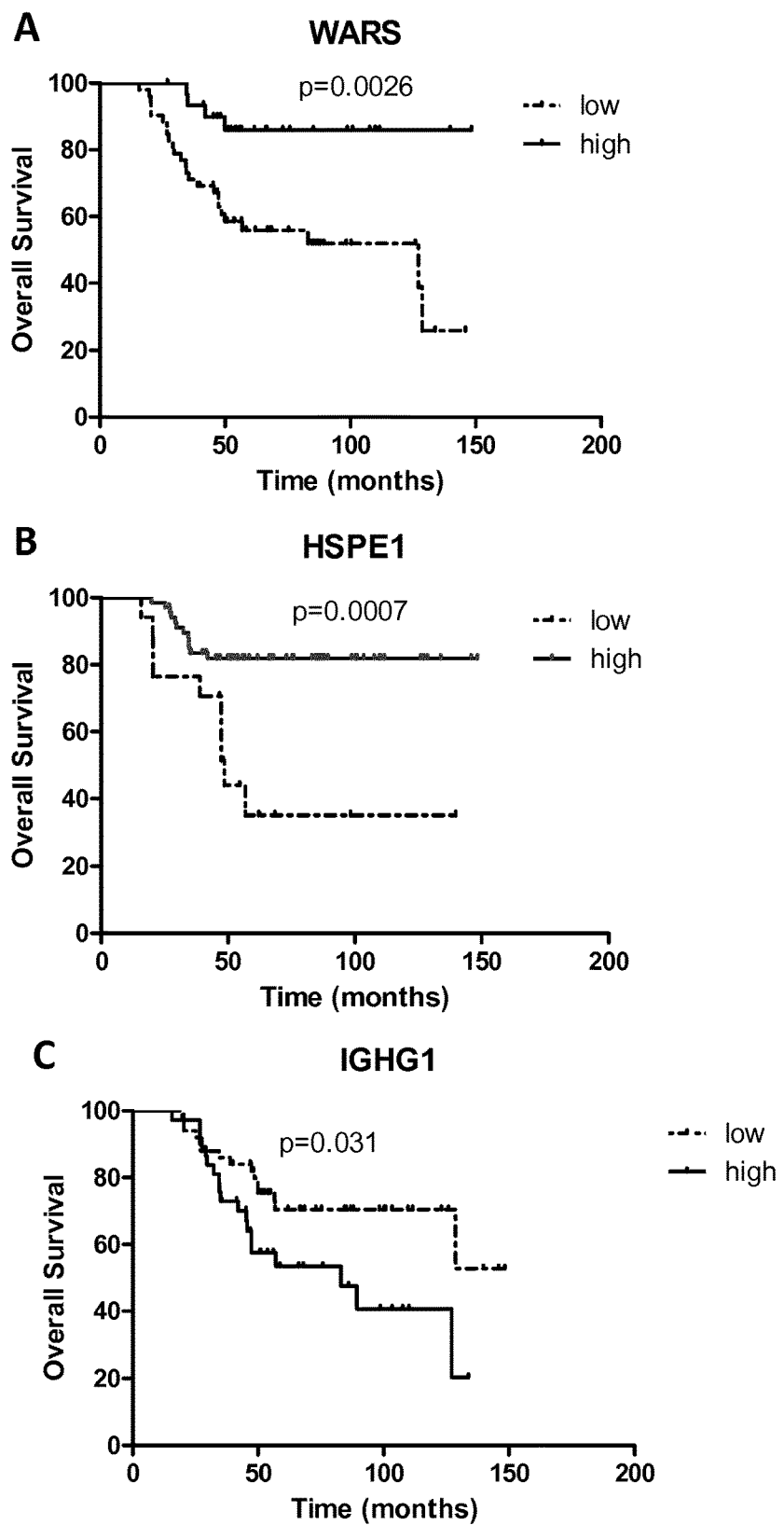
FIG. 5. Kaplan-Meier estimates of overall survival for WARS (A), HSPE1 (B) and IGHG1 (C) expression.

For the "No relapse" group, patients' tumor with high expression levels of Tryptophanyl-tRNA synthetase (WARS), 10 kDa heat shock protein (HSPE1), SAM domain and HD domain-containing protein 1 (SAMHD1) and Hexokinase-1 (HK1) experienced a significantly better DFS (Disease Free Survival) compared with those with low expression (p=0.0017, p=0.0042, p=0.0073, p=0.0124 respectively), and inversely, patients' tumor with low expression levels of Ig gamma-1 chain C region (IGHG1) showed a significant better DFS compared with those with high expression (p=0.0339), in agreement with iTraq results (FIG. 4). Furthermore, tumors with high Tryptophanyl-tRNA synthetase (WARS)(p=0.0026), 10 kDa heat shock protein (HSPE1) (p=0.0067) and Ig gamma-1 chain C region (IGHGI) (p=0.031) expression were also associated with higher OS (overall survival) rates (FIG. 5).

Figure 6:
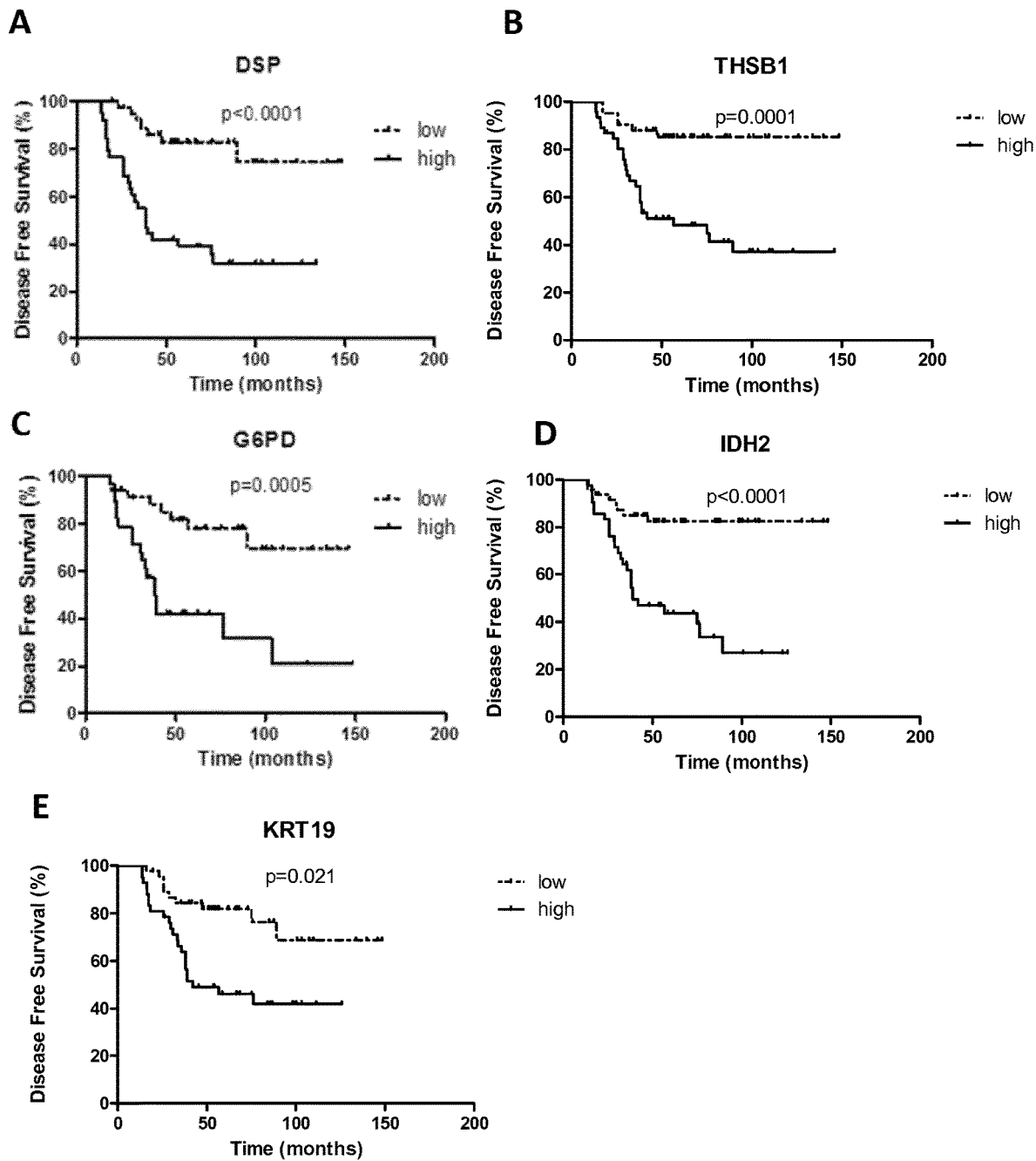
FIG. 6. Kaplan-Meier estimates of disease-free survival for DSP (A), THBS1 (B), G6PD (C), IDH2 (D), KRT19 (E), KRT8 (F), EPPK1 (G), ARHGAP1 (H) and DPYSL3 (I) expression.
Figure 6:
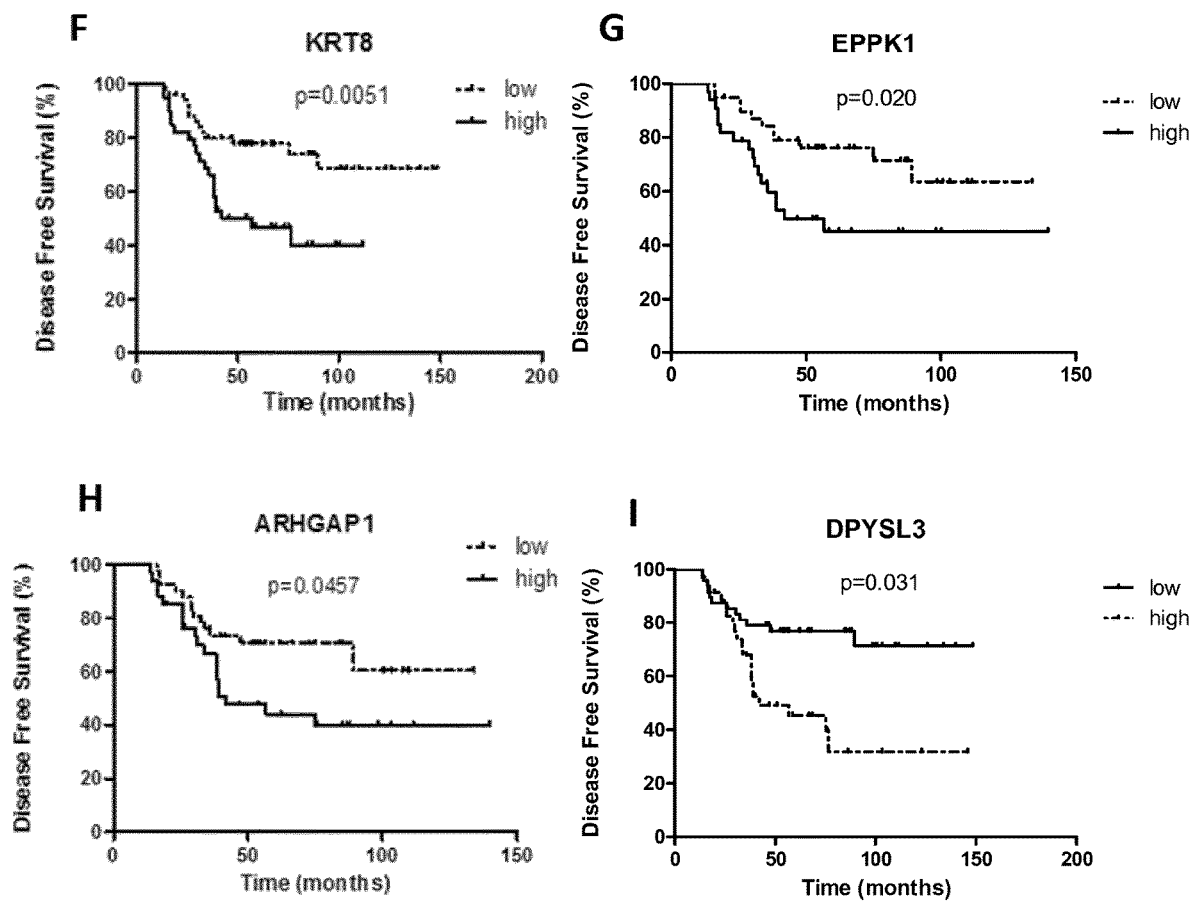
Figure 7:
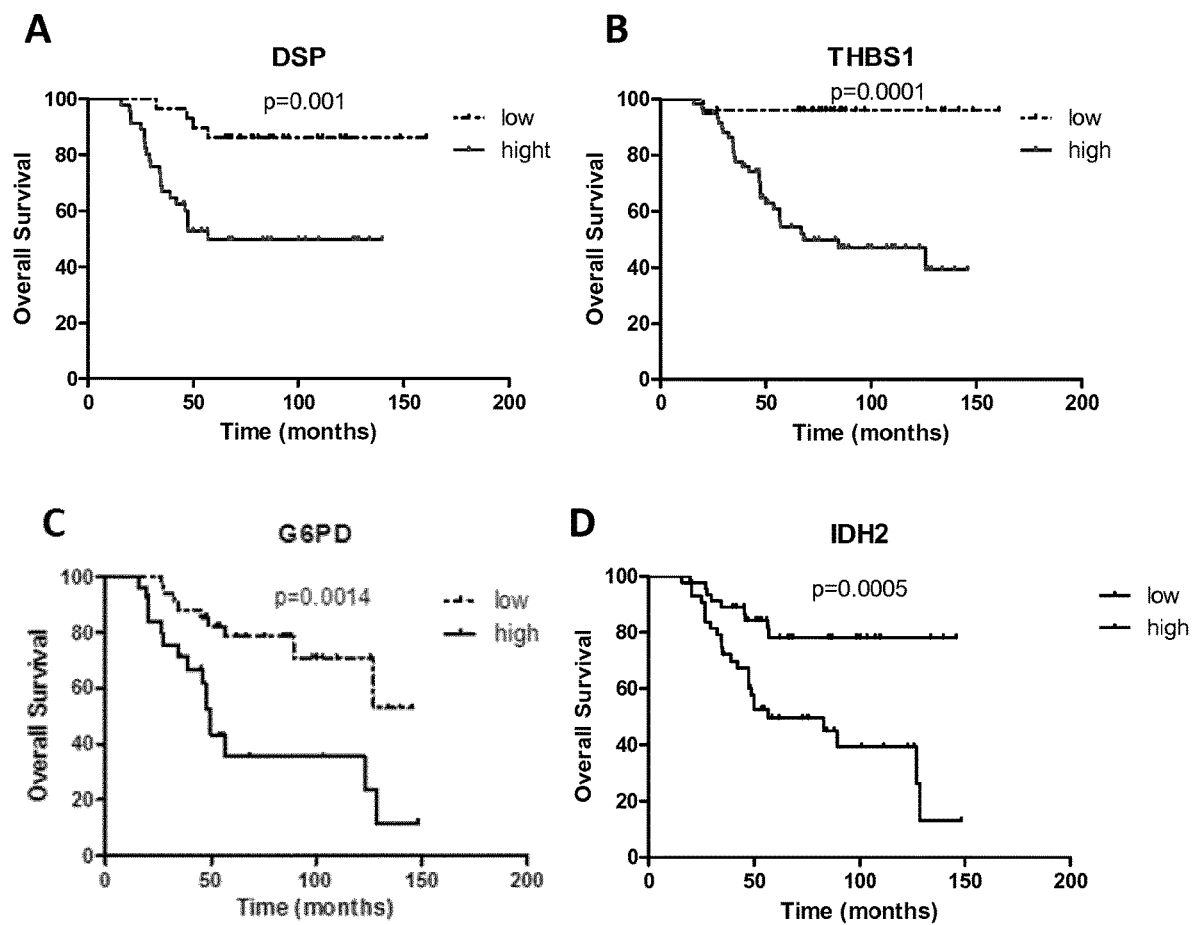
FIG. 7. Kaplan-Meier estimates of overall survival for DSP (A), THBS1 (B), G6PD (C), and IDH2 (D) expression.

For the "Relapse" group, patients' tumors with high expression level of any of the 9 proteins experienced a significantly worse DFS compared with those with low expression (p<0.0001, p=0.0001, p=0.0005, p<0.0001, p=0.021, p=0.0051, p=0.020, p=0.0457 and p=0.031) for pourquoi Desmoplakin (DSP), Thrombospondin-1 (THBS1), Glucose-6-phosphate 1-dehydrogenase (G6PD), Isocitrate dehydrogenase [NADP] (IDH2), Keratin type I cytoskeletal 19 (KRT19), Keratin type II cytoskeletal 8 (KRT8), Epiplakin (EPPK1), Rho GTPase-activating protein 1 (ARHGAP1), and Dihydropyrimidinase-related protein 3 (DPYSL3), respectively (FIG. 6). Furthermore, tumors with high Desmoplakin (DSP) (p=0.001), Thrombospondin-1 (THSB1) (p=0.0001), Glucose-6-phosphate 1-dehydrogenase (G6PD) (p=0.0014) and Isocitrate dehydrogenase [NADP] (IDH2) (p=0.0005) expression were also associated with lower OS rates (FIG. 7). Accordingly, the respective hazard ratios for disease progression or death were also significantly higher for patients whose tumors had high expression of these proteins. Specifically, elevated Thrombospondin-1 (THSB1) (HR=3.91–HR: Hazard rate ratio) Desmoplakin (DSP) (HR=4.36), Glucose-6-phosphate 1-dehydrogenase (G6PD) (HR=4.18), Isocitrate dehydrogenase [NADP] (IDH2) (HR=4.42), Keratin type I cytoskeletal 19 (KRT19) (HR=2.97), Keratin type II cytoskeletal 8 (KRT8) (HR=2.70), Epiplakin (EPPK1) (HR=2.47), Rho GTPase-activating protein 1 (ARHGAP1) (HR=5.06) or Dihydropyrimidinase-related protein 3 (DPYSL3) (HR=2.98) were associated with increased risk of disease progression. Similar association were observed for increased risk of death for Thrombospondin-1 (THSB1) (HR=4.30), Desmoplakin (DSP) (HR=3.67), Glucose-6-phosphate 1-dehydrogenase (G6PD) (HR=3.90), Isocitrate dehydrogenase [NADP] (IDH2) (HR=3.32), or Keratin type I cytoskeletal 8 (KRT8) (HR=2.50). In opposition, the hazard ratios for non-recurrent group were significantly higher for patients whose tumors had high expression of Tryptophanyl-tRNA synthetase (WARS), 10 kDa heat shock protein (HSPE1), SAM domain and HD domain-containing protein 1 (SAMHD1), Hexokinase-1 (HK1) and a low expression of Ig gamma-1 chain C region (IGHG1). Specifically, elevated Tryptophanyl-tRNA synthetase (WARS)(HR=3.12) and 10 kDa heat shock protein (HSPE1) (3.67) were associated with a weak risk of disease progression or death.

Figure 8:
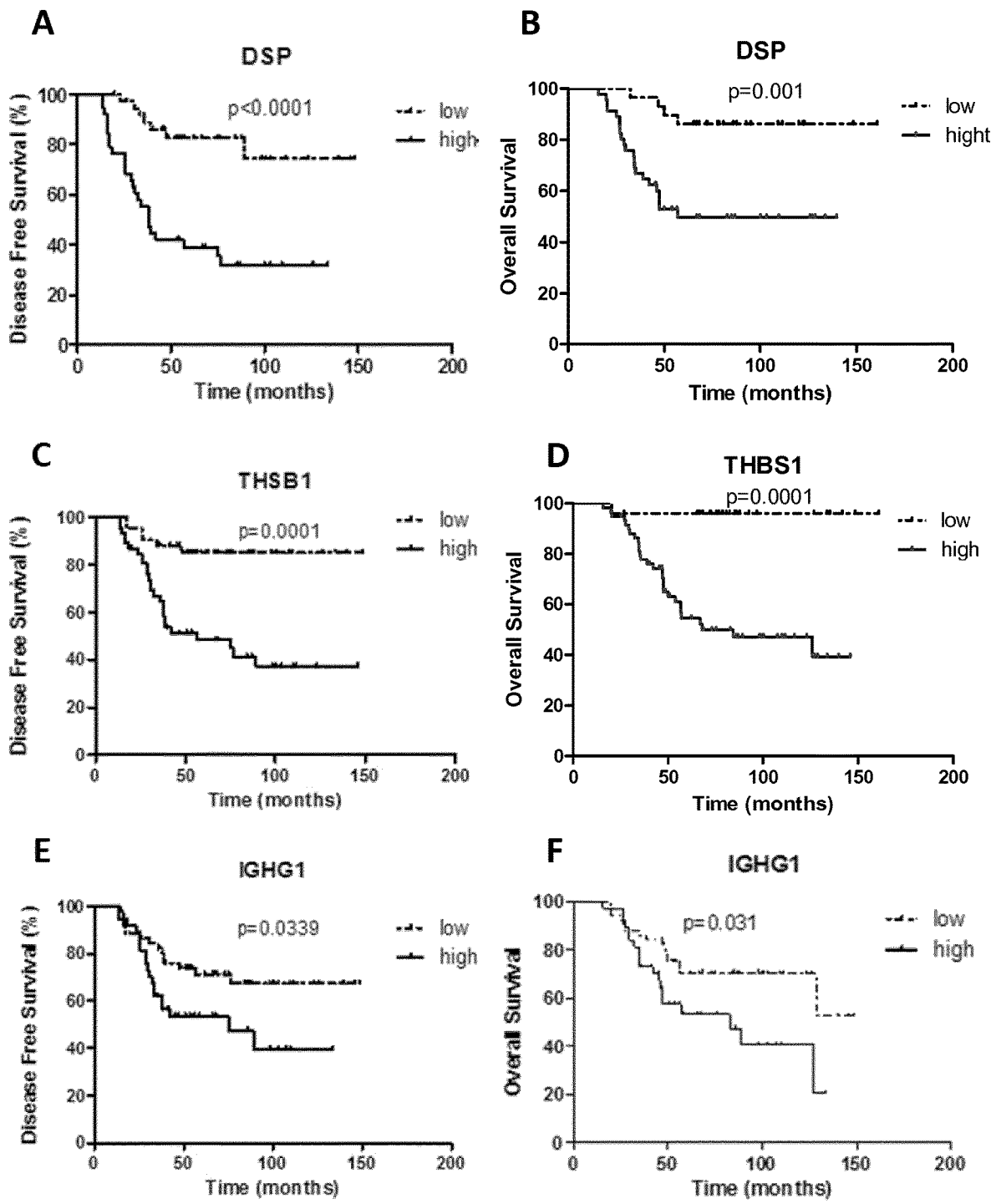
FIG. 8. Kaplan-Meier curves for the biomarkers DSP (A,B), THBS1 (C,D) and IGHG1 (E,F) (disease free survival on the left (A,C,E) and overall survival on the right (B,D,F)).

The FIG. 8 summarizes these Kaplan-Meier curves for three secreted proteins: Desmoplakin (DSP), THSB1 and Ig gamma-1 chain C region (IGHG1).

2.8. Preliminary Validation in Patient-Derived Serum Samples

The inventors then questioned whether any of secreted protein could be measured in the serum of TNBC patients, notably in TNBC relapsing patients.

Figure 9:
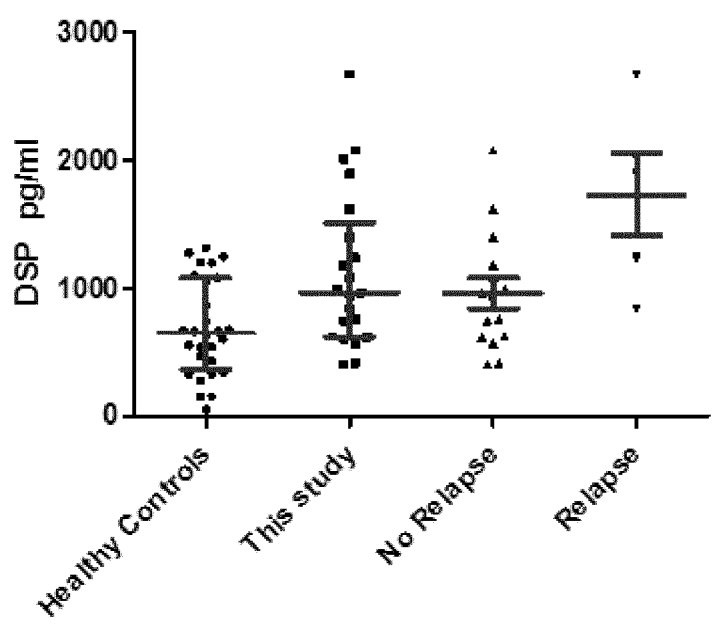
FIG. 9. Validation of DSP in the serum samples of a triple-negative breast cancer cohort.

The determination of the amount of Desmoplakin in the serum of the TNBC cohort corresponding to the triple-negative tumors studied in this paper, showed that Desmoplakin is more concentrated in the "Relapse" group (p=0.01) than in the "No-Relapse" group, according to the proteomic results disclosed herein (FIG. 9).

As very little serum samples were available in this cohort, the inventors extended the determination of Desmoplakin expression in a newer TNBC serum cohort. Based on this new cohort, the inventors demonstrated a significant over-expressed amount of Desmoplakin in TNBC serums compared with healthy controls (p=0.0008).

3. Discussion

Despite the many recent advances in breast tumors treatments through targeted therapies, no specific treatment exists for the triple-negative breast tumors and there are no prognostic molecular markers that would predict whether a tumor will behave aggressively or remain indolent. It is abundantly clear that tumor biology plays a significant role in resultant tumor behaviour. Unfortunately, triple-negative breast primary tumors that are placed in the same prognostic category based on currently used parameters, may behave differently. It is the inventors' hypothesis that the underlying biology of these tumors and differences in its detail will determine a particular tumor's potential for aggressiveness. In addition, these biological differences can be used to identify novel molecular markers that may be useful for diagnostic, prognostic, or predictive purposes, the success of which would pave the road to a new era of personalized medicine in breast cancer.

In this study, the inventors performed quantitative proteomic profiling of 80 triple-negative breast tumors to identify first differential protein expression between triple-negative breast tumors and normal tissues and second, to identify potential prognostic markers of recurrence. To the inventors' knowledge, this study represents the largest proteomic analysis of triple-negative breast tumors ever realized.

From all the triple negative breast tumors, 219 proteins with significant differential expression in tumors compared to normal tissues were identified. Among these proteins, 58 proteins had previously been reported to be involved in breast tumors.

Another aim of this study was to identify differential protein expression between no relapse patients' group and relapse patients' group. The inventors characterized 5 proteins associated with the no-relapse group (i.e. Hexokinase-1, 10 kDa heat shock protein, Ig gamma-1 chain C region, SAM domain and HD domain-containing protein 1, and Tryptophanyl-tRNA synthetase) and 9 proteins associated with the relapse group (i.e. Desmoplakin, Rho GTPase-activating protein 1, Epiplakin, Glucose-6-phosphate 1-dehydrogenase, Isocitrate dehydrogenase [NADP], Keratin type I cytoskeletal 19, Keratin type I cytoskeletal 8, Dihydropyrimidinase-related protein 3, and Thrombospondin-1). It is thus proposed herein that the above group of proteins is a protein signature of the no-relapse group and relapse group of triple negative breast tumors, respectively.

Among these proteins, it was shown that Desmoplakin could be easily detected in serum of patients, and was also differentially expressed in "Relapse" group compared to "No-Relapse" group. As previously mentioned, this protein is a key component of desmosomes, and belong to the pathway cytoskeleton Remodeling_Keratins-filaments and Gap junctions found in Metacore analysis, that is in agreement with the fact that this pathway is the top-ranked pathway characterizing the "Relapse" group in our proteomic approach. Expanding the assays on a larger cohort sera of patients with breast cancer, the inventors demonstrated that this protein is differentially over-expressed in TNBC sera compared to healthy controls.

REFERENCES

Brenton J. D., Carey L. A., Ahmed A. A., and Caldas C. (2005). *J. Clin. Oncol.;* 23(29):7350-60.

Hudis C. A., and Gianni L. (2011). *Oncologist;* 16 Suppl 1:1-11.

Ernoult E., Gamelin E., and Guette C. (2008). *Proteome Sci.;* 13; 6:27.

Ernoult E., Bourreau A., Gamelin E., Guette C. (2010). *J Biomed Biotechnol.;* 2010:927917.

Rakha E. A., Reis-Filho J. S., and Ellis I. O. (2008). *J. Clin. Oncol.;* 26(15):2568-81.

López-Farré A. J., Zamorano-León J. J., Segura A., Mateos-Cáceres P. J., Modrego J., Rodríguez-Sierra P., Calatrava L., Tamargo J., and Macaya C. (2012). *J. Neurochem.;* 121(2):314-25.

Hou H. W., Warkiani M. E., Khoo B. L., Li Z. R., Soo R. A., Tan D. S., Lim W. T., Han J., Bhagat A. A., Lim C. T. (2013). *Sci. Rep.;* 3:1259.

Reeves J. R. and Bartlett J. M. S. (2000). *Methods in Molecular Medicine;* vol. 39, chapter 51, 471-483.

Schena M. (2005). *Protein microarrays;* Jones and Bartlett Learning.

Hamelinck D., Zhou H., Li L., Verweij C., Dillon D., Feng Z., Costa J., and Haab B. B. (2005). *Mol. Cell Proteomics;* 4(6):773-84.

Köhler G. and Milstein C. (1975). *Nature;* 256 (5517): 495-7.

Kozbor D., Roder J. C. (1983). *Immunology Today;* 4: 72-79.

Roder J. C., Cole S. P., and Kozbor D. (1986). *Methods Enzymol.;* 121:140-167.

Huse W. D., Sastry L., Iverson S. A., Kang A. S., Alting-Mees M., Burton D. R., Benkovic S. J., and Lerner R. A. (1989). *Science;* 246:1275-1281.

Weigelt B. and Bissell M. J. (2008). *Semin Cancer Biol.;* 18(5): 311-321.

Kenny P. A., Lee G. Y., Myers C. A., Neve R. M., Semeiks J. R., Spellman P. T., Lorenz K., Lee E. H., Barcellos-Hoff M. H., Petersen O. W., Gray J. W., and Bissell M. J. (2007). *Mol Oncol.;* 1(1):84-96.

Li Q., Chow A. B., and Mattingly R. R. (2010). *J Pharmacol Exp Ther.;* 332(3): 821-828.

Liu B., Fan Z., Edgerton S. M., Deng X. S., Alimova I. N., Lind S. E., and Thor A. D. (2009). *Cell Cycle;* 8(13): 2031-40.

Mitchell P. (2002). *Nature Biotech;* 20: 225-229.

Haab B. B. (2005). *Mol Cell Proteomics;* 4(4):377-83.

Eckel-Passow J. E., Hoering A., Therneau T. M., and Ghobrial I. (2005). *Cancer Res.;* 65(8):2985-9.

Kingsmore S. F. (2006). *Nat Rev Drug Discov.;* 5(4):310-20.

Chandra H., Reddy P. J., and Srivastava S. (2011). *Expert Rev Proteomics;* 8(1):61-79.

Wisniewski J. R., Zougman A., Nagaraj N., and Mann M. (2009). *Nat. Methods;* 6 (5): 359-62.

Ernoult E., Guette C. (2011) OFFGEL-Isoelectric Focussing Fractionation for the Analysis of Complex Proteome. Neuroproteomics, Edited by Ka Wan Li, Humana Press Inc, U.S. 145-158.

Shilov I. V., Seymour S. L., Patel A. A., Loboda A., Tang W. H., Keating S. P., Hunter C. L., Nuwaysir L. M., and Schaeffer D. A. (2007). *Mol Cell Proteomics;* 6: 1638-1655.

Schwacke J. H., Hill E. G., Krug E. L., Comte-Walters S., and Schey K. L. (2009). *BMC Bioinformatics;* 10: 342.

Grant J. E., Bradshaw A. D., Schwacke J. H., Baicu C. F., Zile M. R., and Schey K. L. (2009). *J Proteome Res;* 8: 4252-4263.

Besson D., Pavageau A. H., Valo I., Bourreau A., Bélanger A., Eymerit-Morin C., Moulière A., Chassevent A., Boisdron-Celle M., Morel A., Solassol J., Campone M., Gamelin E., Barré B., Coqueret O., and Guette C. (2011). *Mol Cell Proteomics;* 10(12): M111.009712.

Zeeberg B. R., Qin H., Narasimhan S., Sunshine M., Cao H., Kane D. W., Reimers M., Stephens R. M., Bryant D., Burt S. K., Elnekave E., Hari D. M., Wynn T. A., Cunningham-Rundles C., Stewart D. M., Nelson D., and Weinstein J. N. (2005). *BMC Bioinformatics;* 6: 168.

The invention claimed is:

1. An in vitro method for diagnosing and/or prognosing and treating a recurrent triple-negative breast cancer in a subject, comprising the steps of:
   a) obtaining a biological sample from a subject,
   b) detecting the expression levels of three biomarkers comprising Desmoplakin, Thrombospondin-1 and Isocitrate dehydrogenase [NADP] in the biological sample,
   c) diagnosing and/or prognosing a recurrent triple-negative breast cancer when the expression levels of the three biomarkers comprising Desmoplakin, Thrombospondin-1 and Isocitrate dehydrogenase [NADP] are superior to the expression levels of the three biomarkers comprising Desmoplakin, Thrombospondin-1 and Isocitrate dehydrogenase [NADP] in a biological sample of at least one healthy subject, and
   d) administering an effective amount of a chemotherapeutic agent to the diagnosed subject.

2. The method according to claim 1, further comprising detecting the expression levels of at least two biomarkers selected from the group consisting of Hexokinase-1, 10 kDa heat shock protein, Ig gamma-1 chain C region, SAM domain and HD domain-containing protein 1, and Tryptophanyl-tRNA synthetase in the biological sample in step b).

3. The method according to claim 2, wherein the expression level of Hexokinase-1, 10 kDa heat shock protein, SAM domain and HD domain-containing protein 1, or Tryptophanyl-tRNA synthetase, is superior to a reference expression level obtained from a biological sample of at least one healthy subject.

4. The method according to claim 2, wherein the expression level of Ig gamma-1 chain C region is inferior to a reference expression level obtained from a biological sample of at least one healthy subject.

5. The method according to claim 2, wherein one of said at least two biomarkers is Tryptophanyl-tRNA synthetase.

6. The method according to claim 1, further comprising detecting the expression levels of at least one biomarker selected from the group consisting of Rho GTPase-activating protein 1, Epiplakin, Glucose-6-phosphate 1-dehydrogenase, Keratin type I cytoskeletal 19, Keratin type I cytoskeletal 8, and Dihydropyrimidinase-related protein 3 in the biological sample in step b).

7. The method according to claim 1, further comprising measuring the expression level of the biomarkers Hexokinase-1, 10 kDa heat shock protein, SAM domain and HD domain-containing protein 1, and Tryptophanyl-tRNA synthetase, and Ig gamma-1 chain C region in the biological sample in step b).

8. The method according to claim 1, further comprising detecting the expression level of biomarkers Glucose-6-phosphate 1-dehydrogenase in the biological sample in step b).

9. The method according to claim 1, further comprising detecting the expression level of biomarkers Glucose-6-phosphate 1-dehydrogenase, and Keratin type II cytoskeletal 8 in the biological sample in step b).

10. The method according to claim 1, wherein the expression level is determined by a method selected from the group consisting of Western blot, immunoblot, enzyme-linked immunosorbant assay (ELISA), enzyme-linked immunospot (ELISPOT), radioimmunoas say (RIA), immunohistochemistry, immunoprecipitation, fluorescence activated cell sorting (FACS), microscopy, flow cytometry, microcytometry, protein binding assay, ligand binding assay, microarray, polyacrylamide gel electrophoresis such as SDS-PAGE, surface plasmon resonance (SPR), Förster resonance energy transfer (FRET), Bioluminescence resonance energy transfer (BRET), chemiluminescence, fluorescent polarization, phosphorescence, mass spectrometry, magnetic resonance imaging (MRI), and any combination thereof.

* * * * *